US008846624B2

(12) United States Patent
Chaikof et al.

(10) Patent No.: US 8,846,624 B2
(45) Date of Patent: Sep. 30, 2014

(54) MODIFIED PROTEIN POLYMERS

(75) Inventors: Elliot L. Chaikof, Atlanta, GA (US);
Vincent P. Conticello, Decatur, GA (US)

(73) Assignee: Emory University, Atlanta, GA (US)

( * ) Notice: Subject to any disclaimer, the term of this patent is extended or adjusted under 35 U.S.C. 154(b) by 1544 days.

(21) Appl. No.: 12/440,670

(22) PCT Filed: Sep. 11, 2007

(86) PCT No.: PCT/US2007/078172
§ 371 (c)(1),
(2), (4) Date: Apr. 10, 2009

(87) PCT Pub. No.: WO2008/033847
PCT Pub. Date: Mar. 20, 2008

(65) Prior Publication Data
US 2010/0048473 A1    Feb. 25, 2010

Related U.S. Application Data

(60) Provisional application No. 60/825,255, filed on Sep. 11, 2006, provisional application No. 60/863,117, filed on Oct. 26, 2006.

(51) Int. Cl.
| A61K 38/16 | (2006.01) |
| A61K 48/00 | (2006.01) |
| A61K 38/39 | (2006.01) |
| C07K 14/00 | (2006.01) |
| A61L 31/04 | (2006.01) |
| A61L 15/32 | (2006.01) |
| A61L 27/22 | (2006.01) |

(52) U.S. Cl.
CPC .............. *A61L 31/047* (2013.01); *A61L 15/32* (2013.01); *A61L 27/227* (2013.01)
USPC ......... 514/21.2; 530/324; 530/353; 514/44 R; 524/423

(58) Field of Classification Search
None
See application file for complete search history.

(56) References Cited

U.S. PATENT DOCUMENTS

| 4,485,045 A | 11/1984 | Regen |
| 4,522,803 A | 6/1985 | Lenk et al. |
| 4,560,599 A | 12/1985 | Regen |
| 4,880,883 A | 11/1989 | Grasel et al. |
| 4,906,465 A | 3/1990 | Chaikof et al. |
| 5,071,532 A | 12/1991 | Taillet et al. |
| 5,288,517 A | 2/1994 | Kanno et al. |
| 5,399,331 A | 3/1995 | Loughrey et al. |
| 5,417,969 A | 5/1995 | Hsu et al. |
| 5,429,618 A | 7/1995 | Keogh |
| 5,741,325 A | 4/1998 | Chaikof et al. |
| 5,755,788 A | 5/1998 | Strauss |
| 5,911,942 A | 6/1999 | Fofonoff et al. |
| 6,071,532 A | 6/2000 | Chaikof et al. |
| 6,171,614 B1 | 1/2001 | Chaikof et al. |
| 6,583,251 B1 | 6/2003 | Chaikof et al. |
| 7,244,830 B2 | 7/2007 | Chaikof et al. |
| 2004/0063200 A1 | 4/2004 | Chaikof et al. |
| 2004/0110439 A1 | 6/2004 | Chaikof et al. |
| 2004/0171545 A1 | 9/2004 | Chaikof et al. |

FOREIGN PATENT DOCUMENTS

| FR | 2533222 | 3/1984 |
| WO | WO 96/21469 | 7/1996 |
| WO | WO 98/16198 | 4/1998 |
| WO | WO 00/00239 | 1/2000 |
| WO | WO 01/78800 | 10/2001 |
| WO | WO 01/80921 | 11/2001 |
| WO | WO 02/09647 | 2/2002 |
| WO | WO 02/055021 | 7/2002 |
| WO | WO 03/082900 | 10/2003 |
| WO | WO 2005/089816 | 9/2005 |
| WO | WO 2008/033847 | 3/2008 |

OTHER PUBLICATIONS

US 5,556,632, 09/1996, Kohler et al. (withdrawn).
Akagawa et al. (2000) "Mechanism of formation of elastin crosslinks," *Connect. Tissue Res.* 41(2):131-141.
Akita et al. (1994) "Effect of FK506 and anti-CD4 therapy on fetal pig pancreas xenografts and host lymphoid cells in NOD/Lt, CBA, and BALB/c mice," *Cell Trans.* 3(1):61-73.
Anderson et al. (1994) "Bioactive silk-like protein polymer films on silicon devices," Alper, M., Bayby, H., Kaplan, D. and Navia, M., ed.; Materials Research Society Symp Proc.: Pittsburgh, PA; 1994, 330:171-177.
Andree et al. (1994) "Transport rate limited catalysis on macroscopic surfaces: the activation of factor X in a continuous flow enzyme reactor," *Biochemistry* 33(14):4368-4374.
Aoi et al. (1994) "Glycopeptide synthesis by an α-amino acid N-carboxyanhydride (NCA) method: ring-opening polymerization of a sugar-substituted NCA," *Macromolecules* 27(3):875-877.
Aoi et al. (1992) "Architectural control of sugar-containing polymers by living polymerization: ring-opening polymerization of 2-oxazolines initiated with carbohydrate derivatives," *Macromolecules* 25(25):7073-7075.

(Continued)

*Primary Examiner* — Satyanarayana R Gudibande
(74) *Attorney, Agent, or Firm* — Emory Patent Group

(57) ABSTRACT

In an embodiment, a number of synthetic protein triblock copolymers are provided comprising first and second end hydrophobic blocks separated by a central hydrophilic block. In particular, the synthetic proteins are elastin-mimetic proteins having improved mechanical characteristics and related methods of making the proteins with the capability of providing precise control over the mechanical properties. Provided are proteins used in a number of medical devices such as artificial blood vessels, shunts, stents or as embolic agents in situations where it is desired to stop or reduce blood flow or pressure in a localized region.

4 Claims, 26 Drawing Sheets

(56) References Cited

OTHER PUBLICATIONS

Arnander et al. (1988) "Influence of blood flow and the effect of protamine on the thromboresistant properties of a covalently bonded heparin surface," *J. Biomed. Mater. Res.* 22(10):859-868.

Arruda et al. (Feb. 1993) "A Three-Dimensional Constitutice Model for the Large Stretch Behavior of Rubber Elastic Materials," *J. Mech. Phys. Solids* 41(2):389-412.

Badylak et al. (1989) "Small Intestinal Submucosa as a Large Diameter Vascular Graft in the Dog," *J. Surg. Res.* 47:74-80.

Baim, DS (2003) "Percutaneous Treatment of Saphenous Vein Graft Disease," *J. Am. College Cardiol.* 42(8):1370-1387.

Balachander et al. (1990) "Monolayer transformation by nucleophilic substitution: applications to the creation of new monolayer assemblies," *Langmuir* 6(11):1621-1627.

Ballyk et al. (1998) "Compliance Mismatch May Promote Graft-Artery Intimal Hyperplasia by Altering Suture-Line Stresses," *J. Biomechanics* 31:229-237.

Barnes et al. (1979) "Platelet-Reactivity of Isolated Constituents of the Blood Vessel Wall," *Haemostasis* 8:158-170.

Basmadjian et al.(1997) "Coagulation on biomaterials in flowing blood: some theoretical considerations," *Biomaterials* 18(23):1511-1522.

Basmadjian et al. (1983) "Relationship between release rate and surface concentration for heparinized materials," *J. Biomed. Mater. Res.* 17(3):509-518.

Bellingham et al. (Dec. 2003) "Recombinant Human Elastin Polypeptides Self-Assemble into Biomaterials with Elastin-Like Properties," *Biopolymers* 70(4):445-455.

Bergland et al. (2003) "A Biological Hybrid Model for Collagen-Based Tissue Engineered Vascular Constructs," *Biomaterials* 24:1241-1254.

Beyer et al. (1996) "Covalently attached polymer mono- and multilayers on silanized glass substrates," *Thin Solid Films* 285:825-828.

Bierbaum et al. (1995) "A near edge X-ray absorption fine structure spectroscopy and X-ray photoelectron spectroscopy study of the film properties of self assembled monolayers of organosilanes on oxidized Si(100)," *Langmuir* 11(2):512-518.

Biessen et al. (1995) "Synthesis of cluster galactosides with high affinity for the hepatic asialoglycoprotein receptor," *J. Med. Chem.* 38(9):1538-1546.

Billy et al. (Jan. 20, 1995) "Prothrombin activation by prothrombinase in a tubular flow reactor," *J. Biol. Chem.* 270(3):1029-1034.

Biro et al. (Mar. 1994) "Expression and subcellular distribution of basic fibroblast growth factor are regulated during migration of endothelial cells," *Circ. Res.* 74(3):485-494.

Bitomsky et al. (Web Release Mar. 19, 1999) "Docking of glycosaminoglycans to heparin binding proteins: validation for aFGF, bFGF, and antithrombin and application to IL-8," *J. Am. Chem. Soc.* 121:3004-3103.

Björquist et al. (1997) "Determination of the inetic constants of tissue factor/factor VII/factor VIIA and antithrombin/heparin using surface plasmon resonance," *Thromb. Res.* 85(3):225-236.

Blezer et al. (1998) "Initiation and propagation of blood coagulation at artificial surfaces studied in a capillary flow reactor," *Thromb. Haemostasis* 79(2):296-301.

Blezer et al. (1997) "Activation of blood coagulation at heparin-coated surfaces," *J. Biomedical Materials Research* 37(1):108-113.

Bon (1999) "Amphiphilic copolymers by atom transfer polymerization with carbohydrate-based initiators and monomers," *Polym. Prepr. (Am. Chem. Soc., Div. Polym. Chem.)* 40(2):248-249.

Bos GW, P.A. (1998) "Small Diameter Vascular Graft Prosthesis: Current Status," *Arch. Physiol. Biochm.* 106(2):100-115.

Bourin et al. (1993) "Glycosaminoglycans and the regulation of blood coagulation," *Biochemical J.* 289(Pt2):313-330.

Brittain et al. (Oct. 1992) "Sickle erythrocyte adherence to large vessel and microvascular endothelium under physiologic flow is qualitatively different," *J. Lab. Clin. Med.* 120(4):538-545.

Broch et al.(1998) "Quantum molecular modeling of the elastinic tetrapeptide Val-Pro-Gly-Gly," *J. Biomol. Struct. & Dyn.* 15(6):1073-1091.

Brown, D.F.M. (Nov. 2001) "Treatment options for deep venous thrombosis," *Emerg. Med. Clin. North Am.* 19(4):913-923.

Brummel et al. (Aug. 6, 1999) "An integrated study of fibrinogen during blood coagulation," *J. Biol. Chem.* 274(32):22862-22870.

Buller et al. (1999) "Primary stenting versus balloon angioplasty in occluded coronary arteries," *Circulation* 100(3):236-242.

Byun et al. (1996) "Binding of antithrombin III and thrombin to immobilized heparin under flow conditions," *Biotechnology Progress* 12(2):217-225.

Byun et al. (1996) "Mechanism of thrombin inactivation by immobilized heparin," *J. Biomed. Mater. Res.* 30:423-427.

Cadroy et al. (Apr. 1989) "Discrimination Between Platelet and Coagulation-Mediated Mechanisms in a model of Complex Thrombus Formation in Vivo," *J. Lab. Clin. Med.* 113(4):436-449.

Cadroy et al. (Jun. 1, 1990) "Effects of Red Blood Cell Concentration on Hemostasis and Thrombus Formation in a Primate Model," *Blood* 75:2185-2193.

Cai, W.Z. et al. (1993) "A solid-state n.m.r. study of microphase structure and segmental dynamics of poly(styrene-b-methylphenylsiloxane) diblock copolymers," *Polymer* 34(2):267-276.

Calistri-Yeh et al. (1996) "Thermal Stability of Self-Assembled Monolayers from Alkylchlorosilanes," *Langmuir* 12(11):2747-2755.

Campbell et al. (1994) "Biocompatible Surfaces Using Methacryloylphosphorylcholine Laurylmethacrylate Copolymer," *ASAIO J.* 40(3):M853-M857.

Cao et al. (1997) "Sequence of Abductin, the Molluscan 'Rubber' Protein," *Curr. Biol.* 7:R677-678.

Cappello et al. (Apr. 30, 1998) "In-Situ Self-Assembling Protein Polymer Gel Systems for Administration, Delivery, and Release of Drugs," *J. Controlled Release* 53(1-3):105-117.

Cappello et al. (1990) "Genetic Engineering of Structural Protein Polymers," *Biotechnol. Prog.* 6:198-202.

Chaikof et al. (Jul. 1990) "Platelet Interaction with Poly(ethylene Oxide)-polysiloxane Networks," *AIChE J.* 36(7):994-1002.

Chaikof, E.L. (1996) "Biomaterials that Imitate Cell Microenvironments," *Chemtech.* 26:17-24.

Chaikof et al. (1992) "PEO Enhancement of Platelet Deposition, Fibrinogen Deposition, and Complement C3 Activation," *J. Biomed. Mater. Res.* 26:1163-1168.

Chang et al. (1989) "Nuclear Overhauser Effect and Computational Characterization of the β-Spiral of the Polypentapeptide of Elastin," *J. Biomol. Struct. Dyn.* 6(5):851-858.

Chang et al. (Jun. 10, 1988) "Molecular Dynamics Calculations on Relaxed and Extended States of the Polypentapeptide of Elastin," *Chem. Phys. Lett.* 147:395-400.

Chapman, D. (1993) "Biomembranes and New Hemocompatible Materials," *Langmuir* 9(1):39-45.

Chen et al. (1997) "Phosphorylcholine Coating of ePTFE Grafts Reduces Neointimal Hyperplasia in Canine Model," *Ann. Vasc. Surg.* 11(1):74-79.

Chen, T-M et al. (1996) "Studies on the Synthesis and Properties of Novel Phospholipid Analogous Polymers," *J. Appl. Polym. Sci.* 60:455-464.

Cheung et al. (1994) "Molecular Self-Assembly of Conducting Polymers," *Thin Solid Films* 244:985-989.

Cho et al. (Web Release Jul. 20, 2004) "Vascular Patches Tissue-Engineered with Autologous Bone Marrow-Derived Cells and Decellularized Tissue Matrices," *Biomaterials* 26:1915-1924.

Chon et al. (1999) "Cytomimetic Biomaterials. 3. Preparation and Transport Studies of an Alginate/Amphiphilic Copolymer/Polymerized Phospholipid Film," *J. Biomater. Sci. Polymer. Ed.* 10:95-107.

Chon et al. (1998) "α4β1 and α5β1 Control Cell Migration on Fibronectin by Differentially Regulating Cell Speed and Motile Cell Phenotype," *Ann. Biomed. Eng.* 26:1091-1101.

Chon et al.(Sep. 1997) "Role of Fibronectin and Sulfated Proteoglycans in Endothelial Cell Migration on a Cultured Smooth Muscle Layer," *J. Surg. Res.* 72(1):53-59.

Christianson et al. (Jan. 1993) "Adoptive Transfer of Diabetes into Immunodeficient NODscid/ scid Mice: Relative Contributions of

(56) References Cited

OTHER PUBLICATIONS

CD4+ and CD8+ T-Cells from Diabetic Versus Prediabetic NOD. NON-Thy-$1_a$ Donors," *Diabetes* 42:44-55.
Ciancarini et al. (Oct. 1, 1993) "Linda Meets Minix," *Operating Syst. Rev.* 27(4):76-92.
Cima et al. (1995) "Network Structures of Radiation-Cross-Linked Star Polymer Gels," *Macromolecules* 28:6787-6794.
Clark JM, G.S. (1985) "Transmural Organization of the Arterial Media: The Lamellar Unit Revisited," *Arteriosclerosis* 5:19-34.
Clowes et al. (Jun. 1986) "Mechanisms of Arterial Graft Failure. II. Chronic Endothelial and Smooth Muscle Cell Proliferation in Healing polytetrafluoroethylene Prostheses," *J. Vasc. Surg.* 3(6):877-884.
Clowes et al. (Jan. 1985) "Mechanism of arterial graft failure. 1. Role of cellular proliferation in early healing of PTFE prostheses," *Am. J. Pathol.* 118(1):43-54.
Clowes et al. (Feb. 17, 1977) "Suppression by heparin of smooth muscle cell proliferation in injured arteries," *Nature* 265:625-626.
Colton, C.K. (1992) "The engineering of xenogeneic islet transplantation by immunoisolation," *Diab. Nutr. Metabol.* 5(Supp 1):145-149.
Colton et al. (May 1991) "Bioengineering in the development of the hybrid artificial pancreas I" *Biochem. Eng.* 113:152-70.
Conte, M.S. (Jan. 1998) "The Ideal Small Arterial Substitute: A Search for the Holy Grail," *FASEB J.* 12:43-35.
Contino et al. (Sep. 1994) "Use of an oriented transmembrane protein to probe the assembly of a supported phospholipid bilayer," *Biophys. J.* 67:1113-1116.
Courtman et al. (2001) "The Role of Crosslinkng in Modification of the Immune Response Elicited Against Xenogenic Vascular Acellular Matrices," *J. Biomed. Mater. Res.* 55:576-586.
Crooks et al. (1990) "Microencapsulation of mammalian cells in a HEMA-MMA copolymer: effects on capsule morphology and permeability," *J. Biomed. Mater. Res.* 24: 1241-1262.
Cruise et al. (Mar. 20, 1998) "A sensitivity study of the key parameters in the interfacial photopolymerization of poly(ethylene glycol) diacrylate upon porcine islets," *Biotechnol. Bioeng.* 57(6):655-665.
Daniell et al. (1997) "Hyperexpression of a Synthetic Protein-Based Polymer Gene," *Methods Mol. Biol.* 63:359-371.
Dardik, H. (1995) "The Second Decade of Experience with the Umbilical Vein Graft for Lower-Limb Revascularization," *Cardiovasc. Surg.* 3(3):265-269.
Daugherty et al. (Jan. 19, 1999) "A fluorescence assay for leucine zipper dimerization: avoiding unintended consequences of fluorophore attachment," *J. Am. Chem. Soc.* 121:4325-4333.
Dautzenberg et al. (1996) Polyelectrolyte complex formation at the interface of solutions, *Polym. Sci.* 101:149-156.
Debelle et al. A.M. (Dec. 23, 1999) "Elastin: molecular description and function," *Internat. J. Biochem. & Cell Biol.* 31:261-272.
Decher, G. (1997) "Fuzzy nanoassemblies: toward layered polymeric multicomposites," *Science* 277:1232-1237.
Defife et al. (Dec. 22, 1999) "Photochemically Immobilized Polymer Coatings Effects on Protein Adsorption, Cell Adhesion and Leukocyte Activation," *J. Biomater. Sci. Polym. Ed.* 10(10):1063-1074.
Defrees et al. (Dec. 7, 1996) "Sialyl lewis x liposomes as a multivalent ligand and inhibitor of E-selectin mediated cellular adhesion," *J. Am. Chem. Soc.* 118:6101-6104.
Deming, T. J. (1999), "Mussel byssus and biomolecular materials," *Curr. Opin. Chem. Biol.* 3: 100-5.
Dingemans et al. (2000) "Extracellular Matrix of the Human Aortic Media: An Ultrastructural Histochemical and Immunohistochemical Study of the Adult Aortic Media," *Anatomical Record* 258:1-14.
Dixon, W. T. (Nov. 20, 1982) "Spinning-sideband-free and spinning-sideband-only NMR spectra in spinning samples," *J. Chem. Phys.* 77:1800-1809.
Dixon, W.T. (Apr. 16, 1982), "Total suppression of sidebands in CPMAS C-13 NMR," *J. Magn. Reson.* 49:341-345.
Dluhy, R.A. (1986)"Quantitative external reflection infrared spectroscopic analysis of insoluble monolayers spread at the air-water interface," *J. Phys. Chem.* 90:1373-1379.

Dodson et al. (1993), "molecular recognition in insulin assembly," (1993) *Biochem. Soc. Trans.* 21:609-614.
Doshi et al. (1995) "Electrospinning process and applications of electrospun fibers," *J. Electrostatics* 35:151-160.
Dutoya et al. (Mar. 31, 2000) "Elastin-Derived Protein Coating onto Poly(ethylene terephthalate): Technical, Microstructural and Biological Studies," *Biomaterials* 21:1521-1529.
Eaton, D. F. (1986) "Dye sensitized photo polymerization," *Advances in Photochemistry* 13:427-487.
Egger et al. (1992) "Solid state NM investigation of cationic polymerized epoxy resins," *J. Appl. Poly. Sci.* 44:289-295.
Einaga et al. (Jul. 13, 1999) "Photofunctional vesicles containing Prussian blue and azobenzene," *J. Am. Chem. Soc.* 121:3745-3750.
Eitzman et al. (1994), "Heparin neutralization by platelet-rich thrombi," *Circulation* 89(4):1523-1529.
Ejaz, M. et al. (2000) "Controlled Grafting of a Well-Defined Glycopolymer on a Solid Surface by Surface-Initiated Atom Transfer Radical Polymerization", *Macromolecules* 33:2870.
Elbert et al. (Nov. 9, 1999) "Thin polymer layers formed by polyelectrolyte multilayer techniques on biological surfaces," *Langmuir* 15:5355-5362.
Elender et al. (1996) "Functionalisation of Si/$SiO_2$ and glass surfaces with ultrathin dextran films and deposition of lipid bilayers," *E. Biosensors Bioelectronics* 11(6/7):565-577.
Elliott et al. (2000) "Maleimide-functionalized lipids that anchor polypeptides to lipid bilayers and membranes," *Bioconjugate Chem.* 11:832-841.
Esmon et al. (1999) "Regulation and functions of the protein C anticoagulant pathway," *Haematologica* 84(4):363-368.
Esmon et al. (1997), "The protein C pathway: new insights," (1997) *Thromb. Haemostasis* 78(1):70-74.
Esmon, C.T. (1995) "Thrombomodulin as a model of molecular mechanisms that modulate protease specificity and function at the vessel surface," *FASEB Journal* 9(10):946-955.
Esmon et al. (1981), "Identification of an endothelial cell cofactor for thrombin-catalyzed activation of protein C," *Proc. Natl. Acad. Sci. USA* 78(4):2249-2252.
Esmon et al. (1983) "Proteolytic formation and properties of (-carboxyglutamic acid-domainless protein C," *J. Biol. Chem.* 258(9):5548-5553.
Esmon et al. (May 5, 1983) "Thrombomodulin blocks the ability of thrombin to activate platelets," *J. Biol. Chem.* 258(20):12238-12242.
Esmon et al. (Jul. 9, 1982) "Isolation of a membrane-bound cofactor for thrombincatalyzed activation of protein C," *J. Biol. Chem.* 257(2):859-864.
España et al. (1991) "In vivo and in vitro complexes of activated protein C with two inhibitors in baboons," *Blood* 77(8):1754-1760.
Esquivel CO, B.F. (Oct. 1983) "Why Small Caliber Vascular Grafts Fail: A Review of Clinical and Experimental Experience and the Significance of the Interaction of Blood et the Interface," *J. Surg. Res.* 41:1-15.
European Patent Office, Communication of Mar. 19, 2004 with Enclosed European Search Report (including Annex) for Application No. EP 03 25 7349, 4 pages.
Faham et al. (Feb. 23, 1996) "Heparin structure and interactions with basic fibroblast growth factor," *Science* 271:1116-1120.
Feingold et al.(1986) "Coagulation assays and platelet aggregation patterns in human, baboon, and canine blood," *Am. J. Vet. Res.* 47:2197-2199.
Feng et al. (2000) "Reconstitution of thrombomodulin into polymerizable phospholipid vesicles," *Polymer Preprints* 41(2):1653-1654.
Flitsch, S.L. (Dec. 2000) "Chemical and enzymatic synthesis of glycopolymers," *Current Opinion in Chem. Biol.* 4(6):619-625.
Florin et al. (1993) "Painted supported lipid membranes," *Biophys J.* 64:375-383.
Fong et al. (1999), "Beaded nanofibers formed during electrospinning," *Polymer* 40:4585-4592.
Foster et al. (1973) "Isolation and amino acid sequences of tropoelastin peptides," *J. Biol. Chem.* 24:2876-2879.
Frank et al. (1991) "The role of complement in inflammation and phagocytosis," *Immunol. Today* 12:322-326.

(56) References Cited

OTHER PUBLICATIONS

Franzblau et al. (1977) "Role of crosslinking in fiber formation," *Adv. Exp. Med. Biol.* 79:313-327.
Galvin et al. (1987) "Reconstitution of rabbit thrombomodulin into phospholipid vesicles," *J. Biol. Chem.* 262(5):2199-2205.
Gemmell et al. (Feb. 7, 1990) "The effects of shear rate on the enzymatic activity of the tissue factor-factor VIIa complex," *Microvasc. Res.* 40(30):327-340.
Gemmell et al. (Aug. 1990), "Utilization of a continuous flow reactor to study the lipoprotein-associated coagulation inhibitor (LACI) that inhibits tissue factor," *Blood* 76(11):2266-2271.
Gentry et al. (1995) "Surface-mediated enzymatic reactions: simulations of tissue factor activation of factor X on a lipid surface," *Biophys. J.* 69(2):362-371.
Gerling et al. (1994) "Multiple low-dose streptozocin-induced diabetes in NODscid/scid mice in the absence of functional lymphocytes," *Diabetes* 43:433-440.
Gill et al. (1994) "CD4+ T cells are both necessary and sufficient for islet xenograft rejection," *Transplantation Proceedings* 26:1203.
Gir et al. (1996) "A numerical analysis of factor X activation in the presence of tissue factor-factor VIIa complex in a flow reactor," *Ann. Biomed. Eng.* 24(3):394-399.
Girton et al. (2000) "Mechanisms of Stiffening and Strengthening in Media-Equivalents Fabricated Using Glycation," *J. Biomech. Eng.* 122:216-223.
Gnanou et al. (May 3, 1998), "Synthesis of star-shaped poly(ethylene oxide)," *Makromol. Chem.* 189:2885-2892.
Goeden-Wood et al. Jul./Aug. 2002) "Improved assembly of multimeric genes for the biosynthetic production of protein polymers," *Biomacromolecules.* 3(4):874-879.
Golden, M.A. (1990) "Healing of polytetrafluoroethylene arterial grafts is influenced by graft porosity," *J. Vascular Surgery* 11(6):838-844.
Goldsmith et al. (1986) "Rheological aspects of thrombosis and haemostasis: basic principles and applications," *Thromb. Haemostasis* 55(3):415-435.
Goosen, M.F.A. (1985) Optimization of microencapsulation parameters: semipermeable microcapsules as a bioartificial pancreas, *Biotech. Bioeng.* 27:146-150.
Goosen et al. (1980) "Inactivation of thrombin by antithrombin III on a heparinized biomaterial," *Thrombosis Research* 20(5/6):543-554.
Grande et al. (2001) "Glycosaminoglycan mimetic biomaterials. 2. Alkene- and acrylate-derivatized glycopolymers via cyanoxyl-mediated free-radical polymerization," *Macromolecules* 34:1640-1646 (tentatively published on Web Feb. 13, 2001).
Grande et al. (Sep. 2000), "Glycosaminoglycan mimetic biomaterials. 1. Nonsulfated and sulfated glycopolymers by cyanoxyl-mediated free-radical polymerization," *Macromolecules* 33:1123-1125.
Grande et al. (Feb. 2000), "Synthesis of non-sulfated and sulfated glycopolymers," *Polymer Preprints* 41(1):1000-1001.
Gray et al. (1973), "Molecular model for elastin structure and function," *Nature* 246:461-466.
Greisler et al. (1996) "Biointeractive Polymers and Tissue Engineered Blood Vessels," *Biomaterials* 17:329-336.
Gruber et al. (1991) "Antithrombotic effects of combining activated protein C and urokinase in nonhuman primates," *Circulation* 84(6):2454-2462.
Gruber et al. (1990), "Inhibition of thrombus formation by activated recombinant protein C in a primate model of arterial thrombosis," *Circulation* 82(2):578-585.
Gruber et al. (1989) "Inhibition of platelet-dependent thrombus formation by human activated protein C in a primate model," *Blood* 73(3):639-742.
Hall et al. (1998), "Factor Xa generation at the surface of cultured rat vascular smooth muscle cells in an in vitro flow system," (1998) *J. Biomech. Eng.* 120(4):484-490.
Hall et al. (1980) "Biomembranes as models for polymer surfaces," *Biomaterials* 10(4):219-224.

Halle et al. (Feb. 1993) "Protection of islets of Langerhans from antibodies by microencapsulation with alginate-poly-L-lysine membranes," *Transplantation*, 55 (2):350-354.
Hanson et al. (1998) "Blood flow and antithrombotic drug effects," *Am. Heart Journal* 135(5 Pt 2 Su):S132-145.
Hanson et al. (1993) "Antithrombotic effects of thrombin-induced activation of endogenous protein C in primates," *J. Clin. Invest.* 92(4):2003-2012.
Hanson et al. (1991) "Effects of angiotensin converting enzyme inhibition with cilazapril on intimal hyperplasia in injured arteries and vascular grafts in the baboon," *Hypertension* 18(4Suppl):II-70-II-76.
Hanson et al. (1985) "Platelet interactions with Dacron vascular grafts; a model of acute thrombosis in baboons," *Arteriosclerosis* 5(6):595-603.
Harker et al. Apr. 2000) "Effects of megakaryocyte growth and development factor on platelet production, platelet life span, and platelet function in healthy human volunteers," *Blood* 95(8):2514-2522.
Hasegawa et al.(Mar. 22, 1995) "Quantitative analysis of uniaxial molecular orientation in Langmuir-Blodgett films by infrared relection spectroscopy," *Langmuir* 11:1236-1243.
Haskins et al. M. (1990) "Acceleration of diabetes in young NOD mice with $CD4_+$ islet-specific T cell clone," *Science* 249:1433-1436.
Hayashi et al. (Sep. 21, 1999) "Hypotheses that correlate the sequence, structure, and mechanical properties of spider silk proteins," *Int. J. Biol. Macromol.* 24:271-275.
Hayashi et al. (1998) "Evidence from flagelliform silk cDNA for the structural basis of elasticity and modular nature of spider silks," *J. Mol. Biol.* 275: 773-84.
Hayward et al. (1986), "Biomembranes as models for polymer surfaces," *Biomaterials* 7:252-258.
Hayward et al. (1984) "Biomembrane surfaces as models for polymer design: the potential for haemocompatibility," *Biomaterials* 5:135-142.
Hayzer et al. (1999) "cDNAs encoding the baboon thrombin receptor indicate a primate transcription start site upstream of putative sites reported for the human gene," *Throm. Res.* 98:195-201.
Hayzer et al. (1993), "Characterization of a cDNA encoding the β-chain of baboon receptor glycoprotein BPIb," *Gene* 127:271-272.
Hébert et al.(1992) "A new reagent for the removal of the 4-methozybenzyl ether: application to the synthesis of unusual macrocyclic and bolaform phosphatidylcholines," *J. Org. Chem.* 57:1777-1783.
Helm et al. (1991), "Measurement of ligand-receptor interactions," (1991) *Proc. Natl. Acad. Sci. USA* 88:8169-8173.
Hergenrother et al. (2000), "Small-molecule microarrays: covalent attachment and screening of alcohol-containing small molecules on glass slides," *J. Am. Chem. Soc.* 122:7849-7850.
Heroguez et al. (1997) "Novel amphiphilic architectures by ring-opening metathesis polymerization of macromonomers," *Macromolecules* 30:4791-4798.
Huang et al. (2000) "Generation of synthetic elastin-mimetic small diameter fibers and fiber networks," *Macromolecules* 33: 2989-2997 (published on Web Mar. 24, 2000).
Hubbell et al. (1991),"Endothelial cell-selective materials for tissue engineering in the vascular graft via a new receptor," *Biotechnology* 9:568-572.
Hudson, S.M. (1997) "The spinning of silk-like proteins into fibers," Protein-Based Materials, McGrath, K. and Kaplan, D., Ed.: Birkhauser: Boston, 1997, pp. 313-337.
Hurt et al. (1983) "Bovine Carotid Artery Heterografts Versus Polytetrafluoroethylene Grafts," *Am. J. Surg.* 146:844-847.
Indik et al. (1987) "Alternative Splicing of Human Elastin mRNA Indicated by Sequence Analysis of Cloned Genomic and Complementary DNA," *Proc. Nat. Acad. Sci. USA* 84(16):5680-5684.
International Preliminary Report on Patentability, Corresponding to International Application No. PCT/US2007/078172, Mailed Mar. 26, 2009.
Ishihara, K. (1997) "Novel polymeric materials for obtaining blood-compatible surfaces," *TRIP* 5(12):401-407.

(56) References Cited

OTHER PUBLICATIONS

Ishihara et al. (1995) "Synthesis of phospholipid polymers having a urethane bond in the side chain as coating material on segmented polyurethane and their platelet adhesion-resistant properties," *Biomaterials* 16:873-879.

Ishihara et al. (1994), "Hemocompatibility on graft copolymers composed of poly(2-methacryloyloxyethyl phosphorylcholine) side chain and poly(n-butyl methacrylate) backbone," *J. Biomed. Mater. Res.* 28:225-232.

Ishihara et al. (1992), "Hemocompatibility of human whole blood on polymers with a phospholipid polar group and its mechanism," *J. Biomed Mat. Res.* 26:1543-1552.

Ishihara et al. (1990) "Reduced thrombogenicity of polymers having phospholipid polar groups," *J. Biomed Mat. Res.* 24:1069-1077.

Ito Y. (1992), Section/Chapter 5.2, "Cell growth factor immobilized materials," p. 285-310; in Imanishi, Y. Synthesis of Biocomposite Materials: Chemical and Biological Modified Natural Polymers. Boca Raton, FL, CRC Press, 314 p. ISBN 0849367719.

Ito et al. (1998) "Application of Coacervated Alpha-Elastin to Arterial Prostheses for Inhibition of Anastomotic Intimal Hyperplasia," *ASAIO J* 4(5):M501-M505.

Iwia et al. (2005) "Novel Tissue-Engineered Biodegradable Material for Reconstruction of Vascular Wall," *Soc. Thoracic Surgeons* 80:1821-1828.

Jackson et al. (1991) "Glycosaminoglycans: molecular properties, protein interactions, and role in physiological processes," *Physiol. Rev.* 71(2):481-539.

Janeway et al. (1994) "Signals and signs for lymphocyte responses," *Cell* 76:275-285.

Japanese Official Action Corresponding to Japanese Patent Application No. 2003-98691, Mailed Oct. 20, 2008.

Japanese Official Action Corresponding to Japanese Patent Application No. 2003-98691, Mailed May 22, 2009.

Jarpe et al. (1990) "Flow cytometric enumeration of mononuclear cell populations infiltrating the islets of Langerhans in prediabetic NOD mice: Development of model of autoimmune insulinitis for Type I diabetes," *Regional Immunology* 3:305-317.

Jenney CR, A.J. (1999) "Alkysilane-Modified Surfaces: Inhibition of Human Macrophage Adhesion and Foreign Body Giant Cell Formation," *J. Biomed. Mater. Res.* 46(1):11-21.

Jordan et al. (2007) "The Effect of a Recombinant Elastin-Mimetic Coating of an ePTFE Prosthesis on Acute Thrombogenicity in a Baboon Arteriovenous Shunt," *Biomaterials* 28:1191-1197.

Joseph et al. (1987) "Prostacyclin Immobilized Albuminated Surfaces," *J. Biomed. Mater. Res.* 21(7):937-945.

Kagan et al. (1980) "Repeat polypeptide models of elastin as substrates for lysyl oxidase," *J. Biol. Chem.* 255:3656-3659.

Kalafatis et al. (1996), "Regulation and regulatory role of (-carboxyglutamic acid containing clotting factors," *Critical Reviews in Eukaryotic Gene Expression* 6(1):87-101.

Kalafatis et al. (1997), "The regulation of clotting factors," *Crit. Rev. Eukaryotic Gene Expression* 7(3):241-280.

Kannan et al. (2005) "Current Status of Prosthetic Bypass Grafts: A Review," *J. Biomed. Mater. Res. Part B. Appl. Biomater.* 74B:570-581.

Kawamoto et al. (1992) "Reconstituted collagen is not capable of activating factor XII but causes intrinsic coagulation by activating platelets," *Blood Coagulation & Fibrinolysis* 3(4):371-379.

Ke et al. (1995), "Ovalbumin injected with complete Freund's adjuvant stimulates cytolytic responses," (1995) *Eur. J. Immunol.* 1995:549-553.

Khaled et al. (1976) "Proton magnetic resonance and conformational energy calculations of repeat peptides of tropoelastin: the tetrapeptide," *J. Am. Chem. Soc.* 98: 7547-7553.

Kim et al. (2000 "The influence of tiered layers of surface-grafted poly(ethylene glycol) on receptor-ligand-mediated adhesion between phospholipid monolayerstabilized microbubbles and coated glass beads," *Langmuir* 16:2808-2817.

Kim et al. (Feb. 2001) "Characterizing structural changes in point-bonded nonwoven fabrics during load-deformation experiments," *Textile Res. J.* 71(2):157-164.

Kim et al. (Web Release Dec. 2, 2005) "A Stereoelectronic Effect on Turn Formation Due to Proline Substitution in Elastin-Mimetic Polypeptides," *J. Am. Chem. Soc.* 127(51):18121-18132.

Kimura et al. (1992) "High-resolution solid-state $_{13}$C nuclear magnetic resonance study of the combined process of $_1$H spin diffusion and $_1$H spin-lattice relaxation in semicrystalline polymers," *Polymer* 33(3):493-497.

King et al (1987), "Alginate-polylysine microcapsules of controlled membrane molecular weight cutoff for mammalian cell culture engineering," *Biotech Progress* 3:231-240.

Kishida et al. (1995) "In vivo and ex vivo evaluation of the antithrombogenecity of human thrombomodulin immobilized biomaterials," *ASAIO Journal* 41:M369-374.

Kishida et al. (1994), "Immobilization of human thrombomodulin onto biomaterials," *ASAIO Journal* 40(3):M840-845.

Kishida et al. (1994), "Immobilization of human thrombomodulin on biomaterials: evaluation of the activity of immobilized human thrombomodulin," *Biomaterials* 15(14):1170-1174.

Kishida et al. (1994), "Immobilization of human thrombomodulin onto poly(ether urethane urea) for developing antithrombogenic blood-contacting materials," *Biomaterials* 15(10):848-852.

Kobayashi et al. (1974), "Theory of the kinetics of reactions catalyzed by enzymes attached to membranes," (1974) *Biotech. Bioeng.* 16(1):77-97.

Kobayashi et al. (1974) "Theory of the kinetics of reactions catalyzed by enzymes attached to the interior surfaces of tubes," *Biotech. Bioeng.* 16(1):99-118.

Köhler et al. (1996) "Platelet adhesion to novel phospholipid materials: modified phosphatidylcholine covalently immobilized to silica, polypropylene, and PTFE materials," *J. Biomed. Mat. Res.* 32:237-242.

Kojima et al. (1991), "Interaction between phospholipids and biocompatible polymers containing a phosphorylcholine moiety," *Biomaterials* 12:121-124.

Korbutt et al. (1996) "Large scale isolation, growth, and function of porcine neonatal islet cells," *J. Clin. Invest.* 97(9):2119-2129.

Korbutt et al. (1995) "Porcine islet cell antigens are recognized by xenoreactive natural human antibodies of both IgG and IgM subtypes," *Transplantation Proceedings* 28:821-823.

Korbutt et al. (1995) "Successful reversal of diabetes in nude mice by transplantation of microencapsulated porcine neonatal islet cell aggregates," *Transplantation Proceedings* 27:3212.

Krejchi et al. (1994) "Chemical sequence control of β-sheet assembly in macromolecular crystals of periodic polypeptides," *Science* 265:1427-1432.

Krych et al. (1992), "Complement receptors," (1992) *Curr. Opin. Immunol.* 4:8-13.

Kuhlenschmidt et al. (1983) "Specificity of chicken liver carbohydrate binding protein," *Biochem.* 23(16):3569-3575.

Kühner et al. (1994) "Lipid mono- and bilayer supported on polymer films: composite polymer-lipid films on solid substrates," *E. Biophys. J.* 67:217-226.

Kwon et al. (2005) "Electrospun Nano- to Microfiber Fabrics Made of Biodegradable Copolyesters: Structural Characteristics, Mechanical Properties, and Cell Adhesion Potential," *Biomaterials* 26(18);3929-3939.

Lamparski et al. (Sep. 1993) "Thermotropic Properties of Model Membranes Composed of Polymerizable Lipids. 1. Phosphatidylcholines Containing Terminal Acryloyl, Methacryloyl, and Sorbyl Groups," *J. Am. Chem. Soc.* 115(18):8096-8102.

Lamparski et al. (1992), "Photoinduced destabilization of liposomes," *Biochemistry* 31:685-694.

Laster et al. (1988) "Heparin-coated catheters and heparin-induced thrombocytopenia," *J. Vasc. Surg.* 7(5):667-672.

Lee et al. (Aug. 2000), "Thermo-reversible self-assembly of nanoparticles derived from elastin-mimetic polypeptides," *Advanced Materials* 12(15):1105-1110.

Lee et al. (2001) "Elastomeric Polypentapeptides Cross-Linked into Matrixes and Fibers," *Biomacromolecules* 2:170-179.

(56) References Cited

OTHER PUBLICATIONS

Lee et al. (2000) "Improved Calcification Resistance and Biocompatibility of Tissue Patch Grafted with Sulfonated PEO or Heparin After Gluteraldehyde Fixation," *J. Biomed. Mater. Res.* 58(1):27-35.

Lee et al. (2001) "Mechanical Properties of Crosslinked Synthetic Elastomeric Polypentapeptides," *Macromolecules* 34:5968-5974.

Lee et al. (2001) "Swelling Behavior of Gamma-Irradiation Cross-Linked Elastomeric Polypentapeptide-Based Hydrogels," *Macromolecules* 34:4114-4123.

Lenschow et al. (1992) "Long-term survival of xenogeneic pancreatic islet grafts induced by CTLA4Ig," *Science* 257:789-795.

Lerouge et al. (2004) "Endovascular Aortic Aneurysm Repair with Stent-Grafts: Experimental Models can Reproduce Endoleaks," *J. Vasc. Interv. Radiol.* 15:971-979.

L'Heureux et al. (1998) "A Completely Biological Tissue-Engineered Human Blood Vessel," *FASEB J.* 12:47-56.

L'Heureux et al. (2001) "A Human Tissue-Engineered Vascular Media A new Model for Pharmacological Studies on Contractile Responses," *FASEB J.* 15:515-524.

Li et al. (2005) "Electrospun Protein Fibers as Matrices for Tissue Engineering," *Biomaterials* 26:5999-6008.

Li et al. (1998) "Novel Arterial Pathology in Mice and Humans Hemizygous for Elastin," *J. Clin. Invest.* 102(10):1783-1787.

Li et al. (1998) "Elastin is an Essential Determinant of Arterial Morphogenesis," *Nature* 393:276-280.

Lillie MA, G.J. (2002) "The Viscoelastic Basis for the Tensile Strength of Elastin," *Int. J. Biological Macromol.* 30:119-127.

Lim et al. (1980) "Microencapsulated islets as a bioartificial endocrine pancreas," *Science* 210:908-910.

Lindhout et al. (1995) "Antithrombin activity of surface-bound heparin studied under flow conditions," *J. Biomed. Mater. Res.* 29(10):1255-1266.

Lindner et al. (1990), "Basic fibroblast growth factor stimulates endothelial regrowth and proliferation in denuded arteries," (1990) *J. Clin. Invest.* 85:2004-2008.

Loudovaris et al. (1992) "The role of T cells in the destruction of xenografts within cell impermeable membranes," *Transplantation Proceedings* 24:2938.

Loykulnant et al. (2000) "Protection and polymerization of functional monomers. 30. Anionic living polymerization of 4-alkylstyrenes containing acetal-protected monosaccharide residues," *Macromolecules* 33:4757-4764.

Loykulnant et al. (1998) "Protection and polymerization of functional monomers. 28. Anionic living polymerization of styrene derivatives containing acetal-protected monosaccharide residues," *Macromolecules* 31:9121-9126.

Lu et al. (1996) "Comparison of activated protein C/protein S-mediated inactivation of human factor VIII and factor V," *Blood* 87(11):4708-4717.

Lvov et al. (1993), "Assembly, structural characterization, and thermal behavior of layer-by-layer deposited ultrathin films of poly(vinyl sulfate) and poly(allylamine)," (1993) *Langmuir* 9:481-486.

MacDonald et al. (1991) "Small-volume extrusion apparatus for preparation of large, unilamellar vesicles," *Biochim. Biophys. Acta* 1061:297-303.

Mann et al. (1988) "Cofactor proteins in the assembly and expression of blood clotting enzyme complexes," *Ann. Rev. Biochemistry* 57:915-956.

Mao et al. (1995) "Interactions, structure, and stability of photoreactive bolaform amphiphile multilayers," *Langmuir* 11:942-952.

Maoz et al. (1984) "On the formation and structure of self-assembling monolayers," *J. Colloid Interface Sci.* 100(2):456.

Markovich et al. (1991) "Silica subsurface amine effect on the chemical stability and chromatographic properties of end-capped immobilized artificial membrane surfaces," *Anal. Chem.* 63:1851-1860.

Marra et al. (1997), "Cytomimetic biomaterials. 1. In-Situ polymerization of phospholipids on an alkylated surface," (1997) *Macromolecules* 30:6483-6488.

Marra et al. (1997) "Cytomimetic biomaterials. 2. In-Situ polymerization of phospholipids on a polymer surface," *Langmuir* 13:5697-5701.

Marra et al. (1997) "Stabilized phosphatidylcholine surfaces via in-situ polymerization at a solid-liquid interface," *Polymer Preprints* 38(2):682-683.

Marsh et al. (1999) "Atom transfer polymerization: use of uridine and adenosine derivatized monomers and initiators," *J. Macromolecules* 32:8725-8731.

Marsh et al. (2004) "Ultrasonic Delineation of the Aortic Microstructure: The Relative Contributions of Elastin and Collagen to Aortic Elasticity," *J. Acoust. Soc. Am.* 115(5):2032-2040.

Marshall et al. (2000) "An Alternative to Synthetic Aortic Grafts Using Jejunum," *J. Invest. Surg.* 13:333-341.

Martin et al. (1997), "Processing and Characterization of Protein Polymers," Protein-Based Materials, McGrath, K. and Kaplan, D., Eds.; Birkhauser: Boston, pp. 339-370.

Martin et al. (1994), "General method for the synthesis of phospholipid derivatives of 1,2-O-diacyl-sn-glycerols," *J. Org. Chem.* 59:4805-4820.

Massia and Hubbell, J.A. (1992) "Vascular endothelial cell adhesion and spreading promoted by the peptide REDV of the IIICS region of plasma fibronectin is mediated by integrin $_2\beta_1$," *J. Biol. Chem.* 267:14019-14026.

Matthew et al (1993) "Complex coacervate microcapsules for mammalian cell culture and artificial organ development," *Biotechnol. Prog.* 9:510-519.

Mauk et al. (1998) "Structural characterization of self-assembled lipid monolayers by NBT simulation," *Langmuir* 14:5255-5266.

Mauk et al. (1980) "Vesicle targeting: timed release and specificity for leukocytes in mice by subcutaneous injection," *Science* 207:309-311.

McGrath et al. (1990) "Chemical and Biosynthesis Approached to the Production of Novel Polypeptide Materials," *Biotechnol. Prog.* 6:188-192.

McLean et al. (1983) "Preparation of stable polar surfaces using polymerizable long-chain diacetylene molecules," *Thin Solid Films* 99:127-131.

McMillan et al. (2000) "Synthesis and characterization of elastinmimetic protein gels derived from a well-defined polypeptide precursor," *Macromolecules* 33:4809-4821.

McMillan et al. (1999) "High-resolution topographic imaging of environmentally responsive, elastin-mimetic hydrogels," *Macromolecules* 32:9067-9070.

McMillan et al. (1999) "Rapid assembly of synthetic genes encoding protein polymers," *Macromolecules* 32: 3643-3648.

McPherson et al. (1996) "Product purification by reversible phase transition following *Eschericia coli* expression of genes encoding up to 251 repeats of the elastomeric pentapeptide GVGVP," *Protein Expression Purification* 7: 51-57.

McPherson et al. (1992) "Production and purification of a recombinant elastomeric polypeptide, G-(VPGVG)$_{19}$-VPGV, from *Escherichia coli*," *Biotechnology Progress* 8:347-352.

Meinhart et al. (2001) "Clinical Autologous In Vitro Endothelialization of 153 Infrainguinal ePTFE Grafts," *Ann. Thorac. Surg.* 71:S327-S331.

Merrill et al. (1970), "Polyvinyl alcohol-heparin hydrogel 'G'," *J. Applied Physiology* 29(5):723-730.

Meuse et al. (1998) "Hybrid bilayer membranes in air and water: infrared spectroscopy and neutron reflectivity studies," *Biophys J.* 74:1388-1398.

Meyer DE, C.A. (2002) "Genetically Encoded Synthesis of Protein-Based Polymers with Precisely Specified Molecular Weight and Sequence by Recursive Directional Ligation: Examples from the Elastin-Like Polypeptide System," *Biomacromolecules* 3:357-367.

Mielczarski et al. (1989) "Fourier transform infrared external reflection study of molecular orientation in spontaneously adsorbed layers on low absorption substrates," *J. Phys. Chem.* 93:2034-2038.

Miller et al. (1988) "Both the Lyt-2$_+$ and L3T4$_+$ T cell subsets are required for the transfer of diabetes in nonobese diabetic mice" *J. Immunol.* 140:52-8.

(56) References Cited

OTHER PUBLICATIONS

Minoda et al. (1997) "Synthesis of functional polymers bearing pendant mono-andoligo-saccharide residues," *Macromol. Symp.* 99:169-177.
Miyata et al. (1995), "Polymers with pendent saccharides—'glycopolymers'," *Trends Polym. Sci.* 5:198-206.
Miyoshi et al. (1976) "A rapid formation of lysine-derived crosslinks by chick embryo aorta," *J. Biochem.* (Tokyo) 79: 235-1243.
Monshipouri et al. (1995) "Liposome-encapsulated alginate: controlled hydrogel particle formation and release," *J. Microencapsulation* 12(2):117-127.
Moses et al. (1990), "Xenogeneic proliferation and lymphokine production are dependent upon CD4+ helper T cells and self antigen-presenting cells in the mouse. I," *Exp. Med.* 172:567-75.
Moya et al. (2000) "Lipid coating on polyelectrolyte surface modified colloidal particles and polyelectrolyte capsules," *Macromolecules* 33:4538-4544.
Müller-Eberhard, H.I. (1988) "Molecular organization and function of the complement system," *Ann. Rev. Biochem.* 57:321-347.
Nagahori et al. (2001) "Tailored glycopolymers: controlling the carbohydrate-protein interaction based on template effect," *Biomacromolecules* 2:22-24 (published on Web Dec. 28, 2000).
Nagapudi et al. (2005) "Protein-Based Thermoplastic Elastomers," *Macromolecules* 38:345-354.
Nagapudi et al. (2005) "Viscoelastic and Mechanical Behavior of Recombinant Protein Elastomers," *Biomaterials* 26(23):4695-4706.
Nagapudi et al. (2002) "Photomediated Solid-State Cross-Linking of an Elastin-Mimetic Recombinant Protein Polymer," *Macromolecules* 35:1730-1737.
Nagarsekar et al. (2003) "Genetic Engineering of Stimuli-Sensitive Silkelastin-Like Protein Block Copolymers," *Biomacromolecules* 4:602-607.
Nagarsekar et al. (Nov. 2002) "Genetic Synthesis and Characterization of pH- and Temperature-Sensitive Silk-Elastinlike Protein Block Copolymers," *J. Biomed. Mater. Res.* 62(2):195-203.
Nagle et al. (1996) "X-ray structure determination of fully hydrated L phase dipalmitoylphosphatidylcholine bilayers," *Biophys. J.* 70:1419-1431.
Nah et al. (2000), "Polymeric micelle formation of multiblock copolymer composed of poly((-benzyl L-glutamate) and poly(ethylene oxide)," *Bull. Korean Chem. Soc.* 21(4):383-388.
Nah et al. (2000) "Drug-delivery system based on core-shell-type nanoparticles composed of poly((-benzyl L-glutamate) and poly(ethylene oxide)," *J. App. Polymer Sci.* 75:115-112.
Nemerson et al. V.T. (1991) "The effect of flow on hemostasis and thrombosis," *Thromb. Haemostasis* 66(3):272-276.
Nerem, RM, E.A. (2004) "The Tissue Engineering of Blood Vessels and the Heart," *Am. J. Transplant.* 4(supp 6):36-42.
Nerem RM, S.D. (2001) "Vascular Tissue Engineering," *Ann. Rev. Biomed. Eng.* 3:225-243.
Nickerson, P. et al. (1993 "Analysis of cytokine transcripts in pancreatic islet cell allografts during rejection and tolerance induction," *Transplantation Proceedings* 25:984-985.
Niklason et al. (1999) "Functional Arteries Grown in Vitro," *Science* 284(5413):489.
Nojiri et al. (1996) "Can heparin immobilized surfaces maintain nonthrombogenic activity during In Vivo long-term implantation?" *ASAIO Journal* 42(5):M468-475.
Nojiri et al. (1990) "In vivo nonthrombogenicity of heparin immobilized polymer surfaces," *ASAIO Transactions* 36(3):M168-172.
Nomura et al. (1996) Preparation of 'sugar-coated' homopolymers and multiblock ROMP copolymers, *Macromolecules* 29:540.
Nowatzki et al. (2004) "Physical Properties of Artificial Extracellular Matrix Protein Films Prepared by Isocyanate Crosslinking," *Biomaterials* 25:1261-1267.
O'Brien et al. (1998) "Polymerization of preformed self-organized assemblies," *Acc. Chem. Res.* 31:861-868.
O'Connell et al. (1993) "Unmodified pancreatic islet allograft rejection results in the preferential expression of certain T cell activation transcripts," *J. Immunol.* 150:1093-1104.
O'Donnell et al. (1992), "Radiation degradation of linear low density polyethylene: determination of lamellae thickness, crystallinity and crosslinking by solid-state $_{13}$C NMR and DSC," *Radiat. Phys. Chem.* 36(20:209-214.
O'Donnell et al. (1992) "A solid-state $_{13}$C-NMR study of crosslinking in polybutadiene by ( radiation: effect of microstructure and dose," *J. Polym. Chem. Ed.* 30:185-195.
Office Action Corresponding to Australian Patent Publication No. 2003236491, May 19, 2009.
Ohno et al. (1999), "Nitroxide-controlled free radical polymerization of a sugar-carrying acryloyl monomer," *Macromol. Chem. Phys.* 200:1619-1625.
Ohno et al. (1998) "Synthesis of a well-defined glycopolymer by nitroxide-controlled free radical polymerization," *Macromolecules* 31:1064-1069.
Ohno et al. (1998), "Synthesis of a well-defined glycopolymer by atom transfer radical polymerization," *J. Polym. Sci., Part A: Polym. Chem.* 36:2473-2481.
Ohno et al. (1998) "Free radical polymerization of a sugar residue-carrying styryl monomer with a lipophilic alkoxyamine initiator: synthesis of a well-defined novel glycolipid," *Macromol. Chem. Phys.* 199:2193-2197.
Ohno et al. (1987) "Polymerization of liposomes composed of diene-containing lipids by UV and radical initiators: evidence for the different chemical environment of diene groups on 1- and 2-acyl chains," *Macromol.* 20:929-933.
Ohno et al. (1987) "Polymerization of liposomes composed of diene-containing lipids by radical initiators. II. Polymerization of monodiene-type lipids as liposomes," *J. Polym. Sci.: Part A: Polym. Chem.* 25:2737-2746.
Orban et al. (2000) "Cytomimetic biomaterials. 4. In-situ photo polymerization of phospholipids on an alkylated surface," *Macromolecules* 33:4205-4212 (published on Web May 6, 2000).
Ornitz et al. (1995) "FGF binding and FGF receptor activation by synthetic heparan-derived di- and trisaccharides," *Science* 268:432-434.
Otani et al. (1996) "Rapidly curable biological glue composed of gelatin and poly(Lglutamic acid)," *Biomaterials* 17(14):1387-1391.
Ottani et al (2001) "Collagen Structure and Functional Implications," *Micron* 32:251-260.
Owen et al. (1981) "Functional properties of an endothelial cell cofactor for thrombin-catalyzed activation of protein C," *J. Biol. Chem.* 256(11):5532-5535.
Packer et al. (1984) "The effects of morphology on $_1$H NMR spectra and relaxation in semicrystalline polyolefins," *J. Polym. Sci.: Polym. Phys.* 22:589-616.
Panitch et al. (1999) "Design and biosynthesis of elastin-like artificial extracellular matrix proteins containing periodically spaced fibronectin CS5 domains," *Macromolecules* 32:1701-1703.
Parikh et al. (1994), "An intrinsic relationship between molecular structure in self assembled n-alkysiloxane monolayers and deposition temperature," *J. Phys. Chem.* 98:7577.
Parker et al. (1996) "Transplantation of discordant xenografts: a challenge revisited," *Immunology Today* 17:373-378.
Pasquali-Ronchetti et al. (1998) "Study of elastic fiber organization by scanning force microscopy," *Matrix Biology* 17:75-83.
Pasquali-Ronchetti et al. (1995) "Ultrastructure of elastin," *Ciba Foundation Symposium* 192:31-50.
Patel et al. (Web Release Feb. 28, 2006) "Elastin Biosynthesis: The Missing Link in Tissue-Engineered Blood Vessels," *Cardiovasc. Res.* 71(1):40-49.
Pearce et al. (1993) "Comparison of the membrane binding kinetics of bovine prothrombin and its fragment 1," *J. Biol. Chem.* 268:22984-22991.
Peterson et al. (1996) "Transfer of diabetes in the NOD-scid mouse by CD4 T-cell clones: differential requirement for CD8 T-cells," *Diabetes* 45:328-36.
Petka et al. (1998) "Reversible hydrogels from self-assembling artificial proteins," *Science* 281:389-392.
Petitou et al. (1999) "Synthesis of thrombin-inhibiting heparin mimetics without side effects," *Nature* 398:417-422.
Petitou et al. (1998) "First synthetic carbohydrates with the full anticoagulant properties of heparin," *Chem. Int. Ed.* 37:3009-3014.

(56) References Cited

OTHER PUBLICATIONS

Pierson et al. (1989), "CD4₊ lymphocytes play a dominant role in murine xenogeneic responses," *Transplantation Proceedings* 21:519.
Plant et al. (1995) "Phospholipid/alkanethiol bilayers for cell-surface receptor studies by surface plasmon resonance," *Anal. Biochem.* 226:342-348.
Plant, A. L. (1993) "Self-assembled phospholipid/alkanethiol biomimetic bilayers on gold," *Langmuir* 9: 2764-2767.
Plant et al. (1989), "Generic liposome reagent for immunoassays," *Anal. Biochem.* 176:420-426.
Ponpipom et al. (1980) "Isolation of 1,3-distearoyl-glycero-2-phosphocholine (β-lecithin) from commercial 1,2-distearoyl-sn-glycero-3-phosphocholine," *Lipid Res.* 21:136-139.
Pourdeyhimi et al. (1999) "Measuring fiber diameter distribution in nonwovens," *Textile Res. J.* 69:233-236.
Qiu et al. (1994) "Protein kinase C-dependent and -independent pathways of mitogen-activated protein kinase activation in macrophages by stimuli that activate phospholipase $A_2$," *J. Biol. Chem.* 269:19480-19487.
Rand et al. (1996) "Blood clotting in minimally altered whole blood," *Blood* 88(9):3432-3445.
Rapaka et al. (1978), "Non-elastomeric polypeptide models of elastin," *Int. J. Pept. Protein Res.* 11:109-127.
Rashid et al. (2004) "The Use of Animal Models in Developing the Discipline of Cardiovascular Tissue Engineering," *Biometerials* 25:1627-1637.
Regen et al. (1983) Polymer-supported membranes. A new approach for modifying polymer surfaces, *Macromolecules* 16:335-338.
Reneker et al. (1996) "Nanometre diameter fibres of polymer, produced by electrospinning," *Nanotechnology* 7: 216-223.
Reneker et al. (1995) "Electrospun polyaramid fibers: structure and morphology," *Bull Am. Phys. Soc.* 40:351.
Rifkin et al. (1989), "Recent developments in the cell biology of basic fibroblast growth factor," *J. Cell. Biol.* 109:1-6.
Ringsdorf et al. (1988) "Molecular architecture and function of polymeric oriented systems: models for the study of organization, surface recognition, and dynamics of biomembranes," *Angew. Chem. Int. Ed. Engl.* 27:113-158.
Roach et al. (1957) "The reason for the shape of the distensibility curves of arteries," *Can. J. Biochem. Physiol.* 35:681-690.
Roberts et al. (1996) "Dopamine secretion by PC12 cells microencapsulated in a hydroxymethyl methacrylate-methyl methacrylate copolymer," *Biomaterials* 17:267-275.
Robins, S. P. (1982), "Analysis of the crosslinking components in collagen and elastin," *Methods Biochem. Anal.* 28:329-379.
Robinson et al. (1988) "Intro-Arterial Stenting in the Atherosclerotic Rabbit," *Circulation* 78:646-653.
Rosen et al. (1991), "Regulation of motility in bovine brain endothelial cells," *J. Cell Physiol.* 146:325-35.
Rosenbloom et al. (1995) "Structure of the Elastin Gene," *Ciba Foundation Symposium* 192:59-74.
Rosenbloom et al. (1993) "Extracellular Matrix 4: The Elastic Fiber," *FASEB J* 7:1208-1218.
Roy et al. (2000) "Synthesis and fluorescence properties of new fluorescent, polymerizable, metal-chelating lipids," *J. Org. Chem.* 65:3644-3651.
Roy, R. (1997) "Recent developments in the rational design of multivalent glycoconjugates," *Topics in Current Chem.* 187:241-274.
Roy, R. (1996) "Syntheses and some applications of chemically defined multivalent glycoconjugates," *Current Opinion in Structural Biology* 6:692-702.
Rucker RB, D.M. (1984) "Elastin Metabolism and Chemistry: Potential Roles in Lung Development and Structure," *Environ. Health Perspectives* 55:179-191.
Sabatani et al. (1987) "Organized self-assembling monolayers on electrodes. 2. Monolayer-based ultramicroelectrodes for the study of very rapid electrode kinetics," *J. Phys. Chem.* 91:6663-6669.
Sackmann et al. (2000) Supported membranes on soft polymer cushions: fabrication, characterization and applications, *Trans Biotechnol.* 18:58-64.

Sadler, J.E. (1997), "Thrombomodulin structure and function," (1997) *Thromb. Haemostasis* 78(1):392-395.
Sakai et al. (1998) "Molecular orientation in Langmuir films of 12-hydroxystearic acid studied by infrared external-reflection spectroscopy," *Langmuir* 14:6249-6255.
Sakata et al. (1985) "Activated protein C stimulates the fibrinolytic activity of cultured endothelial cells and decreases antiactivator activity," *Proc. Natl. Acad. Sci. USA* 82(4):1121-1125.
Sallach et al. (2006) "Size Variable Micelle Density Regulated by a reversible Switch of Protein Secondary Structure," *J. Am. Chem. Soc.* 128(36):12014-12019.
Sandberg et al. (1985), "Elastin covalent structure as determined by solid phase amino acid sequencing," *Pathol. Biol.* 33:266-274.
Sandberg et al. (1981) "Elastin structure, biosynthesis, and relation to disease states," *N. Engl. J. Med.* 304:566-579.
Sandberg et al. (1977) "Primary structure of porcine tropoelastin," *J. Adv. Exp. Med. Biol.* 79:277-284.
Santin et al. (1996), "Synthesis and characterization of a new interpenetrated poly(2-hydroxyethylmethacrylate)-gelatin composite polymer," *Biomaterials* 17(15):1459-1467.
Sato et al. (1988) "Autocrine activities of basic fibroblast growth factor: regulation of endothelial cell movement, plasminogen activator synthesis, and DNA synthesis," *J. Cell. Biol.* 107:1199-1205.
Schmidt, R.R. (1989) "Recent developments in the synthesis of glycoconjugates," *Pure Appl. Chem.* 61(7):1257-70.
Schmit et al. (2000) "Acellular Vascular Tissues: Natural Biomaterials for Tissue Repair and Tissue Engineering," *Biomaterials* 21:2215-2231.
Sefton, M.V., (Oct. 1989) "Blood, Guts and Chemical Engineering," *Can. J. Chem. Eng.* 67(5):705-712.
Seifert et al. (1993) "Charge transport by ion translocating membrane proteins on solid supported membranes," *Biophys. J.* 64:384-391.
Seitz et al. (1998) "Formation of tethered supported bilayers via membrane inserting reactive lipids," *Thin Solid Films* 329:767-771.
Seliktar et al. (2000) "Dynamic Mechanical Conditioning of Collagen-Gel Blood Constructs Induces Remodeling In Vitro," *Ann. Biomed. Eng.* 28:351-362.
Sells (1994) "Two-dimensional polymerization of lipid bilayers: degree of polymerization of acryloyl lipids," *Macromolecules* 27:226-233.
Serruys et al.(1998), "Randomized comparison of implantation of heparin-coated stents with balloon angioplasty in selected patients with coronary artery disease (Benestent II)," *Lancet* 352:673-681.
Shen et al. (2001), "Polymer-supported lipid bilayers on benzophenonemodified substrates," *Biomacromolecules* 2:70-79.
Shi et al. (2001) "Release behavior of thin-walled microcapsules composed of polyelectrolyte multilayers," *Langmuir* 17:2036-2042.
Shoji et al. (1993) "Human and baboon integrin $β_5$ subunit-encoding mRNAs have alternative polyadenylation sites," (1993) *Gene* 133:307-308.
Shultz et al. (1995) "Multiple defects in innate and adaptive immunologic function in NOD/LtSz-scid mice," *J. Immunology* 154:180-191.
Siedlecki et al. (1994) "Interactions of human von Willebrand factor with a hydrophobic self-assembled monolayer studied by atomic force microscopy," *Biomed. Mater. Res.* 28:971.
Silver et al. (2003) "Mechanical Behavior of Vessel Wall: A Comparative Study of Aorta, Vena Cava, and Carotid Artery," *Annals Biomed. Eng.* 31:793-803.
Silver et al. (2001) "Viscoelasticity of the Vessel Wall: The Role of Collagen and Elastin Fibers," *Crit. Rev. Biomed. Eng.* 29(3):279-302.
Slack et al. (1993) "The effects of flow on blood coagulation and thrombosis," *Thromb. Haemostasis* 70(1):129-134.
Slack et al. (1994) "Flow chambers and their standardization for use in studies of thrombosis," *Thromb. Haemostasis* 72(5):777-781.
Smirnov et al. (1999) "The effect of membrane composition on the hemostatic balance," *Biochemistry* 38(12):3591-3598.
Smirnov et al. (1994) "Phosphatidylethanolamine incorporation into vesicles selectively enhances factor Va inactivation by activated protein C," *J. Biol. Chem.* 269(2):816-819.
Snyder et al. (1978) "Vibrational spectra in the CōH stretching region and the structure of the polymethylene chain," *Spectrochim. Acta, Part A* 34A:395-406.

(56) References Cited

OTHER PUBLICATIONS

Solletti et al. (1996) "Elaboration and characterization of phospholipid Langmuir-Blodgett films," *Langmuir* 1:5379-5386.
Spinke et al. (1992) "Polymer-supported bilayer on a solid substrate," *Biophys. J.* 63:1667-1671.
Stoll et al. (1988) "Improved procedure for the construction of neoglycolipids having antigenic and lectin-binding activities, from reducing oligosaccharides," *Biochemical J.* 256:661-664.
Sun et al. (1993) "Ultrathin self-assembled polymeric films on solid surfaces. 2. Formation of 11-(n-pentyldithio)undecanoate-bearing polyacrylate monolayers on gold," *Langmuir* 9:3200-3207.
Sun et al. (1996) "Spontaneous polymer thin film assembly and organization using mutually immiscible side chains," *J. Am. Chem. Soc.* 118:1856-1866.
Sun et al. (1994) "Ultrathin self-assembled polymeric films on solid surfaces. III. Influence of acrylate dithioalkyl side chain length on polymeric monolayer formation on gold," *J. Vac. Sci. Technol.* 12:2499-2506.
Sun et al. (1998) "The synthesis of neoglycophospholipid conjugates via reductive amination of ω-oxoalkylglycosides and phosphatidylethanolamines," *Carbohydrate Res.* 370:77-81.
Sun et al. (1997) "Neoglycophospholipids with alkyl spacers: synthesis via an improved reductive amination and monolayer properties," *Bioconjugate Chem.* 8:567-571.
Sun et al. (1996), "Normalization of diabetes in spontaneously diabetic cynomologus monkeys by xenografts of microencapsulated porcine islets without immune suppression," *J. Clin. Invest.* 98:1417-1422.
Sun et al. (2005) "One-Pot Glyco-Affinity Precipitation Purification for Enhanced Proteomics: The Flexible Alignment of Solution-Phase Capture/Release and Solid-Phase Separation," *J. Proteome. Res.* 4(6):2355-2359.
Tai et al. (2000) "Compliance Properties of Conduits Used in Vascular Reconstruction," *Brit. J. Surg.* 87:1516-1524.
Takeuchi et al. (1992), "Heart allografts in murine systems: The differential activation of Th2-like effector cells in peripheral tolerance," *Transplantation* 53:1281-1294.
Tasumi et al. (1962), "Normal vibrations and force constants of polymethylene chain," *J. Mol. Spectrosc.* 9:261-287.
Tendian et al. (1991), "Evidence from total internal reflection fluorescence microscopy for calcium-independent binding of prothrombin to negatively charged planar phospholipid membranes," *Biochemistry* 30:10991-10999.
Terranova et al. (1985) "Human endothelial cells are chemotactic to endothelial cell growth factor and heparin," *Cell Biol.* 101:2330-2334.
Thomas et al. (1987) "Raman amide bands of type-II β-turns in cyclo-(VPGVG)$_3$ and poly-(VPGVG), and implications for protein secondary-structure analysis," *Biopolymers* 26:921-934.
Tobias et al. (1991) "The N-End Rule in Bacteria," *Science* 254:1324-1377.
Toshima et al. (1993) "Recent progress on O-glycosylation methods and its application to natural products synthesis," *Chem. Rev.* 93:1503-1531.
Trabbic-Carlson et al. (2003) "Swelling and Mechanical Behaviors of Chemically Cross-Linked Hydrogels of Elastin-Like Polypeptides," *Biomacromolecules* 4(3):572-580.
Turitto et al. (1998) "Mechanical factors affecting hemostasis and thrombosis," *Thromb. Res.* 92(6 Suppl.2):S25-310.
Ueda et al. (1992) "Preparation of 2-methacryloyloxyethyl phosphorylcholine copolymers with alkyl methacrylates and their blood compatibility," *Polym. J.* 24(11):1259-1269.
Uludag et al. (1993), "Metabolic activity and proliferation of CHO cells in hydroxyethyl methacrylate-methyl methacrylate (HEMA-MMA) microcapsules," *Cell Transplantation* 2:175-182.
Urry et al. (1997) "Protein-based materials with a profound range of properties and applications: the elastin $T_t$ hydrophobic paradigm," In *Protein-Based Materials*, K. McGrath and D.Kaplan, Ed., Birkhauser: Boston, pp. 133-177.

Urry et al. (1995) "Molecular biophysics of elastin structure, function and pathology," *Ciba Foundation Symposium* 192:4-30.
Urry, D.W. (1993) "Molecular machines: how motion and other functions of living organisms can result from reversible chemical changes," *Angew. Chem. Int. Ed. Engl.* 32:819-841.
Urry et al. (1989) "Two-dimensional proton NMR studies on poly(VPGVG) and its cyclic conformational correlate, cyclo(VPGVG)$_3$," *Biopolymers* 28:819-833.
Urry, D.W. (1988) "Entropic elastic processes in protein mechanisms. I. Elastic structure due to an inverse temperature transition and elasticity due to internal chain dynamics," *J. Prot. Chem.* 7(1):1-34.
Urry et al. (1986) "Polytetrapeptide of Elastin. Temperatire-Correlated Elastomeric Force and Structure Development," *Int. J. Pept. Protein Res.* 28(6):649-660.
Urry et al. (1985) "Polypentapeptide of elastin: temperature dependence of ellipticity and correlation with elastomeric force," *Biochem. Biophys. Res. Commun.* 130:50-57.
Urry et al. (1985) "Phase-structure transitions of the elastin polypentapeptidewater system within the framework of composition-temperature studies," *Biopolymers* 24:2345-2356.
Urry et al. (1975) "Studies on the conformation and interactions of elastin secondary structure of synthetic repeat hexapeptides," *Biochim. Biophys. Acta* 393:296-306.
Urry et al. (1974) "Studies on the conformation and interactions of elastin. Proton magnetic resonance of the repeating pentapeptide," *Biochemistry* 13:609-616.
Urry et al. (1974) "The Synthetic Polypentapeptide of Elastin Coacervates and Forms Filamentous Aggregates," *Biochim. Biophys. Acta* 371(2):597-602.
Urry et al. (1977) "On the Conformation, Coacervation and Function of Polymeric Models of Elastin," *Adv. Exp. Med. Biol.* 79:685-714.
Urry et al. (1984) "Polypentapeptide of Elastin: Temperature Dependence Correlation of Elastomeric Force and Dielectric Permittivity," *Biochem. Biophys. Res. Commun.* 125(3):1082-1088.
Urry et al. (1992) "Hydrophobicity Scale for Proteins Based on Inverse Transition Temperature," *Biopolymers* 32:1243-1250.
Urry et al. (1991) "Temperature of Polypeptide Inverse Temperature Transition Depends on Mean Residue Hydrophobicity," *J. Am. Chem. Soc.* 113:4346-4348.
Urry, D.W. (Web Release Dec. 18, 1997) "Physical Chemistry of Biological Free Energy Transduction as Demonstrated by Elastic Protein-Based Polymers," *J. Phys. Chem. B.* 101(51):11007-11028.
van Ackern et al. (1998) Ultrathin membranes for gas separation and pervaporation prepared upon electrostatic self-assembly of polyelectrolytes, *Thin Solid Films* 329:762-766.
Van Boeckel et al. (1993) "The unique antithrombin III binding domain of heparin: a lead to new synthetic antithrombotics," *Chem. Int. Ed. Engl.* 32(12):1671-1690.
Van Den Bulcke et al. (2000) "Structural and rheological properties of methacrylamide modified gelatin hydrogels," *Biomacromolecules* 1:31-38.
Vanderhart, D. L. (1990) "Proton spin diffusion as a tool for characterizing polymer blends," *Makromol. Chem., Macromol. Symp.* 34:125-159.
van Hest, JCM, T.D. (2001) "Protein-Based Materials, Toward a New Level of Structural Control," *Chem. Commun.* :1897-1904.
van't Veer et al. (1997) "Inhibitory mechanism of the protein C pathway on tissue factor-induced thrombin generation," *J. Biol. Chem.* 272(12):7983-7984.
Vasilets et al. (1997) "Microwave $CO_2$ plasma-initiated vapour phase graft polymerization of acrylic acid onto polytetrafluoroethylene for immobilization of human thrombomodulin," *Biomaterials* 18(17):1139-1145.
Viitala et al. (2000) "Protein immobilization to a partially cross-linked organic monolayer," *Langmuir* 16:4953-4961.
Wagenseil et al. (2005) "Effects of Elastin Haploinsufficiency on the Mechanical Behavior of Mouse Arteries," *Am. J. Physiol. Heart Circ. Physiol.* 289:H1209-H1217.
Wagenseil et al. (Oct. 2003) "One-Dimensional Viscoelastic Behavior of Fibroblast Populated Collagen Matrices," *J. Biomech. Eng.* 125(5):719-725.
Wall et al. (1978), "Human endothelial cell migration: stimulation by a released platelet factor," (1978) *Lab Invest.* 39(5):523-529.

(56) References Cited

OTHER PUBLICATIONS

Wang et al. (1993) "Synthesis of phospholipid-inhibitor conjugates by enzymatic transphosphatidylation with phospholipase D," *J. Am. Chem. Soc.* 115:10487-10491.
Wasserman et al. (1990) "A molecular dynamics investigation of the elastomeric restoring force in elastin," *Biopolymers* 29:1613-1631.
Wasserman et al. (1989) "The structure of self-assembled monolayers of alkylsiloxanes on silicon: a comparison of results from ellipsometry and lowangle X-ray reflectivity," *J. Am. Chem. Soc.* 111:5852-5861.
Weber et al. (1997) "CTLA4-Ig prolongs survival of microencapsulated neonatal porcine islet xenografts in diabetic NOD mice," *Cell Transplantation* 6(5):505-508.
Weber et al. (1995) "Encapsulated islet iso-, allo-, and xenografts in diabetic NOD mice," *Transplantation Proceedings* 27:3308-3311.
Weber et al. (1994) "NOD mouse peritoneal cellular response to poly-Llysine-alginate microencapsulated rat islets," *Transplantation Proceedings* 26:1116-1119.
Weber et al. (1990), "Microencapsulated dog and rat islet xenografts into streptozotocin-diabetic and NOD mice," *Horm. Metab. Res.* 35:219-226.
Weber et al. (1990) "The role of $CD4_+$ helper T cells in destruction of microencapsulated islet xenografts in NOD mice," *Transplantation* 49(2):396-404.
Weinberg CB, B.E. (1986) "A Blood Vessel Model Constructed from Collagen and Cultured Vascular Cells," *Science* 231(4736):397-400.
Weiner et al., (1985) "Liposome-collagen gel matrix: A novel sustained drug delivery system," *J. Pharm. Sci.* 74(9):922-925.
Welsh et al. (2000) "Engineering the extracellular matrix: A novel approach to polymeric biomaterials. I. Control of the physical properties of artificial protein matrices designed to support adhesion of vascular endothelial cells," *Biomacromolecules* 1:23-30.
Westerduin et al. (1996), "Synthesis of tailor-made glycoconjugates showing AT Illmediated inhibition of blood coagulation factors Xa and thrombin," *Chem. Int. Ed. Engl.* 35:331-333.
Westman et al. (1995) "Synthesis and fibroblast growth factor binding of oligosaccharides related to heparin and heparan sulphate," *J. Carbohydr. Chem.* 14:95-113.
Wet et al. (1999) "Polymeric Biomaterials with Degradable Sites for Proteases Involved in Cell Migration," *Macromolecules* 32:241-244.
Wick et al. (1987) "Unusually large von Willebrand factor multimers increase adhesion of sickle erythrocytes to human endothelial cells under controlled flow," *J. Clin. Invest.* 80:905-910.
Wilbur et al. (2000) "Biotin reagents for antibody pretargeting. 4. Selection of biotin conjugates for in vivo application based on their dissociation rate from avidin and streptavidin," *Bioconjugate Chem.* 11:569-583.
Winger et al. (1999) "Formation and stability of complex membrane-mimetic monolayers on solid supports," *Langmuir* 15:3866-3874.
Winger et al. (1998) "Synthesis and characterization of supported phospholipid monolayers: a correlative investigation by radiochemical titration and atomic force microscopy," *Langmuir* 14:4148-4155.
Winger et al. (1998) "Synthesis and characterization of supported bioactive lipid membranes," In: Materials Science of the Cell, A. Plant and V. Vogel (Ed.), MRS Publications, Pittsburgh, pp. 113-118.
Winger et al. (1997) "Behavior of lipid-modified peptides in membrane-mimetic monolayers at the air/water interface," *Langmuir* 13:3256-3259.
Winger et al. (1996) "Lipopeptide conjugates: Biomolecular building blocks for receptor activating membrane-mimetic structures," *Biomaterials* 17:443-449.
Winger et al. (1995) "A convenient route to thiol terminated peptides for conjugation and surface functionalization strategies," *Bioconjug. Chem.* 6:323-326.
Winger et al. (1995) Purification of synthetic lipopeptide conjugates by liquid chromatography, *J. Liquid Chromatogr.* 18:4117-4125.
Wolinsky H, G.S. (1967) "A Lamellar Unit of Aortic Medial Structure and Function in Mammals," *Circ. Rev.* 20:99-111.
Wong et al. (1988) "Intriguing absorption band behavior of IR reflectance spectra of silicon dioxide on silicon," *Appl. Spectrosc.* 42(4):598-604.
Wood et al. (1986) "In Vitro Calcification and In Vivo Biocompatibility of the Crosslinked Polypentapeptide of Elastin," *J. Biomed. Mater Res.* 20(3):315-335.
Woodhouse et al. (2004) "Investigation of Recombinant Human Elastin Polypeptides as Non-Thrombogenic Coatings," *Biomaterials* 25:4543-4553.
Wright et al. (Oct. 2002) "Self-assembly of block copolymers derived from elastin-mimetic polypeptide sequences," *Adv. Drug Deliv. Rev.* 54(8):1057-1073.
Wright et al. (Feb. 2002), "Thermoplastic elastomer hydrogels via self-assembly of an elastinmimetic triblock polypeptide," *Adv. Funct. Mater.* 12(2):149-154.
Wright et al. (2002) "Self-Assembly of Hydrogels from Elastin-Mimetic Block Copolymers," *Mat. Res. Soc. Symp. Proc.* 724:161-166.
Wu et al. (No./Dec. 2005) "Alterations in Physical Cross-Linking Modulate Mechanical Properties of Two-Phase Protein Polymer Networks," *Biomacromolecules* 6(6):3037-3044.
Wu et al. (Web Release Jun. 18, 2008) "Deformation Responses of a Physically Cross-Linked High Molecular Weight Elastin-Like Protein Polymer," *Biomacromolecules* 9(7):1787-1794.
Xiao et al. (1995), "Preparation, structure, and mechanical stability of alkylsilane monolayers on mica," *Langmuir* 11(5):1600-1604.
Yamada et al. (1999) "Controlled synthesis of amphiphilic block copolymers with pendant N-acetyl-D-glucosamine residues by living cationic polymerization and their interaction with WGA lectin," *Macromolecules* 32:3553.
Yamada et al. (1997) "Controlled synthesis of glycopolymers with pendant D-glucosamine residues by living cationic polymerization," *J. Polym. Sci. Part A: Polym. Chem.* 35:751-757.
Yen et al. (Oct. 1989) "Infrared Reflectance Properties of Surface Thin Films," *J. Phys. Chem.* 93(20):7208-7216.
Yoshioko et al. (1990) "Encapsulation of mammalian cell with chitosan-CMC capsule," *Biotechnol. Bioeng.* 35:66-72.
Yu et al. (1997) "Smectic ordering in solutions and films of a rod-like polymer owing to monodispersity of chain length," *Nature* 389:167-170.
Zhang et al. (1989) "Synthesis of 4% glu-containing $Val_1$ and $Ile_1$-polypentapeptides: model protein systems for demonstrating mechanochemical coupling," *J. Protein Chem.* 8:173-182.
Zierler et al. (1992) "Accuracy of duplex scanning for measurement of arterial volume flow," *J. Vasc. Surg.* 16(4):520-526.

{[VPAVG(IPAVG)$_4$][(IPAVG)$_5$]$_{33}$} – [X] – {[VPAVG(IPAVG)$_4$][(IPAVG)$_5$]$_{33}$VPGVG}

[X] = (IPGAG)(VPGAG)VPGEG(VPGAG)$_2$ [(VPGAG)$_2$VPGEG(VPGAG)$_2$]$_{20}$

{VPAVG[(IPAVG)$_4$(VPAVG)]$_{16}$IPAVG} – [X] – {VPAVG[(IPAVG)$_4$(VPAVG)]$_{16}$IPAVG}

[X] = VPGVG[(VPGVG)$_2$VPGEG(VPGVG)$_2$]$_{48}$VPGVG

■ Plastin Domain
☐ Elastin Domain
▨ Crosslinking Domain

MODIFIED PROTEIN POLYMERS

CROSS-REFERENCE TO RELATED APPLICATIONS

This application is the U.S. national stage application under 35 U.S.C. §371 of International Application No. PCT/US2007/078172, filed Sep. 11, 2007, which claims the benefit of priority to U.S. Provisional Patent Application Ser. Nos. 60/863,117 filed Oct. 26, 2006 and 60/825,255 filed Sep. 11, 2006, which are hereby incorporated by reference in their entireties to the extent they are not inconsistent with the disclosure herein.

ACKNOWLEDGEMENT

This invention was made with government support under Grant No. RO1HL71336 awarded by the National Institutes of Health. The government has certain rights in the invention.

STATEMENT REGARDING FEDERALLY SPONSORED RESEARCH OR DEVELOPMENT

This invention was made with government support under Grant No. RO1HL71336 awarded by National Institutes of Health. The Government has certain rights in the invention

BACKGROUND OF THE INVENTION

The invention generally relates to proteins, particularly elastin-mimetic proteins, and methods of producing and using the same, such as in medical devices and/or medical procedures, and other applications.

Cardiovascular disease is a growing concern whose importance in the health care field is evidenced by the effort directed at tissue engineering of artificial blood vessels. Current procedures for alleviating cardiovascular disease such as coronary artery disease involves use of a variety of stents, bypass vessels and/or angioplasty. A common problem with these techniques is the high rate of restonosis that requires one or more additional procedures to ensure blood flow through the region remains effective. One method to assist in reducing subsequent adverse outcome or failure of the procedure is to ensure any implanted device be mechanically matched to the surrounding vessel. In addition, any implanted material must also be biocompatible to avoid or minimize an unwanted immune response and anti-thrombogenic to minimize unwanted platelet adhesion.

One difficulty with producing biocompatible and mechanically matched devices such as grafts, stents and artificial blood vessels is that the physical characteristics of the blood vessel is rather complex due to the interaction of a number of different biological materials including elastin, collagen and glucoseaminoglycans, for example. Elastin provides initial elasticity to the vessel wall in the lower strain regime, while collagen prevents overextension of the blood vessel. Accordingly, elastin is an important material that provides elasticity to the blood vessel wall and any implantable medical device in the cardiovascular should model elastin's physical characteristics.

Although elastin-mimetic proteins are generally known in the art (see, e.g., U.S. Pub. No. 2004/0171545 published Sep. 2, 2004), there is a need for such proteins having improved mechanical performance that better match the surrounding in vivo environment while being durable and readily and reliably made. In particular, the cardiovascular system has a wide range of operating parameters depending on the location within the vascular tree. For example, the stress exerted on a blood vessel wall in the heart or aorta is very different in terms of magnitude and oscillation than those stresses exerted in the venous system. The venous system tends to be of lower and constant pressure whereas upstream in the arterial system the systolic and diastolic pressures provide continuous and significant cyclic strain on the vessel wall. In addition, the pressure and time-dependent forces exerted in a neurovascular defect (e.g., aneurysm) region may be quite different than that in other blood vessels. These difference in the mechanical environment are optionally addressed herein by artificial elastin-mimetic proteins (and related methods of manufacture) that are readily modified to provide a mechanical parameter that is matched to the in vivo environment.

SUMMARY OF THE INVENTION

The disclosure herein includes, inter alia, synthetic elastin-mimetic proteins, and various polypeptides useful for incorporation into the synthetic proteins, that are biocompatible and useful for medical applications including as implantable devices. Further, the elastin mimetic proteins can have selectable physical characteristics so that the proteins (and specifically the medical devices/procedures comprising the proteins) may be tailored to better match the physical environment in which the elastin mimetic proteins are to be implanted. Also disclosed are a variety of related methods for making the proteins, selectively tuning one or more physical characteristics of the protein, methods of casting the protein into a film or fiber network useful for making medical devices and/or coatings thereof.

In a broad embodiment, the invention is a triblock protein copolymer having hydrophobic end block regions separated by a hydrophilic center block. Further provided are polymers corresponding to the end region and polymers corresponding to the center region. In various aspects of the invention, chemical cross-linking sites are provided for further tuning of the material's physical parameters. In addition, manipulation of the center and end block regions (relative to each other) provides another mechanism for tuning one or more physical parameters. For example, the respective lengths and/or the hydrophobicity/hydrophilicity are increased or decreased to alter a physical parameter. In an embodiment, the invention is a triblock protein copolymer A-B-C, where the end blocks A and C are hydrophobic and the central block B is hydrophilic. In an embodiment, the central block provides elasticity to the protein, and the end block provides plasticity to the protein.

In an aspect, the invention is recombinant protein polymers that are biocompatible and have improved mechanical stability and deformation responses and related recombinant methods for expressing and making the polymers. In particular, the polymers relate to artificial proteins that are capable of physical and/or chemical cross-links to mimic the mechanical properties of elastin, but are capable of long-term functionality when implanted under relatively demanding in vivo applications, for example.

In an embodiment, the invention is a synthetic protein triblock copolymer comprising first and second end hydrophobic blocks separated by a central hydrophilic block, wherein:

the central block comprises the sequence:

(IPGAG)(VPGAG)VPGEG(VPGAG)$_a$[(VPGAG)$_b$VPGEG (VPGAG)$_c$]$_d$ (SEQ ID NO. 8)

the first and second end blocks each independently comprise the sequence:

[VPAVG(IPAVG)$_x$][(IPAVG)$_y$]$_z$ (SEID NO. 7)

and wherein:
a has a value from about 1 to about 10;
b has a value from about 1 to about 10;
c has a value from about 1 to about 10;
d has a value from about 10 to about 50;
x has a value from about 1 to about 10;
y has a value from about 1 to about 10; and
z has a value from about 20 to about 100;

The first and second endblocks of any of the proteins provided herein have the same amino acid sequence or have a different amino acid sequence.

In an embodiment, at least one the first and second endblocks of the protein comprises the sequence (SEQ ID NO:6, which itself is made from a plurality of 5-mers from SEQ ID NOs:4-5):

[VPAVG(IPAVG)$_4$][(IPAVG)$_5$]$_{33}$

In an embodiment, the central block of any of the proteins provided herein comprise the sequence (SEQ ID NO:7, which itself is made from a plurality of 5-mers from SEQ ID NOs: 1-3):

(IPGAG)(VPGAG)VPGEG(VPGAG)$_2$

[(VPGAG)$_2$VPGEG(VPGAG)$_2$]$_{20}$

In an embodiment, the protein triblock copolymer comprises the sequence of B10 (SEQ ID NO:9):

[VPAVG(IPAVG)$_4$][(IPAVG)$_5$]$_{33}$-X-

[VPAVG(IPAVG)$_4$][(IPAVG)$_5$]$_{33}$ wherein X=(IPGAG)(VPGAG)VPGEG(VPGAG)$_2$ [(VPGAG)$_2$VPGEG(VPGAG)$_2$]$_{20}$ In an aspect, any of the proteins disclosed herein are further characterized in terms of the relative lengths of the endblocks to the central block. For example, the protein is described as having an end block length parameter corresponding to the total number of amino acids in the first and second end blocks, and a central block length parameter corresponding to the number of amino acids in the central block. In this aspect, a ratio of the end block length parameter to the central block length parameter has a selected value, wherein the ratio has a value that is about 1, greater than 1, greater than 1.5, from about 1:1 to about 10:1, or about 2:1 to about 10:1.

In another aspect, any of the proteins are described in terms of the amount of isoleucine, such as a mole fraction of isoleucine of greater than about 18%, between about 18% to about 25%, or about 20%.

In an embodiment, any of the proteins are hydrated. Such hydration provides the capacity of at least one of the end hydrophobic blocks to form physical crosslinks that provide improved mechanical stability under sustained or repeated mechanical loading such as, for example, the sustained repeated load experienced by the blood vessel wall, a tissue, or an organ in a living system.

In an embodiment, any of the proteins are described in terms of any one or more of a physical parameter. In an aspect of this embodiment, any of the proteins have an inverse transition temperature, such as a transition temperature that is between about 15° C. and about 27° C., or selected from a range that is between about 19° C. and about 23° C.

In another embodiment, the invention is a hydrated film or fiber network comprising any of the proteins disclosed herein. Optionally, the film or fiber network is cast from a solution comprising TFE or water, such as by electrospinning, and the film or fiber network has a cast temperature. The cast temperature may be of any value so long as suitable elastin-mimetic materials having suitable mechanical properties are obtained, such as a cast temperature selected from a range that is between about 2° C. and about 35° C. In an aspect, any of these films or fiber networks is formed into a tissue engineering scaffold capable of supporting cell growth. A useful property of the proteins disclosed herein is their capacity of having a user-selected physical parameter by selection of appropriate amino acids, amino acid sequences and amino acid configurations. For example, the film or fiber network of any of the proteins optionally have a tunable physical parameter, such as a physical parameter that is a: Young's modulus that is greater than 0.3 MPa; ultimate tensile stress greater than 1 MPa; strain at failure selected from a range that is between 100% and 200%; resilience that is greater than 70% over a strain of 30 to 45%; and creep resistance that is less than 10% at an applied stress greater than 0.3 MPa. Of course, any of the materials described herein may be subject to any one or more post-processing techniques known in the art to further effect a change in one or more physical parameters (e.g., post-processing that changes porosity).

The ability to tune one or more physical property parameters of the film or fiber network that is made from any of the disclosed proteins provides the capability of tailoring the material to a particular application. For example, any of the films or fiber networks is formed into a medical device that may be implanted into the body, such as a vascular graft. Depending on the location of the vascular graft, however, the desired mechanical properties can be very different. Some applications may require resistance to high loads, other low lows, and others a repeated cycling of loads. An embodiment of the present invention provides the ability to tune any one or more of these parameters by varying one or more of end block to central block length, end block hydrophobicity, center block hydrophilicity, and degree of cross-linking.

In an embodiment, the invention is a medical device comprising any of the proteins provided herein, such as B9, B10, R1, R2 or R4, or a film or fiber network of any of the proteins. Examples of medical devices of particular utility include, but are not limited to, an artificial blood vessel; a stent; a graft; a wound dressing an embolic agent; and a drug delivery device. Any of the medical devices may have a protein, film, or fiber network comprising a protein of the present invention that at least partially coats one or more surfaces of the medical device. In an aspect the protein, film, or fiber network of the medical device retains physical integrity under sustained mechanical load.

In another embodiment, the film or fiber network has a cast temperature is greater than the inverse transition temperature. In an embodiment, any of the proteins comprise one or more chemical cross-linking sites flanking each block. "Chemical cross-linking" refers to covalent interactions, van der Waals interactions, dipole-dipole interactions and/or hydrogen bonding interactions within the proteins that provide the capability of effecting a measurable change in one or more physical parameters, and is different from the "physical cross-linking" arising from the physical interaction of hydrophobic and hydrophilic regions which causes conformational changes. In an embodiment, the chemical cross-linking site comprises an amino acid that is lysine. Lysine can be suitably processed to mediate chemical cross-linking, such as by gluteraldehyde or a photocross-linkable acrylate functionalized lysine.

In another embodiment, the invention is nucleic acid sequence that encodes the any one or more of the first endblock, the second endblock (SEQ ID NO:14), the central block (SEQ ID NO:15) and/or any of the proteins disclosed herein.

In an embodiment, the nucleic acid sequence encodes the protein having the amino acid sequence of B10 (SEQ ID NOs:9-10), or any blocks thereof (DNA cross-referenced as SEQ ID NOs:11-17, 19 or repeating combinations thereof).

In an embodiment, the invention is a synthetic protein copolymer triblock having a plurality of chemically cross-linkable sites, such as the protein of SEQ ID NO:33 or:

K[(IPAVG)$_5$]$_{26}$-KK[(VPGAG)$_4$(VPGEG)]$_{26}$KK-[(IPAVG)$_5$]$_{26}$
KK

In an embodiment, the invention is a synthetic protein copolymer triblock comprising end hydrophobic blocks (SEQ ID NO:23 and/or SEQ ID NO:24) separated by a central hydrophilic block, with a plurality of cross-linkable sites (SEQ ID NO:25), for example the protein having the sequence of lysB10 (SEQ ID NO:26 or 71):

[VPAVGKVPAVG(IPAVG)$_4$][(IPAVG)$_5$]$_{33}$-X-[VPAVGKAAKVPGA

GVPAVG(IPAVG)$_4$][(IPAVG)$_5$]$_{33}$[IPAVGKAAKA]

wherein X is (SEQ ID NO:25) IPAVGKAAKVPGAG][(VP-GAG)$_2$VPGEG(VPGAG)$_2$]$_{28}$ In another embodiment, the invention is an isolated and purified nucleic acid sequence, that encodes for any one or more of the first endblock (SEQ ID NO:23), the second endblock (SEQ ID NO:24), the central block (SEQ ID NO: 25), repeated any number of times as desired, such as from about 10 to 50, or about 28 as exemplified, or the protein lysB10 (SEQ ID NOs:26 or SEQ ID NO: 71), and mixtures of any of the endblocks and central blocks as disclosed herein repeated any number of times to form copolymers having more than 3 blocks.

In an aspect, the invention is a synthetic protein copolymer triblock comprising end hydrophobic blocks separated by a central hydrophilic block, said protein comprising the sequence of R4 or SEQ ID NO:34:

VPAVGKVPAVG[(IPAVG)$_5$]$_{16}$ (IPAVGIPAVG)KAAK(VPGAGVPGIG) [(VPGIG)$_5$]$_{15}$ (VPGIGVPAVG)KAAK(VPGAGVPAVG) [(IPAVG)$_5$]$_{16}$

IPAVGVPAVGKAAKA

In another embodiment, the invention is an isolated and purified nucleic acid sequence, the sequence encoding for any one or more of the first endblock, the second endblock, the central block and/or the entire R4 protein, such as the nucleic acid sequence of SEQ ID NO:42.

In another embodiment, the invention is a peptide capable of establishing elastic-like behavior when incorporated into an elastin-mimetic protein, such as a peptide comprising the sequence R1 protein has in the amino acid sequence of SEQ ID NO. 43.

K$_a$[(VPGIG)$_b$]$_c$K$_d$

Wherein a has a value from about 1 to about 5; b has a value from about 1 to about 10; c has a value from about 5 to about 50; d has a value from about 1 to about 5.

In an aspect R1 has the amino acid sequence of SEQ ID NO:44:

K[(VPGIG)$_5$]$_{15}$KK

In an embodiment, the invention is a peptide capable of establishing plastic-like behavior when incorporated into an elastin-mimetic protein, such as a peptide comprising the sequence of R2 protein has in the amino acid sequence of SEQ ID NO. 45

K$_a$[(IPAVG)$_b$]$_c$K$_d$

Wherein a has a value from about 1 to about 5; b has a value from about 1 to about 10; c has a value from about 5 to about 50; d has a value from about 1 to about 5.

In an aspect, R2 has the amino acid sequence of SEQ ID NO:46:

K[(IPAVG)$_5$]$_{16}$KK

In another embodiment, the invention comprises a multi-block elastin mimetic protein having the formula:

R2-R1-R2 or (R2-R1)$_n$;

R1 and R2 are as defined above and wherein n is greater than or equal to 2, or is selected from a range that is between 2 and 10

In an aspect, R1 comprises the sequence of SEQ ID NO:44 and R2 comprises the sequence of SEQ ID NO:46:

([(IPAVG)$_5$]$_{16}$)-KK[(VPGIG)$_5$]$_{15}$KK-([(IPAVG)$_5$]$_{16}$)KK

In an embodiment, the invention is a medical device, cell, tissue, or organ comprising any one or more of the proteins disclosed herein, such as any one or more of B9 (SEQ ID NO:50), B10 (SEQ ID NOs:9, 26, 33), R1 (SEQ ID NO:44), R2 (SEQ ID NO:46), or R4 (SEQ ID NO:34), any combinations thereof, or spun fiber or fiber networks thereof. In an embodiment, the protein is one or more of B10, R1, R2, or R4. One example of a medical device is a vascular graft, such as a shunt. The graft or shunt optionally comprises a base scaffold material that is coated and/or impregnated with any one or more of the proteins or films and/or fiber networks thereof. One example is a shunt that is made of ePTFE. In an aspect, the coating is a multi-layer coating. In an embodiment, the medical device comprises a woven collagen graft.

In another embodiment, the invention is an embolic agent, wherein the embolic agent comprises one or more of the proteins of the present invention, such as any one or more of the amino acid sequences in Table 16 alone or in combination with each other, or SEQ ID NOs:9, 10, 26, 33, 34, 44, 46, 47, 48, 50, B9, B10, R1, R2, R4, or a blend thereof. In an aspect, the embolic agent has an inverse transition temperature, said temperature selected from a range that is between about 19° C. and about 23° C. Such an inverse temperature may be used to readily administer the embolic agent in a liquid form, and upon administration, the embolic agent gels or solidifies.

In an embodiment, the invention is a method of applying an embolic agent to a patient in need of an embolic agent by providing an embolic agent, wherein the embolic agent is any of the proteins disclosed herein, such as B9, B10, R1, R2, R4 or mixtures thereof. The embolic agent is applied to the patient. In an aspect, the embolic agent is applied in a solid or a gel form. Alternatively, the embolic agent is injectable and has an inverse phase transition temperature that is less than the environment in which the agent is applied, so that upon or after application said embolic agent undergoes a phase transition from liquid to a gel or solid form. In an aspect, the patient in need suffers from a cardiovascular defect. One example of such a defect is a neurovascular aneurysm.

In another embodiment, the invention is a method of producing a fiber network having improved mechanical properties from a triblock copolymer of any of the proteins provided herein, or any mixture thereof. The triblock copolymer is provided and thermally annealed. The triblock copolymer is electrospun, as known in the art (see, e.g., U.S. Pat. App. US-2004-0110439 published Jun. 10, 2004 (ref. 29-01) for various methods of making fibers, fiber networks, and fabrics), to form a fiber or fiber network. The fiber is optionally incubated in an aqueous solution at an annealing temperature sufficient to anneal the fiber network and thereby improve the mechanical properties compared to a fiber network that is not thermally annealed. Examples of specific triblock copolymers has an amino acid sequence selected from the group consisting of B10, B9, R1, R2, R1-R2, R4. In an aspect, the method improves a mechanical property that is an elastic modulus, and the elastic modulus increases by at least 30% compared to a nonannealed fabric. In an aspect, the annealing temperature is greater than 50° C. In another aspect, the method of annealing generates a decrease in water swelling ratio, selected from a range that is between 30% and 70%, or about 50%. Optionally, the method further comprises preconditioning the fiber network by repeated stress-relaxation cycling. In an aspect, the number of repeats is less than 10, such as between the range of about 4 and about 8.

In an embodiment, the invention is a method of controllably tuning a creep response parameter in an elastin-mimetic protein triblock copolymer. This is useful for tailoring a protein to the environment in which it will operate (e.g., high load, long term versus low loads). For example, a triblock copolymer A-B-C, having a central block region B and endblock regions A and C, wherein the central region is hydrophilic and the endblock regions are hydrophobic is provided. Varying at least one of endblock region size, endblock region hydrophobicity, or both, provides the capability of tuning creep response of the triblock copolymer. Optionally, the sum of the number of amino acid residues of said endblock regions have a length that is at least two times greater than the number of amino acid residues in the length of the central block region. The triblock optionally comprises any one or more of the proteins disclosed herein, such as B9, B10, R1, R2, R4, etc.

In an embodiment, the invention is a method of making a shunt for insertion into a patient having a cardiovascular defect. An expanded polytetrafluroethylene (ePTFE) graft having a wall and a lumen is provided. The graft is impregnating and/or coated with any one or more proteins disclosed herein. For impregnation of the graft, a protein solution is introduced to a surface wall of the graft under positive pressure so that the protein solution is capable of traversing from one surface of the graft wall to the other surface via a plurality of pores in the graft. Examples of appropriate protein solutions include, but are not limited to the protein of any of B9, B10, R1, R2, R4, or any mixture thereof. The protein solution and graft are contacted for a contact time sufficient to ensure the protein solution impregnates the wall.

The graft is optionally coated on a surface, such as the lumen facing surface, with the protein solution by introducing the protein solution to the graft lumen-facing wall surface; removing excess protein solution from the lumen; incubating the graft for a coating time period; and optionally repeating the coating steps to generate a multi-layer coated shunt. Any proteins disclosed herein may be provided in the solution, such as a protein comprising B10, R1, R2, and/or R4.

In an embodiment, the invention is an elastin-mimetic protein polymer, and related methods for synthesizing the elastin-mimetic protein polymers disclosed herein, such as by recombinant expression. One class of elastin-mimetic protein analog comprises analogs with elastic-like behavior based on the sequence:

BRIEF DESCRIPTION OF THE DRAWINGS

FIG. 22B scale is 40 μm; FIG. 22C scale is 2.0 μm; FIG. 22D scale is 333 μm; FIG. 22E scale is 40 μm; and, FIG. 22F scale is 2.0 μm.

Figure 1:
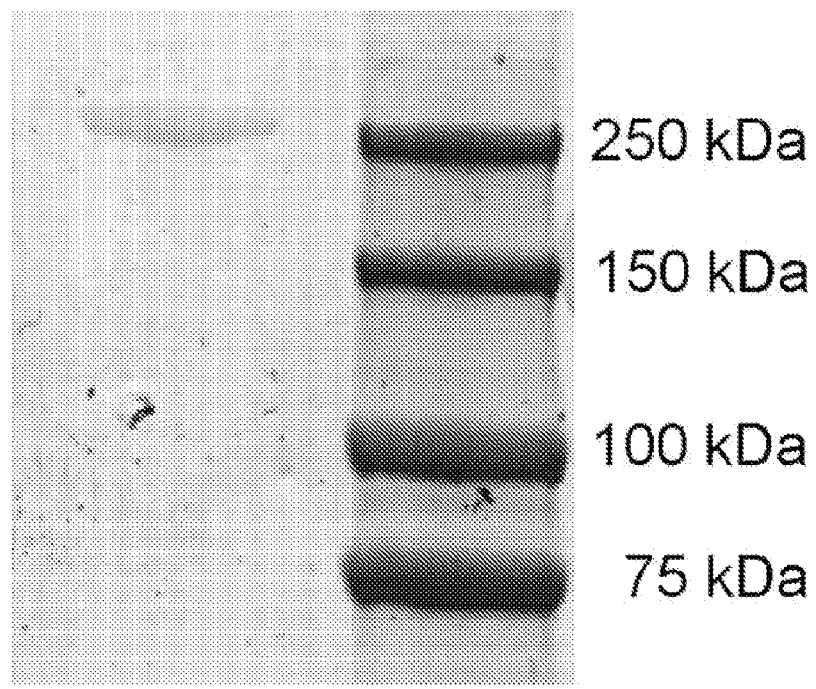
FIG. 1. Sodium dodecyl sulfate-polyacrylamide gel electrophoresis (SDS-PAGE) analysis of B10 copolymer. B10 was run on a 5% SDS-PAGE and stained with Coomassie G250 (BioRad). Molecular weight markers were Precision Plus Protein Kaleidoscope (BioRad).

Table 1. Coding Sequences of Oligonucleotide Cassettes Employed for the Construction of Protein Triblock (PEP) B10.

Table 2. Comparison of Young's Modulus of B9 and B10 Films.

Table 3. Tensile Behavior for Electrospun B9 Fabrics.

Table 4. Absorption Data for B9 Fabrics Hydrated in PBS and Water.

Table 5. Elastin-Mimetic Protein Classifications.

Table 6. Yeast B9 Elastin-block Monomer Library.

Table 7. Lysine Insert and Adaptor Sequences for B10.

Table 8. Coding sequences of R1 and R2 monomer blocks.

Table 9. Summary of Features Integral to the Design of an Elastin-Based Arterial Conduit.

Table 10. Experimental Design for characterization of the mechanical properties of elastin-mimetic nanofiber networks.

Table 11. Targeted Design Criteria.

Tables 12-16. Amino acid and nucleotide sequence listings in table form.

DETAILED DESCRIPTION OF THE INVENTION

"Synthetic" refers to an isolated artificial protein that is not normally made by an organism. A synthetic protein may be made by an organism or manufactured outside an organism. For example, the protein may be a recombinant protein in that a organism has been genetically engineered to express the protein or a precursor thereof.

"Triblock" refers to a protein having at least three distinct regions, such as a hydrophobic central block that separates end blocks that tend to be more hydrophilic. Optionally, a triblock amino acid sequence has additional material inserted between one or more of the blocks or at the block ends. For example, a cross-linkable amino acid or modified amino acid that is capable of cross-linking may be inserted between the blocks to facilitate cross-linkage manipulation. Such chemical cross-linking may be in addition to the physical cross-linking that tends to occur naturally with the amphilic triblocks and provides ability to tailor a mechanical property to the end-application to which the protein may be used.

"Creep" refers to a mechanical property of a material that is time-dependent. In particular, creep relates to the tendency of a material to permanently deform in response to an applied force or stress applied over time, or a time-dependent deformation of the material under stress.

"Inverse transition temperature" refers to the property where a material is a liquid at a lower temperature, but changes state to a gel or solid at a higher temperature. The temperature at which such a change of state begins is referred to as the "inverse transition temperature" and is useful for assisting in placement of an embolic agent into a cardiovascular defect as a liquid initially that later changes to a gel or solid, thereby providing therapeutic benefit.

"Young's modulus" is a mechanical property of a material, device or layer which refers to the ratio of stress to strain for a given substance. Young's modulus may be provided by the expression;

$$E = \frac{(stress)}{(strain)} = \left(\frac{L_0}{\Delta L} \times \frac{F}{A}\right); \quad (II)$$

wherein E is Young's modulus, $L_0$ is the equilibrium length, $\Delta L$ is the length change under the applied stress, F is the force applied and A is the area over which the force is applied.

"Physical parameter" refers to a property of the protein or material made from the protein and includes mechanical parameters provided herein (e.g., Young's modulus, bending modulus, compressability, ultimate tensile stress, fracture or failure strain, resilience, permeability, swelling ratio, and other parameters and particularly those parameters used in the art to describe biological systems and materials). A "tunable physical parameter" refers to a parameter that can be controllably adjusted by any of the methods disclosed herein or that depends on the structure or sequence of the proteins that make up a film or fiber network. For example, adjusting the properties of the end and/or central blocks (e.g., length, hydrophobicity) permits tuning of a physical parameter that describes the environment or surrounding tissue in which the film or fiber network is to be used or implanted into (e.g., a blood vessel or a portion of the cardiovascular system). Optionally, further tuning is accomplished by any processing or post-processing known in the art thereby providing further control of the mechanical properties of the medical device.

"Embolic agent" refers to a material that is capable of physically impacting blood flow or altering hemodynamics in and around a blood vessel. The embolic agent may be applied to a blood vessel or blood vessel wall, such as a wall rupture or aneurysm, in a liquid form that subsequently gels or solidifies, thereby displacing or preventing further blood flow in a region. Alternatively, the embolic agent may be applied as a gel, semi-solid or solid in a blood vessel or blood vessel wall, such as a wall rupture or aneurysm to provide a therapeutic benefit.

Example 1

Mechanical Stability and Deformation Responses of Physically Crosslinked Protein-Based Materials Recombinant protein polymers are synthesized and examined under various loading conditions in order to assess the mechanical stability and deformation responses of physically crosslinked, hydrated, protein polymer networks designed as triblock copolymers with central elastomeric and flanking plastic-like blocks. Uniaxial stress-strain properties, creep and stress relaxation behavior, as well as the effect of various mechanical preconditioning protocols on these responses are characterized. An analysis of viscoelastic behavior demonstrates that an increase in endblock size improves network stability and that mechanical preconditioning significantly enhances the resilience of hydrated films. Furthermore, the presence of three distinct phases of deformation behavior is revealed upon subjecting physically crosslinked protein networks to step and cyclic loading protocols in which the magnitude of the imposed stress is incrementally increased over time. Without being bound to a particular theory, we believe that these phases correspond to the stretch of polypeptide bonds, the conformational changes of polypeptide chains, and the disruption of physical crosslinks. The capacity to select a genetically engineered protein polymer that is suitable for its intended application requires an appreciation of its viscoelastic characteristics and the capacity of both molecular structure and conditioning protocols to influence these properties.

The emergence of genetically engineered synthetic polypeptides has enabled the design of protein polymers composed of complex peptide sequences in which individual peptide repeat sequences can be selected with distinct mechanical, chemical, or biological properties. While a large variety of recombinant protein polymers have been reported, those composed of distinct block structures are typically characterized by relatively short block sequences. For example, Cappello and colleagues have produced a series of silk-elastinlike block copolymers (SELPs) in which silk-like regions, consisting of between 12 and 48 alternating alanine and glycine residues, are found between elastin-mimetic sequences comprised of 8 or 16 repeat sequences of Val-Pro-Gly-Val-Gly. We have synthesised high molecular weight recombinant protein block copolymers using an approach, which affords significant flexibility in the selection and assembly of blocks of diverse size and structure. This has led to the synthesis of a new class of BAB protein triblock copolymer composed of large polypeptide block sequences ranging from 400 to 1200 amino acids in length. This class of protein block copolymers are derived from elastin-mimetic polypeptide sequences in which identical endblocks of a hydrophobic, plastic-like sequence are separated by a central hydrophilic, elastomeric block. The triblock protein copolymer acts as a two-phase network when hydrated, in that the hydrophilic block remains conformationally flexible and elastomeric, while the hydrophobic block forms physical or virtual crosslinks through hydrophobic aggregation.

Physically crosslinked protein-based materials possess a number of advantages over their chemically crosslinked counterparts, including ease of processing and the ability to avoid the addition or removal of chemical reagents or unreacted intermediates. However, physical crosslinks formed as a result of hydrophobic aggregation are often deformed or disrupted under external stresses that may be substantially lower than the forces required to disrupt covalent crosslinks. This feature may limit the capacity of physically crosslinked protein-based materials to retain material integrity under sustained mechanical loading that is often an essential requirement for their application in tissue engineering or regenerative medicine or use as a component of an implanted medical device.

Studies suggest that the density and strength of the physical crosslinks are important determinants of both mechanical responses and long-term material stability of two-phase protein networks. Therefore, in order to enhance the mechanical behavior of these materials a new elastin-mimetic triblock copolymer is synthesized that contains hydrophobic endblocks, which are nearly twice as large as prior versions of this triblock protein polymer. Hydrophobic aggregation of the endblocks is examined using differential scanning calorimetry and rheology, and material stability of the physically crosslinked protein networks is accessed through mechanical analysis. In particular, the deformation mechanisms of these protein networks and the conditions under which the physical crosslinks are disrupted are thoroughly examined under creep and stress relaxation protocols, as well as under conditions of cyclic and step loading. The resilience of a material, which characterizes its capacity for shape and energy recovery under mechanical loading, provides another crucial criterion that dictates the applications for which it may be suitable. Moreover, the magnitude of preconditioning strains and the off-loading period between loading cycles strongly influences the viscoelastic properties of a variety of protein and tissue derived materials. Thus, in this investigation we also explore the resilience and viscoelastic behavior of two-phase elastin-mimetic protein polymer networks and the capacity of distinct mechanical preconditioning protocols to affect these properties.

Synthesis of Protein Triblock Polymer B10.

Synthetic methods used to produce the DNA inserts that encode the various elastin-mimetic block copolymers have been described. Oligonucleotide cassettes encoding elastic-like (E) and plastic-like (P) repeat units (Table 1) are independently synthesized and inserted into the BamH I and HinD III sites within the polylinker of pZErO-2. Recombinant clones are isolated after propagation in *E. coli* strain Top10F', double-stranded DNA sequence analysis verified the identity of the DNA inserts E and P. DNA monomers E and P are liberated from the respective plasmids via sequential restriction digestion with Bbs I and BsmB I, respectively. Self-ligation of each DNA cassette affords a population of concatemers.

Concatemers derived from DNA monomers E and P are inserted into the BsmB I site of their original plasmid containing the monomer cassette. Concatemers encoding 31 repeats of the P monomer and 21 repeats of the E monomer are isolated and identified via restriction cleavage with BamH I and HinD III. Double-stranded DNA sequence analysis confirm the integrity of the concatemers within the recombinant plasmids, which were labeled pE and pP, respectively. Restriction cleavage of plasmid pE with Bbs I/Xma I and plasmid pP with BsmB I/Xma I afforded two fragments, which are separated via preparative agarose gel electrophoresis. Enzymatic ligation of pE and pP afforded the recombinant plasmid pPE, which encoded the diblock PE as a single contiguous reading frame within plasmid pZErO-2. The diblock, pPE, is used for subsequent construction of the triblock pPEP using the same biosynthetic scheme. Restriction cleavage of plasmid pP with Bbs I/Xma I and plasmid pPE with BsmB I/Xma I afforded two fragments, which are separated via preparative agarose gel electrophoresis. Enzymatic ligation of pP and pPE afforded the recombinant plasmid pPEP, which encoded the triblock PEP as a single contiguous reading frame within plasmid pZErO-2.

The triblock concatemer is liberated from pPEP via restriction cleavage with Bbs I and BsmB I and purified via preparative agarose gel electrophoresis. Enzymatic ligation is used to join the concatemer cassette to the Bbs I sites within the modified polylinker C in plasmid pBAD-A. Double stranded DNA sequence analysis confirms the integrity of the concatemer within the recombinant plasmid, which is subsequently transferred to the expression plasmid, pET-24 (d) via restriction cleavage with Nco I and HinD III. Double stranded DNA sequence analysis confirms the integrity of the concatemer within the recombinant plasmid, which is labeled pB10.

Figures 26, 27, 28:
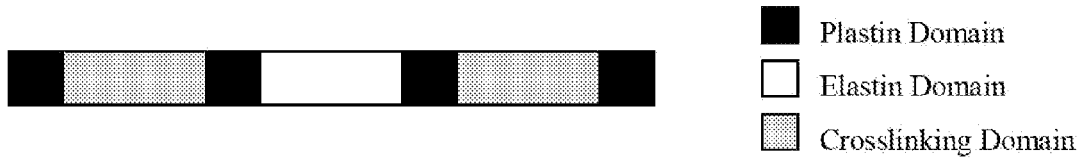
FIG. 26. Amino Acid Sequence of Protein-Based Block Copolymer B10.
FIG. 27. Amino Acid sequence of triblock copolymer B9, constructed from plastic and elastic [X] elastin sequences.
FIG. 28. Molecular Assembly of Modified B10 gene. Crosslinking regions inserted between the plastin and elastin domains in addition to flanking the gene.

Plasmid pB10 encodes the triblock copolymer protein B10 as a single contiguous reading frame within plasmid pET-24 (d) and is used to transform the *E. coli* expression strain BL21(DE3). This affords a protein triblock containing flanking endblock sequences [VPAVG(IPAVG)$_4$][(IPAVG)$_5$]$_{33}$ (SEQ ID NO:7) and a midblock sequence (IPGAG)(VPGAG) VPGEG(VPGAG)$_2$[(VPGAG)$_2$VPGEG(VPGAG)$_2$]$_{20}$ (SEQ ID NO:8) (FIG. 26, Table 2). Large-scale fermentation (4 L) is performed at 37° C. in Terrific Broth (TB) medium supplemented with kanamycin (50 µg/mL). The fermentation cultures are incubated under antibiotic selection for 48 h at 37° C. with agitation at 225 rpm in an orbital shaker. Cells are harvested via centrifugation at 4° C. and 4,000 g for 20 min and the cell pellet resuspended in lysis buffer (150 mL; 100 mM NaCl, 50 mM Tris-HCl, pH 8.0) and stored at −80° C. The frozen cells are lysed by three freeze/thaw cycles. Lysozyme (1 mg/mL), protease inhibitor cocktail (5 mL), benzonase (25 units/mL), and MgCl$_2$ (1 mM) is added to the lysate and the mixture is incubated at 25° C. for 30 min. The cell lysate is incubated for 12 h at 4° C. and is centrifuged at 18,000 g for 30 min at 4° C. to pellet the cell debris. The target protein is purified from the clarified cell lysate by three to five cycles of temperature-induced precipitation (4° C./37° C.) from 5 M NaCl solution. Dialysis and lyophilization afforded protein B10 as a fibrous solid in isolated yields of 250 mg/L of culture. MALDI-TOF mass spectrometry, Obs. (Calc.): B10, 177,608 (176,924.3). Sodium dodecyl sulfate-polyacrylamide gel electrophoresis (SDS-PAGE) analysis reveals a single protein band for B10 that migrated higher than its predicted molecular weight (FIG. 1).

Synthesis of Triblock Protein Polymer B9 (SEQ ID NO:50)

A recombinant protein that contains flanking hydrophobic endblocks of sequence VPAVG[(IPAVG)$_4$(VPAVG)]$_{16}$IPAVG (SEQ ID NO:51) separated by a central hydrophilic block [(VPGVG)$_2$(VPGEG)(VPGVG)$_2$]$_{48}$ (SEQ ID NO:52) is expressed from *E. coli* and purified, as detailed elsewhere. Amino acid compositional analysis. B9; Calc. (mol.-%): Ala, 8.1; Glx, 2.4; Gly, 31.9; Ile, 6.4; Pro, 20.0; Val, 31.2. Obs.

(mol.-%): Ala, 10.8; Glx, 2.0; Gly, 28.3; Ile, 7.0; Pro, 22.8; Val, 28.2. MALDI-TOF mass spectrometry, Obs. (Calc.): B9, 165,356 (165,564).

Differential Scanning Microcalorimetry (Micro-DSC).

Differential scanning microcalorimetry is recorded on a Setaram Micro DSC III calorimeter (Setaram Inc., France) at a scan rate of 1° C./min from 4 to 70° C. Lyophilized proteins are dissolved at a concentration of 1 mg/mL in distilled, deionized water. MicroDSC data is analyzed using SET-SOFT 200 software (Setaram Inc, France).

Rheological Analysis of Concentrated Protein Polymer Solutions.

Rheological data are acquired on an Advanced Rheological Expansion System III rheometer (ARES III, TA instrument, NJ) in parallel plate geometry with a plate diameter of 25 mm. The testing protocol for rheological analysis is detailed elsewhere. In brief, 100 mg/mL protein solutions are prepared by adding distilled, deionized water to lyophilized protein at 4° C., shaking the solution for 48 h, and then allowing the solution to equilibrate for 72 h. The gap between parallel plates is adjusted between 0.2-0.35 mm and dynamic mechanical experiments were performed in shear deformation mode. An initial strain amplitude ($\gamma$) sweep is performed at 4° C. and 37° C. at different frequencies to determine the linear viscoelastic range for the protein polymer.

The gelation temperature is determined by heating samples from 4° C. to 40° C. at a rate of 1° C. per minute. Following temperature equilibration at 37° C., viscoelastic properties are examined by a strain sweep at a fixed frequency of 1 Hz and a frequency sweep at fixed strain amplitude of 2%. Experiments are repeated on 5 to 6 samples and representative data presented.

Mechanical Analysis of Hydrated Protein Polymer Films.

For mechanical property analysis, films are cast from protein solutions. In brief, lyophilized proteins were dissolved at a concentration of 100 mg/mL either in 2,2,2-trifluoroethanol (TFE) at 23° C. or in water at 4° C. The protein solution is then poured into Teflon casting molds and solvent evaporation performed either at 23° C. or at 4° C. Test samples are referred to as TFE-23, water-23, or water-4, indicating the casting solvent and evaporation temperature used for film formation. After complete solvent evaporation, films are hydrated in phosphate buffered saline (PBS) at 37° C., which contains $NaN_3$ at 0.2 mg/mL to prevent biological contamination. Samples are cut into a dumbbell shape using a stainless steel die with gauge dimensions of 13 mm×4.75 mm. Hydrated film thickness, as measured by optical microscopy, is typically 0.1 mm for TFE-23 and water-5 films and 0.5 mm for water-23 films.

Mechanical characterization of protein films is performed using a dynamic mechanical thermal analyzer DMTA V (Rheometric Scientific Inc., Newcastle, Del.) with a 15 N load cell in the inverted orientation, so that samples could be immersed in a jacketed beaker filled with PBS at 37° C. The maximum travel distance of the drive shaft of DMTA was 23 mm, which limited maximum strain to 70% of engineering strain. Samples are evaluated by a several mechanical test protocols including: (i) Uniaxial tension. Loading and unloading is controlled by displacement at a fixed rate of 5 mm/min. Five to six samples are monotonically stretched to 65% of maximum strain for uniaxial stress-strain analysis. (ii) Creep and stress relaxation. Six to ten samples are prepared for creep analysis. Constant engineering stresses are applied for time periods of up to 30 hours. Four to six samples are prepared for stress-relaxation analysis. Each sample is stretched at 5 mm/min to a fixed strain and the evolution of stress over time is examined. Measurement of stress-relaxation is limited to 30 minutes. (iii) Preconditioning protocols. Five to six samples cast under different conditions are cyclically stretched to 30% strain for 20 cycles with an off-loading period of 5 minutes between cycles. Water-23 films are also stretched to 30% strain for one cycle and then cyclically stretched to 10% strain for 20 cycles; or stretched to 50% strain for one cycle and then cyclically stretched to 30% strain for 20 cycles with an off-loading period of 5 minutes. Resilience is calculated from loading and under the loading curves. (iv) Cyclic loading with increasing stress magnitude. Water-4 samples preconditioned at 30% strain for 20 cycles with an off-loading period of 5 minutes are subjected to cyclic stress of increasing magnitude. Stress is applied for one hour and then removed for one hour followed by reimposition of the load at a higher stress. Reproducibility is examined in three replicate samples. (v) Step loading. Water-4 samples preconditioned at 30% strain for 20 cycles with an off-loading period of 5 minutes are subjected to step loading, in which stress is increased by 50 kPa every two hours. Reproducibility is examined in three replicate samples.

Figure 2:
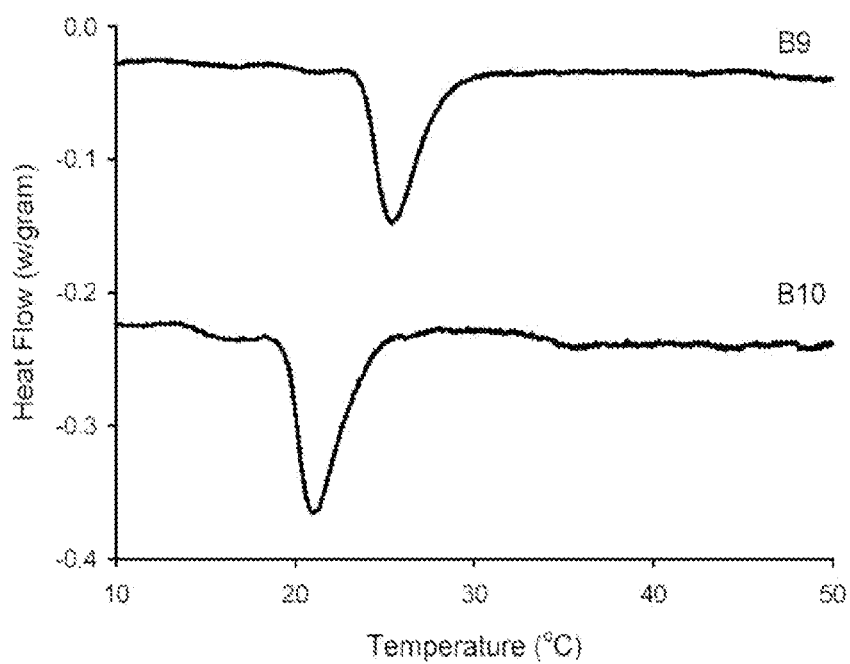
FIG. 2. Differential scanning microcalorimetry of B9 and B10. Signals are shifted for clarity.

The inverse transition temperature is consistent with protein block structure. Differential scanning microcalorimetry of dilute aqueous solutions of B10 (1 mg/mL) confirms the presence of a single endothermic transition at 21° C. consistent with coacervation of the hydrophobic endblocks (FIG. 2). The inverse transition temperature of B10 is 4° C. lower than that observed for B9 due to an increase in the size and hydrophobicity of the endblocks. Specifically, the B10 endblocks are nearly twice as large as those of the B9 triblock copolymer and contained a larger mole fraction of isoleucine (20 vs. 16 mol %). Reversibility of the phase transition is confirmed upon repeating microcalorimetry measurements after a 12 h equilibration at 4° C. (data not shown).

Figure 3:
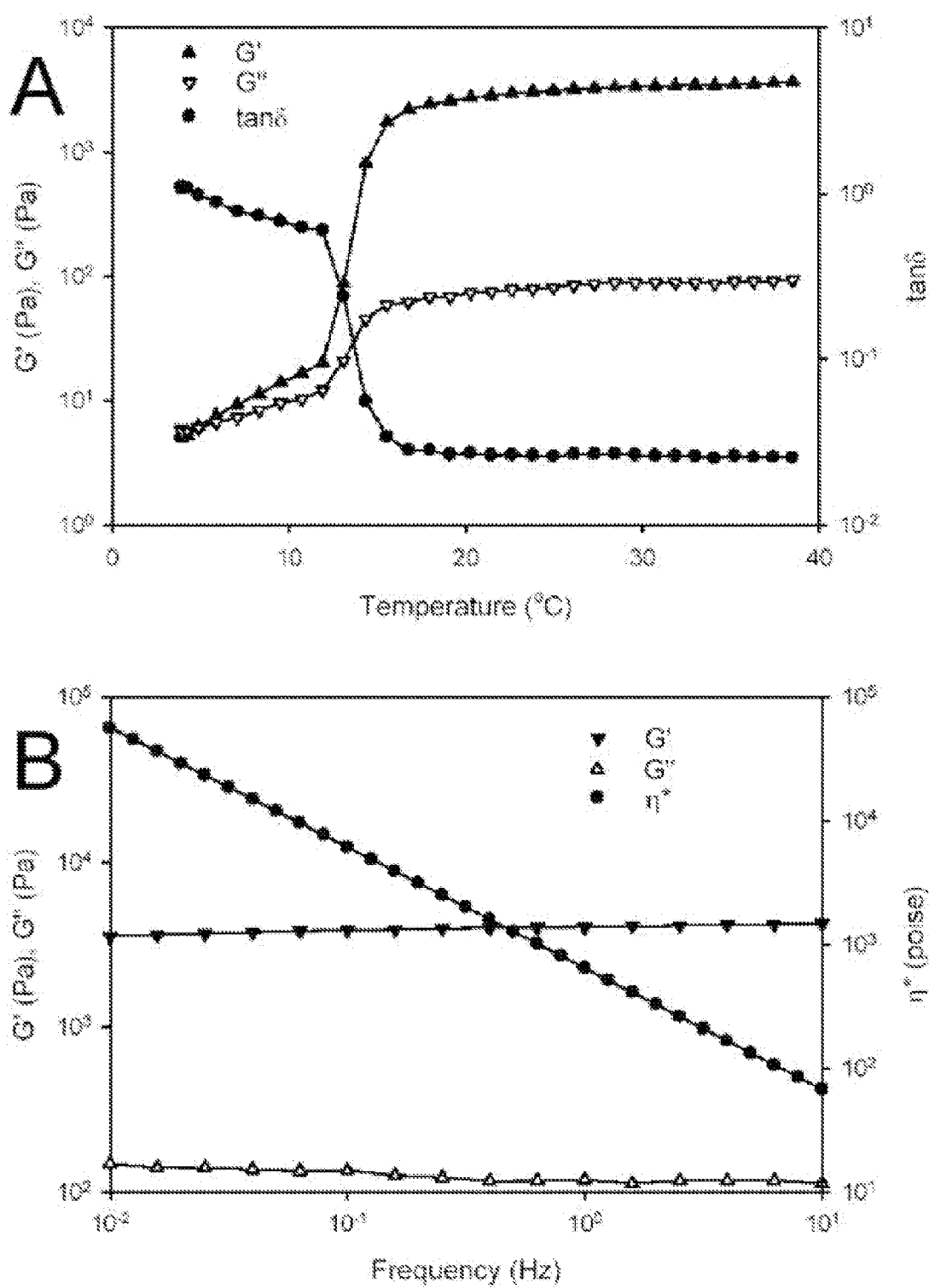
FIG. 3A shows dynamic shear storage (G'), loss modulus (G"), and tan $\delta$ are plotted as a function of temperature ($\gamma$ 2%, $\omega$ 1 Hz).
FIG. 3B shows dynamic shear storage (G'), loss modulus (G"), and complex viscosity ($\eta$*) are plotted as a function of frequency ($\gamma$ 2%, 37° C.). The figures shows the rheological behavior of B10 in water FIG. 4. Uniaxial stress-strain analysis. The Young's modulus was 87±9 MPa for TFE-23 and 60±8 MPa for water-4 measured from the first linear range, and was 0.71±0.12 MPa for water-23 film measured from the first 10% of deformation.

Rheological analysis confirms formation of a protein gel. Above 18° C., the shear storage (G') and loss (G") modulus of concentrated solutions of B10 increased by a factor of approximately $10^3$ and 10, respectively, while tan $\delta$ (G'/G") decreased, consistent with the formation of a viscoelastic gel (FIG. 3A). Observation of a lower transition temperature for protein gelation than that noted by microcalorimetry studies of dilute protein solutions was likely due to the effect of extensive intermolecular interactions present in the concentrated protein solution used for rheological studies. At 37° C., G' and G" were independent of frequency between 0.01 to 10 rad/s at a fixed strain amplitude of 2% (FIG. 3B). In addition, the logarithm of complex viscosity ($\eta^*$) was a linear function of the logarithm of frequency with a slope of −1. All of this suggests that within this frequency range the mechanical response of the protein hydrogel is consistent with a rubbery solid.

Figure 4:
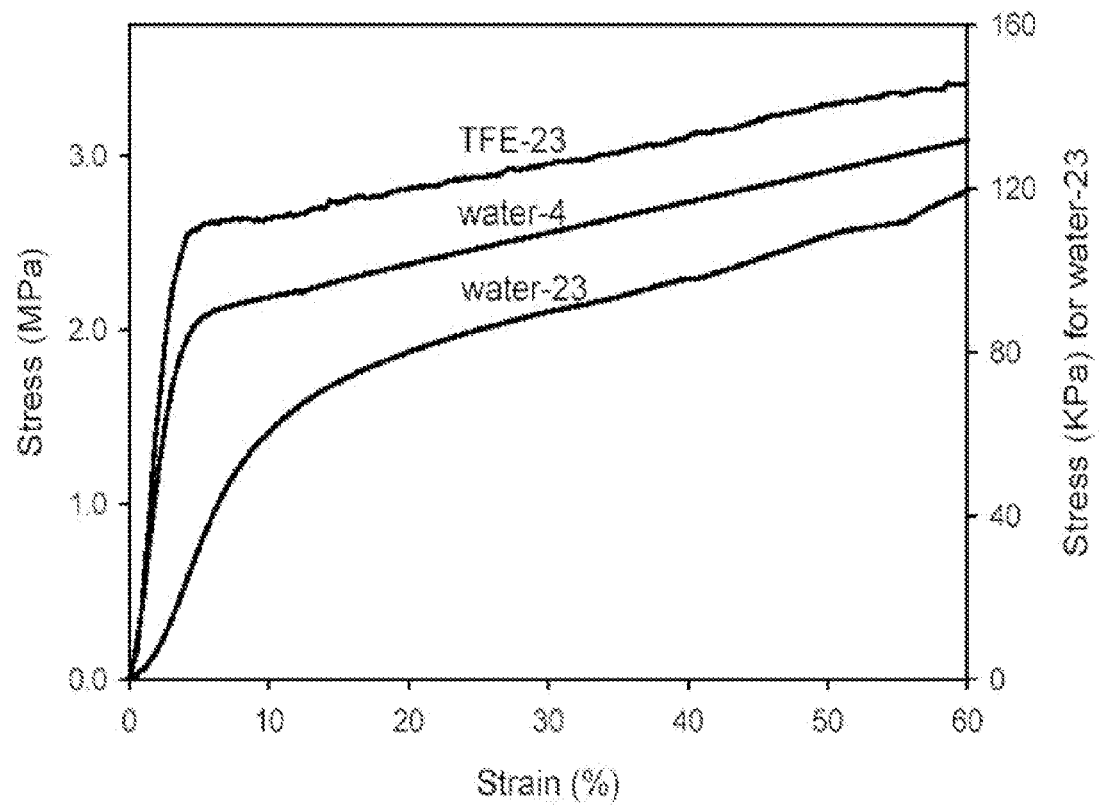

Block structure alters the Young's modulus of elastin-mimetic triblock protein polymers. Load-extension curves at 37° C. of hydrated B10 films cast either from TFE at 23° C. or water at 4° C. reveals plastic-like deformation behavior, such that, stress increases linearly with increasing strain until a yield point is reached between 2-2.5 MPa, after which elongation occurs with the imposition of a relatively low increment in load. In contrast, hydrated B10 films produced from an aqueous protein solution cast at 23° C. displays rubber-like behavior with homogeneous deformation occurring in response to low stress levels. Corresponding values of Young's modulus are 87 MPa, 60 MPa, and 0.71 MPa for hydrated TFE-23, water-4, and water-23 B10 films, respectively. Of note, these values are two- to 60-fold greater than the Young's modulus measured for B9 films processed under identical casting conditions (FIG. 4, Table 2).

Prior studies of B9 triblock copolymers demonstrate that solvent type and casting temperature profoundly influences microphase protein block mixing with a commensurate effect on mechanical responses. Specifically, films cast from TFE, which solvates both mid and endblock sequences, promotes significant interphase mixing in cast films. As a result, the hydrophobic, semi-rigid endblocks are organized as a dispersed microphase and thereby contribute to the mechanical response of the material as load bearing elements leading to plastic-like deformation behavior. In contrast, water preferentially solvates the hydrophilic midblock. Thus, films cast from water at 23° C. display a microphase separated structure with well segregated endblocks that act as relatively discrete virtual crosslinks within an elastomeric protein matrix. Moreover, in casting the aqueous protein solution above the inverse transition temperature of the protein polymer (23° C.>18° C.), microphase separation of the endblocks is further promoted due to a coacervation effect. Given the greater degree of microphase separation, the contribution of the elastomeric midblock to the mechanical response of the material is enhanced with a corresponding rubber-like stress-strain profile. The influence of casting temperature is demonstrated by the behavior of films cast from water at 4° C. In the absence of the coacervation effect present above 18° C., we believe that films are produced with a lower degree of microphase separated structure and, therefore, display a higher Young's modulus. As compared to B9, the presence of substantially larger endblocks and a relatively smaller midblock accentuates the proportion of plastic-like domains in B10 films and, as a consequence, the generation of materials with a higher elastic modulus under all film forming conditions.

Creep responses are modulated by protein block structure. Prior studies characterized creep responses of B9 films cast from water at 4° C. or TFE at 23° C. and revealed substantial deformation responses above 0.2 MPa. As a virtually crosslinked protein network, it is presumed that time-dependent changes in strain in response to stress will be influenced by the density, size, and chemical nature of the physical crosslinks. Thus, by increasing both the hydrophobicity of the endblock, as well as the relative size of the endblock by altering the weight ratio of endblock to midblock segments, the creep response behavior is controllably modified.

Figure 5:
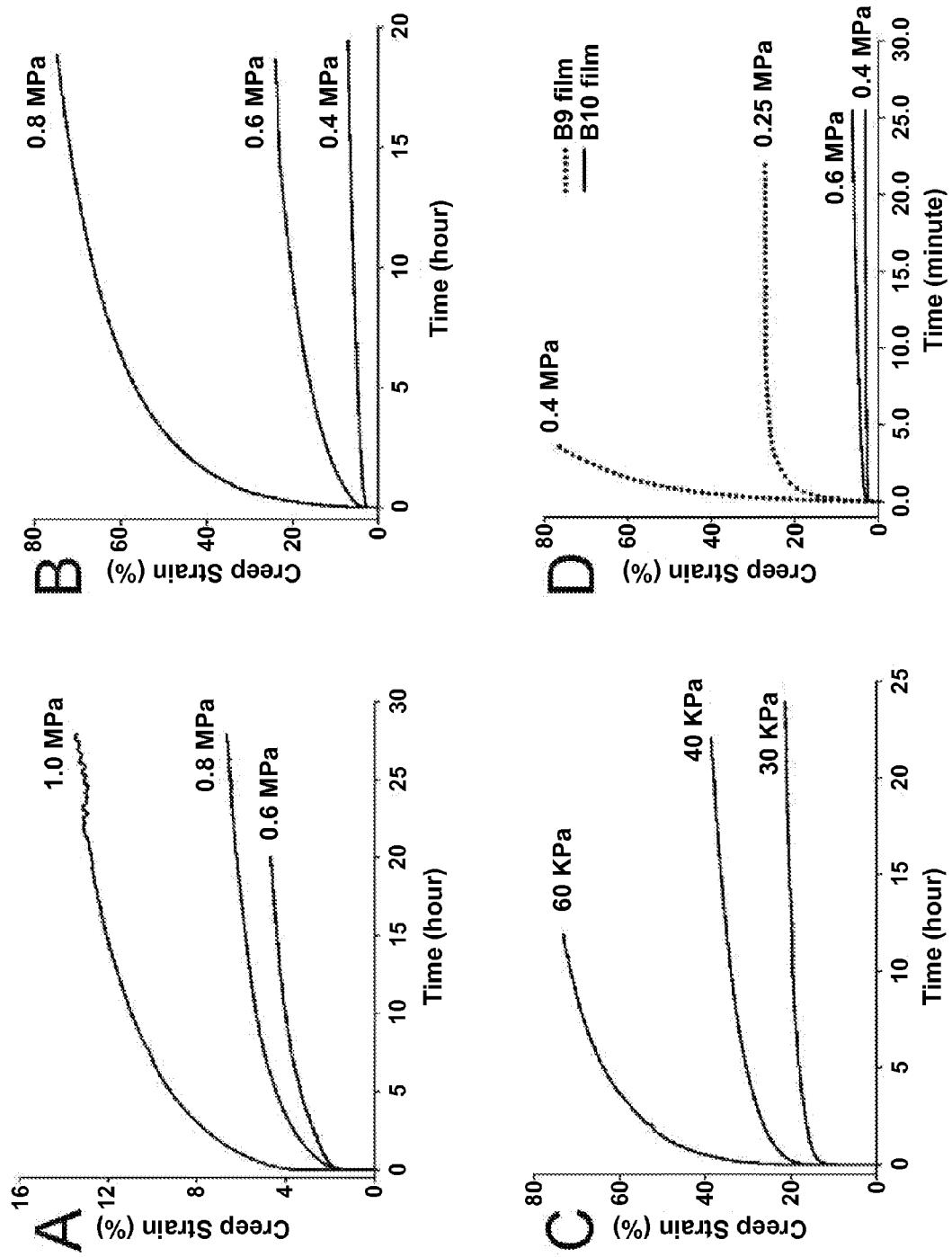
FIG. 5A. shows creep of TFE-23 film. From top to bottom, creep was examined as tensile stress was maintained at 1.0 MPa, 0.8 MPa and 0.6 MPa, respectively.
FIG. 5B shows creep of water-4 film. From top to bottom, creep was examined as tensile stress was maintained at 0.8 MPa, 0.6 MPa and 0.4 MPa, respectively.
FIG. 5C shows creep of water-23 films. From top to bottom, creep was examined as tensile stress was maintained at 60 KPa, 40 KPa and 30 KPa, respectively. Under 60 KPa stress, creep reached the maximum strain that was allowed on the current testing facility within 12 hours.
FIG. 5D shows comparison of the creep behaviors of water-4 films derived from B10 and B9. The short-term creep behaviors demonstrated that films derived from B10 are more stable under mechanical loading. The figures shows the creep analysis of B10 films

Creep analysis was performed on hydrated B10 films at 37° C. that were initially produced under a variety of film casting conditions (FIG. 5). Water cast films produced at 4° C. demonstrated limited creep (<10%) over a 20 h observation period at stress levels at or below 0.4 MPa, nearly double the load for B9 films produced under comparable conditions. Films cast from an aqueous solution of B10 at 23° C. demonstrated comparable levels of creep, but at stress levels that were one order of magnitude lower. B10 films cast from TFE demonstrated the lowest level of creep with an observed strain of less than 10% when subjected to a stress of 0.8 MPa; an approximately four-fold greater load than that sustained by similarly fabricated B9 films. Given that the magnitude of the observed deformation response was not directly proportional to the applied stress, these materials behaved as non-linear viscoelastic solids. In summary, these data emphasize that time-dependent mechanical properties of protein-based materials containing large, chemically distinct blocks can be modulated by controlling the tendency for block segregation either by selection of processing conditions or by molecular design.

Figure 6:
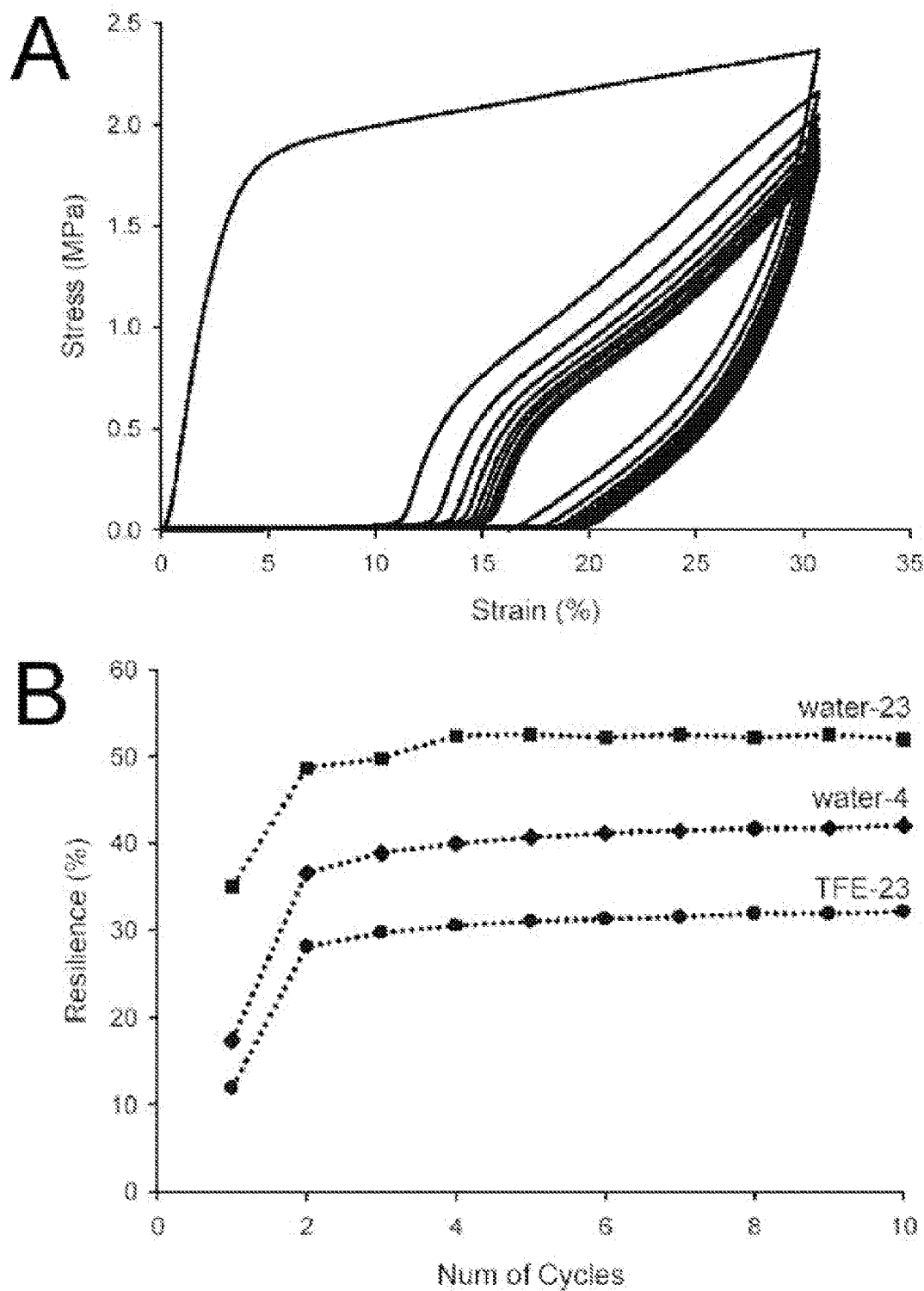
FIG. 6A shows the influence of preconditioning on resilience of water-4 film. A water-4 sample was cyclically stretched to 30% strain, with an off-loading period of 5 minutes between cycles. Plotted are the stress-strain curves from the first ten cycles of stretches, because stress-strain responses were stabilized after the eight cycles of stretch. Similar responses were also observed for TFE-23 and water-23 samples.
FIG. 6B shows the dependence of resilience on the number of preconditioning cycles. Samples cast in different conditions are cyclically stretched to 30% strain, with an off-loading period of 5 minutes between cycles. Plotted is resilience after each cycle against the number of the preconditioning cycles.

Preconditioning by an imposed cyclic stress enhances the resilience of protein polymer films. Upon subjecting B10 films to periods of repetitive cyclic deformation to 30% strain, we observed the accumulation of residual deformation and a decline in peak stress that stabilized after several cycles (FIG. 6). In the process, resilience was significantly enhanced over 10 loading cycles with an increase from 11±2% to 30±2% for TFE-23 films, from 18±2% to 39±2% for water-4 samples, and from 35±2% to 51±2% for water-23 films. The greatest increase in resilience largely occurred after the first loading cycle, presumably due to stabilization of load induced changes in microstructure.

Figure 7:
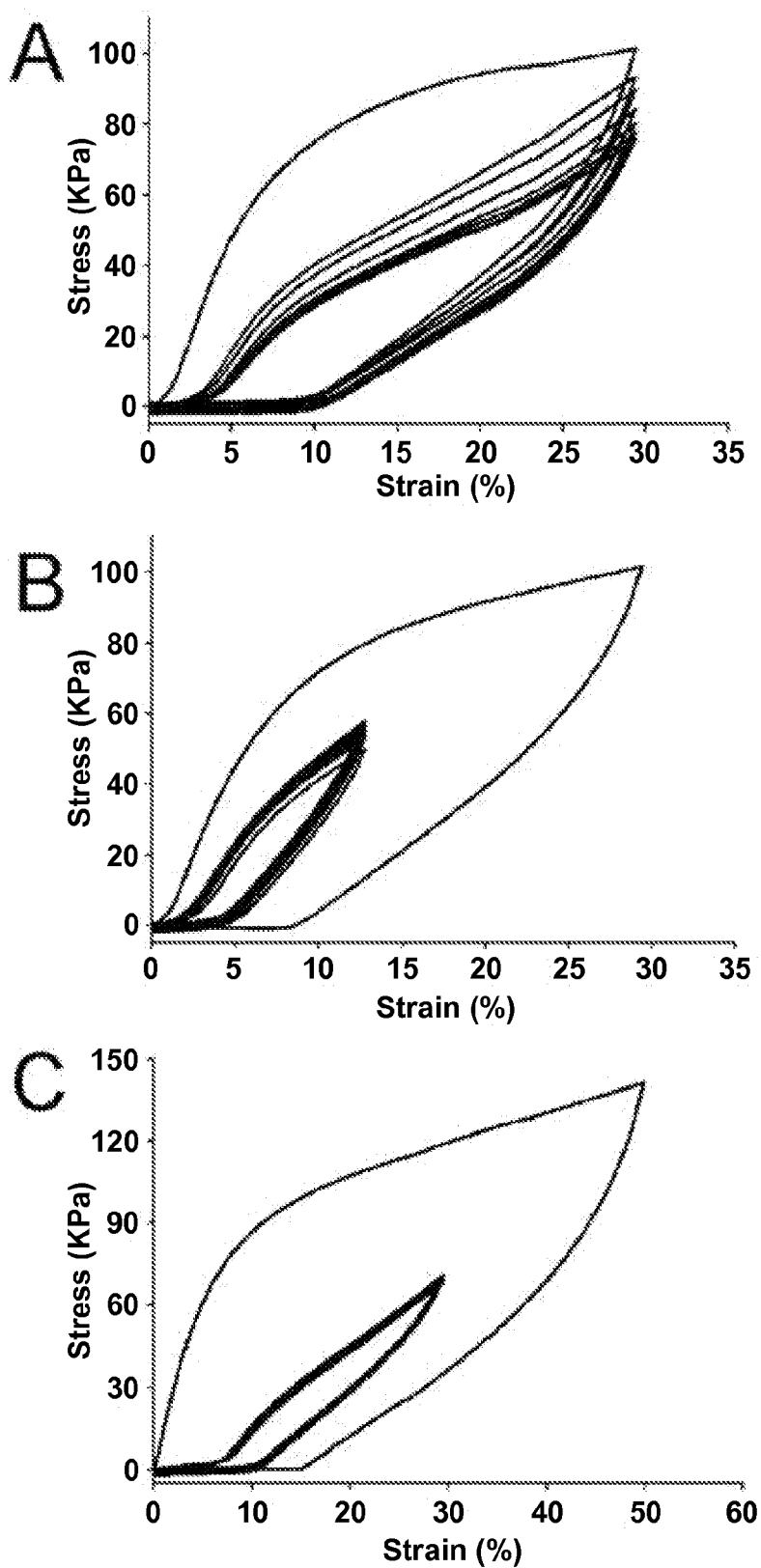
FIG. 7A shows a water-23 sample was cyclically stretched to 30% strain for 21 cycles, with an off-loading period of 5 minutes between cycles. Plotted are the stress-strain curves from the first 10 cycles, because the material response to the external loading is stabilized after 8 cycles of stretch.
FIG. 7B shows a water-23 sample was cyclically stretched to 30% strain and then to 12% strain for 20 cycles, with an off-loading period of 5 minutes between cycles.
FIG. 7C shows a water-23 sample was cyclically stretched to 50% strain and then to 30% strain for 20 cycles, with an off-loading period of 5 minutes between cycles. The figures shows the influence of preconditioning on the resilience of water-23 films.

The effects of varying mechanical preconditioning protocols on resilience are further examined using films initially cast from water at 23° C. (FIG. 7). In all protocols, stabilization of mechanical behavior is largely observed after the initial loading cycle with accumulation of residual strain of 5-10% and a decline in peak stress. As previously stated, the resilience of water-23 films subjected to a repetitive cyclic strain of 30% was 51±2%. When films are subjected to an initial elongation of 30% followed by cyclic stretch at 12% strain, the resilience increases to 58±2%, which is attributed, at least in part, to a reduction in energy dissipation at reduced strain. Nonetheless, the influence of initial deformation history on resilience is evident when films are subjected to an initial strain of 50% and subsequently exposed to 30% cyclic stretch. Although permanent strain is unaffected, as compared to films subjected to 30% cyclic stretch alone, resilience increases to 67±1%. Thus, a significant degree of change in protein microstructure can be induced not only by the conditions of film casting, but also through the effects of mechanical deformation or annealing protocols. As mechanical preconditioning stabilized the microstructures and mechanical properties of protein polymer films, the deformation plasticity tends to decrease. For instance, the yielding behaviors of TFE-23 films diminished and nearly linear behaviors are observed in water-23 films over 10 loading cycles.

Figure 8:
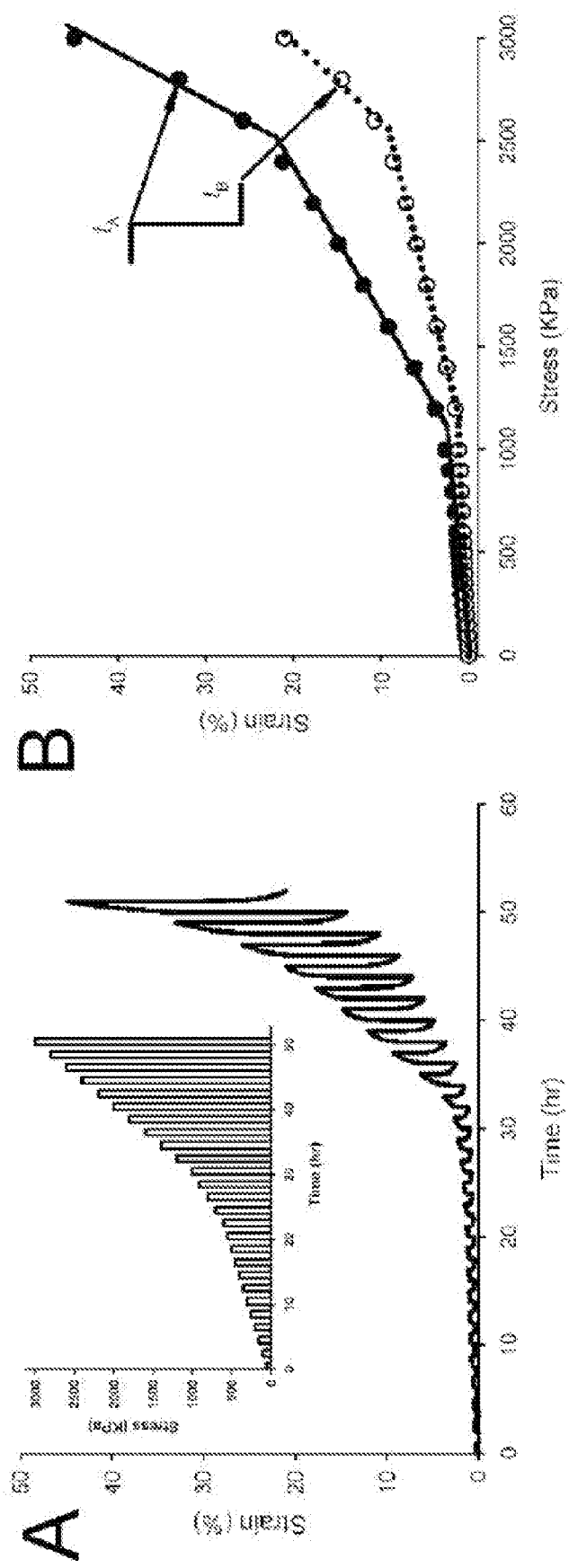
FIG. 8A shows a water-4 sample was subjected to cyclic stress of increasing magnitudes (shown in inset), and the deformation history was recorded. Reproducibility was examined on three replicate samples, which were preconditioned at 30% strain for 20 cycles with an off-loading period of 5 minutes between cycles and a two hour recovery time.
FIG. 8B shows deformation at the end of each loading (filled circles) and off-loading (open circles) period were plotted against the magnitude of cyclic stress. The figures show the deformation behaviors of preconditioned water-4 films under cyclic stress of increasing magnitude FIG. 9. Deformation behavior of preconditioned water-4 films subjected to a step loading protocol. A water-4 sample was subjected to step stress (shown in inset), and strains at the end of each loading step represented by open circles in water-4 films and by crosses in TFE-23 films were plotted against the magnitude of stress. Reproducibility was examined on three replicate samples, which were preconditioned at 30% strain for 20 cycles with an off-loading period of 5 minutes between cycles.
Figure 9:
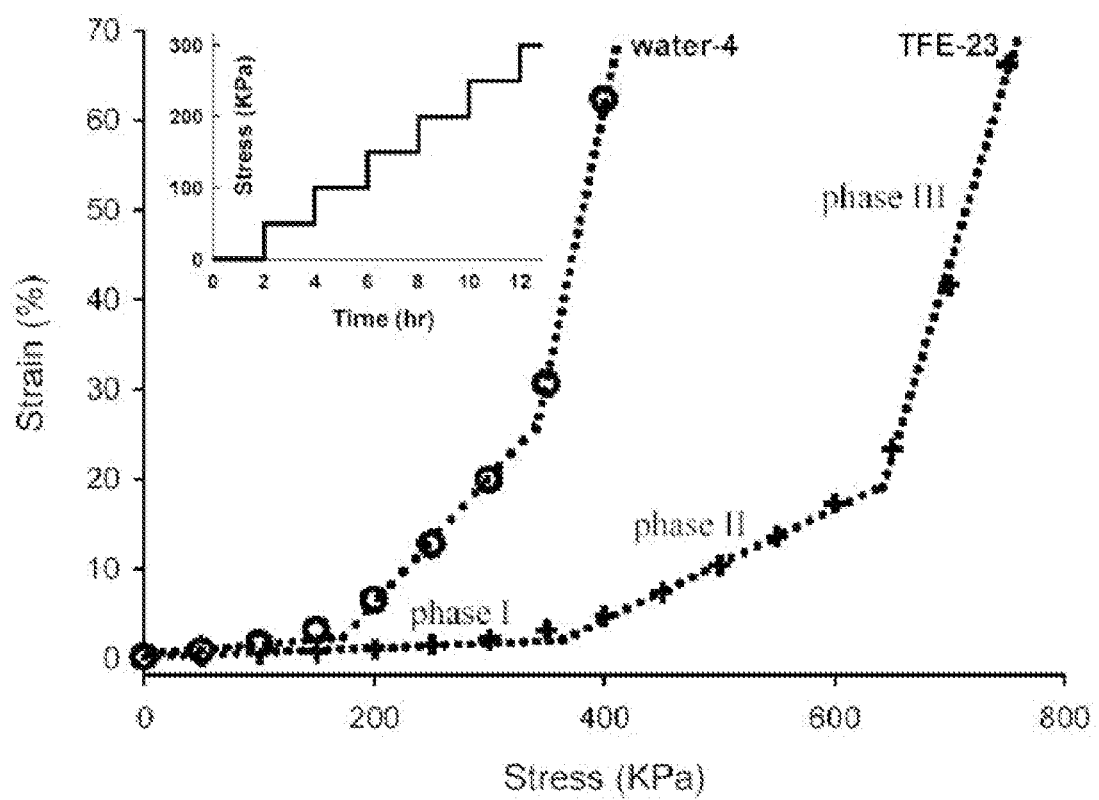
Figure 10:
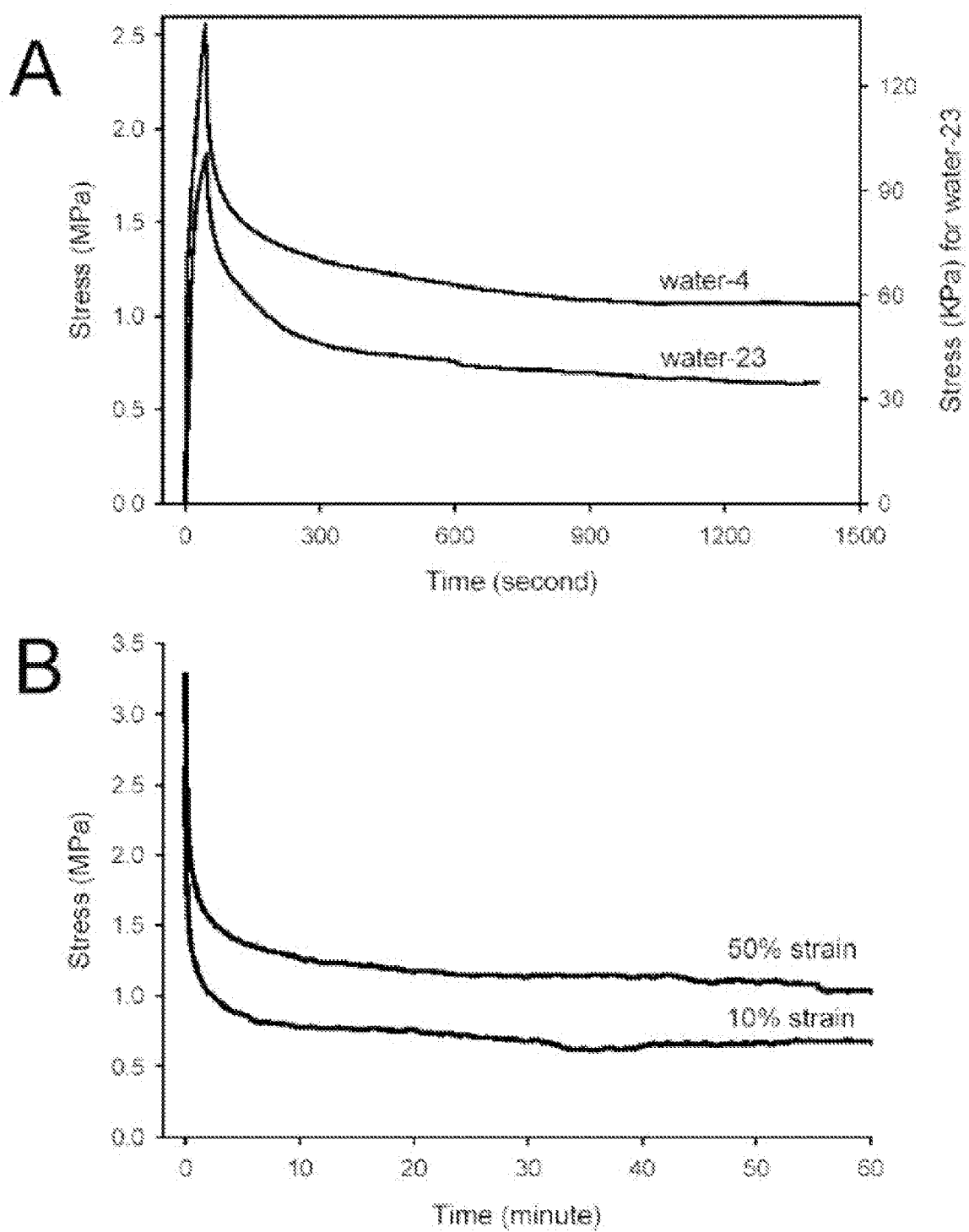
FIG. 10A shows stress-relaxation response for films cast in water at 4° C. and 23° C., following deformation to 30% strain at constant rate of 5 mm/min. The rapid stress relaxation took place in the first few hundreds of seconds. At 20 minutes, stress dropped from 2.6 MPa to 1.1 MPa in water-4 film, and from 100 KPa to 35 KPa in water-23 film, respectively.
FIG. 10B shows Stress relaxation responses of TFE-23 film, following deformation at a constant rate of 5 mm/min to 10% and 50% strain.

Under what circumstances will physical crosslinks be broken? Three phases of deformation behavior are observed when preconditioned B10 water-4 films are exposed to cyclic loads of increasing magnitude (FIG. 8). The first phase, which extends up to an imposed load of 1.2 MPa over a 30 h period, is characterized by small elastic deformation responses, as both the total and residual deformations are small. In the second phase, over a load range between 1.2 and 2.7 MPa, both the total and residual deformation increase linearly with increasing magnitude of cyclic stress and appreciable residual deformation is observed. A more rapid increase in the total and residual deformation occurs in the third phase consistent with disruption of physical crosslinks. Films examined under step loading also display three similar phases of deformation behavior (FIG. 9). Remarkably, strain levels at each transition point are similar for both protocols, although stress levels were significantly different. Three phases of deformation behavior are also observed for preconditioned films cast from TFE at 23° C.

It bears comment that during off-loading periods water-4 films demonstrate "recovery" of deformation after imposed cyclic loading and, therefore, are able to sustain larger subsequent stresses, when compared to deformation induced by direct step loading. For example, when accumulated strain reaches the onset of the second deformation phase, the exerted stress is approximately 1200 kPa and 200 kPa under cyclic and step loading conditions, respectively. The observed recovery effect is likely a consequence of limited polypeptide chain rearrangement, in which the capacity of the material to carry loads is partially recovered and is clearly dependent on the characteristics of both loading and off-loading conditions.

We believe that in a manner akin to synthetic polymers, the deformation behavior in the first phase may be attributable to an initial stretching of polypeptide bonds. Inevitably, bond stretch is limited and further deformation must arise from conformational changes in the polymer chain, which likely occurs in the second phase of deformation. Differences in the stress required to induce conformational changes of protein polymer within films processed under different casting conditions are likely related to differences in the mixing of semi-rigid endblocks and flexible midblocks that create energy or stereoelectronic barriers. Under both loading protocols, substantial film deformation is observed after an initial 22-25% strain, which appears to designate the stress level associated with disruption or damage to physical crosslinks. Given that samples are preconditioned at 30% strain for 20 cycles, these data suggest that "new" disruption or damage may occur when deformation approaches or exceeds preconditioning strains.

Micro-DSC and rheology studies confirm the presence of an inverse-temperature transition for the elastin-mimetic protein polymer B10 in aqueous solutions with gelation of concentrated solutions at ambient temperatures. Mechanical analysis, particularly studies of creep behavior, demonstrate enhanced mechanical stability of physically crosslinked protein networks derived from B10 compared to a triblock copolymer designed with a lower relative content of hydrophobic, plastic-like endblocks. Moreover, resilience is significantly enhanced by mechanical preconditioning. Newly designed tests consisting of cyclic loading of increasing magnitude and step loading further reveal the presence of three phases of deformation behavior, which likely correspond to peptide bond stretching, conformational changes of polypeptide chains, and disruption of physical crosslinks. Significantly, the breakage of physical crosslinks strongly depends on the imposed pattern of load, as well as preconditioning protocols.

TABLE 1

Coding Sequences of Oligonucleotide Cassettes for Repeating Sequences Employed for the Construction of a Protein Triblock (PEP) B10

E Block

| Val Pro Gly Ala | Gly | Val Pro | Gly Ala | Gly Val | Pro Gly |
|---|---|---|---|---|---|
| GTT CCA GGT GCA | GGC | GTA CCG | GGT GCT | GGC GTT | CCG GGT |
| CAA GGT CCA CGT | CCG | CAT GGC | CCA CGA | CCG CAA | GGC CCA |
| Glu Gly Val Pro | Gly | Ala Gly | Val Pro | Gly Ala | Gly |
| GAA GGT GTT CCA | GGC | GCA GGT | GTA CCG | GGT GCG | GGT |
| CTT CCA CAA GGT | CCG | CGT CCA | CAT GGC | CCA CGC | CCA |

P Block

| Ile Pro Ala Val | Gly | Ile Pro | Ala Val | Gly Ile | Pro Ala |
|---|---|---|---|---|---|
| ATT CCT GCT GTT | GGT | ATT CCG | GCT GTT | GGT ATC | CCA GCT |
| TAA GGA CGA CAA | CCA | TAA GGC | CGA CAA | CCA TAG | GGA CGA |
| Val Gly Ile Pro | Ala | Val Gly | Ile Pro | Ala Val | Gly |
| GTT GGT ATC CCA | GCT | GTT GGC | ATT CCG | GCT GTA | GGT |
| CAA CCA TAG CGA | GCA | CAA CCG | TAA GGC | CGA CAT | CCA |

Modified Polylinker

| Met Val Pro Glu | Ser | Ser Gly | Thr Glu | Asp Val | Pro |
|---|---|---|---|---|---|
| ATG GTT CCA GAG | TCT | TCA GGT | ACC GAA | GAC GTT | CCA |
| TAC CAA GGT CTC | AGA | AGT CCA | TGG CTT | CTG CAA | GGT |

TABLE 1-continued

Coding Sequences of Oligonucleotide Cassettes for Repeating Sequences Employed for the Construction of a Protein Triblock (PEP) B10

| Gly Val Gly Stop | Stop |
|---|---|
| GGT GTA GGC TAA | TAA |
| CCA CAT CCG ATT | ATT |

TABLE 2

Comparison of Young's Modulus of B9 and B10 Films

| | Cast in TFE at 23° C. | Cast in water 4° C. | Cast in water 23° C. |
|---|---|---|---|
| B10 (MPa) | 87 ± 9 | 60 ± 8 | 0.71 ± 0.12 |
| B9 (MPa) | 35 ± 3 | 1.3 ± 0.3 | 0.01~0.03 |

Example 2

Elastin Fibers as Design Elements for an Arterial Substitute

With statistics indicating approximately 500,000 procedures for coronary bypass surgery performed in over 300,000 patients each year, cardiovascular disease (CVD) is an unmistakably a growing concern. Since 1900 CVD has been the leading cause of death in the United States, plaguing 70 million Americans and claiming over one million lives per year. Specifically, coronary artery disease accounts for 54% of the CVD deaths annually [1].

Consequently, the need for a small diameter arterial prosthesis is apparent. Although employing polymers such as polytetrafluoroethylene (PTFE) have been successful in the development of large diameter vascular grafts, the fabrication of a durable small diameter prosthesis remains an elusive goal. Biological reactions at the tissue material interface resulting from mechanical or compliance mismatch between native artery and the arterial replacement material lead to their ultimate failure. Presently, autologous vessels (i.e. saphenous veins and internal mammary arteries) are vascular replacements of choice, though even these vessels are not sufficient for long term patency. Of the 600,000 coronary bypass operations performed annually, 10-20% of patients will require a second operation within 10 years [2].

In response to these limitations, strategies to mimic some or all of the characteristics of the arterial wall have been pursued. Current tissue engineering strategies provide an opportunity to circumvent maladaptive responses, though adequate replacements could be decades away. Alternatively, the generation of protein polymers that mimic native structural proteins offers a replacement strategy to develop a vascular graft with clinical performance results that match or exceed those of a native vessel. The reformulation of these proteins into nanofiber networks provides an opportunity to optimize the mechanical properties of an arterial bioprosthesis, as well as other biologically related characteristics, thus creating an optimal vascular replacement material.

This work can be divided into four areas: (i) to synthesize a family of recombinant elastin-mimetic proteins; (ii) to define their molecular level structure-property relationships; (iii) to develop nanofabrication strategies to create organized fiber networks, and (iv) to characterize the capacity of these artificial proteins for the generation of non-thrombogenic small diameter blood vessel substitutes with mechanical properties that closely match those of native blood vessels. Utilizing recombinant proteins based on consideration of the structural properties of the native matrix leads to the creation of vascular conduits with better defined mechanical properties and enhanced biodegradation with improved clinical performance characteristics.

The assembly of nanofiber protein networks comprised of recombinant elastin proteins provides a rational approach for generating a tissue engineered vascular graft with enhanced biostability and mechanical properties that closely match those of a native artery.

Disclosed herein are synthesize of recombinant elastin-mimetic protein polymers capable of forming both physical and chemical crosslinks. Using genetic engineering approaches elastin-mimetic fibers are produced with controlled elastomeric properties and enhanced biostability through appropriate choice of recombinant peptide sequences that facilitate both chemical and physical crosslink formation.

Characterize the mechanical properties of elastin-mimetic nanofiber networks. The presence of chemical and physical crosslinks can act synergistically to improve compliance, resilience, and ultimate tensile strength of elastin networks. Creep and stress-relaxation responses of elastin fiber networks are further improved with the incorporation of chemical crosslinks.

We assess the biocompatibility of elastin based fiber networks after in vivo implantation and the ability of such networks to retain primary elastomeric responses. Elastin-mimetic fiber networks have sufficient biostability for use in a vascular construct. In addition, a recombinant protein fiber patch retains initial elastomeric properties after in vivo implantation.

Development of a small diameter vascular replacement for coronary bypass surgery has been described as the 'Holy Grail' for cardiovascular tissue engineering [3]. It is recognized that adverse events leading to vascular graft failure are related to destructive biological reactions at the blood-material and tissue-material interface. Specifically, synthetic materials which have been successfully applied to large diameter replacements fail when applied to the small diameter with insufficient patency rates limited by thrombosis and compliance mismatch [4-8]. Over the past three decades, vascular graft design has adapted more of a tissue engineering approach with new graft design inspired by characteristics of the arterial wall.

Earliest efforts endeavored to functionalize synthetic graft prostheses with a luminal layer of endothelial cells. Though this strategy has several limitations, i.e. issues with cell sourcing, cell retention, and procoagulant tendencies, it has found success as larger peripheral artery replacements [9, 10]. The inherent limitations of synthetic polymers have motivated investigation to take a completely biological approach to the development of vascular grafts. Early work explored collagen gel technology in which constructs were developed consisting of cell populated collagen gels [11]. This research has served as the foundation for subsequent innovation. Extensions of this technology have incrementally enhanced the material integrity of the construct, through strategies to increase fiber alignment of the collagen[12, 13], strength via mechanical conditioning[14], crosslinking[15], and others, yet constructs exhibit inferior mechanical properties as compared to native vessels. Other approaches have utilized native vascular cells in the production of 'cell secreted scaffolds' [16-18] Though these tissue engineering strategies have reported promising results, each poses unique challenges. Specifically, the duration of incubation time, immunologic challenges associated with the use of allogeneic cells, and suboptimal compliance has limited the application of these strategies to create a clinically applicable small diameter replacement.

Decellularized allo- and xenogeneic tissue have alternatively been investigated as materials for vascular grafts. These decellularized natural matrices contain the intact extracellular matrix and associated attachment proteins and have been used to produce structures with increase degradation resistance, decreased thrombogenicity, and decreased inflammatory reactions. Human umbilical vein, bovine carotid artery and small intestine submucosa, chemically crosslinked using gluteraldehyde, have been employed in clinical application though their use has been limited due to suboptimal patency rates via dilation and aneurysm formation [19-24].

Biosynthetic Approach to the Development of an Engineered Vascular Graft: Allogeneic and xenogeneic strategies indicate native fiber networks can be used to fabricate a vascular graft prosthetic, though the inability to tailor matrix composition and content, fiber size and architecture, limits the applicability of these materials. As a result, strategies to design a prosthesis with precisely defined mechanical and biological properties has been pursued via a 'ground-up' design. Recent developments in recombinant protein engineering now offer the opportunity to construct new proteins with near absolute control over molecular architecture [25-28]. Employing biosynthetic routes to the design of structural proteins for vascular prosthetics afford the ability to modulate material properties at the level of the primary amino acid sequence, thus affording the ability to engineer recombinant proteins to meet physiologic requirements. Additionally, this strategy enables the elucidation of structure-property relationships and ultimately, control over these properties. Currently, structural proteins have been generated in this way consisting of sequentially repeated amino acid blocks derived from analysis of native protein molecular structure [29, 30]. This strategy not only allows for control of sequence and size, it also facilitates incorporation of additional functional groups, in particular, the placement of crosslinks at well defined intervals along the peptide chain allowing for the additional control over material properties of the protein. Thus, recombinant proteins that mimic structural matrix proteins can be engineered with a precisely tailored design to modulate tensile strength, elastic modulus, viscoelasticity, and in vivo stability, as well as desired host response. These mimics are optimal candidates in the design of the next generation vascular graft.

Rational Design of an Arterial Prosthesis with Mechanically Matched Properties of the Arterial Wall: The inherent elasticity of blood vessels arises from the structure of the medial layer. The media is composed of concentric layers of elastic lamellar units each composed of smooth muscle cells, elastin fibers, and collagen fibrils. Elastin and collagen function in a concerted action in response to imposed deformations. Elastin is primarily responsible for distensibility and elastic recovery of the vessel in the low-strain regime while collagen responds by limiting deformation during excessive strain [31-35]. Thus, the lamellar unit of the aortic media serves as a foundation in the design of a vascular graft prosthetic [36-38]. Furthermore, the elastin protein network appears to be integral to mechanically match the native blood vessel and for the prevention of intimal hyperplasia and potential graft failure.

Native elastin is a highly insoluable matrix protein that is responsible for providing extensibility and resilience to most tissues of the body. In the vascular system, elastin fiber networks appear in large densities (over 50%) and function to provide resilience to the artery to absorb dynamic systolic stresses of the cardiac cycle and to release energy in the form of blood pressure during diastole [39]. Therefore, elastin networks maximize the durability of tissues that are loaded by repetitive forces by minimizing the conversion of mechanical energy to heat which would ultimately result in tissue damage [35]. In addition to its structural role, elastin creates an environment which promotes proper cell function. Specifically within the vascular system, elastin regulates smooth muscle cell phenotype and proliferation, and in this way is responsible for stabilizing arterial structure [39-41].

Elastin fibers appear to exist as two morphologically different components, a highly isotropic amorphous elastin constituent within an organized microfibrilar scaffold [42]. Understanding the mechanism of fiber assembly in native elastin is limited. Fiber assembly appears to take place in proximity to the cell membrane where microfibrils appear first, grouped in small bundles. Amorphous elastin is synthesized by smooth muscle cells as the soluble monomer, the 72 kDa precursor tropoelastin, and is secreted within each fiber bundle. Here it is organized into insoluble networks reminiscent of natural rubber. Microfibrils function to properly align tropoelastin to facilitate enzymatic crosslinking via oxidation by lysyl oxidase [43].

The distinctive composition of tropoelastin affords unique physical properties of this structural protein. Tropoelastin is rich in glycine (33%), proline (10-13%), and other hydrophobic residues (44%) rendering elastin an extremely hydrophobic protein [44]. Tropoelastin contains distinct crosslinking and hydrophobic domains. Crosslinking domains are alanine rich, containing pairs of lysine residues facilitating intermolecular crosslinking. Specifically, lysine residues are separated by either two or three alanine residues allowing for retention of an a-helical conformation in this region. The sequence within the crosslinking domains appears to be conserved as a consequence of the conformational constraints of crosslinking [43]. Alternatively, the hydrophobic domains within tropoelastin are composed of three-quarters of valine, glycine, proline, and alanine. Investigations have determined that precise sequence and size of this region are not critical for appropriate function. However, the total size of the protein polymer, 750-800 residues, is highly conserved among species [43].

Rational Design of Peptide Sequence for Elastin-Mimetic Protein Polymers: Limitations to the use of elastin in biomedical and tissue engineering applications are a consequence of its intrinsic insolubility and inability to be processed. But through the structural characterization of the hydrophobic domains, the ability to base synthetic protein polymers on native elastin sequences is feasible. The pioneering work of Urry elucidated the elastomeric pentapeptide repeat, VPGVG, from human elastin which now serves as the basic sequence extensively investigated by both chemical methodologies and recombinant technology [46-51]. VPGVG is a common repeat unit within the hydrophobic domain of human elastin and is responsible for resultant elastic properties. Additionally, this domain is responsible for facilitating fiber formation through coacervation phenomena, behaviors consistent with native elastin. Spectroscopic analysis has revealed that native elastin, and likewise, protein polymers containing this repeat, exhibit β-turns and helical β-spiral conformations and display an inverse temperature transition defined by the generation of a more ordered system upon increasing temperature. This loss of entropy is a consequence of protein folding into β-spiral conformation and the subsequent reorientation of water from the elastin chain [45].

Studies have indicated that the amino acid in the fourth (X) position (VPGXG) modulates the coacervation temperature with more polar amino acids increasing transition temperature [46, 47]. As long as glycine and proline residues are preserved the structure and function of elastin is maintained [48]. This discovery has led to the generation of recombinant elastin analogs designed for biomedical applications. For instance, Conticello et al have employed recombinant techniques to design amphiphilic elastin protein polymers consisting of hydrophobic and hydrophilic domains. Through precise sequence design and control of processing conditions, these elastin analogs exhibit a wide range of properties advantageous for biomedical applications, as micelles or physically crosslinked hydrogels [49, 50]. Additionally, groups have incorporated cell binding domains, RGD or REDV, into elastin sequences to functionalize elastin matrix components for endothelial cell attachment [51, 52].

Genetic engineering strategies afford the capability to modulate macroscopic properties on the molecular level. Specifically, it is feasible to alter the molecular architecture to control biologically important parameters of these materials including permeability, swelling ratios, viscoelasticity, strength, and biostability. For instance, residues may be incorporated into the polymer backbone which can be post-translationally modified to promote crosslinking into a protein network [53].

In its native form, elastin is present as a network of elastic fibers crosslinked through lysine residues. Characteristically, crosslinking of native elastin is accomplished via enzymatic modification of amino acid side chains of lysine residues in the solid state, i.e. after secretion by cells into the extracellular space. Briefly, crosslinks are formed through the deamination of the ε-amino group of the lysine side chains by the enzyme lysyl oxidase. The reaction occurs in two ways: (i) the reactive aldehyde group condenses with a second aldehyde residue to form allysine aldol or (ii) with the ε-amino group on the lysine to form dehydrolysinonoleucine. These two precursors condense to form the pyridium cross-links esmosine and isodesmosine [13].

Incorporation of reactive lysine residues into recombinant elastin design provides the ε-amino moiety of lysine for crosslinking using a variety of approaches. Crosslinking of synthetic elastin-mimetic protein polymers has been investigated using solution phase systems; either gamma irradiation [54-56], chemical [53, 57-60], or enzymatic based approaches [61], as well as solid state photocrosslinking [62]. Specific investigations into reactive group spacing as well as crosslinking strategies on the modulation of important biological behaviors of elastin analogs has been conducted with the general conclusion that the placement of well defined crosslinks enhance the biostability of elastin and improve biologically relevant properties.

Fabrication of Structural Proteins into Nanofiber Networks: As material for tissue engineering applications, elastin is intended to provide both mechanical support and potentially act as a scaffold for cellular repopulation. As such, it is likely that its versatility as a scaffold for tissue engineering applications will be significantly enhanced when reformulated into fiber networks. Electrospinning is a technique for generating fibers with diameters <1 μm. Briefly, the electrospinning technique relies on electrostatic forces to produce sub-micron diameter fibers from protein solutions. A high voltage is applied to a spinneret while a protein solution is slowly being pumped through it. This induces evenly dispersed charges in a pendent drop at the tip of the spinneret, relaxing the fluid surface. This surface charge and the external Coulombic forces from the electric field combine to form a tangential stress. This causes the drop to become distorted into a shape referred to as a Taylor cone. At a threshold value, the electric field strength will overcome that of surface tension and the protein solution is ejected as a charged jet from the spinneret tip. As the jet travels to the grounded collector it undergoes stretching and whipping phenomena which reduces the diameter of this fiber. It is then collected, usually in a random orientation, on the grounded collector, creating a nonwoven protein mat. The applied voltage, concentration of protein solutions, flow rate, and deposition distance all effect the morphology of the fiber. When proteins are reformulated as fiber systems desired mechanical and biological properties can be achieved for biomedical applications. For instance, flexibility of a fibrous system can be controlled by either a decrease in fiber diameter or an increase in fiber number [63]. Thus, reformulating recombinant proteins into fiber networks provides an additional level of control over the properties of the system. Specifically, studies have indicated electrospun fabrics composed of small diameter fibers (<1 um) were found to have decreased porosity, increased fiber density, increased mechanical strength, as well as an optimized biological environment for promoting endothelial cell adhesion as compared to larger diameter fibers (7 um) [64, 65].

The assembly of recombinant elastin fiber networks provides an important new design strategy for generating a clinically durable small diameter arterial substitute. This approach yields an arterial prosthesis with mechanical properties that closely match those of a native artery, along with enhanced biostability as compared to allogeneic or xenogeneic tissue. Specifically, in employing a biosynthetic strategy, elastin-mimetic protein polymers can be designed to facilitate both covalent and physical crosslink formation thus enhancing static and dynamic material behavior. These protein polymers may be formulated into nano-fiber networks with improved compliance, resilience, creep, stress relaxation and biostability. Significantly, this strategy can be integrated into schemes which are ultimately driven either by a desire to generate a cell containing arterial construct or a non-thrombogenic acellular conduit.

Data are divided into three areas (i) characterization of first generation elastin-mimetic protein polymers reformulated as fiber networks, (ii) genetic modification of first generation elastin-mimetic protein polymers, and (iii) synthesis of second generation elastin-mimetic protein polymers.

Characterization of First Generation Elastin-Mimetic Protein Polymers Reformulated into Fiber Networks: Initial studies select a unique recombinant elastin protein from a family of recombinant proteins, exhibiting properties relevant to the fabrication of a bioengineered vascular prosthesis. This triblock protein co-polymer, designated B9 (FIG. 27), is uniquely designed with distinct hydrophobic and hydrophilic domains to facilitate physical crosslinking via coacervation of hydrophobic endblocks above the inverse transition temperature. Initial investigations reveal the capacity of this protein to be processed into hydrogels or micelles for drug delivery applications [49, 66] and nanofiber networks for tissue engineering scaffolds [67, 68]. Additionally, B9 studies provide understanding of the relationship between macroscale material properties and microscale features, such as block size and sequence, in engineered proteins [69]. More recent work investigated modulating mechanical properties of B9 films by preferential solvent casting and the impact of casting conditions on static and transient properties of B9 films [70]. These investigations serve as the foundation for subsequent B9 studies and also in the rational design of second generation proteins.

Figure 11:
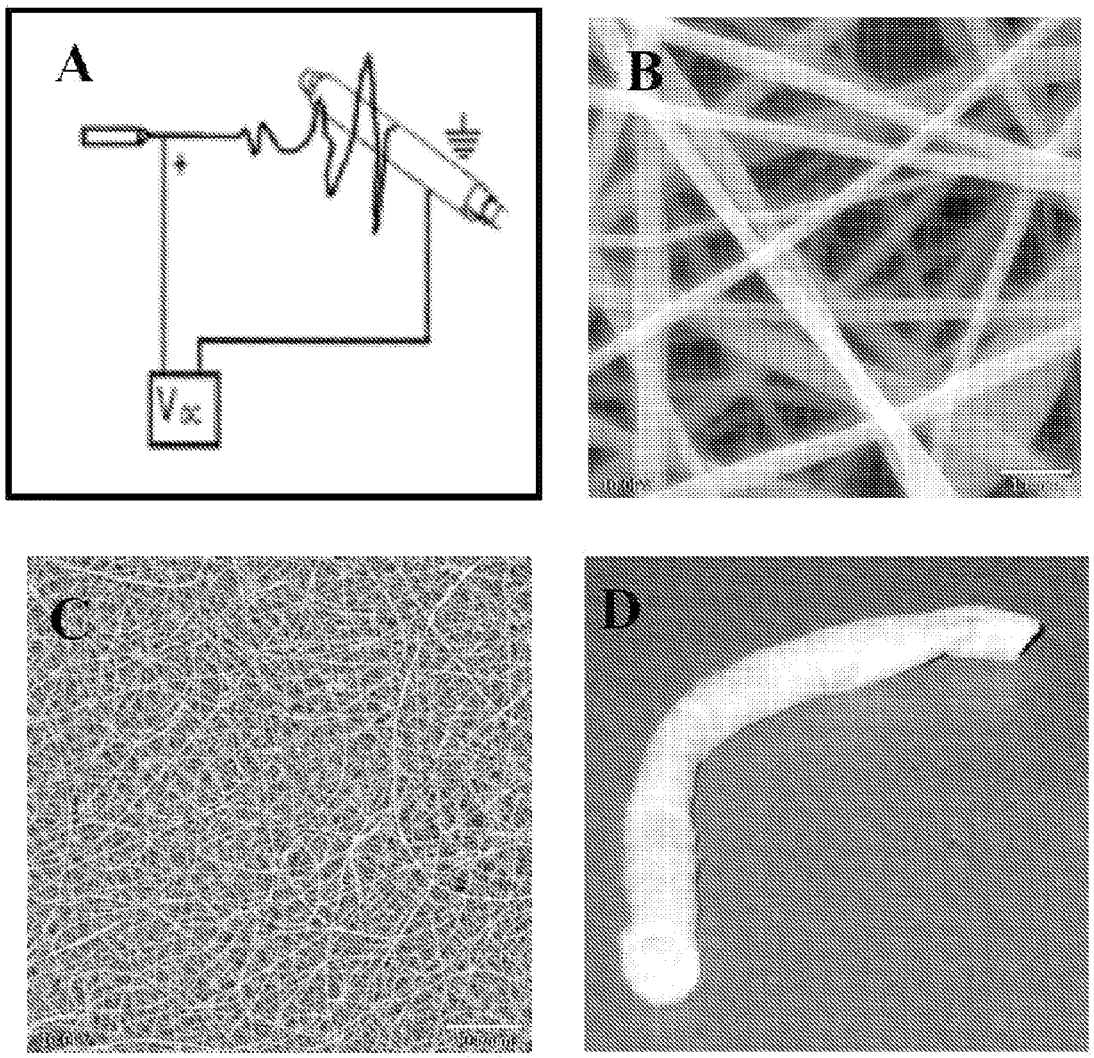
FIG. 11A shows electrospinning experimental setup.
FIG. 11B shows Electrospun B9 fibers.
FIG. 11C shows electrospun B9 network.
FIG. 11D shows electrospun B9 conduit.

Fabrication of B9 Nanofibers and Networks: Lyophillized B9 protein is reformulated into fiber networks using electrospinning techniques (FIG. 11A). A solvent system is employed to allow for interphase mixing of the incompatible blocks of the copolymer on the nanoscale which influenced and enhanced B9's material properties as fibers. Sub-micron diameter B9 fibers are produced from a 12 wt % protein solution using a trifluoroethanol (TFE) solvent system (FIG. 11 B,C). By controlling the rotational and translational speeds of the collecting mandrel, an elastin conduit is created (FIG. 11D).

Figure 12:
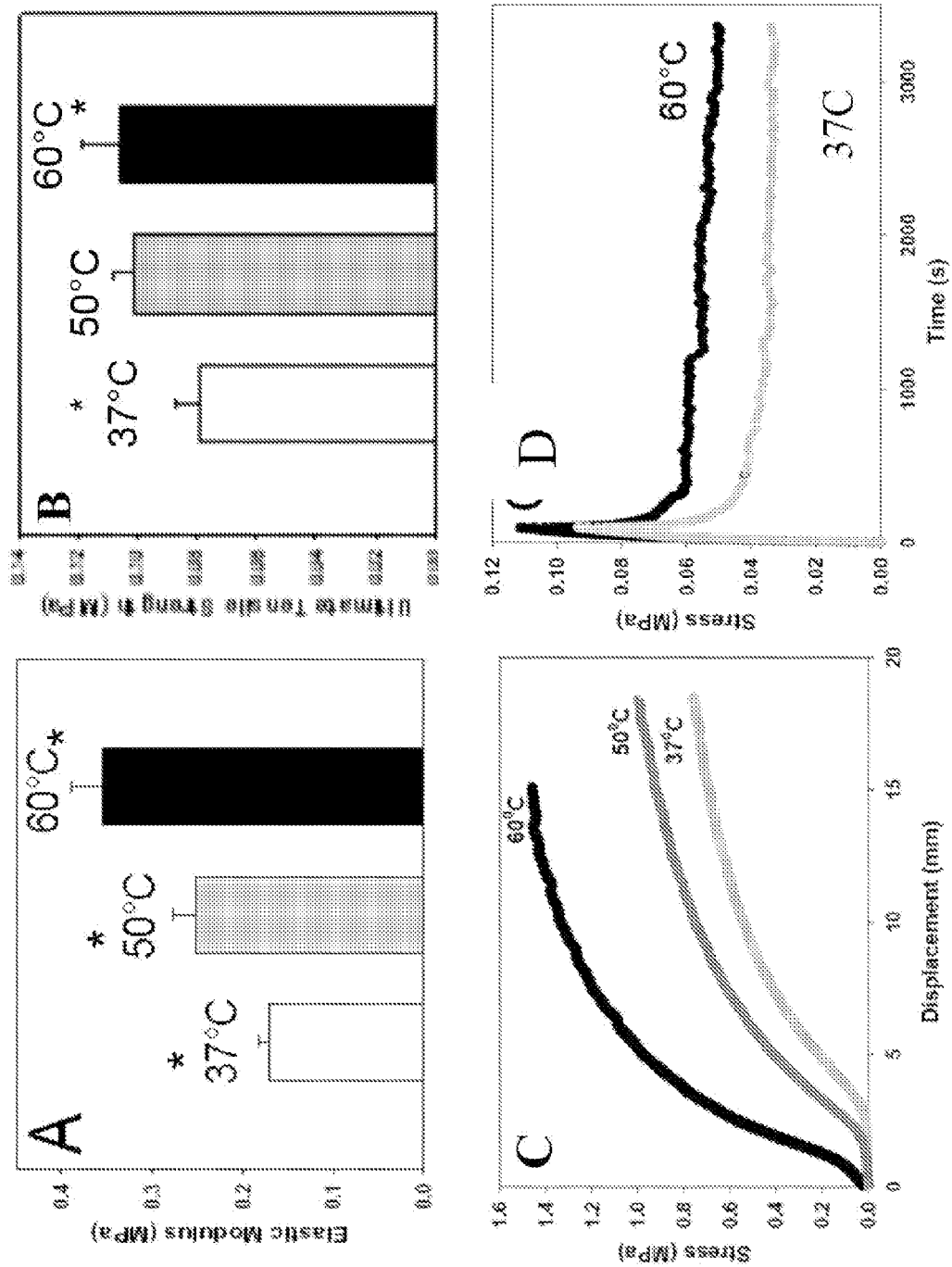
FIG. 12A shows Young's modulus and FIG. 12B shows ultimate tensile strength of thermally annealed B9 fiber networks, tested at 37° C. in PBS.
FIG. 12C shows characteristic uniaxial stress-strain curves for electrospun B9 fabrics generated from ring testing of annealed and non-annealed samples.
FIG. 12D shows stress relaxation curves for B9 electrospun fiber networks. Annealing temperature is indicated for each curve.

Mechanical Properties of Elastin-Mimetic Fiber Networks: Uniaxial Stress-Strain Behavior of B9 Fiber Networks: The mechanical response of electrospun B9 networks under physiological conditions (37° C., PBS pH 7.0) is evaluated by uniaxial (ring) stress-strain testing [14, 71]. Hydrated samples displayed an elastic modulus of 0.17±0.01 MPa and ultimate tensile strength of 0.079±0.008 MPa (FIG. 12); values comparable to the elastin component of the arterial wall (Young's modulus~0.3 MPa) [18]. As electrospinning creates randomly oriented fiber fabrics, similar properties are expected in the longitudinal and circumferential directions. Uniaxial tensile testing using traditional dogbone shaped samples is conducted on a Dynamic Materials Thermal Analyzer (DMTA) and a Minimat Testing Apparatus to assess longitudinal properties. Circumferential and longitudinal mechanical properties of B9 fabrics are summarized in Table 3. Elastic moduli and tensile strengths obtained from samples strained along the longitudinal axis of the conduit are not statistically different than values measured when stress was imposed in the circumferential direction. The isotropy of electrospun materials is consistent with the mechanical response of native elastin [72].

Time-Dependent Mechanical Properties of B9 Fiber Networks: When deformation is held constant, a relaxation of the imposed tensile stress is observed. This phenomenon is a result of the disappearance of frictional forces, rearrangement of polymer chains, and possibly micro-damage to the protein. Stress relaxation of B9 fiber networks reveals rapid relaxation of imposed tensile stress following deformation to 64% strain. The stress relaxation took place in the first two hundred seconds. At ten minutes, engineering stress had dropped approximately 45% and stabilized indicating structural reorientation of anisotropic fibers in the direction of deformation followed by conformational rearrangements of protein chains and network entanglements (FIG. 12D).

Modulation of Mechanical Properties of B9 Fiber Networks via Thermal Annealing: A comparative analysis of annealed and non-annealed fabrics indicates thermal annealing significantly alters the mechanical behavior of electrospun B9 fabrics. Subjecting electrospun fiber networks to incubation in PBS at 60° C. for 4 hours appeared to enhance both static and time-dependent mechanical properties. Detailed investigations of tensile properties of annealed and non-annealed samples are reported in FIGS. 12A and 12B and critical parameters are summarized in Table 3. Annealing induced a graduated increase in both elastic modulus and tensile strength commensurate with temperature at which annealing occurred. The greatest effect was observed in elastic modulus of the fabric with an approximate doubling of modulus to 0.366±0.05 MPa as result of annealing at 60° C. for 4 hours (p<0.005) as compared to a non-annealed sample maintained at 37° C. Under similar conditions, tensile strength increased 30% from 0.079±0.008 MPa to 0.119±0.015 MPa (p<0.01). Additionally, the characteristic non-linear toe region, typical of native arteries and biological tissues, is observed in electrospun fabrics and appears to be influenced by annealing temperature. Structural reorientation of the randomly oriented fibers account for this phenomena as verified by SEM of critical point dried (CPD) mechanically strained fibers (data not shown). Interestingly, the non-linear toe region decreased significantly with an increase in annealing temperature.

TABLE 3

Tensile Behavior for Electrospun B9 Fabrics

| Treatment | | Elastic Modulus (MPa) | Tensile Strength (MPa) |
|---|---|---|---|
| 37° C. Incubation | Circumferential | 0.170 ± 0.01 | 0.079 ± 0.008 |
| | Longitudinal | 0.190 ± 0.026 | 0.108 ± 0.05 |
| 60° C. Anneal | Circumferential | 0.366 ± 0.05 | 0.119 ± 0.015 |
| | Longitudinal | 0.294 ± 0.03 | 0.111 ± 0.01 |

Evaluation of Thermally Induced Structural Changes in Annealed B9 Fiber Networks: Preliminary investigations indicate that this change in protein polymer behavior after thermal annealing treatment is due, at least in part, to a reduction in water uptake in hydrated B9 fiber networks that may be related to a conformational rearrangement in protein microstructure. Significantly, investigations of the absorptive properties of electrospun fabrics indicate a change in hydration characteristics of the fabric upon thermal annealing. The data summarized in Table 4 indicates a ~50% decrease in the water swelling ratio of annealed fabrics. Similar trends were observed with samples hydrated in PBS. A well documented inverse relationship between material stiffness and water content has been observed in biological materials and this phenomena likely contributes to the increase strength and modulus of annealed B9 electrospun fabrics. Interestingly, the impact of annealing on the mechanical properties and hydration characteristics of B9/TFE cast films was not significant. $^1$H NMR studies indicate all solvent was removed by the electrospinning process. Alternatively, evaluation of B9/TFE films revealed the presence of residual TFE. It is suggested that the polar nature of TFE induces hydrogen bonding between the TFE molecules and residues within the protein chain which could stabilize the microstructure within the films thus preventing thermally induced chain reorientation.

TABLE 4

Absorption Data for B9 Fabrics Hydrated in PBS and Water

| Sample Conditions | Water Swelling Ratio |
|---|---|
| 37° C. H$_2$O | 28.75 + 2.80* |
| 60° C. H$_2$O | 13.55 + 1.39* |

*indicates p < 0.006

Solid-State Circular Dichromy (CD) spectroscopy and Attenuated Total Reflectance Infrared (IR) spectroscopy are used to investigate potential changes in secondary protein structure induced by thermal annealing (data not shown). Data indicates only subtle changes in secondary structure.

Figure 13:
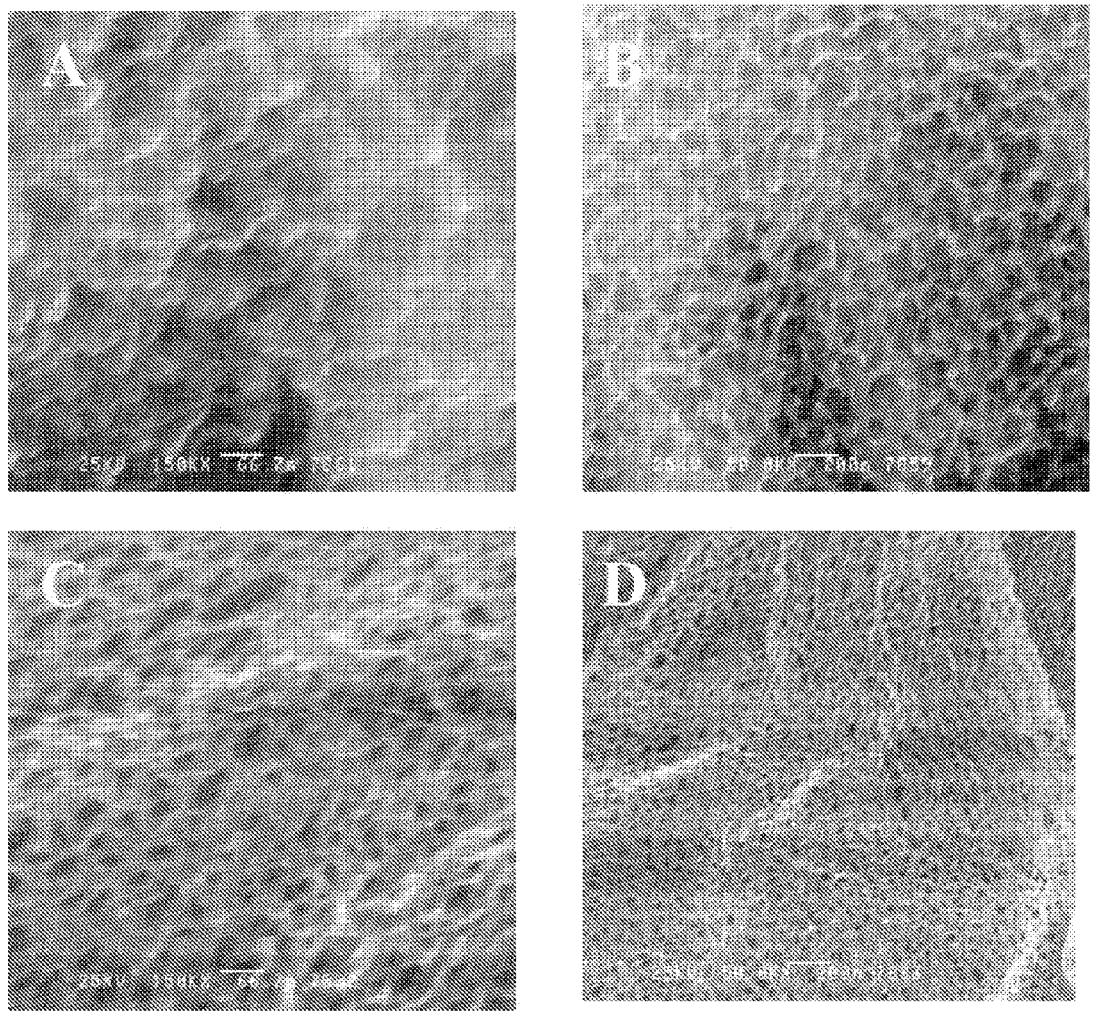
FIG. 13A and FIG. 13B are plates showing Cryo-HRSEM micrographs of B9 electrospun fibers hydrated at 37C.
FIG. 13C and FIG. 13D are places showing Cryo-HRSEM micrographs of B9 electrospun fibers annealed at 60C.

Cryo-High Resolution SEM is used to inspect the hydrated morphology of electrospun fiber networks. A freeze-drying protocol was designed to remove of water from the surface of the specimen leaving bulk water/ice at larger depths. Cryo-EM sample preparation indicates similar effects of annealing on water content as longer freeze drying times a necessary to remove bulk water and the hydration shell from non-annealed fibers. A comparative analysis of annealed and non-annealed networks reveals subtle differences in microstructure (FIG. 13). Annealing appears to increase the degree of interpenetration of the elastic and plastic blocks, as observed by a loss of molecular architecture in fibers receiving the annealing treatment (FIG. 13C,D).

Figure 14:
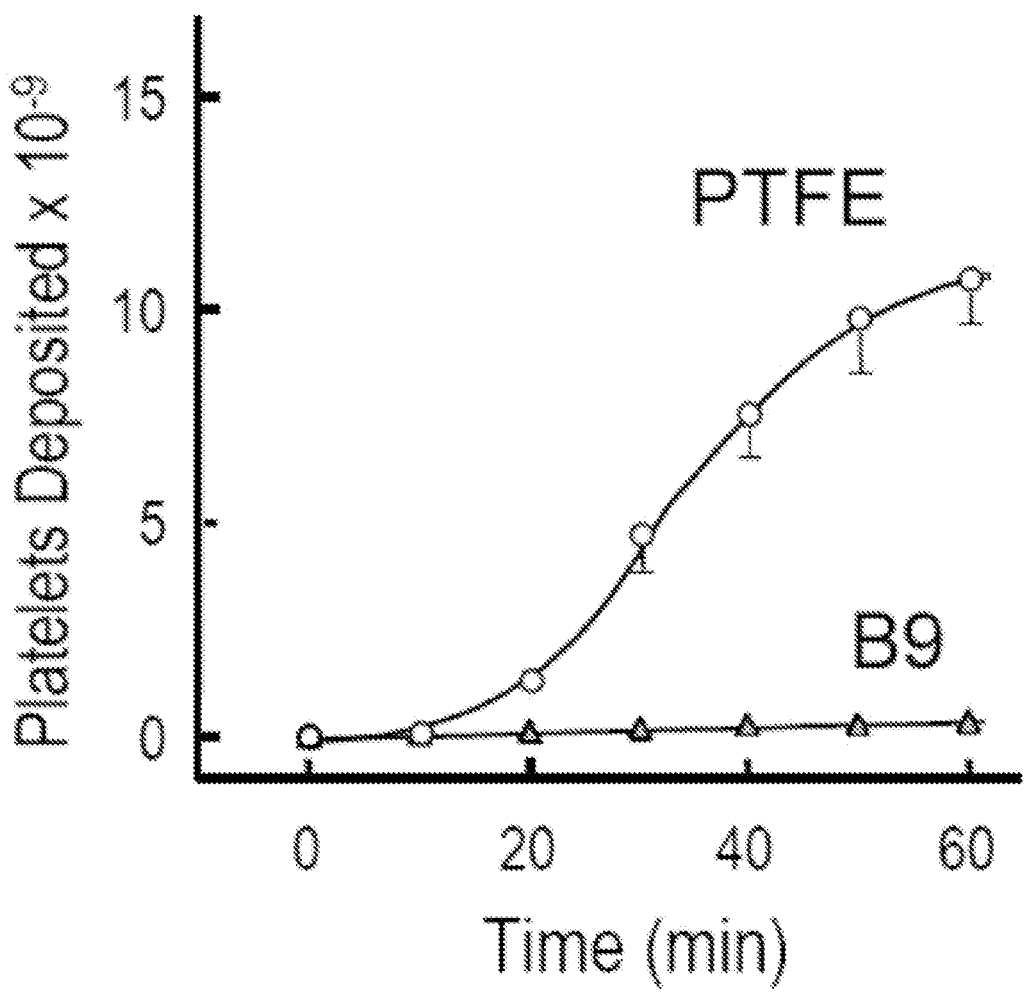
FIG. 14. Platelet deposition on B9 and ePTFE in a baboon ex vivo shunt model.

Blood-Contacting Properties of B9 in a Baboon Shunt Model: Platelet accumulation is measured on expanded PTFE (ePTFE) vascular grafts (i.d. 4 mm) interposed in surgically implanted chronic exteriorized AV access shunts, as described previously [73]. Segments of ePTFE vascular graft with or without a luminal coating of B9 are examined at a blood flow of 100 mL/min in the absence of systemic anticoagulation. Autologous baboon platelets are labeled with 1 mCi $^{111}$In and platelet deposition measured throughout a 60-min contact period. Investigations indicate B9 is non-thrombogenic in a baboon shunt model and therefore provides a durable long-term blood-contacting interface (FIG. 14).

Investigations of first generation protein, B9, supports the proposed mechanistic basis that physical crosslinks, afforded by the presence of relatively rigid endblock domains, provides a mechanism for tailoring protein polymer mechanical responses. Moreover, the current mechanical responses of these elastin-mimetic proteins (i.e. Young's modulus, tensile strength, creep, and resilience) are suited for fabrication as the basis for the elastomeric matrix of a prototype small diameter vascular conduit based on "artificial" proteins. These first generation proteins provide a further basis for the design of new recombinant proteins ("second generation proteins") that are capable of both covalent and physical crosslinks. In particular, such a strategy further optimizes creep resistance and resilience for maximum long-term durability of these implants. Table 5 outlines proteins used in subsequent experiments and their classification as a first or second generation protein.

TABLE 5

Elastin-Mimetic Protein Classifications

| Protein | Classification |
|---|---|
| B9 | First Generation |
| B10 | First Generation |
| Yeast-B9 | Modified First Generation |
| Lys-B10 | Modified First Generation |
| R1/R2 | Second Generation |

Figure 15:
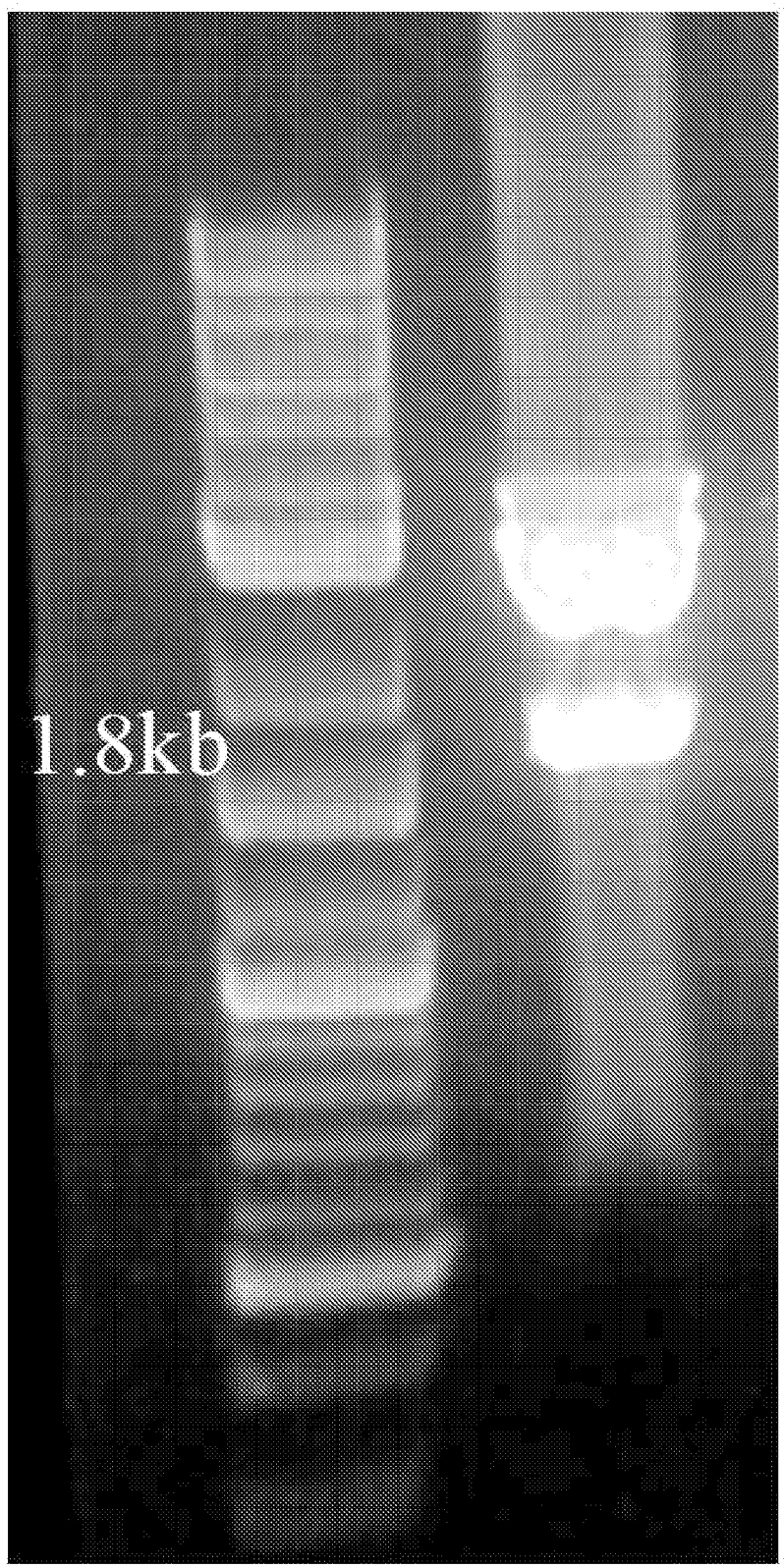
FIG. 15. 1800 bp B9 midblock gene concatemer.

Genetic Modification of First Generation Elastin-Mimetic Protein Polymers: Modified B9 for Yeast Expression. Recently, investigations to employ alternate microbial expression systems for recombinant elastin proteins have been launched. Specifically, an analog to the B9 gene is designed for expression from *Pichia pastoris*. As yeast systems are not as proficient in handling highly repetitive sequences, we present a unique strategy to reduce sequence repetition by creating a library of monomer repeat units with varying nucleotide sequences encoding the same monomer (Table 6; amino acid of SEQ ID NO:53; DNA sequence of SEQ ID NO:54) [74]. This is accomplished through the use of wobble bases. Due to the degeneracy of the genetic code, different nucleotide sequences code for the same amino acid. These coding differences are restricted to usually one position in the codon triplet and incorporate multiple nucleotides thus increasing variability of the protein. The wobble base concept can be incorporated through chemical synthesis of the monomer repeat units thus providing monomer with varied nucleotide sequence based on the preferred codon usage of *Pichia pastoris*. A detailed description of the recombinant approaches employed to generate this analog is provided herein. Briefly, seven monomers are identified and via cleavage with type II restriction endonucleases (which cut downstream of the recognition site), monomer repeat units (RU) with cohesive ends were generated enabling ligation of the monomer library. This method affords a population of concatemers varying in size from 500-2500 base pairs with random incorporation of each monomer. Thus this is a versatile approach for generating a population of synthetic genes that encode repetitive peptides with decreased repetition in primary sequence. As such, a series of recombinant proteins based upon a repeating elastomeric peptide sequence of elastin can be expressed and purified from *Pichia*. To date, a 1500 bp plastin gene encoding the redesigned B9 endblocks and 1800 bp elastin gene encoding the redesigned B9 midblock (FIG. 15) is identified.

TABLE 6

Yeast B9 Elastin-block Monomer Library

| Monomer RU | Coding Sequence |
|---|---|
| | Val Pro Gly Val Gly Val Pro Gly Val Gly Val Pro Gly Glu Gly Val Pro Gly Val Gly Val Pro Gly Val Gly |
| 1 | GTT CCA GGA GTC GGA GTT CCT GGT GTT GGA GTA CCA GGT GAA GGT GTT CCT GGT GTA GGA GTC CCT GGT GTA GGT |
| 2 | GTT CCA GGT GTC GGA GTA CCA GGT GTT GGA GTC CCT GGA GAA GGT GTA CCT GGT GTT GGT GTT CCT GGA GTA GGT |
| 3 | GTT CCA GGT GTC GGT GTA CCT GGT GTA GGT GTT CCT GGT GAA GGT GTA CCA GGT GTC GGT GTA CCT GGT GTA GGA |
| 4 | GTT CCA GGT GTC GGA GTA CCT GGA GTT GGT GTC CCT GGT GAA GGT GTT CCA GGA GTT GGA GTC CCA GGT GTA GGA |
| 5 | GTT CCA GGT GTT GGA GTT CCT GGA GTT GGT GTC CCT GGA GAA GGA GTT CCT GGT GTT GGA GTA CCT GGA GTC GGT |
| 6 | GTT CCA GGT GTT GGT GTT CCT GGT GTT GGT GTT CCC GGA GAA GGA GTC CCT GGA GTC GGA GTT CCT GGT GTA GGT |
| 7 | GTT CCA GGT GTT GGA GTT CCT GGA GTA GGT GTT CCT GGA GAA GGA GTA CCT GGT GTT GGT GTA CCA GGT GTT GGT |

Modified B10, Incorporation of Chemically Crosslinkable Sites: Work on various elastin-mimetic proteins indicates that through selective engineering of block structure, a wide range of mechanical responses can be produced. In recent studies we have demonstrated that relatively limited changes in chemistry, including midblock size or amino acid sequence, provide an additional mechanism for tailoring protein elasticity, resilience, tensile strength, or strain at failure [67]. In this way, an elastomer, designated B10, was produced with endblocks that were significantly larger in size than those of B9. As a consequence, significant increases in both tensile strength and creep resistance were observed [75]. In light of improved mechanical properties, B10 is under investigation with outcomes that will shape the design of R1 and R2 analogs. Chemically crosslinkable sites are incorporated within the B10 polymer chain at specified locations and gluteraldehyde crosslinked. An adaptor is prepared to incorporate a single lysine near the N-terminus and a pair of lysine residues at the C-terminus of the gene (Table 7; SEQ ID NO:56). This scheme provides four crosslinking sites: three from the lysine side chains and one from the amino termini. The B10 genes are ligated into the adapter sequence within an expression plasmid. Likewise, an insert containing a pair of lysine residues are designed for incorporation of crosslinks between the elastin and plastin blocks. To date, insert and adaptor sequences are developed and the molecular re-assembly is delineated as described in FIG. 28.

tein Polymers R1 and R2: Proteins designated R1 and R2 are specifically designed to facilitate physical and/or covalent crosslinking. Specifically, lysine (K) residues will be incorporated at selective sites to facilitate chemical (e.g. gluteraldehyde) crosslinking with precise control over crosslink density. R1 and R2 exemplify two classes of elastin-mimetic protein analogs: (i) The first class, R1, comprises analogs with elastic-like behavior based upon the elastin-mimetic sequence $K[(VPGIG)_5]_{n=5, 15}KK$. (ii) The second class, R2, is comprised of analogs with plastic-like behavior of sequence $K[(IPAVG)_5]_{n=16}KK$. Two unique sequences were designed for both R1 and R2 based on preferred codon usage to enable expression from both *E coli* and *Pichia* expression systems. Coding sequences for these analogs are outlined in Table 8 (SEQ ID NOs:57, 59, 61, 63). Specifically, these proteins (SEQ ID NOs:58, 60, 62, 64) can be varied and combined into multiblock systems (R2-R1-R2, R2-R1-R2-R1) or applied as independent blocks (R1, R2) (SEQ ID NOs:44, 46) either alone or in formulated blends. Of course, any of the proteins disclosed herein may be applied as formulated blends of one another and optional other components as desired.

R1 and R2 protein polymers are synthesized using a genetic engineering strategy which affords near absolute control of macromolecular architecture. The plastic-like and elastic-like segments were designed independently following an identical protocol as described herein and detailed in the 'Methods' section. DNA monomer units encoding R1 and R2 and concatemerization of this cassette produce a family of

TABLE 7

Lysine Insert and Adaptor Sequences for B10

Coding Sequence

Insert   5' TCCAGCTGTTGTTAAGGCCGCGAAGGTTCCAGGTGCAGGCGT 3'

Adapter 5' GATCCAAGGTTCCAAGAGACGGTACCCGTCTCTTCCAAAGGCCGCGAA 3'

*Note:
Highlighted nucleotides code for Lysine residues.

Figure 16:
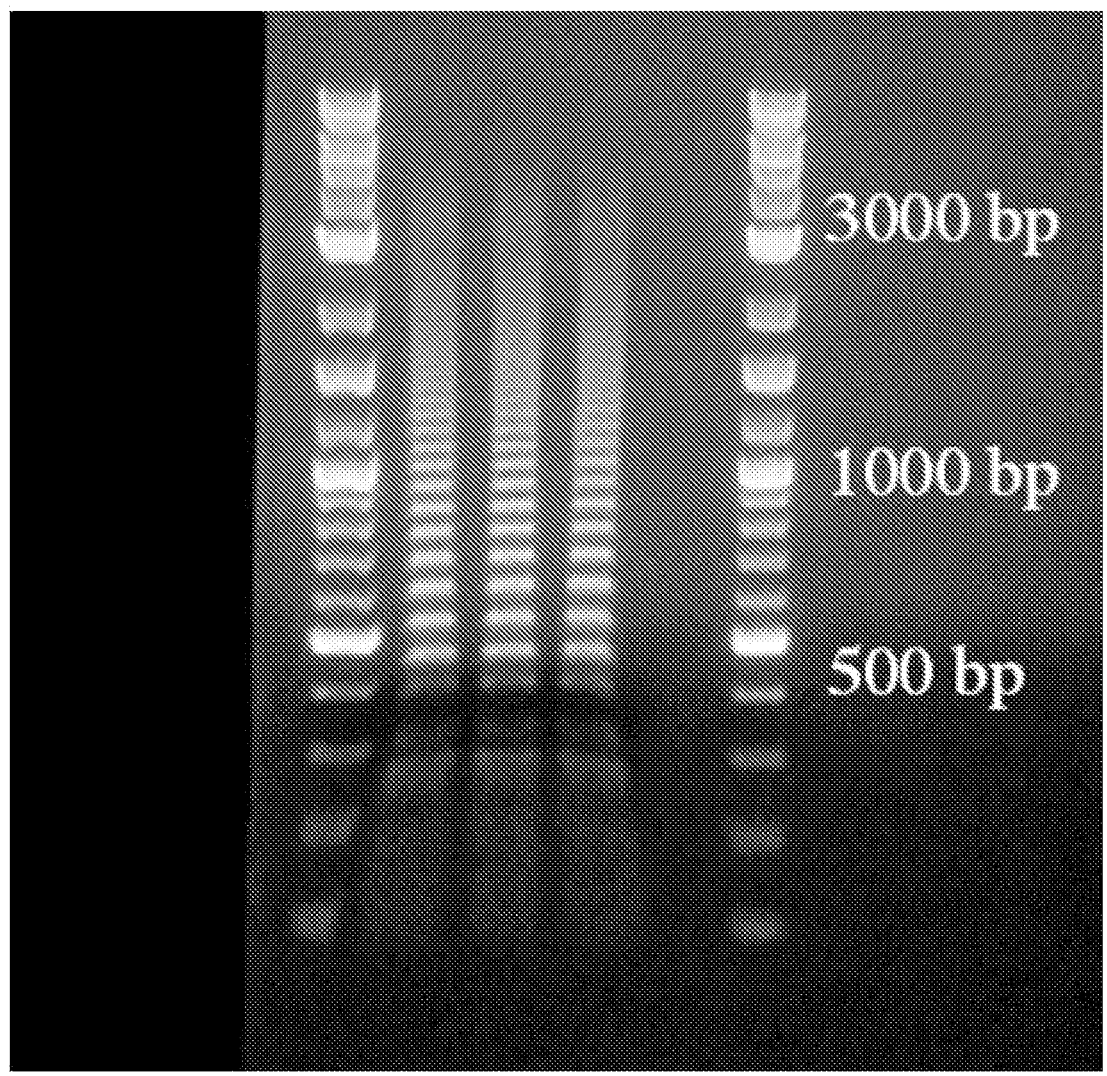
FIG. 16. Concatemers created via ligation of monomer library.

Synthesis of Second Generation Elastin-Mimetic Protein Polymers: Synthesis of Recombinant Elastin-Mimetic Pro-genes differing in size by multiples of the repeat unit (75 bp) (FIG. 16). Additionally, cloning of concatamers into the pZero-1 cloning plasmid (Invitrogen) and screening for requisite sizes via double digestion and agarose gel analysis are performed.

Subsequent work involves designing adaptor sequences to incorporate lysine residues into selective sites as described herein. Small scale expressions are initially pursued to verify protein expression from *E coli* (BL21(DE3)) and *Pichia* (XL100) expression systems and for structural analysis of the protein products. Protein scale-up and purification protocols provide sufficient protein materials for subsequent experiments.

gral to the design of elastin fiber analogs for the fabrication of a small diameter vascular graft with mechanical properties matching a native blood vessel. The significance of mechanically matched properties is primarily to minimize compliance mismatch, which leads to neointimal hyperplasia and late graft failure. Table 9 provides a summary of structural parameters and describes how they are managed in the experiments (i.e. fixed or variable). Parameters that are fixed in these

TABLE 8

Coding sequences of R1 and R2 monomer blocks

| Block Type | Expression System | Sequence |
|---|---|---|
| R1 | *E coli* (BL21) | GTA CCT GGT ATT GGC GTT CCG GGT ATC GGT GTG CCA GGC ATC GGT GTA CCG GGT ATT GGC GTT CCA GGC ATT GGC |
| | *Pichia* (XL100) | GTT CCA GGT ATT GGT GTC CCA GGA ATC GGT GTT CCT GGA ATT GGA GTC CCA GGT ATT GGA GTT CCA GGT ATA GGT |
| R2 | *E coli* (BL21) | ATT CCG GCT GTT GGT ATC CCA GCT GTT GGT ATC CCA GCT GTT GGC ATT CCG GCT GTA GGT ATC CCG GCA GTG GGC |
| | *Pichia* (XL100) | ATT CCA GCT GTT GGT ATC CCT GCC GTC GGT ATT CCT GCT GTT GGA ATC CCA GCA GTC GGT ATT CCA GCC GTT GGA | experiments have been investigated and have exhibit promising results for vascular graft applications.

TABLE 9

Summary of Features Integral to the Design of an Elastin-Based Arterial Conduit

| | Fixed or Variable Parameters | Explanation of Experimental Design |
|---|---|---|
| | | Molecular Level Features |
| Sequence | Fixed | 1$^{st}$ Generation: B10 Triblock (P-E-P)of sequence [(IPAVG)$_5$]$_{26}$-[(VPGAG)$_4$(VPGEG)]$_{26}$-[(IPAVG)$_5$]$_{26[75]}$ |
| | | 2$^{nd}$ Generation: Elastin (E) and plastin (P) block sequences based on VPGIG and IPAVG, respectively [52, 70] |
| Molecular Weight | Fixed | 1$^{st}$ Generation: 170 kDa [75] |
| | Variable | 2$^{nd}$ Generation: Type 1 ~75 kDa, Type 2 ~150 kDa |
| Block Size | Fixed | 1$^{st}$ Generation: 26 elastin repeat units (RU), 26 plastic RU |
| | Variable | Two 2$^{nd}$ Generation options will be investigated: |
| | | Type 1: 5 or 15 elastin RU |
| | | Type 2: 15 elastin RU flanked by 16 plastin RU yielding P-E-P triblock, established from previous work [75] |
| Presence of Crosslinks | Variable | All first and second generation proteins will contain crosslinkable lysine (K) residues affording the ability to chemically crosslink the protein [26, 52, 53, 60] |
| | | Crosslinking Strategies: |
| | | [primary] Glutaraldehyde crosslinking-through lysine residues |
| | | [alternate] Photocrosslinking-following acrylate functionalization of lysine residues |
| Density of Crosslinks | Fixed | Two adjacent amine moieties for crosslinking [26, 52] |
| Location of Crosslinks | Fixed | Two sites-flanking elastin block KEKK [2nd generation, Type I] |
| | | Four sites-flanking each block KP-KKEKK-PKK [1$^{st}$ generation, and 2$^{nd}$ generation Type 2] [26, 52] |
| | | Supramolecular Features |
| Fiber Diameter | Fixed | ~100-300 nm |
| | | Function of electrospinning parameters (concentration of protein, flow rates, applied voltage, etc), to be optimized for new protein solution to yield fiber diameters of several hundred nanometers to micrometers |
| Fiber Orientation | Fixed | Randomly oriented as a result of the electrospinning process |
| Pore Size | Fixed | ~60 μm - Function of electrospinning parameters. |

Experimental Design: Investigations described herein determines both molecular and supramolecular features inte Synthesize recombinant elastin-mimetic protein polymers that have the capacity to form both physical and chemical crosslinks: Previous investigations have supported the hypothesis that physical crosslinks, afforded by the presence of relatively rigid endblock domains, provides an important mechanism for tailoring protein polymer mechanical responses [67-70]. Current mechanical responses of these elastin-mimetic proteins (i.e. Young's modulus, tensile strength, creep, and resilience) appear adequate for the fabrication of the elastomeric matrix of a prototype small diameter vascular conduit. However, the design new recombinant proteins, which include both covalent and physical crosslinks provides a strategy that further optimize creep resistance and resilience for maximum long-term durability of these implants.

Using genetic engineering approaches elastin-mimetic fibers are produced with controlled elastomeric properties and enhanced biostability through appropriate choice of recombinant peptide sequences that facilitate both covalent and physical crosslink formation.

Design and synthesis of modified First Generation elastin-mimetic protein polymers via incorporation of covalent crosslinking sites. The elastin analog, B10, is focus of these investigations. Physically crosslinked B10 has been extensively studied and determined to exhibit improved tensile strength and creep resistance [75]. Through molecular redesign, a modified B10 is constructed to incorporate covalent crosslinking sites at desired locations. Introduction of lysine (K) residues into the cloning sequence facilitates glutaraldehyde crosslinking.

Specifically, modified B10 is redesigned to include crosslinking sites flanking each block of the gene, such as the sequence that is or comprises SEQ ID NO:26:

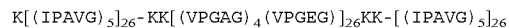

KK

Design and synthesis of Second Generation elastin-mimetic protein polymers with covalent and physical crosslinking sites. Two classes of elastin analogs that are able to form covalent and/or physical crosslinks are examined. The first class (Type I) comprises elastin analogs capable of undergoing covalent crosslinking. Recombinant proteins are synthesized based upon the elastin-mimetic sequence K[(VPGIG)$_5$]$_{n=5, 15}$ KK, (K[X]KK). The second class (Type II) incorporates both physical and covalent crosslinks. Specifically, protein polymer triblocks are synthesized based on the sequence SEQ ID NO:49:

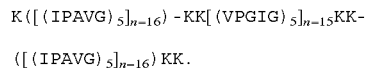

Chemical and structural analysis of recombinant proteins. The chemical and structural properties of synthesized proteins are investigated by automated Edman degradation, MALDI-TOF mass spectroscopy, SDS-PAGE, as well as by NMR spectroscopy. Inverse temperature transitions (ITT) are determined on protein solutions by temperature-dependent turbidity measurements and/or DSC. The transition temperature is integral in determining processing conditions for fiber spinning and refining solvent selection.

Alternative block size option: Similar proteins have been extensively researched and the design of Type 1 and Type 2 proteins are optimized based on these findings. However, this genetic engineering strategy affords a population of concatemerized genes creating a family of elastin genes with varying block size and subsequent molecular weight of the protein. These concatemers can be incorporated into the Type 1 and Type 2 protein design as needed. (ii) Alternative crosslinking options: Through our genetic engineering strategy, we are afforded the ability to incorporate crosslinking sites at additional locations thereby altering the crosslinking density and location of crosslinks. (iii) Alternative applications for Second Generation analogs: These proteins can be varied and combined into multiblock systems (R2-R1-R2, R2-R1-R2-R1) or applied as independent blocks (R1, R2) either alone or in formulated blends. (iv) Composite grafts: Any of these elastin protein polymers are optionally incorporated into woven collagen grafts.

Characterize the mechanical properties of elastin-mimetic nanofiber networks: The relationship of mechanical behavior to protein polymer structure, including molecular weight, fiber architecture, as well as the nature and degree of crosslink formation facilitates the determination of structure-property relationships that are necessary to generate elastin fiber networks that are both mechanically resilient and optimally resist degradation processes. In the first phase of these studies, electrospinning techniques are employed to produce fibers in a form that mimics native elastin fiber diameter using elastin analogues discussed herein. Elastin proteins, as outlined above, with physical and/or covalent crosslinking sites are used for these studies. In preliminary studies, covalent crosslinks are produced by glutaraldehyde crosslinking of lysine amines. Additionally, options for crosslinking via methacrylate derivitization for photocrosslinking exist. Table 10 summarizes the experimental design.

The presence of chemical and physical crosslinks can act synergistically to improve compliance, resilience, and ultimate tensile strength of elastin networks. Creep and stress-relaxation responses of elastin fiber networks are improved with the incorporation of chemical crosslinks.

Mechanical characterization of protein fiber networks. Static mechanical properties are characterized at 37° C. in PBS using model fiber networks, sectioned from electrospun tubes. Stress-strain properties, such as ultimate tensile strength, maximum strain at failure, Young's modulus, as well as mechanical hysteresis, compliance, and % resilience (i.e. the ability of the material to store energy without permanent deformation) is evaluated by uniaxial ring testing.

Characterization of time-dependant mechanical properties. Transient mechanical behavior is defined by stress-relaxation (fixed strain) and creep (fixed stress) studies at small deformations in order to define instantaneous, time-dependent and viscoelastic material behavior. Using a Dynamic Mechanical Thermal Analyzer (DMTA, TA Instruments) these tests are conducted under physiologically relevant conditions.

TABLE 10

Experimental Design

| | Non-crosslinked (Type II protein) | Glutaraldehyde crosslinked (Type I and II) |
|---|---|---|
| Tensile Properties | Ring Testing | Ring Testing |
| Mechanical Hysteresis | Ring Testing | Ring Testing |
| Compliance | Ring Testing | Ring Testing |
| Creep | DMTA | DMTA |
| Stress Relaxation | DMTA | DMTA |

Defining target property endpoints for elastin analogs: Elastin fiber networks that most closely meet target biomechanical endpoints summarized in Table 11 are selected for further biostability studies. Mechanical values comparable to the elastin component of the arterial wall are the desired objective.

TABLE 11

Targeted Design Criteria

| Mechanical Parameter | Target Value |
|---|---|
| Young's Modulus | 0.3-1.3 MPa |
| Ultimate Tensile Stress | >1.0 MPa |
| Strain at Failure | 100-200% |
| Observed Creep | <10% at an applied stress of >0.40 MPa |
| Resilience | >80% over a strain of 30-45% |

(i) Alternatives to glutaraldehyde crosslinking. We focus on the use of glutaraldehyde, which provides a very simple approach for crosslink formation. However, while widely used in the biomaterials industry, limitations of glutaraldehyde do exist. Therefore, methacrylate groups via derivitization of lysine residues provides a good option for chemical crosslinking via photoactivation. (ii) Modulation via thermal annealing: Previous investigations have indicated that brief thermal annealing of protein fibers increases both Young's modulus and ultimate tensile strength. Optionally, this strategy is pursued with Type I and Type II elastin proteins. (iii) Fiber network architecture options: Experimental parameters deemed fixed (Table 9-fiber diameter, orientation, pore size) are modulated as needed. Oriented electrospun fibers can be generated as needed. If necessary, controlled fiber orientation provides a capability to generate a more robust elastomeric construct.

Define the biocompatibility of elastin based fiber networks after in vivo implantation and the ability of such networks to retain primary elastomeric responses: These studies provide insight into material biostability and material-tissue interactions and confirm the fiber networks described above have sufficient biostability for in vivo use. Nonetheless, all proteins are potentially degradable as a consequence of the action of endogenous peptidases. Thus, selected in vivo experiments are designed to define the biostability and biocompatibility of elastin analogues. Additionally, characterization of the behavior and function of elastin fiber networks in vascular applications is investigated. In vivo test samples are selected from elastin analogues that have demonstrated desirable mechanical properties.

Elastin-mimetic fiber networks have sufficient biostability to be used in a vascular construct. A recombinant protein fiber patch retains initial elastomeric properties after in vivo implantation.

Characterization and evaluation of biostability of elastin fiber networks. In vivo implant studies in the subcutaneous space provide preliminary insight into material biostability and material-tissue interactions [76]. In these experiments, 1-cm circular elastin fiber discs are weighed and implanted directly into a subcutaneous pouch of Wistar rats (n=32). Expanded polytetrafluroethylene (ePTFE) discs are implanted as a reference material. Biostability is analyzed over a 4-week implant interval through measurement of the recovered sample's dry weight at 3, 7, 14, and 28 days. TEM is used to observe changes in elastin network architecture induced by the biological environment. Additionally, immunohistochemical staining is employed to evaluate in vivo biocompatibility of fiber networks through analysis of the local cellular response.

Evaluation of elastin fiber networks as a vascular patch. Elastin fiber patches measuring 15×33 mm are implanted into the wall of the inferior vena cava (IVC) of mongrel dogs (n=10), as a high flow, low pressure system. Segments measuring 15×33 mm of the IVC are resected and replaced by the fiber-based patch. Three weeks post implantation the patches are retrieved and examined for patch dilatation followed by immunohistochemical, electron microscopy, and mechanical analysis.

(i) Biocompatibility of elastin analogs: Similar peptide sequences, i.e. VPGVG, VPGKG, VPGEG, IPAVG, and VPAVG, have not elicited an inflammatory response in previous studies. Additionally, these peptides do not appear to be chemotactic to leukocytes or serve as substrates for enzymes commonly released by macrophages or neutrophils at the site of injury [77]. Nevertheless, local inflammatory infiltrates is monitored and humoral responses to the material measured. (ii) Endotoxin. It is not expected that endotoxin will be a major contaminant of these bacterially expressed proteins. However, if endotoxin contamination is significant, purification protocols are optimized for the removal of endotoxin to a level accepted by the FDA for biomaterials. Additionally, proteins of the same sequence have been designed for yeast expression and can be applied analogously to the proteins described above. (iii) Vascular prosthesis studies: Implant studies to assess preclinical performance of small diameter (4 mm i.d., 10 cm length) elastin-collagen composite conduits as both acellular and endothelialized bioprostheses exist.

Experimental Methods:

Synthetic Gene Construction: A single-stranded oligonucleotide corresponding to a monomer repeat unit was chemically synthesized (Sigma Genosys, Inc). The lyophilized sequence was resuspended in elution buffer (10 mM tris-HCl, pH 8.5) to a final concentration of 0.5 ug/uL. DNA Polymerase I Klenow fragment was utilized in a primed extension of the oligonucleotide template for the second strand synthesis yielding the double stranded cassette of the monomer repeat unit. An aliquot of the reaction mixture was analyzed via gel electrophoresis (4% GTG NuSieve, 1×TBE buffer) to verify a single band corresponding to the size of the monomer repeat unit (~75 bp). Subsequently, a preparative gel was utilized to excise DNA from the remainder of the reaction mixture. The corresponding band was excised for purification via Aimcon Ultrafree Centrifugal Filter Units (Milipore) and isolated via enthanol precipitation.

20 ug of the DNA cassette was digested with Bam H I (10 U/ug) and Hin d III (10 U/ug) restriction enzymes, extracted with phenol/chloroform, and isolated via ethanol precipitation. Ligations between the DNA cassette and Bam H I and Hin d III-digested pZErO-1 plasmid (Invitrogen) were performed using T4 DNA Ligase in 1× enzyme ligase buffer with 1 mM ATP at 16° C. for 30 minutes. A 2 ul aliquot of the ligation mixture was used to transform competent cells of E Coli strain Top 10F' (40 uL). 100 ul of the transformation mixture was spread onto low salt LB (LSLB) agar plates (5 g tryptone, 2.5 g yeast extract, 2.5 g NaCl, 7.5 g agar, 200 mL ddH$_2$O, pH 7.5) and incubated 12 hours at 37° C. Twenty-four transformants were used to inoculate separate 7 mL LSLB cultures supplemented with Zeocin (50 ug/mL) for antibiotic selection. Cultures were rotary incubated at 37° C. for 12-14 hours. Plasmid DNA was isolated using Qiagen Spin Mini-Prep protocol (QIAGEN, Inc). Clones were screened by a Bam H I/Hin d III double digestion. Positive clones were identified by analysis of cleavage products with agarose gel electrophoresis (2% GTG Nuseive, 1×TBE buffer) and confirmed by automated DNA sequence analysis (Center for Fundamental and Applied Molecular Evolution, Emory University).

Recombinant plasmids containing correct inserts of for each of the selected sequences were re-transformed into competent Top 10F' cells and plated on LSLB agar plates under Zeocin antibiotic resistance. A single colony from each plate was used to inoculate 500 mL LSLB medium and grown overnight at 37° C. in an orbital shaker at 225 rpm. Preparative amounts of plasmid DNA was isolated using QIAfilter Plasmid Maxi protocol (QIAGEN, Inc). Monomer cassettes were excised from the plasmid via sequential digestion by Bbs I (10 U/uL) and Bsm B I (5 U/uL) restriction enzymes. Fragments of 75 bp were isolated via preparative gel electrophoresis (4% GTG NuSieve, 1×TBE buffer), extracted using Aimcon Ultrafree Centrifugal Filter Units (Milipore) and isolated via enthanol precipitation.

Multimerization reactions utilized 3.0 ug of the BbsI/Bsm BI digested DNA and ligated monomers end-to-end via T4 DNA ligase. Multimer mixtures were separated by size using agarose gel electrophoresis (1% agarose, 1×TBE buffer). Concatemers were excised in blocks, <500 bp, 500-1000 bp, 1000-3000 bp and purified using Zymoclean Gel DNA Recovery protocol (Zymo Research, Inc). Multimers of 500-1000 and 1000-3000 bp in size were ligated into the acceptor plasmid at the Bbs I site at 16° C. for 16 hours. The acceptor plasmid was prepared from the pZErO-1 plasmid containing the original monomer repeat unit associated with each gene, digesting with Bbs I, and dephosphorylated via SAP (Shrimp Alkaline Phosphatase) to prevent self ligation. Ligation mixtures were used to transform competent Top 10F' cells and 100 uL of the transformation mixture was plated on LSLB/Zeocin agar plates. DNA from positive clones were isolated via MacConnell automated miniprep and screened through double digestion using Bam H I and Hin d III restriction enzymes. Clones of predetermined sizes were isolated.

Figure 29:
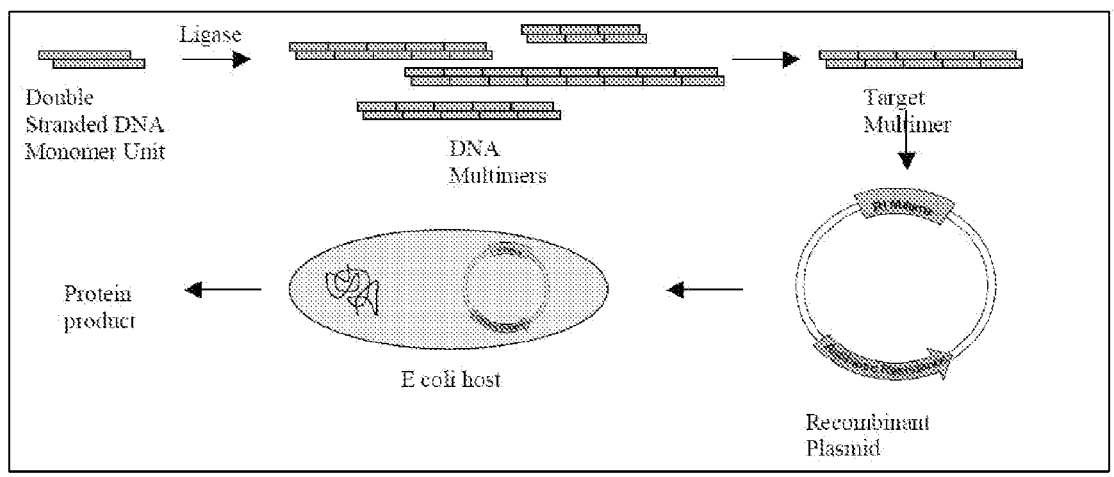
FIG. 29. Synthesis of repetitive polypeptides via multimerization of DNA monomers, adapted from [25].

The recombinant techniques described above were employed in the generation of recombinant proteins R1, R2, and the B9 plastin and elastin blocks for yeast expression. The generation of the B9 plastin and elastin blocks deviated from the described protocol in that a monomer library was initially generated based on a wobble base design and homologous sequences were obtained from SigmaGenosys. Seven recombinant genes were identified and 0.4 ug of each were used in multimerization reactions affording multimers ranging in size from 500-3000 bp with random incorporation of the monomers. The pPICZαA expression vector/XL100 Pichia expression strain will be utilized for yeast-B9 expression (see FIG. 29).

Figure 30:
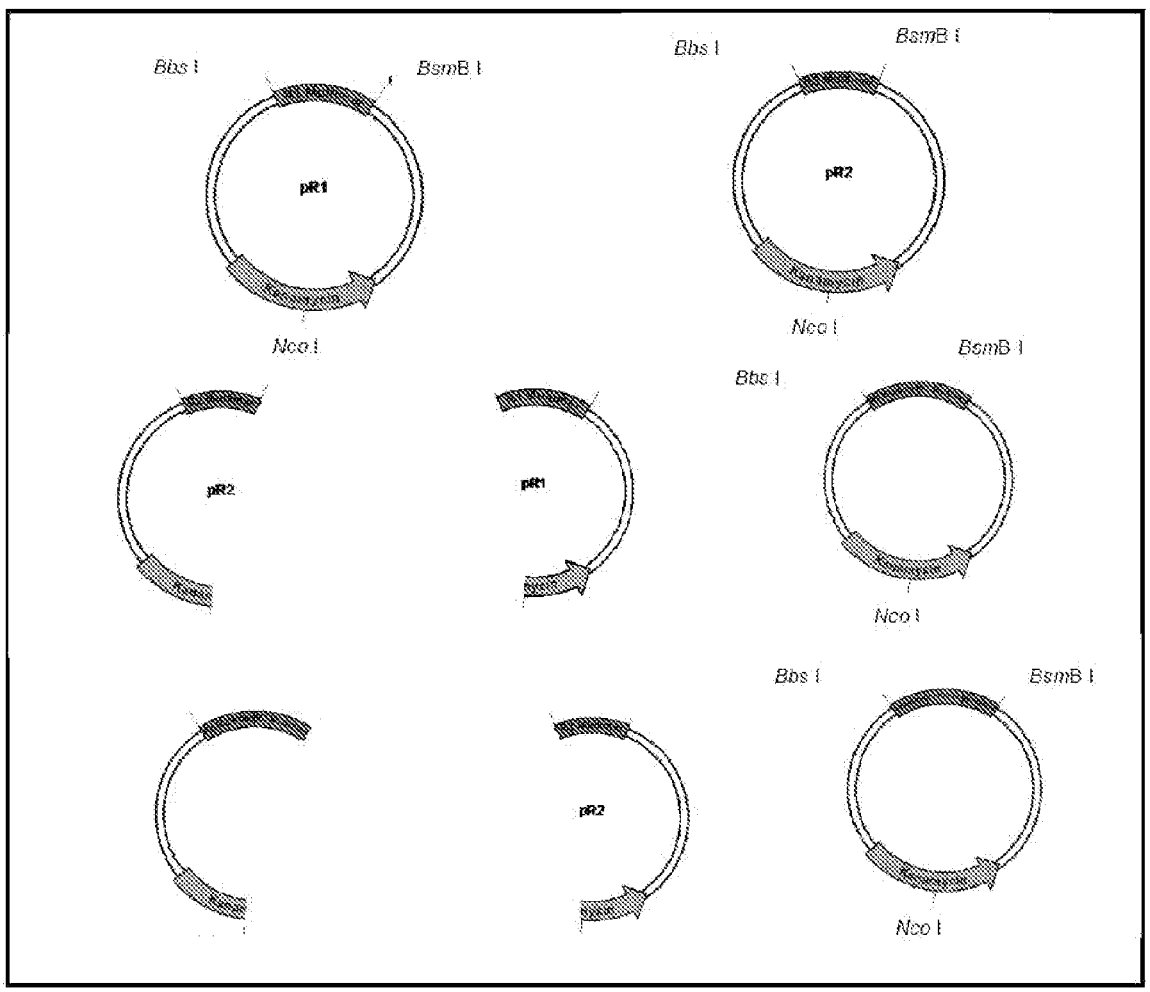
FIG. 30. Genetic assembly of the gene encoding the triblock copolymer R2-R1-R2, adapted from [49].

Assembly of Triblock Copolymers: Recombinant plasmids containing R1 elastin and R2 plastin blocks will be isolated and digested with Bbs I/Xma I and Bsm B I/Xma I, respectively. The large fragment from each of these digestions will be isolate via preparative gel electrophoresis (1% agarose, 0.5×TBE) and purified using the Zymoclean gel recovery kit. R1 and R2 fragments will be ligated by T4 DNA ligase, transformed into Top 10F' and plated on LSLB plates under Zeocin resistance. As the Xma I site cuts within the Zeocin coding region, only clones containing the correctly assembled diblock (R2-R1), and thus, the correctly reassembled antibiotic coding region, will propagate. To form the triblock, the R2-R1 diblock is digested with Bsm B I/Xma I and the plasmid containing the R2 plastin block with Bbs I/Xma I. Similar protocols for ligation, transformation, and propagation will be followed. Via antibiotic selection, only colonies contain the correctly assembled triblock (R2-R1-R2) will survive (see FIG. 30).

Figure 17:
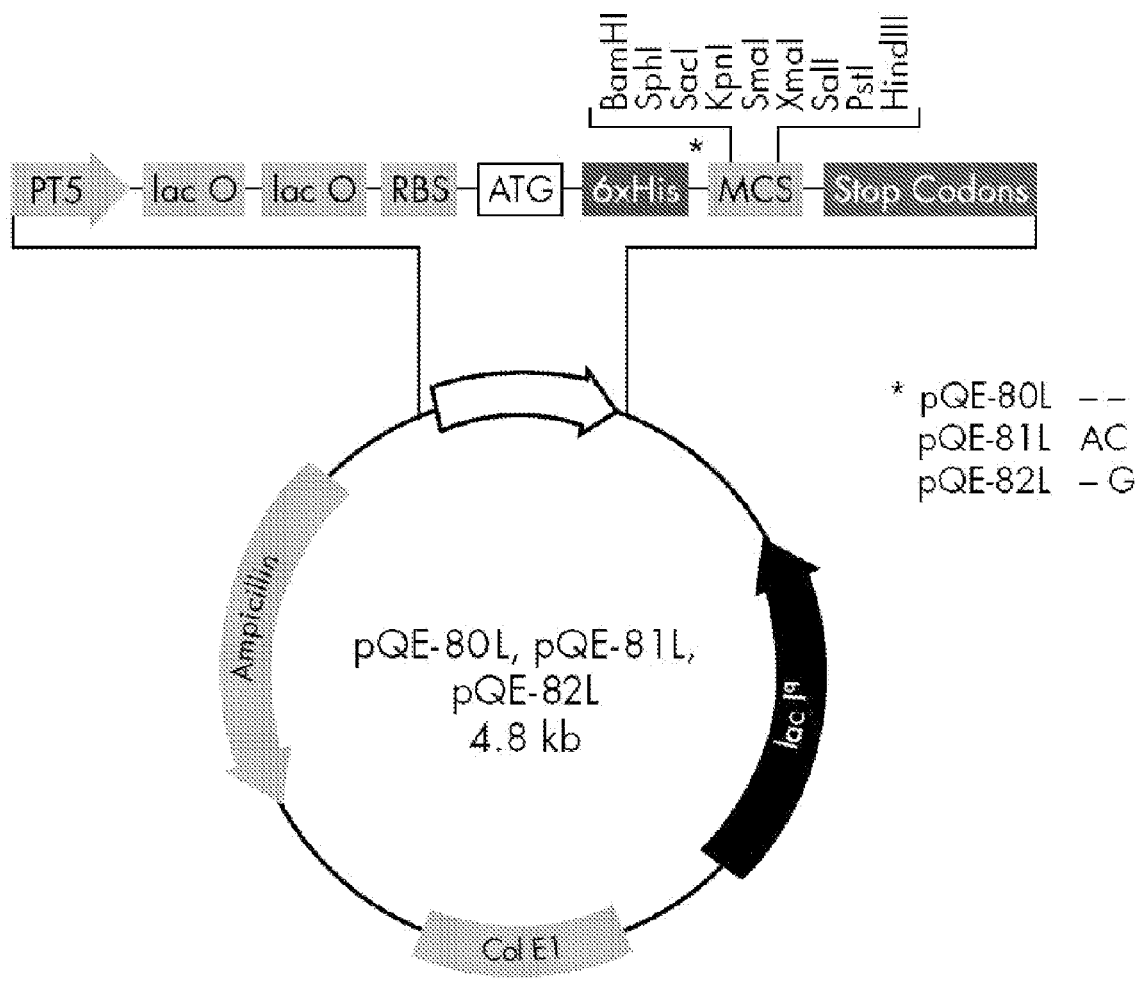
FIG. 17. Plasmid map of commercial expression vector pQE 80L (Qiagen, Inc). Preparation of the plasmid involves the removal of nucleotides between Bam H I and Hin d III restriction sites within the polyclonal region. Contains an N-terminal His-tag.

Construction of Expression Vectors The expression plasmid, pQE 80L (Qiagen, Inc) (see FIG. 17) will be prepared by deletion of the polyclonal region between the Bam H I and Hin d III restriction sites. A 75 bp adaptor containing flanking Lysine residues between which recombinant genes can be cloned will be inserted. The resulting plasmid will be defined as mpQE80L for the modification made to the original pQE 80L vector. This vector will be propagated in Top 10F' and preparative amounts of DNA will be isolated. Adaptor design: In native elastin, crosslinking domains consist of poly-alanine and paired lysines. This composition promotes an alpha helical structure and facilitates positioning for intermolecular crosslinking. Through rational design of the adaptor sequences, lysine residues can be incorporated for crosslinking. Previous studies have indicated proper placement of lysine residues is essential for protein stabilization and adequate expression levels [26, 52, 78]. Thus the pQE 80L expression vector will be utilized encoding an N-terminal oligonucleotide tag affording a strategy to incorporate lysines at the amino-terminus of the elastin genes.

Protein Hyperexpression and Purification: Expression plasmids containing R1 and R2 will be used to transform the E coli expression strain DG99. Purification protocols will be adapted from those employed with BL21 (DE3) strain expressions utilizing elastin's inverse transition temperature, though the ability to purify using affinity chromatography is available. Large scale expression will be performed in an orbital shaker (225 rpm) at 37° C. in Terrific Broth medium supplemented with ampicillin (100 uL/mL) for 36-48 hours. Cells will be harvested via centrifugation (4° C./8000 rpm/20 min) and the cell pellet resuspended in lysis buffer (64 mL; 100 mM NaCl, 50 mM Tris-HCl, pH 8.0) and stored at −80° C. Frozen cells will be lysed via three freeze (−80° C.)/thaw cycles. Lysozme (1 mg/mL), benzonase (1 uL/10 mL), $MgCl_2$ (1 uL/mL), and protease inhibitor cocktail (1.3 mg/mL) will be added to the cell lysate and incubated at 37° C. for 30 minutes with constant agitation. The lysed cells will be incubated at 4° C. for overnight followed by centrifugation (4° C./14000 rpm/20 min) for removal of cellular debris. Repeatable purification protocols have been developed to purify elastin-like proteins by exploiting their solubility characteristics. In this way, proteins will be extracted from the cell lysate by three-five cycles of reversible temperature induced precipitation via centrifugation at 4° C./37° C. from 500 mM NaCl solution. Dialysis and lyophillization will follow with expected yields of 200-500 mg/L.

Gluteraldehyde Crosslinking: Gluteraldehyde crosslinking protocol has been adapted from the work of Welsh and Tirrell on elastin-like proteins [52]. Gluteraldehyde vapor phase crosslinking and solution phase crosslinking will be employed successively to crosslink elastin electrospun fabrics through the amine moieties of lysine residues. Fabrics will be enclosed in a chamber containing a pool of 12.5% gluteraldehyde (GTA) solution. Solution phase crosslinking will follow with submersion of the fabric in 10 mM GTA (in PBS, pH 7.4) for two hours at room temperature. Following the crosslinking steps, fabrics will be exposed to 0.2 wt % dimedone in PBS for 24 hours to quench further crosslinking reactions. Crosslinking efficiency will be assessed using a Trinitrobenzene sulfonate (TNBS) assay to quantify unreacted amine functionalities.

Matrix Assisted Laser Desorption Ionization Time of Flight Mass Spectroscopy (MALDI-TOF)

Experiments will be performed on a Persptive Biosystems Instrument (Voyager-DE STR Biospectroscopy Workstation) at the Mircochemical Facility at Emory University. A matrix of Ferulic acid (4-Hydroxy-3-methoxycinnamic acid), will be mixed with protein solutions (1 mg/100 ul) in a 1:1 ratio, spotted on the target, and dried under vacuum. In order to prevent protein precipitation, the protein samples and matrix will be mixed at 4° C. immediately prior to analysis.

Solution Turbidity Assessment

Turbidity measurements will be assessed as a function of temperature. Solutions of 0.5-0.7 mg/mL will be prepared from water and heated at rate of 1° C./min. The optical density will be measured at 280 nm by an Ultrospec 3000 UV/vis spectrophotometer equipped with a temperature controller (Amersham Pharmacia Biotech, Inc). The inverse transition temperature of the protein will be defined as the temperature associated with half-maximal turbidity [16].

$^1$H NMR $^1$H NMR spectra will be acquired on a Varian INVOA 600 spectrometer operating at a frequency of 599 MHz. Thirty-two scans will be collected for signal-to-noise averaging. Spectra will be collected at 4° C. on protein specimens in solution (10 mg/ml). Chemical shifts (δ) will be referenced and reported relative to an internal standard sodium 2,2-dimethyl-2-silapenta-5-sulfonate.

Differential Scanning Micro-Calorimetry (Micro-DSC)

Experiments will be performed using a Setaram Micro DSC III calorimeter (Setaram Inc, France). Lyophilized protein samples of 1 mg/ml will be dissolved at 4° C. in sterile distilled, deionized water. The thermal transition data will be investigated over a temperature range of 4° C. to 70° C. at a scan rate of 1° C./min. Reversibility will be investigated upon cooling of the sample back to 4° C. following the initial scan. Data will be analyzed using SETSOFT 200 software (Setaram Inc, France).

Fabrication of Elastin-Mimetic Fiber Fabrics—Electrospinning

A 5-18 weight % protein solution will be prepared by dissolving lyophilized protein in 2,2,2 trifluoroethanol (TFE) at room temperature. The solution will be extruded at ambient temperature and pressure using a syringe pump (Havard Apparatus, Inc) at a flow rate of 150 μL/min though a positively charged needle (18G×4 in). A high voltage, low-current power supply (ES30P/DDPM, Gamma High Voltage Research, Inc) will be used to generate an electric potential gradient at approximately 18 kV. Fibers will be collected on a grounded stainless steel mandrel (d=3.18 mm for ring testing studies, d=6 mm for DMTA studies) located 7-10 mm from the needle tip. The mandrel undergoes rotational and translational motion during the electrospinning process to create a nonwoven fabric conduit. The electrospun conduit can be removed from the mandrel in the dehydrated state and used in subsequent experiments.

Mechanical Characterization of Uniaxial Stress-Strain Properties Measured in the Circumferential Direction of the Conduit A uniaxial ring testing apparatus described elsewhere [14, 71] will be used to characterize the mechanical properties of the electrospun conduits as outlined in Table II. Electrospun elastin conduits will be sectioned into rings (n=6), 3 mm in length, hydrated in PBS at 37° C. for great than 24 hours. Four reference beads (~300 μm) will be attached to the surface of the ring, two on each wall. Following the placement of the beads, samples are loaded on two hooks in the ring testing apparatus, and strained to failure at a rate of 0.2 mm/sec. Using a step motor, strain is applied to the sample through downward displacement of the lower hook generating hook displacement data which is recorded through an analog/digital interface. This data is used in conjunction with testing images captured by CCD camera to relate hook displacement to sample wall strain. Force is recorded by a load transducer attached to the top hook and is normalized by initial cross-sectional area of the hydrated construct wall to calculate stress measurements. Ultimate tensile strength is defined as the maximum stress withstood by samples with respect to the original cross-sectional area. The elastic modulus is determined by the slope of the region extending between 25-75% of the ultimate tensile strength.

Mechanical Characterization of Uniaxial Stress-Strain Properties Measured with Respect to the Longitudinal Axis of the Conduit Mechanical characterization of protein fiber networks will be performed on a dynamic mechanical thermal analyzer DMTA V (Rheometric Scientific Inc) with samples submerged in a temperature controlled jacketed beaker filled with 37C PBS. Note that the samples can not be strained to failure as the maximum travel distance of the drive shaft of the DMTA is 23 mm which limits maximum strain to 70% of engineering strain. Sample Thickness. Samples for each experiment will be prepared from sectioned electrospun tubes cut longitudinally, pressed flat and hydrated at 37° C. in PBS for 24 hours. Hydrated samples will be sectioned using a dog-bone shaped stainless steel die with gauge dimensions of 13×4.75 mm. Fabric thickness will be measured in the hydrated state using an Advanced Rheometric Expansion System (ARES) (Rheometric Scientific) and verified by optical microscopy using the standard image analysis protocol. Uniaxial Tension. Six samples will be loaded by controlling displacement at a standard rate of 5 mm/min. As samples can be strained to only 70% engineering strain, only Young's Modulus can be obtained from this data set. To characterize ultimate tensile strength, a miniature materials tester, a Minimat 2000 (Rheometric Scientific) will be used in tensile deformation mode at a rate of 5 mm/min. Samples will be tested under ambient conditions and coated in a thin layer of mineral oil prior to loading to limit water loss during the test. Ultimate tensile strength and elastic modulus data can be obtained. Hysteresis. In these studies, three samples will be stretched to a predetermined strain, unloaded to a zero-stress state, and strained to 70% strain. Stress relaxation. Three samples will be stretched to a predetermined strain and held constant for times greater than one hour. The evolution of stress over time will be examined. Creep. Six samples will be subjected to a range of constant stresses for times approaching 24 hours. Material deformation over time will be assessed. Statistical Analysis. The Student's 2-tailed unpaired t-test will be utilized to evaluate data sets collected from different constructs to assess batch-to-batch variation. Additionally, Student's 2-tailed unpaired t-test will be used to establish statistical significance (p 0.05) of mechanical properties measured for crosslinked and non-crosslinked samples.

In Vivo Biocompatibility and Biostability Studies 1-cm circular disc test samples will be weighed and implanted directly into a subcutaneous pouch of C57BL6 mouse (n=32) [76]. Expanded polytetrafluroethylene (ePTFE) discs will be implanted as a reference material. Biostability will be analyzed over a 4-week implant interval through measurement of the recovered sample's dry weight at day 3, 7, 14, and 28. TEM will be used to observe changes in elastin network architecture induced by the biological environment. Additionally, in vivo biocompatibility of fiber networks will be investigated through an initial H&E stain (hematoxylin and eoxin) and if indicated, further analysis of the local cellular response by immunohistochemical staining. Specifically, myeloperoxidase (MPO) (clone ab15484, Abcam) and Ham 56 (clone ab8186, Abcam) staining for neutrophils and macrophages, respectively, will be used to determine if an inflammatory response is generated. Staining for endothelial factor VIII/von Willebrand factor (clone ab6994, Abcam) will be used to identify endothelial cells. The surrounding tissue and the disc composition will be evaluated for inflammatory response, tissue ingrowth, and capsule formation. The observations will be ranked from 0 to 4, where 0 is a minimal and 4 is a maximal response. All observations will be made at a magnification of 200× with five random areas observed per sample. All scores and measurements will be tabulated for each specimen group with mean and standard errors calculated. An ANOVA using Scheffe's analysis will be used to determine statistical significance between the groups for all measurements ($p<0.05$). The elastin fiber samples will be determined acceptable if ranked statistically similar to positive control (ePTFE).

In Vivo Vascular Patch Studies

Figure 31:
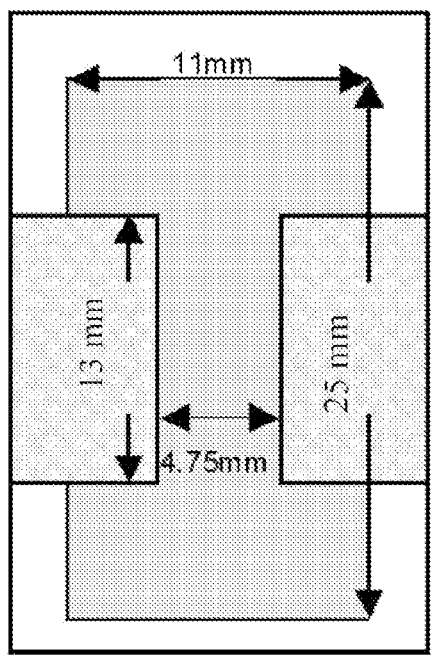
FIG. 31. Diagram detailing sectioning of 15×33 mm elastin fiber patch for immunohistochemical, electron microscopy, and mechanical analysis.

Canines (n=10), weighing 25-30 kg, will be anesthetized, and entered through a vertical midline abdominal incision to expose the infrarenal IVC. The proximal and distal IVC will be clamped and two rectangular segments measuring 15×33 mm of the anterior wall will be resected and replaced by an elastin patch and a control PTFE patch using a running suture technique with 5/0 Prolene. In five of the dogs, the experimental elastin patch will be implanted superior to the control PTFE patch. In the other five dogs, the control patch will be positioned superior to the elastin patch. Three weeks post implantation the animals will be euthanized according to The American Veterinary Medical Association Guidelines. The peritoneal cavity will be reentered though the previous wound and the implanted patches will be removed in an en-block manner [79-81]. The explanted patch will be sectioned according to requirements for mechanical testing as outlined in FIG. 31. This will allow for two 4×13 mm samples to perform immunohistochemistry and microscopy studies. At the time of explantation, specimens will be photographed for measurements of thrombus free surface and overall pannus tissue ingrowth. Serial sections of the adjacent IVC and segments of the patch will be obtained for examination by Scanning Electron Microscopy (SEM), Transmission Electron Microscopy (TEM), and light microscopy. Staining will be performed to examine endothelial and smooth muscle cell coverage, as well as associated cellular and matrix responses. For example, immunohistochemical studies will include staining with endothelial factor VIII/von Willebrand (clone ab6994, Abcam) factor to identify endothelial cells, smooth muscle α-actin (clone ab9465, Abcam) to identify smooth muscle cells, and Ham 56 (clone ab8186, Abcam) to identify macrophages [82, 83]. Biomechanical testing will include tensile, mechanical hysteresis, and creep to be performed in triplicate. Data analysis will be conducted using ANOVA and Student's t-tests.

Transmission Electron Microscopy (TEM)

Sections measuring 3×3 mm will be sectioned from three sample areas within the graft. Samples will be fixed by immersion in 2.5% gluteraldehyde buffered with 0.1 M cacodylate (pH 7.5) for 4-16 hours and postfixed for one hour in 1% osmium tetroxide solution, washed, en block stained with uranyl acetate, dehydrated through graded concentrations of ethanol and embedded in embed 8-12 epoxy resin. Thin sections will be post stained with lead citrate and observed on a JEOL 1210 $LaB_6$ transmission electron microscope. The images will be captured on Kodak film and the negatives converted to digital images using an AGFA Duoscan T2500 scanner. TEM images will be processed using Adobe Photoshop [84].

Scanning Electron Microscopy (SEM)

Two 5×10 mm samples will be sectioned from the proximal and distal segments of the patch and surrounding vascular tissue. These samples will be fixed by immersion in oxygenated 2.5% glutaraldehyde buffered with 0.1 M cacodylate (pH 7.4) at 37° C. for 15 minutes followed by immersion overnight in glutaraldehyde. Tissue will be dehydrated through graded concentrations of ethanol and critical point dried. Samples will be inserted into an acetone filled specimen boat and transferred to a Polaron critical point drying apparatus where the exchange with liquid carbon dioxide was performed followed by decompression of $CO_2$ within the chamber. Dried samples will be mounted on aluminum stubs and coated with a 10 nm thin film of gold palladium with a Denton DV-602 sputter coater. Specimens will be imaged using the in-lens of a DS-130F field emission scanning electron microscope operated at 25 kV. SEM images of low (1000×) and intermediate (50,000×) magnifications will be digitally collected at a 17 Mb file size and Photoshop was used to adjust levels [84-86].

Example 3

The Effect of a Recombinant Elastin-Mimetic Coating of an ePTFE Prosthesis on Acute Thrombogenicity in a Baboon Arteriovenous Shunt The development of durable synthetic vascular grafts has been limited by both surface-induced thrombus formation and anastomotic intimal hyperplasia related, in part, to maladaptive biological responses at the blood-material and tissue-material interfaces. Indeed, within 5 years 30% to 60% of prosthetic vascular grafts implanted in the infrainguinal position will fail [1]. In response to these problems and, in particular, to limit the risk of thrombosis of small caliber prostheses, grafts have been coated with albumin, heparin, or prostacyclin analogues, which inhibit the clotting cascade and platelet reactivity, or with relatively inert materials, such as polyethylene oxide [2-6]. As an alternative strategy to passivate blood-contacting surfaces, several investigators have recently reported that elastin and elastin-derived proteins provide a relatively inert interface when coated on synthetic polymeric surfaces that characteristically initiate thrombogenic responses [7-10].

Elastin, which is derived from the soluble precursor tropoelastin, is widely distributed in vertebrate tissues where it consists of repetitive glycine-rich hydrophobic elastomeric domains of variable length that alternate with alanine-rich, lysine-containing domains that form crosslinks [11-13]. Native elastin's intrinsic insolubility, however, has restricted its capacity to be purified and processed into forms suitable for biomedical or industrial applications without extensive organic solvent and 2-mercatoethanol extractions, cyanogen bromide (CNBr) treatment, and enzymatic digestions. Recently, this limitation has been largely overcome, in part, by the structural characterization of the elastomeric domains. Comprehensive sequence analysis has revealed the presence of consensus tetra- (VPGG), penta- (VPGVG), and hexapeptide (APGVGV) repeat motifs [14-19]. Notably, only polymers of the pentapeptide exhibit elastic behavior with spectroscopic features that are consistent with those of native elastin [20-22]. Thus, the pentapeptide sequence (VPGVG) has formed the basis for the synthesis of protein polymers with elastomeric domains by standard solution and solid phase chemical methodologies and, more recently, by genetic engineering strategies [23-28].

We have recently demonstrated that genetic engineering of polypeptides enables the creation of recombinant amphiphilic protein polymers composed of complex block sequences [29-32]. Notably, the segregation of the protein blocks into compositionally, structurally, and spatially distinct domains affords ordered structures on the nanometer to micrometer size range that may have unique mechanical, chemical, and biological properties. The biosynthetic scheme for generating self-assembling recombinant proteins has been based upon a new convergent strategy for assembling multiple blocks of concatemerized DNA cassettes by sequential ligation. To date this strategy has been used to design amphiphilic multiblock proteins (e.g. diblock, triblock, and tetrablocks) ranging from 100 to 200 kD in molecular weight. The protein sequences used to design these protein block copolymers were derived in part from a consideration of the primary structure of elastin. Specifically, we have synthesized and characterized a series of elastomeric triblock copolymers capable of virtual or physical crosslink formation. Proteins were synthesized that incorporate identical hydrophobic endblocks [VPAVG[(IPAVG)$_4$(VPAVG)]] SEQ ID NO. 7, separated by a central hydrophilic block [(VPGVG)$_2$(VPGEG)(VPGVG)$_2$] SEQ ID NO 52. These protein polymers reversibly self-assemble from concentrated aqueous solution above an inverse transition temperature of the hydrophobic endblocks (~15° C.) to form a stable, water solvated, interlocking network. Of note, recent 2-D FTIR spectroscopy studies reveal a conformational transformation in the protein end block above the inverse transition temperature from helix to sheet-like structures that tightly assemble into physical or virtual crosslinks [33]. Indeed, several investigations have now confirmed robust viscoelastic and mechanical responses of several recombinant elastin-mimetic protein block copolymers that may be processed into a variety of forms including hydrogels, particles, films, and fiber networks [29-31]. In this study, we examined the acute blood-contacting properties of a triblock elastin-mimetic peptide physically gelled and layered onto the luminal surface of a small diameter expanded PTFE vascular graft (4 mm i.d.). Elastin-coated grafts are characterized by contact angle goniometry, Fourier transform infrared (FT-IR) spectroscopy, and scanning electron microscopy (SEM) and their stability tested in a high shear rate environment. Favorable blood contacting properties under flow are observed in a baboon ex vivo femoral arteriovenous shunt model.

Materials and Methods

Figure 18:
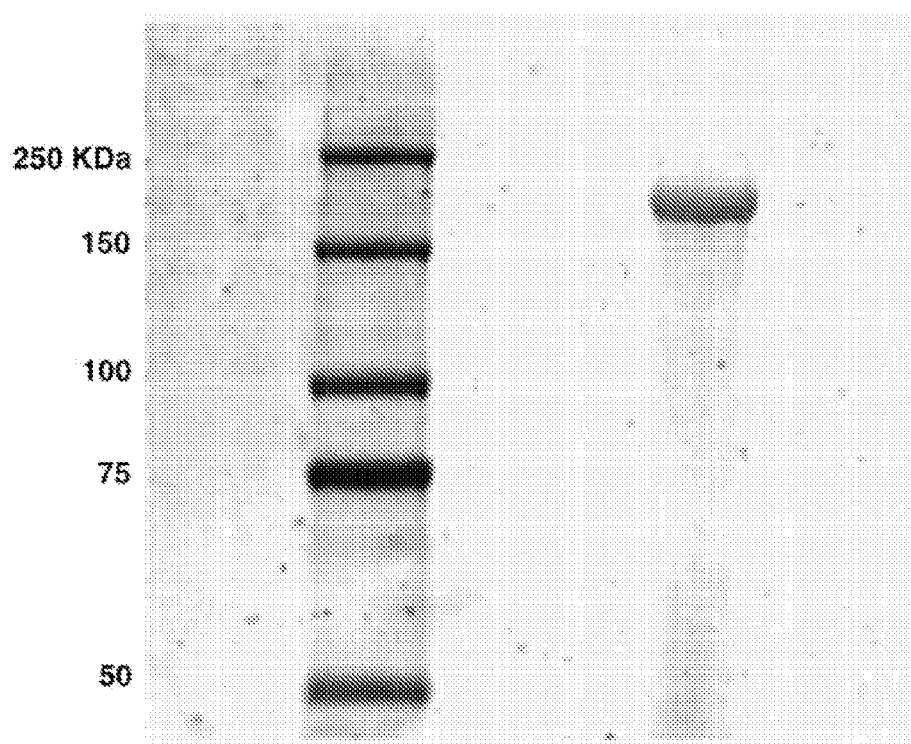
FIG. 18. Sodium dodecyl sulfate-polyacrylamide gel electrophoresis (SDS-PAGE) analysis of elastin-mimetic triblock copolymer run on 7.5% SDS-PAGE stained with Coomassie G250. Marker lane: Precision Plus Protein Kaleidoscope (Bio-Rad).

Synthesis and purification of the elastin-mimetic triblock copolymer The recombinant protein polymer B9 is derived from concatemerization of elastin-mimetic peptide sequences, expressed, and purified, as previously described [29, 34]. The structure consists of a triblock of form of [PN]-[X]-[PC], where
PN=VPAVG[(IPAVG)$_4$(VPAVG)]$_{16}$IPAVG;
X=VPGVG[(VPGVG)$_2$VPGEG(VPGVG)$_2$]$_{48}$VPGVG;
PC=VPAVG[(IPAVG)$_4$(VPAVG)]$_{16}$IPAVG.
The elastin-mimetic polypeptide is run on 7.5% sodium dodecyl sulfate-polyacrylamide gel electrophoresis (SDS-PAGE) and stained with Coomassie G250 stain (Bio-Rad). Molecular weight markers were Precision Plus Protein Kaleidoscope (Bio-Rad). As anticipated, the molecular weight of the recombinant triblock copolymer is ~180 kDa (FIG. 18). Additional structural characterization data is been detailed elsewhere (29).

Physical crosslinking of an elastin protein polymer film onto an ePTFE vascular graft. Elastin impregnation of an ePTFE vascular graft: Impregnation of vascular grafts (4 mm i.d., Atrium Medical, Hudson, N.H.) is performed under positive pressure by clamping one end of the graft and infusing 5 mL of cold elastin polymer solution (6 w/v % in water) through the graft using a Luer-lok syringe. Elastin is extruded through the pores of the graft during this process. The prosthesis is subsequently immersed in an elastin bath at 4° C. for 6 hours to ensure uniform coating. After the 6 hour incubation, the graft is drained, 60 mL of air pushed through the lumen to remove excess elastin protein polymer, and the graft is oriented vertically at 37° C. for 30 min.

Multilayer coating of elastin films: The elastin-impregnated ePTFE graft is post-coated by infusing 3 mL of chilled elastin solution (6 w/v % in water) through the open lumen of the graft. Using a Luer-lok syringe, 60 mL of air is pushed through the lumen to remove excess elastin, and the graft is then oriented vertically at 37° C. for 30 min. This process is repeated twice for a total of two post-coated layers. Samples are stored in warm saline. In order to visualize the protein polymer luminal film, graft samples are incubated for 10 min in Coomassie G250 stain (Bio-rad) in a 37° C. water bath and rinsed extensively with warm deionized water. Graft samples are sectioned lengthwise prior to staining.

Stability of protein polymer coating: Stability of the prosthesis-bound protein film is evaluated in a closed-loop flow system by perfusing phosphate buffered saline (PBS) through the graft at 180 mL/min (500 s$^{-1}$ wall shear rate) at 37° C. for 24 hours.

Instrumentation. Water contact angles. Graft samples are cut into 5×5 mm sections, air-dried, and adhered onto glass slides using double-stick tape and advancing and receding contact angles were obtained using a Rame-Hart goniometer, Model 100-00.

High resolution scanning electron micrographs (HRSEM) Protein polymer coated ePTFE grafts are critical point dried, mounted onto aluminum specimen stubs with double-stick carbon tape, degassed for 30 minutes, and sputter coated with a 1 nm gold (Au) film. The film surface is examined using an in-lens field emission scanning electron microscope (ISI DS-130F Schottky Field Emission SEM) that was operated at 5 kV.

Infrared Spectroscopy: Spectra are acquired using a Bio-Rad FTS-4000 Fourier Transform Infrared (FT-IR) spectrometer equipped with a wide band MCT detector, collected with 100 scans, and 2 cm$^{-1}$ resolution. Attenuated total reflectance (ATR) spectra of protein coated grafts were acquired using a Silvergate ATR anvil press accessory equipped with a germanium prism (Specac Inc., Woodstock, Ga.). The single beam spectrum of the ATR accessory is used as a background. Spectra manipulations performed on the data, such as baseline correction, $CO_2$ peak removal (from 2250-2405 cm$^{-1}$) and center-of-gravity frequency position determination of IR absorption bands were performed using the Grams/AI software package (Thermo Galactic Industries, Salem, N.H.).

Figure 19:
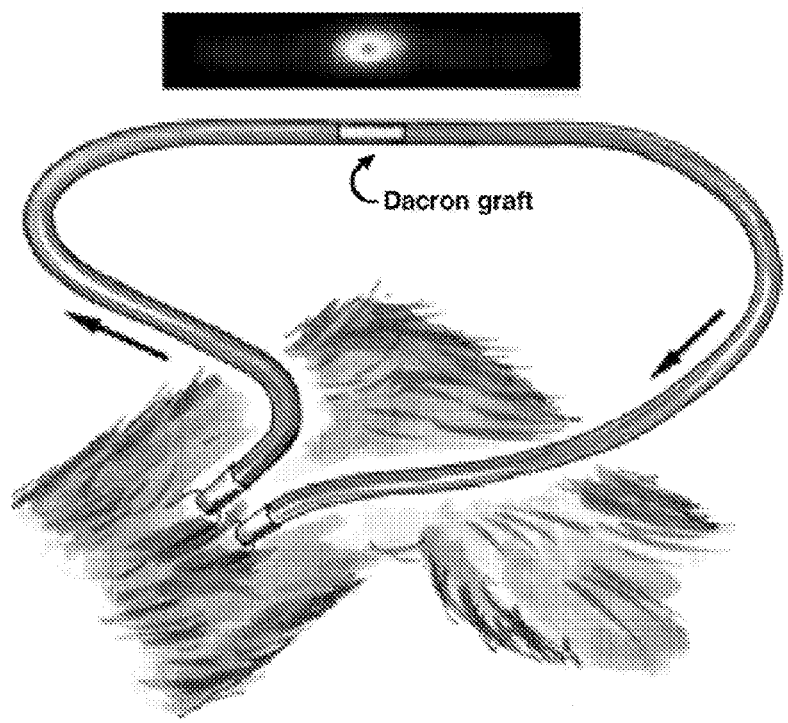
FIG. 19. Schematic representation of the baboon femoral arteriovenous shunt model. Test samples are interposed within an exteriorized silicone shunt and In[111]-platelet deposition on test surfaces monitored by scintillation camera imaging using a SPECT system.

Baboon Model. Arteriovenous shunt: Baboon ex vivo shunt studies are performed, as detailed elsewhere [35]. Briefly, grafts are interposed into a permanent Silastic arteriovenous shunt that had been surgically implanted between the femoral artery and vein in male baboons (*Papio papio*) (FIG. 19). Circulating platelet concentrations averaged 380,000 platelets/µL. Ketamine hydrochloride (10 mg/kg intramuscularly) is given as a pre-anesthetic agent, and the operation is performed under general 1% halothane anesthesia. All procedures are in accordance with institutional guidelines. Mean blood flow rate through the shunt is measured continuously using a Doppler ultrasonic flow meter and held constant by an external screw clamp at 100 mL/min.

Platelet Radiolabeling: Autologous baboon platelets are radiolabeled on the day prior to the shunt study. Forty-five milliliters of whole blood is initially withdrawn into syringes containing 9 mL of acid citrate dextrose anticoagulant. The blood is centrifuged at 160 g for 15 min and the platelet rich plasma removed and centrifuged at 1500 g for 15 min. The platelet pellet is then removed, washed in normal saline solution with 0.1% (w/v) dextrose, and 600 µCi of indium-111 oxine (Amersham Co.) is added to the platelet suspension. Following a 10-min incubation at room temperature, 3 mL of platelet-poor plasma is added and the platelets are incubated for an additional 2 min. The mix is centrifuged at 1500 g for 5 min to form a platelet pellet, the supernatant and excess $^{111}$In oxine removed, and the platelets resuspended in 5 mL of reserved plasma. Approximately 0.5 mCi of indium-111 oxine labeled platelets are reinjected into the baboon. Platelet function is not altered by this technique, when studied by either thrombin stimulated platelet release of $^{14}$C serotonin or by morphological studies of dense body distribution.

Platelet Deposition Measurement: Platelet uptake on test surfaces is monitored over a 60-min period using scintillation camera imaging of the 172 keV In g photon peak. A high-sensitivity $^{99}$Tc collimator was utilized, and images are acquired with a GE 400T scintillation camera (General Electric, Milwaukee, Wis.) interfaced with a Medical Data Systems A3 image processing system (Ann Arbor, Mich.). Immediately before imaging, 5-min images are acquired of the 200 µL sample of platelet concentrate (injection standard) and of a segment of 4.0 mm i.d. Silastic tubing filled with autologous blood and having the same luminal volume as the test graft segment (blood standard). Images are obtained continuously with data storage at 5-min intervals. Deposited $^{111}$In-platelet activity is calculated by subtracting the blood standard activity from all dynamic study images. Data are converted, at each time point, to total platelet deposition per unit test surface, as follows:

$$\text{Platelets/unit surface area} = \frac{\left[\begin{array}{c}\text{test surface area } (cpm) - \\ \text{background activity } (cpm)\end{array}\right]}{\text{blood blood specific activity } (cpm/\text{mL})} \times \text{platelet/mL}$$

where $$\text{Blood specific activity} = \frac{\left[\begin{array}{c}\text{blood } std\ (cpm) - \\ \text{backgournd } (cpm)\end{array}\right](111\text{ln fraction in platelets})}{vol \text{ of the blood } std\ (\text{mL})}$$

Total fibrin deposition: Homologous baboon fibrinogen was purified and labeled with $^{125}$I as described (36). The labeled fibrinogen preparation was 90% clottable. In total, 5 mCi of $^{125}$I-fibrinogen was injected intravenously 10 min prior to shunt studies. After blood exposure for 1 h, the prosthesis was thoroughly rinsed with isotonic saline. After allowing at least 30 days for the $^{111}$In to decay ($t_{1/2}$=2.8 d), $^{125}$I-activity was measured using a gamma counter. Total fibrin accumulation was calculated by dividing the deposited $^{125}$I-radioactivity (cpm) by the clottable fibrinogen radioactivity (cpm/mL) and multiplying by the circulating fibrinogen concentration (mg/mL) as measured in each experiment [36, 37].

Results and Discussion

Figure 20:
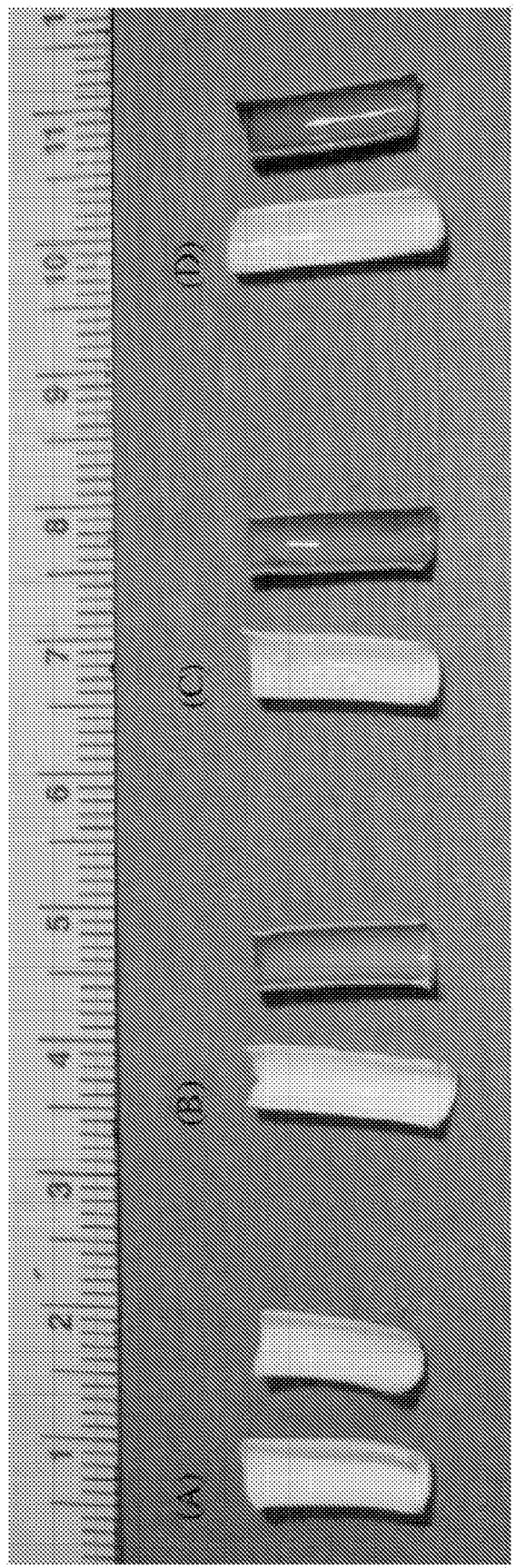
FIG. 20A shows plain ePTFE.
FIG. 20B shows after elastin impregnation.
FIG. 20C shows after layer-by-layer elastin deposition.
FIG. 20D shows after 24-h flow conditioning in PBS at 37° C. The figures shows macroscopic photographs of unstained (left) and Coomassie-stained (right) graft samples

Fabrication of an elastin-impregnated ePTFE vascular graft: Following impregnation and post-coating with the elastin-mimetic polypeptide, the luminal surface of the ePTFE vascular graft is macroscopically smooth. The elastin film stained uniformly with Coomassie G250 (Bio-rad) and remained intact after exposure to PBS at 500 sec$^{-1}$ for 24 hours (FIG. 20). Prior investigations have confirmed that isolated films are stable, without weight loss, when incubated in PBS at 37° C. for periods of up to 3 months [29].

Figure 21:
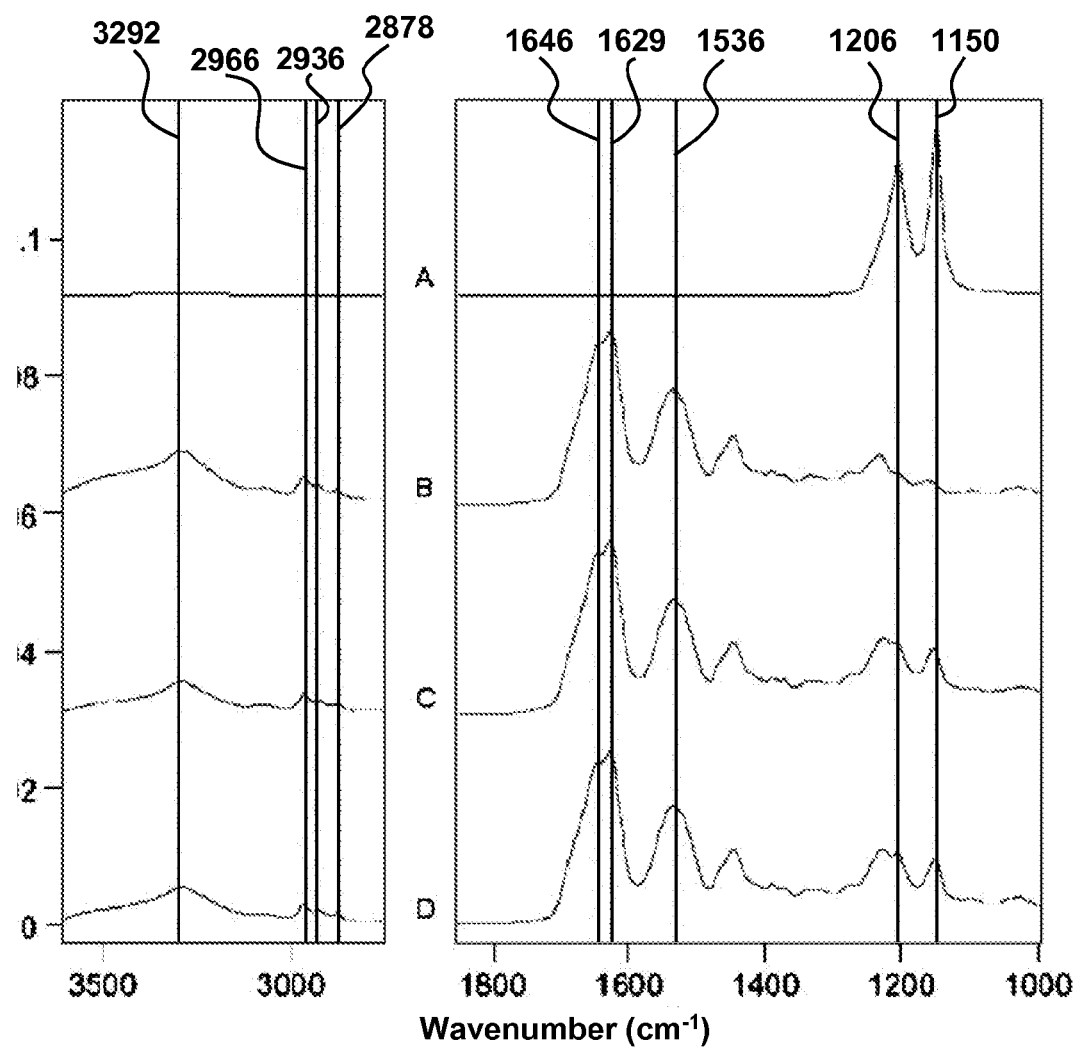
FIG. 21A shows plain ePTFE graft.
FIG. 21B shows plain water-cast elastin-mimetic film.
FIG. 21C shows ePTFE graft after elastin impregnation.
FIG. 21D shows after layer-by-layer elastin deposition. The figures shows infrared ATR spectra from 1800 to 1000 $cm^{-1}$.

Infrared spectra of an uncoated ePTFE graft, a water-cast elastin film, an elastin-impregnated ePTFE graft, and an elastin-impregnated ePTFE graft post-coated with elastin are presented in FIG. 21. Before the graft is coated, characteristic CF$_2$ antisymmetric and symmetric stretching modes at 1208 and 1147 cm$^{-1}$, respectively, are observed from the bare ePTFE graft (FIG. 21A). Amide I and amide II stretching modes at 1646 and 1536 cm$^{-1}$, respectively, are typical of polypeptide films (FIG. 21B). After elastin impregnation and multilayer film coating, amide I and amide II stretching modes appear alongside CF$_2$ stretching modes (FIGS. 21C and D).

Water contact angles were measured on the luminal surface on the graft. As anticipated, advancing/receding contact angles for the bare ePTFE graft were extremely high(125/121° and decreased after elastin impregnation)(43/40° consistent with coverage of the ePTFE surface. These values agree with those measured for B9 elastin films cast from cold water)(47/42°. In contrast, Defife et al. obtained contact angles of 69° for surface grafted-(GVGVP)$_{100}$ on silicone rubber [8]. Contact angles of the post-coated graft could not be measured due to the hydrophilic nature of the coating with complete wetting of the film surface.

Figure 22:
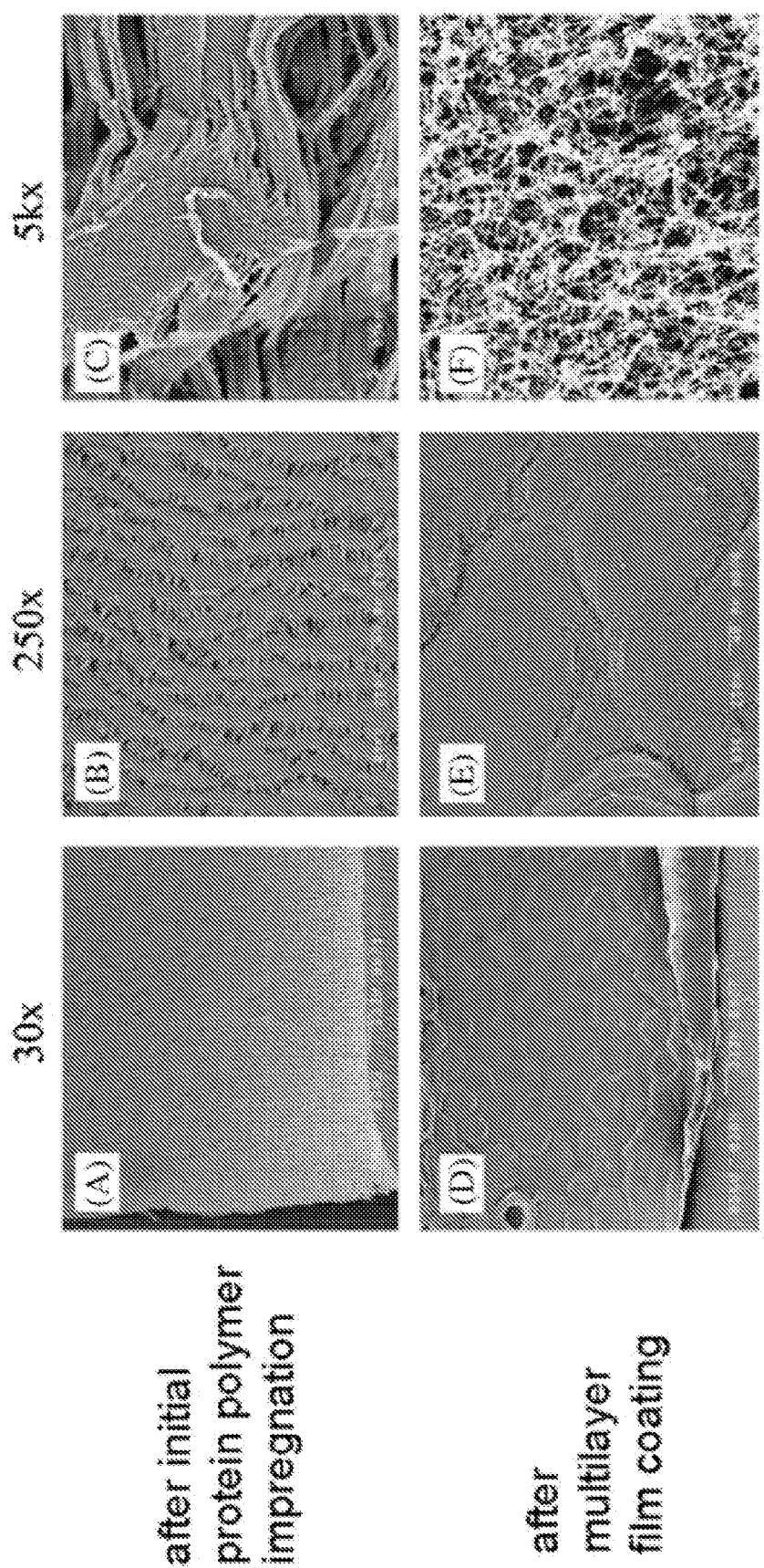
FIG. 22 shows scanning electron micrographs of ePTFE vascular grafts processed by critical point drying. Scale bar in FIG. 22A scale is 333 μm.

Microstructural characterization of the elastin protein polymer film and elastin-mimetic impregnated vascular grafts using scanning electron microscopy Scanning electron micrographs (SEM) of impregnated and post-coated elastin grafts are presented in FIG. 22. Prior to impregnation with the elastin-mimetic protein polymer, ePTFE has a characteristic fibril and node structure. Following the impregnation step, the fibrils are covered with a thin layer of the elastin-mimetic polypeptide (FIG. 22A-C). After application of two post-coated layers, the surface has a smooth cobblestone appearance, and the underlying ePTFE architecture is no longer visible (FIG. 22D-E). As previously observed (18), the elastin-mimetic hydrogel displays an open-cell microstructure, which was well preserved by critical point drying (FIG. 22F).

Figure 23:
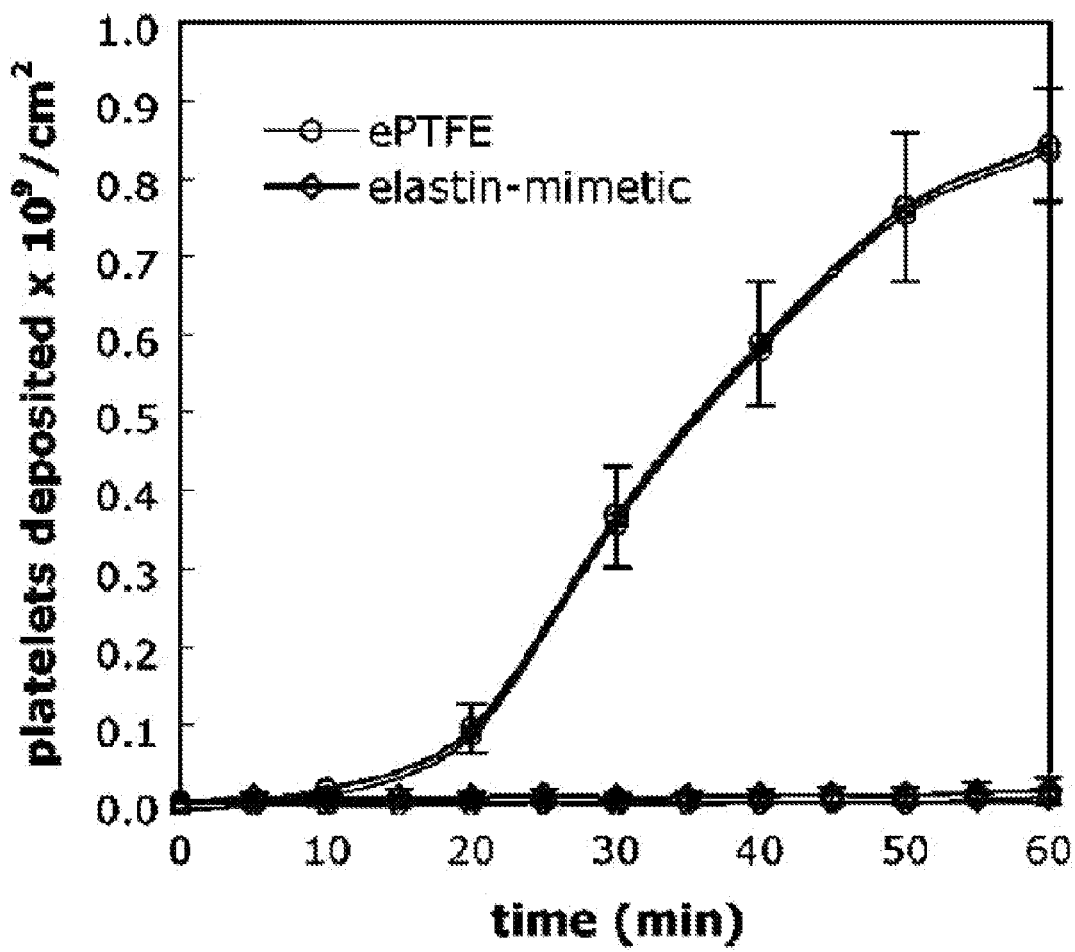
FIG. 23. Platelet deposition normalized by surface area over a 1-h time period (n=6).
Figure 24:
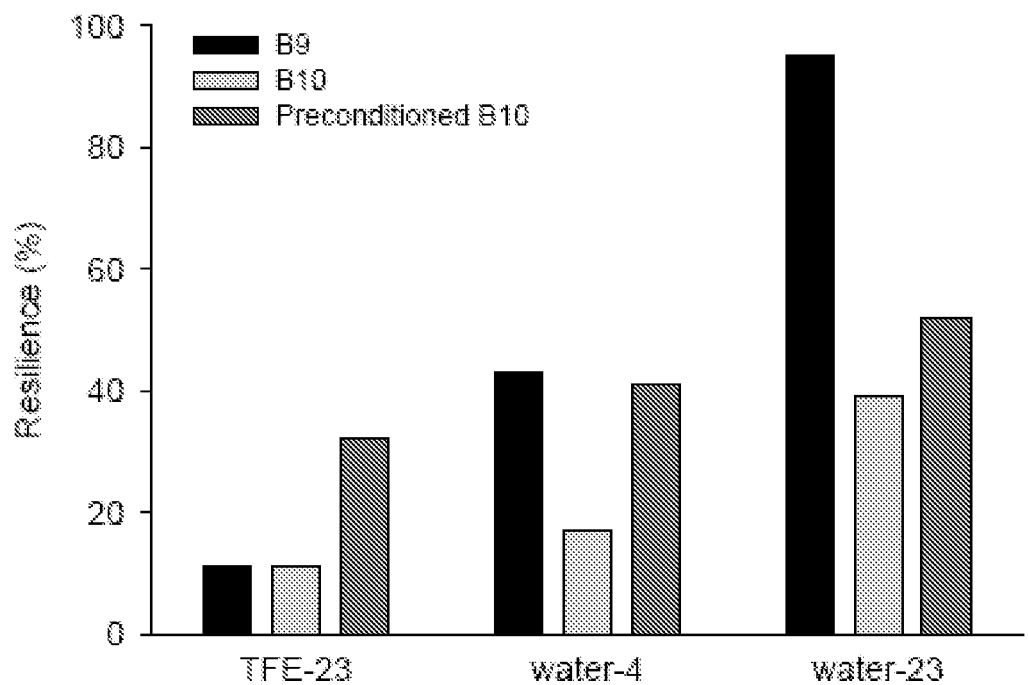
FIG. 24. Resilience of B9 and B10 scaffolds. Samples are cyclically stretched to 30% strain with a rest period of 5 minutes between cycles. Resilience is measured from the first loading loop for non-preconditioned samples and measured from the $10^{th}$ loading loop for preconditioned B10 samples. Data indicate that increased hydrophobicity of endblocks decreases resilience of elastin-mimetic scaffold but mechanical preconditioning enhances resilience.
Figure 25:
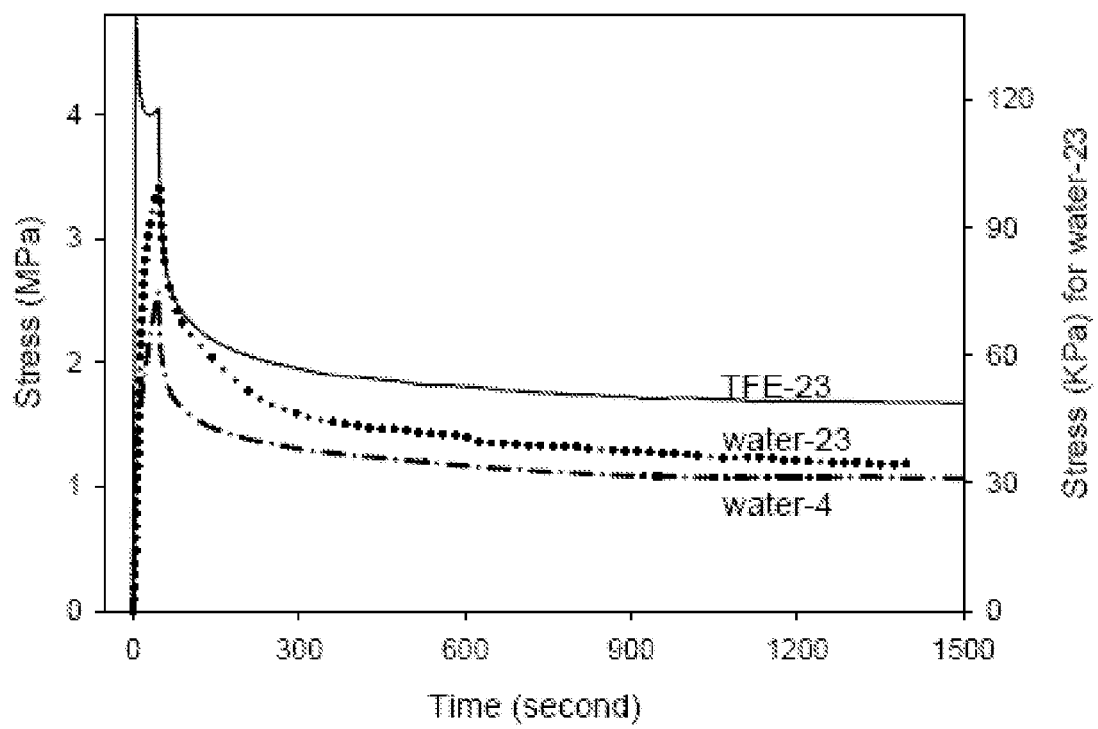
FIG. 25. Stress relaxation of B10 scaffolds under different cast conditions. Samples are stretched to 30% strain at a constant rate of 5 mm/min and then held at this constant strain. Rapid stress relaxation occurs in the first few hundreds of seconds. At 20 minutes, stress decreases from 2.6 MPa to 1.1 MPa, 100 kPa to 35 kPa, and 4.0 Mpa to 1.7 MPa in water-4 scaffold, water-23 scaffold and TFE-23 scaffold, respectively. The first stress drop in TFE-23 scaffold prior to 30% deformation is due to the strain-induced damage effect.

Blood-contacting properties of a small diameter ePTFE graft coated with an elastin-mimetic polypeptide in a baboon ex vivo shunt model: Small-diameter ePTFE vascular grafts (4 mm i.d.) are placed in a femoral arteriovenous shunt at a constant blood flow rate of 100 mL/min. Throughout a 1-hr time period, minimal platelet deposition was observed on elastin-coated ePTFE graft surfaces compared to a reference set of uncoated controls, 4 mm i.d., 30 µm pore size (FIG. 23). Total adsorbed fibrinogen during the test period was 0.03±0.02 mg/cm$^2$ for the elastin-coated grafts compared to 1.44±0.75 mg/cm$^2$ adsorbed on uncoated ePTFE grafts ($p<0.05$).

The generation of elastin-mimetic thin films for blood contacting applications has been motivated by the observation that as a constituent structural protein of the vascular wall, elastin elicits minimal platelet adhesion and aggregation[38, 39]. As such, Ito and colleagues initially coated polyethylene terephthalate vascular grafts with coacervated native α-elastin and noted in vitro inhibition of smooth muscle cell migration without an effect on endothelial cell motility, which suggested that such a coating might inhibit the formation of anastomotic intimal hyperplasia [9]. Subsequently, Defife et al. photochemically linked soluble and crosslinked poly(VPGVG) to silicone via amino-terminal lysine residues and demonstrated reduced fibrinogen and immunoglobulin G adsorption in vitro, as well as decreased release of proinflammatory cytokines by monocytes [8]. Recently, Woodhouse et al. passively adsorbed a recombinant elastin polypeptide, EP20-24-24, that consists of exons 20, 21, 23, and 24 of the human elastin gene onto polyethylene terephthalate (Mylar™), a poly(tetrafluoroethylene-ethylene) copolymer (Tefzel™), and a polycarbonate polyurethane (Corethane™). Decreased platelet deposition and activation was observed in vitro and occlusion times were prolonged on coated polyurethane catheters placed in the right atrium of rabbits [10]. Consistent with these investigations, we have observed that a recombinant elastin-mimetic protein polymer displays minimal thrombogenicity using a primate model. It bears emphasis that the hemostatic system of the baboon most closely resembles that of man[40]. For example, although the prothrombin time (PT) is slightly prolonged in the baboon, the activated partial thromboplastin time (PTT), fibrinogen level, Factor VIII clotting activity, and thrombin time (TT) are similar in both species. Additionally, baboon and human Factor VIII antigen cross-react, and the platelets of both species are equivalent in size distribution, number of dense bodies, and responsiveness to collagen, ristocetin, and arachadonic acid [41].

As illustrated in this report, triblock elastin-mimetic protein polymers is processable into multiple forms, including stable films that can be physically impregnated into ePTFE vascular prostheses generating a smooth luminal surface. Moreover, as demonstrated in previous studies, the capacity to incorporate amphiphilic drugs into these protein-based materials may provide an additional mechanism for the control of biological responses at blood- and tissue-materials [29].

The development of a small diameter vascular prosthesis with favorable blood-contacting properties remains a significant clinical challenge. In this report, we have demonstrated that a recombinant elastin-mimetic copolymer can be used to generate a hydrogel coating on the luminal surface of an ePTFE vascular prosthesis. Elastin-based protein polymers are a promising class of materials characterized by high degree of biocompatibility, a tunable range of mechanical properties from plastic to elastic, a variety of processing options including gels, films, and nanofibers, and the potential for the incorporation of bioactive compounds within the polymer backbone itself or impregnated within a hydrogel. We anticipate that elastin-mimetic materials will find utility in a number of vascular and non-vascular biomaterial applications.

The following U.S. patents and published patent applications are specifically incorporated by reference to the extent not inconsistent with the present disclosure: U.S. Pat. No. 7,244,830; 2004-0110439; 2004-0063200 and 2004-0171545.

A summary of sequence listings is provided in TABLE 16. In an embodiment, the invention is directed to any one or more of these sequences. TABLES 12-15 provide the various amino acid sequences and a corresponding DNA sequence for B10, lysB10, B9, and R4.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated. Although nucleotide sequences are specifically exemplified as DNA sequences, those sequences as known in the art are also optionally RNA sequences (e.g., with the T base replaced by U, for example).

Whenever a range is given in the specification, for example, a temperature range, a time range, or a composition or concentration range, all intermediate ranges and subranges, as well as all individual values included in the ranges given (e.g., within a range and at the ends of a range) are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLE 12

Amino Acid and DNA sequence of B10

```
B10: [VPAVG(IPAVG)4][(IPAVG)5]33(IPGAG)(VPGAG)VPGEG(VPGAG)2
     [(VPGAG)2VPGEG(VPGAG)2]20[VPAVG(IPAVG)4][(IPAVG)5]33VPGVG

Val Pro Ala Val Gly Ile Pro Ala Val Gly Ile Pro
GTT CCT GCT GTT GGT ATT CCG GCT GTT GGT ATC CCA

Ala Val Gly Ile Pro Ala Val Gly Ile Pro Ala
    GCT GTT GGT ATC CCA GCT GTT GGC ATT CCG GCT

Val Gly [Ile Pro Ala Val Gly Ile Pro Ala Val
    GTA GGT ATT  CCT GCT GTT GGT ATT CCG GCT GTT

Gly Ile Pro Ala Val Gly Ile Pro Ala Val Gly
    GGT ATC CCA GCT GTT GGT ATC CCA GCT GTT GGC

Ile Pro Ala Val Gly]5 Ile Pro Gly Ala Gly Val
    ATT CCG GCT GTA GGT]33 ATT CCA GGT GCA GGC GTA

Pro Gly Ala Gly Val Pro Gly Glu Gly Val Pro
    CCG GGT GCT GGC GTT CCG GGT GAA GGT GTT CCA

Gly Ala Gly Val Pro Gly Ala Gly [Val
    GGC GCA GGT GTA CCG GGT GCG GGT [GGT

Pro Gly Ala Gly Val Pro Gly Ala Gly Val Pro
    CCA GGT GCA GGC GTA CCG GGT GCT GGC GTT CCG

Gly Glu Gly Val Pro Gly Ala Gly Val Pro Gly
    GGT GAA GGT GTT CCA GGC GCA GGT GTA CCG GGT

Ala Gly]2 Val Pro Ala Val Gly Ile Pro Ala Val
    GCG GGT]20 GTT CCT GCT GTT GGT ATT CCG GCT GTT

Gly Ile Pro Ala Val Gly Ile Pro Ala Val Gly
    GGT ATC CCA GCT GTT GGT ATC CCA GCT GTT GGC

Ile Pro Ala Val Gly [Ile Pro Ala Val Gly Ile
    ATT CCG GCT GTA GGT [ATT CCT GCT GTT GGT ATT

Pro Ala Val Gly Ile Pro Ala Val Gly Ile Pro
    CCG GCT GTT GGT ATC CCA GCT GTT GGT ATC CCA

Ala Val Gly Ile Pro Ala Val Gly]5
    GCT GTT GGC ATT CCG GCT GTA GGT]33

Val Pro Gly Val Gly Stop Stop
    GTA CCA GGT GTA GGC TAA  TAA
```

TABLE 13

Amino Acid and DNA sequence of lysB10

LysB10:
[VPAVGKVPAVG(IPAVG)$_4$][(IPAVG)$_5$]$_{33}$
[IPAVGKAAKVPGAG][(VPGAG)$_2$VPGEG(VPGAG)$_2$]$_{28}$
[VPAVGKAAKVPGAGVPAVG(IPAVG)$_4$][(IPAVG)$_5$]$_{33}$[IPAVGKAAKA]

```
Val Pro Ala Val Gly Lys Val Pro Ala Val Gly Ile Pro
                                                Ala Val
GTT CCA GCT GTT GGT AAG GTT CCA GCT GTT GGT ATC
                                            CCA GCT GTT
    Gly Ile Pro Ala Val Gly Ile Pro Ala Val Gly Ile
                                                Pro Ala
    GGT ATC CCA GCT GTT GGC ATT CCG GCT GTA GGT
                                            ATC CCG GCA
    Val Gly [Ile Pro Ala Val Gly Ile Pro Ala Val Gly
    Ile Pro
    GTG GGC ATT CCG GCT GTT GGT ATC CCA GCT GTT
    GGT ATC CCA
    Ala  Val Gly Ile Pro Ala Val Gly Ile Pro Ala Val
         Gly]$_{33}$ Ile
    GCT GTT  GGC ATT CCG GCT GTA GGT ATC CCG GCA
    GTG GGC]$_{33}$   ATT
    Pro Ala  Val Gly Lys Ala Ala Lys Val Pro Gly Ala
    Gly [Val

CCA GCT  GTT GGT AAG GCG GCC AAG GTT CCA GGT
    GCT GGC  GTT
    Pro Gly Ala Gly Val Pro Gly Ala Gly Val Pro Gly
    Glu Gly
    CCA GGT GCA GGC GTA CCG GGT GCT GGC GTT CCG
    GGT GAA GGT
    Val Pro Gly Ala Gly Val Pro Gly Ala Gly]$_{28}$ Val Pro
                                                Ala Val
    GTT CCA GGC GCA GGT GTA CCG GGT GCG GGT]$_{28}$
    GTT CCA GCT GTT
    Gly Lys Ala Ala Lys Val Pro Gly Ala Gly Val Pro
                                                Ala Val
    GGT AAG GCG GCC AAG GTT CCA GGT GCA GGC GTT
                                            CCA GCT GTT
    Gly Ile Pro Ala Val Gly Ile Pro Ala Val Gly Ile
                                                Pro Ala
    GGT ATC CCA GCT GTT GGT ATC CCA GCT GTT GGC
    ATT CCG GCT
    Val Gly Ile Pro Ala Val Gly [Ile Pro Ala Val Gly
    Ile Pro
    GTA GGT ATC CCG GCA GTG GGC ATT CCG GCT GTT
    GGT ATC CCA
    Ala Val Gly Ile Pro Ala Val Gly Ile Pro Ala Val
    Gly Ile
    GCT GTT GGT ATC CCA GCT GTT GGC ATT CCG GCT
    GTA GGT ATC
    Pro Ala Val Gly]$_{33}$ Ile Pro Ala Val Gly Lys Ala Ala
    Lys Ala
    CCG GCA GTG GGC]$_{33}$    ATT CCA GCT GTT GGT AAG
    GCG GCC AAG GCG
    Stop
    TAA
```

TABLE 14

Amino Acid and DNA sequence of B9

B9:
{VPAVG[(IPAVG)$_4$(VPAVG)]$_{16}$IPAVG}[VPGVG[(VPGVG)$_2$VPGEG(VPGVG)$_2$]$_{48}$VPGVG]{VPAVG[(IPAVG)$_4$(VPAVG)]$_{16}$IPAVG}

```
Val Pro Ala Val Gly Ile Pro Ala Val Gly Ile Pro Ala
GTA CCT GCT GTT GGT [ATT CCG GCT GTT GGT ATC CCA
    GCT
Val Gly Ile Pro Ala Val Gly Ile Pro Ala Val Gly
GTT GGT ATC CCA GCT GTT GGC ATT CCG GCT GTA GGT
Val Pro Ala Val Gly]$_{16}$ Ile Pro Ala Val Gly
GTA CCT GCT GTT GGT]16 ATT CCG GCT GTT GGT
[Val Pro Gly Val Gly Val Pro Gly Val Gly Val Pro Gly
[GTA CCT GGT GTT GGC GTT CCG GGT GTA GGT GTA CCA
    GGC
```

TABLE 14-continued

Amino Acid and DNA sequence of B9

Glu Gly Val Pro Gly Val Gly Val Pro Gly Val Gly]48
Val Pro Gly
GAA GGT GTA CCG GGT GTT GGC GTA CCA GGC GTT GGC]48
GTA CCT GGT

Val Gly
GTT GGC

Val Pro Ala Val Gly [Ile Pro Ala Val Gly Ile Pro Ala
GTA CCT GCT GTT GGT [ATT CCG GCT GTT GGT ATC CCA
GCT

Val Gly Ile Pro Ala Val Gly Ile Pro Ala Val Gly
GTT GGT ATC CCA GCT GTT GGC ATT CCG GCT GTA GGT

Val Pro Ala Val Gly]16 Ile Pro Ala Val Gly
GTA CCT GCT GTT GGT]16 ATT CCG GCT GTT GGT

TABLE 15

Amino Acid and DNA sequence of R4

R4: VPAVGKVPAVG[(IPAVG)5]16(IPAVGIPAVG)KAAK(VPGAGVPGIG)[(VPGIG)5]15
(VPGIGVPAVG)KAAK(VPGAGVPAVG)[(IPAVG)5]16IPAVGVPAVGKAAKA

Val Pro Ala Val Gly Lys Val Pro Ala Val Gly [Ile Pro
GTT CCA GCT GTT GGT AAG GTT CCA GCT GTT GGT [ATT
CCG

Ala Val Gly Ile Pro Ala Val Gly Ile Pro Ala Val
GCT GTT GGT ATC CCA GCT GTT GGT ATC CCA GCT
GTT

Gly Ile Pro Ala Val Gly Ile Pro Ala Val Gly]16 Ile
GGC ATT CCG GCT GTA GGT ATC CCG GCA GTG GGC]16
ATT

Pro Ala Val Gly Ile Pro Ala Val Gly Lys Ala Ala
CCG GCT GTT GGT ATT CCA GCT GTT GGT AAG GCG
GCC

Lys Val Pro Gly Ala Gly Val Pro Gly Ile Gly
[Val
AAG GTT CCA GGT GCA GGC GTT CCA GGT ATT GGT
[GTA

Pro Gly Ile Gly Val Pro Gly Ile Gly Val Pro Gly
CCT GGT ATT GGT GTT CCG GGT ATC GGT GCG CCA
GGC

Ile Gly Val Pro Gly Ile Gly Val Pro Gly Ile
Gly]15
ATC GGT GTA CCG GGT ATT GGC GTT CCA GGC ATT
GGC]15

Val Pro Gly Ile Gly Val Pro Ala Val Gly Lys Ala
GTA CCT GGT ATT GGT GTT CCA GCT GTT GGT AAG
GCG

Ala Lys Val Pro Gly Ala Gly Val Pro Ala Val Gly
GCC AAG GTT CCA GGT GCA GGC GTT CCA GCT GTT
GGT

[Ile Pro Ala Val Gly Ile Pro Ala Val Gly Ile Pro
[ATT CCG GCT GTT GGT ATC CCA GCT GTT GGT ATC
CCA

Ala Val Gly Ile Pro Ala Val Gly Ile Pro Ala Val
GCT GTT GGC ATT CCG GCT GTA GGT ATC CCG GCA
GTG

Gly]16 Ile Pro Ala Val Gly Ile Pro Ala Val Gly Lys
GGC]16 ATT CCG GCT GTT GGT ATT CCA GCT GTT GGT
AAG

Ala Ala Lys Ala Stop
GCG GCC AAG GCG TAA

TABLE 16

Summary of Sequences

| SEQ ID NO: | Ident. | SEQUENCE | Type |
|---|---|---|---|
| 1 | B10 center1 | IPGAG | PRT |
| 2 | B10 center2 | VPGAG | PRT |

TABLE 16-continued

Summary of Sequences

| SEQ ID NO: | Ident. | SEQUENCE | Type |
|---|---|---|---|
| 3 | B10 center3 | VPGEG | PRT |
| 4 | B10 end1 | VPAVG | PRT |
| 5 | B10 end2 | IPAVG | PRT |
| 6 | B10 END | VPGVG | PRT |
| 7 | B10 end block | [VPAVG(IPAVG)$_4$][(IPAVG)$_5$]$_{33}$ | PRT |
| 8 | B10 center | (IPGAG)(VPGAG)VPGEG(VPGAG)$_2$[(VPGAG)$_2$VPGEG(VPGAG)$_2$]$_{20}$ | PRT |
| 9 | B10 | [VPAVG(IPAVG)$_4$][(IPAVG)$_5$]$_{33}$-X-[VPAVG(IPAVG)$_4$][(IPAVG)$_5$]$_{33}$<br>X = (IPGAG)(VPGAG)VPGEG(VPGAG)$_2$[(VPGAG)$_2$VPGEG(VPGAG)$_2$]$_{20}$ | PRT |
| 10 | B10 plus 5mer | [VPAVG(IPAVG)$_4$][(IPAVG)$_5$]$_{33}$(IPGAG)(VPGAG)VPGEG(VPGAG)$_2$<br>[(VPGAG)$_2$VPGEG(VPGAG)$_2$]$_{20}$[VPAVG(IPAVG)$_4$][(IPAVG)$_5$]$_{33}$VPGVG | PRT<br>PRT |
| 11 | DNA of 1 | ATT CCA GGT GCA GGC | DNA/RNA |
| 12 | DNA of 2 | GTA CCG GGT GCT GGC | DNA/RNA |
| 13 | DNA of 3 | GTT CCG GGT GAA GGT | DNA/RNA |
| 14 | DNA of 4 | GTT CCT GCT GTT GGT | DNA/RNA |
| 15 | DNA of 5 | ATT CCG GCT GTT GGT | DNA/RNA |
| 16 | DNA of 7 (B10 end) | GTT CCT GCT GTT GGT ATT CCG GCT GTT GGT ATC CCA<br>GCT GTT GGT ATC CCA GCT GTT GGC ATT CCG GCT<br>GTA GGT [ATT CCT GCT GTT GGT ATT CCG GCT GTT<br>GGT ATC CCA GCT GTT GGT ATC CCA GCT GTT GGC<br>ATT CCG GCT GTA GGT]$_{33}$ | DNA/RNA |
| 17 | DNA of 7 (B10 end & 5mer) | GTT CCT GCT GTT GGT ATT CCG GCT GTT GGT ATC CCA<br>GCT GTT GGT ATC CCA GCT GTT GGC ATT CCG GCT<br>GTA GGT [ATT CCT GCT GTT GGT ATT CCG GCT GTT<br>GGT ATC CCA GCT GTT GGT ATC CCA GCT GTT GGC<br>ATT CCG GCT GTA GGT]$_{33}$<br>GTA CCA GGT GTA GGC | DNA/RNA |
| 18 | AA seq from 17 | Amino Acid Sequence encoded by SEQ ID NO: 17 | PRT |
| 19 | DNA of 8 (B10 center) | ATT CCA GGT GCA GGC GTA<br>CCG GGT GCT GGC GTT CCG GGT GAA GGT GTT CCA<br>GGC GCA GGT GTA CCG GGT GCG GGT [GGT<br>CCA GGT GCA GGC GTA CCG GGT GCT GGC GTT<br>CCG<br>GGT GAA GGT GTT CCA GGC GCA GGT GTA CCG GGT<br>GCG GGT]$_{20}$ | DNA/RNA |
| 20 | AA seq from 18 | Amino Acid Sequence encoded by SEQ ID NO: 19 | PRT |
| 21 | DNA of 9 | SEQ ID NO: 16-SEQ ID NO: 19-SEQ ID NO: 16 | DNA/RNA |
| 22 | | SEQ ID NO: 16-SEQ ID NO: 19-SEQ ID NO: 17 | DNA/RNA |
| 23 | lysB10 first endblock | [VPAVGKVPAVG(IPAVG)$_4$][(IPAVG)$_5$]$_{33}$ | PRT |
| 24 | lysB10 second endblock | [VPAVGKAAKVPGAGVPAVG(IPAVG)$_4$][(IPAVG)$_5$]$_{33}$[IPAVGKAAKA] | PRT |
| 25 | lysB10 central block | [IPAVGKAAKVPGAG][(VPGAG)$_2$VPGEG(VPGAG)$_2$] | PRT |
| 26 | lysB10 | [VPAVGKVPAVG(IPAVG)$_4$][(IPAVG)$_5$]$_{33}$<br>[VPAVGKAAKVPGAG][(VPGAG)$_2$VPGEG(VPGAG)$_2$]$_{28}$<br>[VPAVGKAAKVPGAGVPAVG(IPAVG)$_4$][(IPAVG)$_5$]$_{33}$ | PRT |
| 27 | B10lys DNA first endblock | GTT CCA GCT GTT GGT AAG GTT CCA GCT GTT<br>GGT ATC CCA GCT GTT<br>GGT ATC CCA GCT GTT GGC ATT CCG GCT GTA<br>GGT ATC CCG GCA<br>GGT GGC [ATT CCG GCT GTT GGT ATC CCA GCT<br>GTT GGT ATC CCA<br>GCT GTT GGC ATT CCG GCT GTA GGT ATC CCG<br>GCA GTG GGC]$_{33}$ | DNA/RNA |

TABLE 16-continued

Summary of Sequences

| SEQ ID NO: | Ident. | SEQUENCE | Type |
|---|---|---|---|
| 28 | AA seq from 27 | Amino Acid Sequence encoded by SEQ ID NO: 27 | PRT |
| 29 | B10lys DNA second endblock | GTT CCA GCT GTT GGT AAG GCG GCC AAG GTT CCA GGT GCA GGC GTT CCA GCT GTT GGT ATC CCA GCT GTT GGT ATC CCA GCT GTT GGC ATT CCG GCT GTA GGT ATC CCG GCA GTG GGC [ATT CCG GCT GTT GGT ATC CCA GCT GTT GGT ATC CCA GCT GTT GGC ATT CCG GCT GTA GGT ATC CCG GCA GTG GGC]$_{33}$ ATT CCA GCT GTT GGT AAG GCG GCC AAG GCG | DNA/RNA |
| 30 | AA seq from 29 | Amino Acid Sequence encoded by SEQ ID NO: 29 | PRT |
| 31 | B10lys DNA central block | ATT CCA GCT GTT GGT AAG GCG GCC AAG GTT CCA GGT GCA GGC GTT CCA GGT GCA GGC GTA CCG GGT GCT GGC GTT CCG GGT GAA GGT GTT CCA GGC GCA GGT GTA CCG GGT GCG GGT]$_{28}$ | DNA/RNA |
| 32 | AA seq from 31 | Amino Acid Sequence encoded by SEQ ID NO: 31 | PRT |
| 33 | B10lys example 2 | K[(IPAVG)$_5$]$_{26}$-KK[(VPGAG)$_4$(VPGEG)]$_{26}$KK-[(IPAVG)$_5$]$_{26}$ KK | PRT |
| 34 | R4 | VPAVGKVPAVG[(IPAVG)$_5$]$_{16}$ (IPAVGIPAVG)KAAK(VPGAGVPGIG) [(VPGIG)$_5$]$_{15}$ (VPGIGVPAVG)KAAK(VPGAGVPAVG) [(IPAVG)$_5$]$_{16}$ IPAVGVPAVGKAAKA | PRT |
| 35 | R4 first endblock | VPAVGKVPAVG[(IPAVG)$_5$]$_{16}$ | PRT |
| 36 | R4 central | (IPAVGIPAVG)KAAK(VPGAGVPGIG) [(VPGIG)$_5$]$_{15}$ | PRT |
| 37 | R4 central2 | VPGIGVPAVG | PRT |
| 38 | R4 lys | KAAK | PRT |
| 39 | R4 endlinker | VPGAGVPAVG | PRT |
| 40 | R4 endblock | [(IPAVG)$_5$]$_{16}$ | PRT |
| 41 | R4 end | IPAVGVPAVGKAAKA | PRT |
| 42 | DNA of R4 | See R4 DNA sequence in Table 15 | DNA/RNA |
| 43 | R1 central | VPGIG | PRT |
| 44 | R1 | K[(VPGIG)$_5$]$_{15}$KK | PRT |
| 45 | R2 central | IPAVG | PRT |
| 46 | R2 | K[(IPAVG)$_5$]$_{16}$KK | PRT |
| 47 | R2-R1-R2 | ([(IPAVG)$_5$]$_{16}$)-KK[(VPGIG)$_5$]$_{15}$KK-([(IPAVG)$_5$]$_{16}$)KK | PRT |
| 48 | R2-R1 | K[(IPAVG)$_5$]$_{16}$KKK[(VPGIG)$_5$]$_{15}$KK | PRT |
| 49 | R2-R1-R2-R1 | K[(IPAVG)$_5$]$_{16}$KK ([(IPAVG)$_5$]$_{16}$)-KK[(VPGIG)$_5$]$_{15}$KK-([(IPAVG)$_5$]$_{16}$)KK | PRT |
| 50 | B9 | {VPAVG[(IPAVG)$_4$VPAVG)]$_{16}$IPAVG}-[X]-{VPAVG[(IPAVG)$_4$VPAVG)]$_{16}$IPAVG}; where [X] is VPGVG[(VPGVG)$_2$VPGEG(VPGVG)$_2$]$_{48}$VPGVG | PRT |
| 51 | B9 endblock | VPAVG[(IPAVG)$_4$(VPAVG)]$_{16}$IPAVG | PRT |
| 52 | B9 central | [(VPGVG)$_2$(VPGEG)(VPGVG)$_2$]$_{48}$ | PRT |
| 53 | B9 Yeast E-block Table 6 | See TABLE 6-Amino Acid sequence | PRT |
| 54 | B9 Yeast E-block Table 6 | See TABLE 6-DNA sequence | DNA/RNA |
| 55 | Lysine insert Table 7 | TCCAGCTGTTGTTAAGGCCGCGAAGGTTCCAGGTGCAGGCGT | DNA/RNA |

TABLE 16-continued

Summary of Sequences

| SEQ ID NO: | Ident. | SEQUENCE | Type |
|---|---|---|---|
| 56 | Lysine adapter Table 7 | GATCCAAGGTTCCAAGAGACGGTACCCGTCTCTTCCAAAGGCCGCGAA | DNA/RNA |
| 57 | R1 ecoli | GTA CCT GGT ATT GGC GTT CCG GGT ATC G-GT GTG CCA GGC ATC GGT GTA CCG GGT ATT GGC GTT CCA GGC ATT GGC | DNA/RNA |
| 58 | R1 ecoli encoded by SEQ ID NO: 57 | Amino Acid Sequence encoded by SEQ ID NO: 57 | PRT |
| 59 | R1 Pichia | GTT CCA GGT ATT GGT GTC CCA GGA ATC G-GT GTT CCT GGA ATT GGA GTC CCA GGT ATT GGA GTT CCA GGT ATA GGT | DNA/RNA |
| 60 | R1 Pichia encoded by SEQ ID NO: 59 | Amino Acid Sequence encoded by SEQ ID NO: 59 | PRT |
| 61 | R2 ecoli | ATT CCG GCT GTT GGT ATC CCA GCT GTT G-GT ATC CCA GCT GTT GGC ATT CCG GCT GTA GGT ATC CCG GCA GTG GGC | DNA/RNA |
| 62 | R2 ecoli encoded by SEQ ID NO: 61 | Amino Acid Sequence encoded by SEQ ID NO: 61 | PRT |
| 63 | R2 Pichia | ATT CCA GCT GTT GGT ATC CCT GCC GTC G-GT ATT CCT GCT GTT GGA ATC CCA GCA GTC GGT ATT CCA GCC GTT GGA | DNA/RNA |
| 64 | R2 Pichia encoded by SEQ ID NO: 59 | Amino Acid Sequence encoded by SEQ ID NO: 63 | PRT |
| 65 | B9 endblock | VPAVG[(IPAVG)$_4$(VPAVG)] | PRT |
| 66 | B9 central | (VPGVG)$_2$(VPGEG)(VPGVG)$_2$ | PRT |
| 67 | B10 endblock | VPAVG(IPAVG)$_4$][(IPAVG)$_5$ | PRT |
| 68 | B10 center | (VPGAG)$_2$VPGEG(VPGAG)$_2$ | PRT |
| 69 | B10 center | (IPGAG)(VPGAG)VPGEG(VPGAG)$_2$ | PRT |
| 70 | B10 center | (VPGAG)$_2$VPGEG(VPGAG)$_2$[(IPGAG)(VPGAG)VPGEG(VPGAG)$_2$] | PRT |
| 71 | lysB10 | [VPAVGKVPAVG(IPAVG)$_4$][(IPAVG)$_5$]$_{33}$-X-[VPAVGKAAKVPGAGVPAVG(IPAVG)$_4$][(IPAVG)$_5$]$_{33}$ [IPAVGKAAKA] wherein X is IPAVGKAAKVPGAG][(VPGAG)$_2$VPGEG(VPGAG)$_2$]$_{28}$ | PRT PRT |

REFERENCES

1. Ferrari, F.; Cappello, J. Biosynthesis of Protein Polymers. In: Protein-Based Materials, McGrath, K. P.; Kaplan, D. L., Eds. Birkhäuser: Boston, 1997; pp 37-117.
2. Petka, W. A.; Harden, J. L.; McGrath, K. P.; Wirtz, D.; Tirrell, D. A. Science 1998, 281, (5375), 389-392.
3. (a) Cappello, J.; Crissman, J. W.; Crissman, M.; Ferrari, F. A.; Textor, G.; Wallis, O.; Whitledge, J. R.; Zhou, X.; Burman, D.; Aukerman, L.; Stedronsky, E. R. J Controlled Release 1998, 53, (1-3), 105-117; (b) Nagarsekar, J.; Crissman, M.; Crissman, F.; Ferrari, J.; Cappello, H.; Ghandehari, H. J. Biomed. Mater. Res. 2002, 62, (2), 195-203.
4. Wright, E. R.; Conticello, V. P. Adv Drug Delivery Rev 2002, 54, (8), 1057-1073.
5. Wright, E. R.; McMillan, R. A.; Cooper, A.; Apkarian, R. P.; Conticello, V. P. Adv Funct Mater 2002, 12, (2), 149-154.
6. Wu, X. Y.; Sallach, R.; Haller, C.; Caves, J.; Nagapudi, K.; Conticello, V. P.; Levenston, M. E.; Chaikof, E. L. Biomacromolecules 2005, 6, 3037-3044.
7. Patel, A.; Fine, B.; Sandig, M.; Mequanint, K. Cardiovascular Research 2006, 71, (1), 40-49.
8. Fung, Y. C., Biomechanics: Mechanical properties of living tissues. 2nd ed.; Springer-Verlag: New York, 1993; p xviii, 568 p.
9. Wagenseil, J. E.; Wakatsuki, T.; Okamoto, R. J.; Zahalak, G. I.; Elson, E. L. J Biomech Eng Trans ASME 2003, 125, (5), 719-725.
10. Nagapudi, K.; Brinkman, W. T.; Thomas, B. S.; Park, J. O.; Srinivasarao, M.; Wright, E.; Conticello, V. P.; Chaikof, E. L. Biomaterials 2005, 26, (23), 4695-4706.
11. Urry, D. W. J Phys Chem B 1997, 101, (51), 11007-11028.
12. Urry, D. W.; Luan, C. H.; Harris, C. M.; Parker, T. M., Protein-based materials with a profound range of properties and applications: the elastin DTt hydrophobic paradigm. In Protein-based materials, McGrath, K.; Kaplan, D., Eds. Birkhauser: Boston, 1997.
13. Nagapudi, K.; Brinkman, W. T.; Leisen, J.; Thomas, B. S.; Wright, E. R.; Haller, C.; Wu, X. Y.; Apkarian, R. P.; Conticello, V. P.; Chaikof, E. L. Macromolecules 2005, 38, (2), 345-354.

14. Ferry, J. Viscoelastic properties of polymers. Wiley: New York, 1961; p 482.
15. Bellingham, C. M.; Lillie, M. A.; Gosline, J. M.; Wright, G. M.; Starcher, B. C.; Bailey, A. J.; Woodhouse, K. A.; Keeley, F. W. Biopolymers 2003, 70, (4), 445-455.
16. Treloar, L. R. G. The physics of rubber elasticity. 3d ed.; Clarendon Press: Oxford, 1975; p xii, 310.
17. Flory, P. J. Principles of polymer chemistry. Cornell University Press: Ithaca, 1953; p 672.
18. De Gennes, P.-G. Scaling concepts in polymer physics. Cornell University Press: Ithaca, N.Y., 1979; p 324.
19. Kim, W.; McMillan, R. A.; Snyder, J. P.; Conticello, V. P. J Am Chem Soc 2005, 127, (51), 18121-18132.
20. Arruda, E. M.; Boyce, M. C. J Mech Phys Solids 1993, 41, (2), 389-412.
21. *Heart Disease and Stroke Statistics.* 2005, American Heart Association.
22. Baim D S, *Percutaneous Treatment of Saphenous Vein Graft Disease.* Journal of the American College of Cardiology, 2003. 42(8): p. 1370-1387.
23. MS, C., *The ideal small arterial substitute: a search for the holy grail?* FASEB J, 1998. 12: p. 43-35.
24. Ballyk P. D., W. C., Butany J., Ojha M., *Compliance mismatch may promote graft-artery intimal hyperplasia by altering suture-line stresses.* Journal of Biomechanics, 1998. 31: p. 229-237.
25. Bos G W, P. A., Beugeling T, van Aken W G, Feijen J, *Small Diameter Vascular Graft Prosthesis: Current Status.* Archives of Physiology and Biochemistry, 1998. 106(2): p. 100-115.
26. Kannan R Y, S. H., Butler P E, Hamilton G, Seifalian A M, *Current Status of Prosthetic Bypass Grafts: A Review.* J Biomed Mater Res Part B: Appl Biomater, 2005. 74B: p. 570-581.
27. Tai N R, S. H., Edwards A, Hamilton G, Seifalian A M, *Compliance Properties of Conduits used in Vascular Reconstruction.* British Journal of Surgery, 2000. 87: p. 1516-1524.
28. Esquivel C O, B. F., *Why Small Caliber Vascular Grafts Fail: A reivew of clinical and experimental experience and the significance of the interaction of blood at the interface.* Journal of Surgical Research, 1983. 41: p. 1-15.
29. Greisler H P, G. C., Ren D, Kang S S, Kim D U, *Biointeractive Polymers and Tissue Engineered Blood Vessels.* Biomaterials, 1996. 17: p. 329-336.
30. Meinhart J G, D. M., Fischlein T, Howanietz N, Froschl A, Zilla P, *Clinical Autologous In Vitro Endothelialization of 153 Infrainguinal ePTFE grafts.* Ann Thorac Surg, 2001. 71: p. S327-331.
31. Weinberg C B, B. E., *A Blood Vessel Model Constructed from Collagen and Cultured Vascular Cells.* Science, 1986. 231(4736): p. 397-400.
32. Nerem R M, E. A., *The tissue engineering of blood vessels and the heart.* American Journal of Transplantation, 2004. 4(supp 6): p. 36-42.
33. Nerem R M, S. D., *Vascular Tissue Engineering.* Annu rev biomed eng, 2001. 3: p. 225-243.
34. Seliktar D, B. R., Vito R P, Nerem R M, *Dynamic Mechanical Conditioning of Collagen-Gel Blood Vessel Constructs Induces Remodeling in Vitro.* Annals of Biomedical Engineering, 2000. 28: p. 351-362.
35. Girton T S, O. T., Grassl E D, Isenberg B C, Tranquillo R T, *Mechanisms of Stiffening and Strengthening in Media-Equivalents Fabricated using Glycation.* J biomech Eng, 2000. 122: p. 216-223.
36. L'Heureux N, P. S., Labbe R, Germain L, Auger F, *A completely biological tissue-engineered human blood vessel.* FASEB J, 1998. 12: p. 47-56.
37. L'Heureux N, S. J., Auger F A, Lagaud G J, Germain L, Andriantsitohaina R, *A Human Tissue-Engineered Vascular Media: a new model for pharmacological studies of contractile responses.* FASEB J, 2001. 15: p. 515-524.
38. Niklason L E, G. J., Abbott W M, Hirschi K K, Houser S, Marini R, Langer R, *Functional Arteries Grown in Vitro.* Science, 1999. 284(5413): p. 489.
39. Badylak S F, L. G., Coffey A, Geddes L A, *Small Intestinal Submucosa as a Large Diameter Vascular Graft in the Dog.* Journal of Surgical Research, 1989. 47: p. 74-80.
40. Dardik, H., *The second decade of experience with the umbilical vein graft for lower-limb revascularization.* Cardiovascular Surgery, 1995. 3(3): p. 265-269.
41. Hurt, A., Batello-Cruz M, Skipper B J, Teaf S R, Sterling W A, *Bovine Carotid Artery Heterografts Versus Polytetrafluoroethylene Grafts.* The American Journal of Surgery, 1983. 146: p. 844-847.
42. Marshall, S., Tweedt S M, Greene C H, Ballestas L Y, Bunning K R, et al, *An Alternative to Synthetic Aortic Grafts Using Jejunum.* Journal of Investigative Surgery, 2000. 13: p. 333-341.
43. Schmit C. E., B. J. M., *Acellular Vascular tissues: natural biomaterials for tissue repair and tissue engineering.* Biomaterials, 2000. 21: p. 2215-2231.
44. Courtman D W, E. B., Wilson G J, *The role of crosslinking in modification of the immune response elicited against xenogenic vascular acellular matrices.* J Biomed Mater Res, 2001. 55: p. 576-586.
45. Ferrari F A, C. J., *Protein Based Materials*, ed. K. D. McGrath K. 1997, Boston, Mass.: Birkhauser. 37-60.
46. Petka W A, H. J., McGrath K P, Wirtz D, Tirrell D A, *Reversible Hydrogels from Self-Assembling Artificial Proteins.* Science, 1998. 281: p. 389-392.
47. Meyer D E, C. A., *Genetically encoded synthesis of protein-based polymers with precisely specified molecular weight and sequence by recursive direcional ligation: examples from the elastin-like polypeptide system.* Biomacromolecules, 2002. 3: p. 357-367.
48. Nagarsekar A, C. J., Crissman M, Ferrari F, Cappello J, Ghandehari H, *Genetic Engineering of Stimuli-Sensitive Silkelastin-like Protein Block Copolymers.* Biomacromolecules, 2003. 4: p. 602-607.
49. Cappello J, C. J., Dorman M, Mikolajczak M, Textor G, Marquet M, Ferrari F, *Genetic Engineering of Structural Protein Polymers.* Biotechnol Progress, 1990. 6: p. 198-202.
50. McGrath K P, T. D., Kawai M, Mason T L, Fournier M J, *Chemical and Biosynthetic Approaches to the Production of Novel Polypeptide Materials.* Biotechnol Progress, 1990. 6: p. 188-192.
51. Humphrey J D, *Mechanics of the Arterial Wall: Review and Directions.* Critical Reviews in Biomedical Engineering, 1995. 23: p. 1-162.
52. Roach M R, B. A., *The Reason for the Shape of the Distensibility Curves of Arteries.* Can J Biochem Physiol, 1957. 35: p. 681-690.
53. Silver, F., Horvath I, Foran D J, *Viscoelasticity of the Vessel Wall: The role of collagen and elastic fibers.* Critical Reviews in Biomedical Engineering, 2001. 29(3): p. 279-302.
54. Silver, F., Snowhill P B, Foran D J, *Mechanical Behavior of Vessel Wall: A Comparative Study of Aorta, Vena Cava, and Carotid Artery.* Annals of Biomedical Engineering, 2003. 31: p. 793-803.

55. Lillie M A, G. J., *The viscoelastic basis for the tensile strength of elastin.* International Journal of Biological Macromolecules, 2002. 30: p. 119-127.
56. Clark J M, G. S., *Transmural Organization of the Arterial Media: The Lamellar unit revisited.* Arteriosclerosis, 1985. 5: p. 19-34.
57. Dingemans K P, T. P., Lagendijk J H, Becker A E, *Extracellular Matrix of the Human Aortic Media: An Ultrastructural Histochemical and Immunohistochemical Study of the Adult Aortic Media.* The Anatomical Record, 2000. 258: p. 1-14.
58. Wolinsky H, G. S., *A Lamellar Unit of Aortic Medial Structure and Function in Mammals.* Circulation Reviews, 1967. 20: p. 99-111.
59. Li D Y, F. G., Taylor D G, Davis E C, Boyle W A, Mecham R P, Stenzel P, Boak B, Keating M T, *Novel Arterial Pathology in Mice and Humans Hemizygous for Elastin.* J Clin INvest, 1998. 102(10): p. 1783-1787.
60. Li D Y, B. B., Davis E C, Mecham R P, Sorenson L K, Boak B B, Eichwald E, Keating M T, *Elastin is an essential determinant of arterial morphogenesis.* Nature, 1998. 393: p. 276-280.
61. Wagenseil J E, N. N., Knutsen R H, Okamoto R J, Li D Y, Mecham R P, *Effects of elastin haploinsufficiency on the mechanical behavior of mouse arteries.* Am J Physiol Heart Circ Physiol, 2005. 289: p. H1209-H1217.
62. Alberts B, J. A., Lewis J, Raff M, Roberts K, Walter P, *Molecular Biology of the Cell.* 4th ed. 2002, New York, N.Y.: Garland Science.
63. Rosenbloom J, A. W., Mecham R, *Extracellular Matrix 4: The elastic fiber.* FASEB J, 1993. 7: p. 1208-1218.
64. Rucker R B, D. M., *Elastin Metabolism and Chemistry: Potential Roles in Lung Development and Structure.* Environmental Health Perspectives, 1984. 55: p. 179-191.
65. Chang D K, U. D., *Molecular Dynamics Calculations on Relaxed and Extended States of the Polypentapeptide of Elastin.* Chem Phys Letters, 1988. 147(4): p. 395-400.
66. Urry D W, G. D., Parker T M, Luan C H, Reid M C, Harris C M, Pattanaik A, Harris R D, *Hydrophobicity Scale for Proteins Based on Inverse Transition Temperature.* Biopolymers, 1992. 32: p. 1243-1250.
67. Urry D W, L. C., Parker T M, Gowda D C, Prasad K U, Reid M C Safavy A, *Temperature of Polypeptide Inverse Temperature Transition Depends on Mean Residue Hydrophobicity.* J Am Chem Soc, 1991. 113: p. 4346-4348.
68. van Hest J C M, T. D., *Protein-Based materials, toward a new level of structural control.* Chem Comm, 2001: p. 1897-1904.
69. Wright, E., Conticello V P, *Self-assembly of block copolymers derived from elastin-mimetic polypeptide sequences.* Advanced Drug Delivery Reviews, 2002. 54: p. 1057-1073.
70. Wright E R, M. R., Cooper A, Apkarian R P, Conticello V P, *Thermoplastic Elastomer Hydrogels via Self-Assembly of an Elastin-Mimetic Triblock Polypeptide.* Advanced Functional Materials, 2002. 12(2): p. 1-6.
71. Panitch A, Y. T., Fournier M J, Mason T L, Tirrell D A, *Design and Biosynthesis of Elastin-like Artificial Extracellular Matrix Proteins Containing Periodically Spaced Fibronectin CS5 Domains.* Macromolecules, 1999. 32: p. 1701-1703.
72. Welsh E R, T. D., *Engineering the Extracellular Matrix: A Novel Approach to Polymeric Biomaterials. I. Control of the Physical Properties of Artificial Protein Matrices Designed to Support Adhesion of Vascular Endothelial Cells.* Biomacromolecules, 2000. 1: p. 23-30.
73. McMillan R A, C. V., *Synthesis and Characterization of Elastin-Mimetic Protein Gels Derived from a Well-Defined Polypeptide Precursor.* Macromolecules, 2000. 33: p. 4809-4821.
74. Lee J, M. C., Urry D W, *Mechanical properties of crosslinked synthetic elastomeric polypentapeptides.* Macromolecules, 2001. 34: p. 5968-5974.
75. Lee J, M. C., Urry D W, *Swelling behavior of gamma-irradiation cross-linked elastomeric polypentapeptide-based hydrogels.* Macromolecules, 2001. 34: p. 4114-4123.
76. Urry D W, H. R., Harris R D, Prasad K U, *Polypentapeptide of Elastin: Temperature Dependence Correlation of Elastomeric Force and Dielectric Permittivity.* Biochemical and Biophysical Research Communications, 1984. 125 (3): p. 1082-1088.
77. Lee J, M. C., Urry D W, *Elastomeric Polypentapeptides Cross-Linked into Matrixes and Fibers.* Biomacromolecules, 2001. 2: p. 170-179.
78. Nowatzki P J, T. D., *Physical Properties of artificial extracellular matrix protein films prepared by isocyanate crosslinking.* Biomaterials, 2004. 25: p. 1261-1267.
79. Trabbic-Carlson K, S. L., Chilkoti A, *Swelling and Mechanical Behaviors of Chemically Cross-linked Hydrogels of Elastin-like Polypeptides.* Biomacromolecules, 2003. 4: p. 572-580.
80. McMillan R A, L. T., Conticello V P, *Rapid Assembly of Synthetic Genes Encoding Protein Polymers.* Macromolecules, 1999. 32: p. 3643-3648.
81. Kagan H M, T. L., Trackman P C, Okamoto K, Rapaka R S, Urry D W, *Repeat Polypeptide Models of Elastin as Substrates for Lysyl Oxidase.* Journal of Biological Chemistry, 1980. 255(8): p. 3656-2659.
82. Nagapudi K, B. W., Leisen J E, Huang L, McMillan R A, Apkarian R P, Conticello V P, Chaikof E L, *Photomediated Solid-State Cross-Linking of an Elastin-Mimetic Recombinant Protein Polymer.* Macromolecules, 2002. 35: p. 1730-1737.
83. Ottani V, R. M., Ruggeri A, *Collagen structure and functional implications.* Micron, 2001. 32: p. 251-260.
84. Kwon I K, K. S., Matsuda T, *Electrospun nano-to microfiber fabrics made of biodegradable copolyesters: structural characteristics, mechanical properties, and cell adhesion potential.* Biomaterials, 2005. 26(18): p. 3929-3939.
85. Li M, M. M., Gandhi M R, Ko F K, Weiss A S, Lelkes P I, *Electrospun protein fibers as matrices for tissue engineering.* Biomaterials, 2005. 26: p. 5999-6008.
86. Wei M, S. R., Biswas N, Conticello V P, Dluhy R A, Chaikof E L, *Size Variable Micelles Regulated by a Reversible Switch of Protein Secondary Structure.* Journal of the American Chemical Society, 2005. In Review.
87. Nagapudi K, B. W., Thomas B S, Park J O, Srinivasarao M, Wright E, Conticello V P, Chaikof E L, *Viscoelastic and mechanical behavior of recombinant protein elastomers.* Biomaterials, 2005. 26: p. 4695-4706.
88. Sallach R E, W. X., Caves J, Conticello V P, Chaikof E L., *Recombinant elastin-mimetic fiber networks: Static and dynamic mechanical properties.* Biomaterials, 2005. In Review.
89. Nagapudi K, B. W., Leisen J E, Thomas B S, Wright E R, Haller C, Wu X, Apkarian R P, Conticello V P, Chaikof E L, *Protein-Based Thermoplastic Elastomers.* Macromolecules, 2005. 38: p. 345-354.
90. Wu X, S. R., Haller C, Caves J, Nagapudi K, Conticello V P, Levenston M E, Chaikof E L, *Alterations in Physical*

*Cross-Linking Modulate Mechanical Properties of Two-Phase Protein Polymer Networks*. Biomacromolecules, 2005. In press.
91. Bergland J D, M. M., Nerem R M, Sambanis A, *A biological hybrid model for collagen-based tissue engineered vascular constructs*. Biomaterials, 2003. 24: p. 1241-1254.
92. Marsh J N, T. S., Lin S J, Lanza G M, Wickline S A, *Ultrasonic delineartion of the aortic microstructure: The relative contributions of elastin and collagen to aortic elasticity*. J Acoust Soc Am, 2004. 115(5): p. 2032-2040.
93. Marra K G, W. T., Hanson S R, Chaikof E L, *Cytomimetic Biomaterials. 1. In-Situ Polymerization of Phospholipids on an Alkylated Surface*. Macromolecules, 1997. 30: p. 6483-6488.
94. *Gene Expression Systems: Using Nature for the Art of Expression*, ed. H. J. Fernandez J M. 1999: Academic Press.
95. Wu X, S. R., Conticello V P, Chaikof E L, *Rheological and Mechanical Properties of a Protein Triblock Copolymer with Enhanced Creep Resistance*. Biomacromolecules, 2005. In Review.
96. Jenney C R, A. J., *Alkylsilane-modified surfaces: inhibition of human macrophage adhesion and foreign body giant cell formation*. Journal of Biomedical Materials Research, 1999. 46(1): p. 11-21.
97. Wood S A, L. J., Prasad K U, Urry D W, *In vitro calcification and in vivo biocompatibility of the crosslinked polypentapeptide of elastin*. J Biomed Mater Res, 1986. 20(3): p. 315-335.
98. Tobias J W, S. T., Rocap G, Varshaysky A, *The N-End Rule in Bacteria*. Science, 1991. 254: p. 1324-1377.
99. Cho S W, P. H., Ruy J H, Kim S H, Kim Y H, CHoi C Y, Lee M J, Kim J S, Jang I S, Kim D I, Kim B S, *Vascular patches tissue-engineered with autologous bone marrow-derived cells and decellularized tissue matrices*. Biomaterials, 2005. 26: p. 1915-1924.
100. Lee W K, P. K., Kim Y H, Suh H, Park J C, Lee J E, Sun K, Baek M J, Kim H M, Kim S H, *Improved calcification resistance and biocompatibility of tissue patch grafted with sulfonated PEO or heparin after gluteraldehyde fixation*. J Biomed Mater Res, 2000. 58(1): p. 27-35.
101. Rashid S T, S. H., Hamilton G, Seifalian A M, *The use of animal models in developing the discipline of cardiovascular tissue engineering*. Biomaterials, 2004. 25: p. 1627-1637.
102. Iwia S, S. Y., Taketani S, Torikai K, Hirakawa K Matsuda H, *Novel Tissue-Engineered biodegradable material for reconstruction of vascular wall*. Society of Thoracic Surgeons, 2005. 80: p. 1821-1828.
103. Lerouge S, R. J., Salazkin I, Qin Z, Gaboury L, Cloutier G, Oliva V, Soulez G, *Endovascular Aortic Aneurysm Repair with Stent-Grafts: Experimental Models an Reproduce Endoleaks*. J vasc Intery Radiol, 2004. 15: p. 971-979.
104. Castejon O J, A. R., Castejon H V, Alvarado M V, *Field Emission scanning electron microscopy and freeze-fracture transmission electron microscopy of mouse cerebellar synaptic contacts*. J submicrosc cytol pathol, 2001. 33(3): p. 289-300.
105. Apkarian R P, B. J., Acland R D, *Scanning Electron Microscopy Study of Disturbances in Arterial Walls Following Microsurgical Needle Perforations*. Scanning Electron Microscopy, 1982: p. 781-787.
106. Robinson K A, R. G., Siegel R J, Black A J, Apkarian R P, King S B, *Intro Arterial Stenting in the Atherosclerotic Rabbit*. Circulation, 1988. 78: p. 646-653.
107. Kannan R Y, Salacinski H J, Butler P E, Hamilton G, Seifalian A M. Current status of prosthetic bypass grafts: a review. J Biomed Mater Res Part B: Appl Biomater, 2005; 74B: 570-81.
108. Joseph G, Sharma C P. Prostacyclin immobilized albuminated surfaces. J Biomed Mater Res 1987; 21(7):937-45.
109. Chaikof E L, Merrill E W, Coleman J E, Ramberg K, Connolly R J, Callow A D. Platelet interaction with poly (ethylene oxide)-polysiloxane networks. AlChEJ 1990; 36:994-1002.
110. van der Giessen W J, van Beusekom H M, Eijgelshoven M H, Morel M A, Serruys P W. Heparin-coating of coronary stents. Seminars in Interventional Cardiology 1998; 3(3-4): 173-6.
111 Serruys P W, van Hout B, Bonnier H, Legrand V, Garcia E, Macaya C, et al. Randomized comparison of implantation of heparin-coated stents with balloon angioplasty in selected patients with coronary artery disease (Benestent II). Lancet 1998; 352(9129): 673-81.
112. Buller C E, Dzavik V, Carere R G, Mancini G B, Barbeau G, Lazzam C. Primary stenting versus balloon angioplasty in occluded coronary arteries: The Total Occlusion Study of Canada (TOSCA). Circulation 1999; 100(3): 236-42.
113 Dutoya S, Verna A, Lefebvre F, Rabaud M. Elastin-derived protein coating onto poly(ethylene terephthalate): Technical, microstructural and biological studies. Biomaterials 2000; 21:1521-9.
114 Defife K M, Hagen K M, Clapper D L, Anderson J M. Photochemically immobilized polymer coatings: Effects on protein adsorption, cell adhesion and leukocyte activation. J Biomater Sci Polym Ed 1999; 10(10): 1063-74.
115. Ito S, Ishimaru S, Wilson S E. Application of coacervated alpha-elastin to arterial prostheses for inhibition of anastomotic intimal hyperplasia. ASAIO J 1998; 44(5): M501-5.
116. Woodhouse K A, Klement P, Chen V, Gorbet M B, Keeley F W, Stahl R, Fromstein J D, Bellingham C M. Investigation of recombinant human elastin polypeptides as non-thrombogenic coatings. Biomaterials 2004; 25: 4543-53.
117. Indik Z, Yeh H, Ornstein-Goldstein N, Sheppard P, Anderson N, Rosenbloom J C, et al. Alternative splicing of human elastin mRNA indicated by sequence analysis of cloned genomic and complementary DNA. Proc of the Nat Acad of Sci USA 1987; 84(16): 5680-4.
118. Rosenbloom J, Abrams W R, Indik Z, Yeh H, Ornstein-Goldstein N, Bashir M M. Structure of the elastin gene. Ciba Foundation Symposium 1995; 192:59-74.
119. Sandberg L B, Soskel N T, Leslie J G. Elastin structure, biosynthesis, and relation to disease states. NEJM 1981; 304(10): 566-79.
120. Sandberg L B, Gray W R, Foster J A, Torres A R, Alvarez V L, Janata J. Primary structure of porcine tropoelastin. Advances in Experimental Medicine & Biology 1977; 79: 277-84.
121. Rapaka R S, Okamoto K, Urry D W. Non-elastomeric polypeptide models of elastin. Synthesis of polyhexapeptides and a cross-linked polyhexapeptide. International Journal of Peptide & Protein Research 1978; 11(2): 109-27.
122. Urry D W, Mitchell L W, Ohnishi T. Studies on the conformation and interactions of elastin secondary structure of synthetic repeat hexapeptides. Biochimica et Biophysica Acta 1975; 393(2): 296-306.
123. Urry D W, Harris R D, Long M M, Prasad K U. Polytetrapeptide of elastin. Temperature-correlated elastomeric force and structure development. International Journal of Peptide & Protein Research 1986; 28(6): 649-60.
124. Broch H, Moulabbi M, Vasilescu D, Tamburro A M. Quantum molecular modeling of the elastinic tetrapeptide Val-Pro-Gly-Gly. Journal of Biomolecular Structure & Dynamics 1998; 15(6): 1073-91.
125. Gray W R, Sandberg L B, Foster J A. Molecular model for elastin structure and function. Nature 1973; 246(5434): 461-6.
126. Urry D W, Long M M, Cox B A, Ohnishi T, Mitchell L W, Jacobs M. The synthetic polypentapeptide of elastin coacervates and forms filamentous aggregates. Biochimica et Biophysica Acta 1974; 371(2): 597-602.
127. Urry D W, Long M M. On the conformation, coacervation and function of polymeric models of elastin. Advances in Experimental Medicine & Biology 1977; 79: 685-714.
128. Urry D W, Luan C H, Peng S Q. Molecular biophysics of elastin structure, function and pathology. Ciba Foundation Symposium 1995; 192: 4-22; discussion 22-30.
129 McMillan R A, Lee T A T, Conticello V P. Rapid assembly of synthetic genes encoding protein polymers. Macromolecules 1999; 32: 3643-3648.
130. McMillan R A, Conticello V P. Synthesis and characterization of elastin-mimetic protein gels derived from a well-defined polypeptide precursor. Macromolecules 2000; 33: 4809-4821.
131. McPherson D T, Morrow C, Minehan D S, Wu J, Hunter E, Urry D W. Production and purification of a recombinant elastomeric polypeptide, G-(VPGVG)19-VPGV, from *Escherichia coli*. Biotechnology Progress 1992; 8(4): 347-52.
132. Daniell H, Guda C, McPherson D T, Zhang X, Xu J, Urry D W. Hyperexpression of a synthetic protein-based polymer gene. Methods in Molecular Biology 1997; 63: 359-71.
133. Panitch A, Yamaoka T, Fournier M J, Mason T L, Tirrell D A. Macromolecules 1999; 32: 1701-1703.
134. Trabbic-Carlson K, Setton L A, Chilkoti A. Swelling and mechanical behaviors of chemically cross-linked hydrogels of elastin-like polypeptides. Biomacromolecules 2003; 4(3): 572-80.
135. Nagapudi K, Brinkman W T, Thomas B S, Wright E R, Conticello V P, Chaikof E L. Protein-based thermoplastic elastomers. Macromolecules 2005; 38: 345-354.
136. Wu X, Sallach R, Haller C A, Caves J A, Nagapudi K, Conticello V P, et al. Alterations in physical cross-linking modulate mechanical properties of two-phase protein polymer networks. Biomacromolecules 2005; 6(6): 3037-44.
137. Nagapudi K, Brinkman W T, Thomas B S, Park J O, Srinivasarao M, Wright E, et al. Viscoelastic and mechanical behavior of recombinant protein elastomers. Biomaterials 2005; 26(23): 4695-706.
138. Sun X L, Haller C A, Wu X, Conticello V P, Chaikof E L. One-pot glyco-affinity precipitation purification for enhanced proteomics: the flexible alignment of solution-phase capture/release and solid-phase separation. J Proteome Res 2005; 4(6): 2355-9.
139. Sallach R E, Wei M, Biswas N, Conticello V P, Lecommandoux S, Dluhy R A, Chaikof E L. Micelle density regulated by a reversible switch of protein secondary structure. In press J Am Chem Soc 2006.
140. Wright E R, McMillan R A, Cooper A, Apkarian R P, Conticello V P. Thermoplastic elastomer hydrogels via self-assembly of an elastin-mimetic triblock polypeptide. Adv Fun Mater 2002; 12:149-54.
141. Hanson S R, Kotze H F, Savage B, Harker L A. Platelet interactions with Dacron vascular grafts. Arteriosclerosis 1985; 5: 595-603.
142. Cadroy Y, Horbett T A, Hanson S R. Discrimination between platelet and coagulation-mediated mechanisms in a model of complex thrombus formation in vivo. J Lab Clin Med 1989; 113: 436-49.
143. Cadroy Y, Hanson S R. Effects of red blood cell concentration on hemostasis and thrombus formation in a primate model. Blood 1990; 75: 2185-93.
144. Baumgartner H R, Muggli R, Tschopp T B, Turitto V T. Platelet adhesion, release and aggregation in flowing blood: Effects of surface properties and platelet function. Thromb Haemost 1976; 35(1): 124-38.
145. Barnes M J, Macintyre D E. Platelet-reactivity of isolated constituents of the blood vessel wall. Haemostasis 1979; 8:158-70.
146. Vecchione J J, Melaragno A J, Hotte C E, Lionetti F J, Kurtz S R, Callow A D. Use of indium-111-oxine to study the circulation and distribution of baboon platelets and granulocytes. In: Thakur M L, Gottschalk A, editors. Indium-111 labeled neutrophils, platelets, and lymphocytes. New York: Trivirium; 1980. p. 7-21.
147. Feingold H M, Pivacek L E, Melaragno A J, Valeri C R. Coagulation assays and platelet aggregation patterns in human, baboon, and canine blood. Am J Vet Res 1986; 47:2197-2199.

We claim:

1. A synthetic protein comprising SEQ ID NO:33.
2. A synthetic protein comprising SEQ ID NO:26.
3. A recombinant nucleic acid sequence that encodes a protein comprising SEQ ID NO: 33.
4. A recombinant nucleic acid sequence that encodes a protein comprising SEQ ID NO: 26.

* * * * *

UNITED STATES PATENT AND TRADEMARK OFFICE
CERTIFICATE OF CORRECTION

PATENT NO. : 8,846,624 B2
APPLICATION NO. : 12/440670
DATED : September 30, 2014
INVENTOR(S) : Chaikof et al.

It is certified that error appears in the above-identified patent and that said Letters Patent is hereby corrected as shown below:

In the Specification

Column 1, Lines 15 through 26:
"ACKNOWLEDGEMENT
This invention was made with with government support under Grant No. RO1HL71336 awarded by the National Institutes of Health. The government has certain rights in the invention.
STATEMENT REGARDING FEDERALLY SPONSORED RESEARCH OR DEVELOPMENT
This invention was made with with government support under Grant No. RO1HL71336 awarded by National Institutes of Health. The Government has certain rights in the invention"

Should read:
STATEMENT REGARDING FEDERALLY SPONSORED RESEARCH OR DEVELOPMENT
This invention was made with government support under HL071336 awarded by the National Institutes of Health. The government has certain rights in the invention.

Signed and Sealed this
Twenty-third Day of August, 2022

Katherine Kelly Vidal
*Director of the United States Patent and Trademark Office*

```
                        SEQUENCE LISTING

<160> NUMBER OF SEQ ID NOS: 71

<210> SEQ ID NO 1
<211> LENGTH: 5
<212> TYPE: PRT
<213> ORGANISM: Artificial Sequence
<220> FEATURE:
<223> OTHER INFORMATION: Synthetic construct

<400> SEQUENCE: 1

Ile Pro Gly Ala Gly
1               5

<210> SEQ ID NO 2
<211> LENGTH: 5
<212> TYPE: PRT
<213> ORGANISM: Artificial Sequence
```

```
<220> FEATURE:
<223> OTHER INFORMATION: Synthetic construct

<400> SEQUENCE: 2

Val Pro Gly Ala Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic construct

<400> SEQUENCE: 3

Val Pro Gly Glu Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic construct

<400> SEQUENCE: 4

Val Pro Ala Val Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic construct

<400> SEQUENCE: 5

Ile Pro Ala Val Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic construct

<400> SEQUENCE: 6

Val Pro Gly Val Gly
1               5

<210> SEQ ID NO 7
<211> LENGTH: 1650
<212> TYPE: PRT
<213> ORGANISM: Artificial Sequence
<220> FEATURE:
<223> OTHER INFORMATION: Synthetic construct

<400> SEQUENCE: 7

Val Pro Ala Val Gly Ile Pro Ala Val Gly Ile Pro Ala Val Gly Ile
1               5                   10                  15

Pro Ala Val Gly Ile Pro Ala Val Gly Ile Pro Ala Val Gly Ile Pro
                20                  25                  30

Ala Val Gly Ile Pro Ala Val Gly Ile Pro Ala Val Gly Ile Pro Ala
            35                  40                  45
```

-continued

Val Gly Val Pro Ala Val Gly Ile Pro Ala Val Gly Ile Pro Ala Val
    50                  55                  60

Gly Ile Pro Ala Val Gly Ile Pro Ala Val Gly Ile Pro Ala Val Gly
65                  70                  75                  80

Ile Pro Ala Val Gly Ile Pro Ala Val Gly Ile Pro Ala Val Gly Ile
                85                  90                  95

Pro Ala Val Gly Val Pro Ala Val Gly Ile Pro Ala Val Gly Ile Pro
            100                 105                 110

Ala Val Gly Ile Pro Ala Val Gly Ile Pro Ala Val Gly Ile Pro Ala
        115                 120                 125

Val Gly Ile Pro Ala Val Gly Ile Pro Ala Val Gly Ile Pro Ala Val
    130                 135                 140

Gly Ile Pro Ala Val Gly Val Pro Ala Val Gly Ile Pro Ala Val Gly
145                 150                 155                 160

Ile Pro Ala Val Gly Ile Pro Ala Val Gly Ile Pro Ala Val Gly Ile
                165                 170                 175

Pro Ala Val Gly Ile Pro Ala Val Gly Ile Pro Ala Val Gly Ile Pro
            180                 185                 190

Ala Val Gly Ile Pro Ala Val Gly Val Pro Ala Val Gly Ile Pro Ala
        195                 200                 205

Val Gly Ile Pro Ala Val Gly Ile Pro Ala Val Gly Ile Pro Ala Val
    210                 215                 220

Gly Ile Pro Ala Val Gly Ile Pro Ala Val Gly Ile Pro Ala Val Gly
225                 230                 235                 240

Ile Pro Ala Val Gly Ile Pro Ala Val Gly Val Pro Ala Val Gly Ile
                245                 250                 255

Pro Ala Val Gly Ile Pro Ala Val Gly Ile Pro Ala Val Gly Ile Pro
            260                 265                 270

Ala Val Gly Ile Pro Ala Val Gly Ile Pro Ala Val Gly Ile Pro Ala
        275                 280                 285

Val Gly Ile Pro Ala Val Gly Ile Pro Ala Val Gly Val Pro Ala Val
    290                 295                 300

Gly Ile Pro Ala Val Gly Ile Pro Ala Val Gly Ile Pro Ala Val Gly
305                 310                 315                 320

Ile Pro Ala Val Gly Ile Pro Ala Val Gly Ile Pro Ala Val Gly Ile
                325                 330                 335

Pro Ala Val Gly Ile Pro Ala Val Gly Ile Pro Ala Val Gly Val Pro
            340                 345                 350

Ala Val Gly Ile Pro Ala Val Gly Ile Pro Ala Val Gly Ile Pro Ala
        355                 360                 365

Val Gly Ile Pro Ala Val Gly Ile Pro Ala Val Gly Ile Pro Ala Val
    370                 375                 380

Gly Ile Pro Ala Val Gly Ile Pro Ala Val Gly Ile Pro Ala Val Gly
385                 390                 395                 400

Val Pro Ala Val Gly Ile Pro Ala Val Gly Ile Pro Ala Val Gly Ile
                405                 410                 415

Pro Ala Val Gly Ile Pro Ala Val Gly Ile Pro Ala Val Gly Ile Pro
            420                 425                 430

Ala Val Gly Ile Pro Ala Val Gly Ile Pro Ala Val Gly Ile Pro Ala
        435                 440                 445

Val Gly Val Pro Ala Val Gly Ile Pro Ala Val Gly Ile Pro Ala Val
    450                 455                 460

Gly Ile Pro Ala Val Gly Ile Pro Ala Val Gly Ile Pro Ala Val Gly

-continued

```
            465                 470                 475                 480
Ile Pro Ala Val Gly Ile Pro Ala Val Gly Ile Pro Ala Val Gly Ile
                    485                 490                 495
Pro Ala Val Gly Val Pro Ala Val Gly Ile Pro Ala Val Gly Ile Pro
                500                 505                 510
Ala Val Gly Ile Pro Ala Val Gly Ile Pro Ala Val Gly Ile Pro Ala
            515                 520                 525
Val Gly Ile Pro Ala Val Gly Ile Pro Ala Val Gly Ile Pro Ala Val
        530                 535                 540
Gly Ile Pro Ala Val Gly Val Pro Ala Val Gly Ile Pro Ala Val Gly
545                 550                 555                 560
Ile Pro Ala Val Gly Ile Pro Ala Val Gly Ile Pro Ala Val Gly Ile
                565                 570                 575
Pro Ala Val Gly Ile Pro Ala Val Gly Ile Pro Ala Val Gly Ile Pro
            580                 585                 590
Ala Val Gly Ile Pro Ala Val Gly Val Pro Ala Val Gly Ile Pro Ala
        595                 600                 605
Val Gly Ile Pro Ala Val Gly Ile Pro Ala Val Gly Ile Pro Ala Val
    610                 615                 620
Gly Ile Pro Ala Val Gly Ile Pro Ala Val Gly Ile Pro Ala Val Gly
625                 630                 635                 640
Ile Pro Ala Val Gly Ile Pro Ala Val Gly Val Pro Ala Val Gly Ile
                645                 650                 655
Pro Ala Val Gly Ile Pro Ala Val Gly Ile Pro Ala Val Gly Ile Pro
            660                 665                 670
Ala Val Gly Ile Pro Ala Val Gly Ile Pro Ala Val Gly Ile Pro Ala
        675                 680                 685
Val Gly Ile Pro Ala Val Gly Ile Pro Ala Val Gly Val Pro Ala Val
    690                 695                 700
Gly Ile Pro Ala Val Gly Ile Pro Ala Val Gly Ile Pro Ala Val Gly
705                 710                 715                 720
Ile Pro Ala Val Gly Ile Pro Ala Val Gly Ile Pro Ala Val Gly Ile
                725                 730                 735
Pro Ala Val Gly Ile Pro Ala Val Gly Ile Pro Ala Val Gly Val Pro
            740                 745                 750
Ala Val Gly Ile Pro Ala Val Gly Ile Pro Ala Val Gly Ile Pro Ala
        755                 760                 765
Val Gly Ile Pro Ala Val Gly Ile Pro Ala Val Gly Ile Pro Ala Val
    770                 775                 780
Gly Ile Pro Ala Val Gly Ile Pro Ala Val Gly Ile Pro Ala Val Gly
785                 790                 795                 800
Val Pro Ala Val Gly Ile Pro Ala Val Gly Ile Pro Ala Val Gly Ile
                805                 810                 815
Pro Ala Val Gly Ile Pro Ala Val Gly Ile Pro Ala Val Gly Ile Pro
            820                 825                 830
Ala Val Gly Ile Pro Ala Val Gly Ile Pro Ala Val Gly Ile Pro Ala
        835                 840                 845
Val Gly Val Pro Ala Val Gly Ile Pro Ala Val Gly Ile Pro Ala Val
    850                 855                 860
Gly Ile Pro Ala Val Gly Ile Pro Ala Val Gly Ile Pro Ala Val Gly
865                 870                 875                 880
Ile Pro Ala Val Gly Ile Pro Ala Val Gly Ile Pro Ala Val Gly Ile
                885                 890                 895
```

```
Pro Ala Val Gly Val Pro Ala Val Gly Ile Pro Ala Val Gly Ile Pro
                900                 905                 910
Ala Val Gly Ile Pro Ala Val Gly Ile Pro Ala Val Gly Ile Pro Ala
        915                 920                 925
Val Gly Ile Pro Ala Val Gly Ile Pro Ala Val Gly Ile Pro Ala Val
    930                 935                 940
Gly Ile Pro Ala Val Gly Val Pro Ala Val Gly Ile Pro Ala Val Gly
945                 950                 955                 960
Ile Pro Ala Val Gly Ile Pro Ala Val Gly Ile Pro Ala Val Gly Ile
            965                 970                 975
Pro Ala Val Gly Ile Pro Ala Val Gly Ile Pro Ala Val Gly Ile Pro
        980                 985                 990
Ala Val Gly Ile Pro Ala Val Gly Val Pro Ala Val Gly Ile Pro Ala
    995                 1000                1005
Val Gly Ile Pro Ala Val Gly Ile Pro Ala Val Gly Ile Pro Ala
    1010                1015                1020
Val Gly Ile Pro Ala Val Gly Ile Pro Ala Val Gly Ile Pro Ala
    1025                1030                1035
Val Gly Ile Pro Ala Val Gly Ile Pro Ala Val Gly Val Pro Ala
    1040                1045                1050
Val Gly Ile Pro Ala Val Gly Ile Pro Ala Val Gly Ile Pro Ala
    1055                1060                1065
Val Gly Ile Pro Ala Val Gly Ile Pro Ala Val Gly Ile Pro Ala
    1070                1075                1080
Val Gly Ile Pro Ala Val Gly Ile Pro Ala Val Gly Ile Pro Ala
    1085                1090                1095
Val Gly Val Pro Ala Val Gly Ile Pro Ala Val Gly Ile Pro Ala
    1100                1105                1110
Val Gly Ile Pro Ala Val Gly Ile Pro Ala Val Gly Ile Pro Ala
    1115                1120                1125
Val Gly Ile Pro Ala Val Gly Ile Pro Ala Val Gly Ile Pro Ala
    1130                1135                1140
Val Gly Ile Pro Ala Val Gly Val Pro Ala Val Gly Ile Pro Ala
    1145                1150                1155
Val Gly Ile Pro Ala Val Gly Ile Pro Ala Val Gly Ile Pro Ala
    1160                1165                1170
Val Gly Ile Pro Ala Val Gly Ile Pro Ala Val Gly Ile Pro Ala
    1175                1180                1185
Val Gly Ile Pro Ala Val Gly Ile Pro Ala Val Gly Val Pro Ala
    1190                1195                1200
Val Gly Ile Pro Ala Val Gly Ile Pro Ala Val Gly Ile Pro Ala
    1205                1210                1215
Val Gly Ile Pro Ala Val Gly Ile Pro Ala Val Gly Ile Pro Ala
    1220                1225                1230
Val Gly Ile Pro Ala Val Gly Ile Pro Ala Val Gly Ile Pro Ala
    1235                1240                1245
Val Gly Val Pro Ala Val Gly Ile Pro Ala Val Gly Ile Pro Ala
    1250                1255                1260
Val Gly Ile Pro Ala Val Gly Ile Pro Ala Val Gly Ile Pro Ala
    1265                1270                1275
Val Gly Ile Pro Ala Val Gly Ile Pro Ala Val Gly Ile Pro Ala
    1280                1285                1290
```

Val Gly Ile Pro Ala Val Gly Val Pro Ala Val Gly Ile Pro Ala
1295            1300            1305

Val Gly Ile Pro Ala Val Gly Ile Pro Ala Val Gly Ile Pro Ala
1310            1315            1320

Val Gly Ile Pro Ala Val Gly Ile Pro Ala Val Gly Ile Pro Ala
1325            1330            1335

Val Gly Ile Pro Ala Val Gly Ile Pro Ala Val Gly Val Pro Ala
1340            1345            1350

Val Gly Ile Pro Ala Val Gly Ile Pro Ala Val Gly Ile Pro Ala
1355            1360            1365

Val Gly Ile Pro Ala Val Gly Ile Pro Ala Val Gly Ile Pro Ala
1370            1375            1380

Val Gly Ile Pro Ala Val Gly Ile Pro Ala Val Gly Ile Pro Ala
1385            1390            1395

Val Gly Val Pro Ala Val Gly Ile Pro Ala Val Gly Ile Pro Ala
1400            1405            1410

Val Gly Ile Pro Ala Val Gly Ile Pro Ala Val Gly Ile Pro Ala
1415            1420            1425

Val Gly Ile Pro Ala Val Gly Ile Pro Ala Val Gly Ile Pro Ala
1430            1435            1440

Val Gly Ile Pro Ala Val Gly Val Pro Ala Val Gly Ile Pro Ala
1445            1450            1455

Val Gly Ile Pro Ala Val Gly Ile Pro Ala Val Gly Ile Pro Ala
1460            1465            1470

Val Gly Ile Pro Ala Val Gly Ile Pro Ala Val Gly Ile Pro Ala
1475            1480            1485

Val Gly Ile Pro Ala Val Gly Ile Pro Ala Val Gly Val Pro Ala
1490            1495            1500

Val Gly Ile Pro Ala Val Gly Ile Pro Ala Val Gly Ile Pro Ala
1505            1510            1515

Val Gly Ile Pro Ala Val Gly Ile Pro Ala Val Gly Ile Pro Ala
1520            1525            1530

Val Gly Ile Pro Ala Val Gly Ile Pro Ala Val Gly Ile Pro Ala
1535            1540            1545

Val Gly Val Pro Ala Val Gly Ile Pro Ala Val Gly Ile Pro Ala
1550            1555            1560

Val Gly Ile Pro Ala Val Gly Ile Pro Ala Val Gly Ile Pro Ala
1565            1570            1575

Val Gly Ile Pro Ala Val Gly Ile Pro Ala Val Gly Ile Pro Ala
1580            1585            1590

Val Gly Ile Pro Ala Val Gly Val Pro Ala Val Gly Ile Pro Ala
1595            1600            1605

Val Gly Ile Pro Ala Val Gly Ile Pro Ala Val Gly Ile Pro Ala
1610            1615            1620

Val Gly Ile Pro Ala Val Gly Ile Pro Ala Val Gly Ile Pro Ala
1625            1630            1635

Val Gly Ile Pro Ala Val Gly Ile Pro Ala Val Gly
1640            1645            1650

<210> SEQ ID NO 8
<211> LENGTH: 525
<212> TYPE: PRT
<213> ORGANISM: Artificial Sequence
<220> FEATURE:
<223> OTHER INFORMATION: Synthetic construct

<400> SEQUENCE: 8

```
Ile Pro Gly Ala Gly Val Pro Gly Ala Gly Val Pro Gly Glu Gly Val
1               5                   10                  15

Pro Gly Ala Gly Val Pro Gly Ala Gly Val Pro Gly Ala Gly Val Pro
            20                  25                  30

Gly Ala Gly Val Pro Gly Glu Gly Val Pro Gly Ala Gly Val Pro Gly
        35                  40                  45

Ala Gly Val Pro Gly Ala Gly Val Pro Gly Ala Gly Val Pro Gly Glu
    50                  55                  60

Gly Val Pro Gly Ala Gly Val Pro Gly Ala Gly Val Pro Gly Ala Gly
65                  70                  75                  80

Val Pro Gly Ala Gly Val Pro Gly Glu Gly Val Pro Gly Ala Gly Val
                85                  90                  95

Pro Gly Ala Gly Val Pro Gly Ala Gly Val Pro Gly Ala Gly Val Pro
            100                 105                 110

Gly Glu Gly Val Pro Gly Ala Gly Val Pro Gly Ala Gly Val Pro Gly
        115                 120                 125

Ala Gly Val Pro Gly Ala Gly Val Pro Gly Glu Gly Val Pro Gly Ala
    130                 135                 140

Gly Val Pro Gly Ala Gly Val Pro Gly Ala Gly Val Pro Gly Ala Gly
145                 150                 155                 160

Val Pro Gly Glu Gly Val Pro Gly Ala Gly Val Pro Gly Ala Gly Val
                165                 170                 175

Pro Gly Ala Gly Val Pro Gly Ala Gly Val Pro Gly Glu Gly Val Pro
            180                 185                 190

Gly Ala Gly Val Pro Gly Ala Gly Val Pro Gly Ala Gly Val Pro Gly
        195                 200                 205

Ala Gly Val Pro Gly Glu Gly Val Pro Gly Ala Gly Val Pro Gly Ala
    210                 215                 220

Gly Val Pro Gly Ala Gly Val Pro Gly Ala Gly Val Pro Gly Glu Gly
225                 230                 235                 240

Val Pro Gly Ala Gly Val Pro Gly Ala Gly Val Pro Gly Ala Gly Val
                245                 250                 255

Pro Gly Ala Gly Val Pro Gly Glu Gly Val Pro Gly Ala Gly Val Pro
            260                 265                 270

Gly Ala Gly Val Pro Gly Ala Gly Val Pro Gly Ala Gly Val Pro Gly
        275                 280                 285

Glu Gly Val Pro Gly Ala Gly Val Pro Gly Ala Gly Val Pro Gly Ala
    290                 295                 300

Gly Val Pro Gly Ala Gly Val Pro Gly Glu Gly Val Pro Gly Ala Gly
305                 310                 315                 320

Val Pro Gly Ala Gly Val Pro Gly Ala Gly Val Pro Gly Ala Gly Val
                325                 330                 335

Pro Gly Glu Gly Val Pro Gly Ala Gly Val Pro Gly Ala Gly Val Pro
            340                 345                 350

Gly Ala Gly Val Pro Gly Ala Gly Val Pro Gly Glu Gly Val Pro Gly
        355                 360                 365

Ala Gly Val Pro Gly Ala Gly Val Pro Gly Ala Gly Val Pro Gly Ala
    370                 375                 380

Gly Val Pro Gly Glu Gly Val Pro Gly Ala Gly Val Pro Gly Ala Gly
385                 390                 395                 400

Val Pro Gly Ala Gly Val Pro Gly Ala Gly Val Pro Gly Glu Gly Val
```

-continued

```
                        405                 410                 415
Pro Gly Ala Gly Val Pro Gly Ala Gly Val Pro Gly Ala Gly Val Pro
            420                 425                 430
Gly Ala Gly Val Pro Gly Glu Gly Val Pro Gly Ala Gly Val Pro Gly
            435                 440                 445
Ala Gly Val Pro Gly Ala Gly Val Pro Gly Ala Gly Val Pro Gly Glu
            450                 455                 460
Gly Val Pro Gly Ala Gly Val Pro Gly Ala Gly Val Pro Gly Ala Gly
465                 470                 475                 480
Val Pro Gly Ala Gly Val Pro Gly Glu Gly Val Pro Gly Ala Gly Val
            485                 490                 495
Pro Gly Ala Gly Val Pro Gly Ala Gly Val Pro Gly Ala Gly Val Pro
            500                 505                 510
Gly Glu Gly Val Pro Gly Ala Gly Val Pro Gly Ala Gly
            515                 520                 525

<210> SEQ ID NO 9
<211> LENGTH: 3825
<212> TYPE: PRT
<213> ORGANISM: Artificial Sequence
<220> FEATURE:
<223> OTHER INFORMATION: Synthetic construct

<400> SEQUENCE: 9

Val Pro Ala Val Gly Ile Pro Ala Val Gly Ile Pro Ala Val Gly Ile
1               5                   10                  15
Pro Ala Val Gly Ile Pro Ala Val Gly Ile Pro Ala Val Gly Ile Pro
            20                  25                  30
Ala Val Gly Ile Pro Ala Val Gly Ile Pro Ala Val Gly Ile Pro Ala
            35                  40                  45
Val Gly Val Pro Ala Val Gly Ile Pro Ala Val Gly Ile Pro Ala Val
            50                  55                  60
Gly Ile Pro Ala Val Gly Ile Pro Ala Val Gly Ile Pro Ala Val Gly
65                  70                  75                  80
Ile Pro Ala Val Gly Ile Pro Ala Val Gly Ile Pro Ala Val Gly Ile
            85                  90                  95
Pro Ala Val Gly Val Pro Ala Val Gly Ile Pro Ala Val Gly Ile Pro
            100                 105                 110
Ala Val Gly Ile Pro Ala Val Gly Ile Pro Ala Val Gly Ile Pro Ala
            115                 120                 125
Val Gly Ile Pro Ala Val Gly Ile Pro Ala Val Gly Ile Pro Ala Val
            130                 135                 140
Gly Ile Pro Ala Val Gly Val Pro Ala Val Gly Ile Pro Ala Val Gly
145                 150                 155                 160
Ile Pro Ala Val Gly Ile Pro Ala Val Gly Ile Pro Ala Val Gly Ile
            165                 170                 175
Pro Ala Val Gly Ile Pro Ala Val Gly Ile Pro Ala Val Gly Ile Pro
            180                 185                 190
Ala Val Gly Ile Pro Ala Val Gly Val Pro Ala Val Gly Ile Pro Ala
            195                 200                 205
Val Gly Ile Pro Ala Val Gly Ile Pro Ala Val Gly Ile Pro Ala Val
            210                 215                 220
Gly Ile Pro Ala Val Gly Ile Pro Ala Val Gly Ile Pro Ala Val Gly
225                 230                 235                 240
Ile Pro Ala Val Gly Ile Pro Ala Val Gly Val Pro Ala Val Gly Ile
```

-continued

```
                245                 250                 255
Pro Ala Val Gly Ile Pro Ala Val Gly Ile Pro Ala Val Gly Ile Pro
                260                 265                 270
Ala Val Gly Ile Pro Ala Val Gly Ile Pro Ala Val Gly Ile Pro Ala
                275                 280                 285
Val Gly Ile Pro Ala Val Gly Ile Pro Ala Val Gly Val Pro Ala Val
                290                 295                 300
Gly Ile Pro Ala Val Gly Ile Pro Ala Val Gly Ile Pro Ala Val Gly
305                 310                 315                 320
Ile Pro Ala Val Gly Ile Pro Ala Val Gly Ile Pro Ala Val Gly Ile
                325                 330                 335
Pro Ala Val Gly Ile Pro Ala Val Gly Ile Pro Ala Val Gly Val Pro
                340                 345                 350
Ala Val Gly Ile Pro Ala Val Gly Ile Pro Ala Val Gly Ile Pro Ala
                355                 360                 365
Val Gly Ile Pro Ala Val Gly Ile Pro Ala Val Gly Ile Pro Ala Val
                370                 375                 380
Gly Ile Pro Ala Val Gly Ile Pro Ala Val Gly Ile Pro Ala Val Gly
385                 390                 395                 400
Val Pro Ala Val Gly Ile Pro Ala Val Gly Ile Pro Ala Val Gly Ile
                405                 410                 415
Pro Ala Val Gly Ile Pro Ala Val Gly Ile Pro Ala Val Gly Ile Pro
                420                 425                 430
Ala Val Gly Ile Pro Ala Val Gly Ile Pro Ala Val Gly Ile Pro Ala
                435                 440                 445
Val Gly Val Pro Ala Val Gly Ile Pro Ala Val Gly Ile Pro Ala Val
                450                 455                 460
Gly Ile Pro Ala Val Gly Ile Pro Ala Val Gly Ile Pro Ala Val Gly
465                 470                 475                 480
Ile Pro Ala Val Gly Ile Pro Ala Val Gly Ile Pro Ala Val Gly Ile
                485                 490                 495
Pro Ala Val Gly Val Pro Ala Val Gly Ile Pro Ala Val Gly Ile Pro
                500                 505                 510
Ala Val Gly Ile Pro Ala Val Gly Ile Pro Ala Val Gly Ile Pro Ala
                515                 520                 525
Val Gly Ile Pro Ala Val Gly Ile Pro Ala Val Gly Ile Pro Ala Val
                530                 535                 540
Gly Ile Pro Ala Val Gly Val Pro Ala Val Gly Ile Pro Ala Val Gly
545                 550                 555                 560
Ile Pro Ala Val Gly Ile Pro Ala Val Gly Ile Pro Ala Val Gly Ile
                565                 570                 575
Pro Ala Val Gly Ile Pro Ala Val Gly Ile Pro Ala Val Gly Ile Pro
                580                 585                 590
Ala Val Gly Ile Pro Ala Val Gly Val Pro Ala Val Gly Ile Pro Ala
                595                 600                 605
Val Gly Ile Pro Ala Val Gly Ile Pro Ala Val Gly Ile Pro Ala Val
                610                 615                 620
Gly Ile Pro Ala Val Gly Ile Pro Ala Val Gly Ile Pro Ala Val Gly
625                 630                 635                 640
Ile Pro Ala Val Gly Ile Pro Ala Val Gly Val Pro Ala Val Gly Ile
                645                 650                 655
Pro Ala Val Gly Ile Pro Ala Val Gly Ile Pro Ala Val Gly Ile Pro
                660                 665                 670
```

-continued

Ala Val Gly Ile Pro Ala Val Gly Ile Pro Ala Val Gly Ile Pro Ala
    675                 680                 685
Val Gly Ile Pro Ala Val Gly Ile Pro Ala Val Gly Val Pro Ala Val
    690                 695                 700
Gly Ile Pro Ala Val Gly Ile Pro Ala Val Gly Ile Pro Ala Val Gly
705                 710                 715                 720
Ile Pro Ala Val Gly Ile Pro Ala Val Gly Ile Pro Ala Val Gly Ile
                725                 730                 735
Pro Ala Val Gly Ile Pro Ala Val Gly Ile Pro Ala Val Gly Val Pro
            740                 745                 750
Ala Val Gly Ile Pro Ala Val Gly Ile Pro Ala Val Gly Ile Pro Ala
        755                 760                 765
Val Gly Ile Pro Ala Val Gly Ile Pro Ala Val Gly Ile Pro Ala Val
    770                 775                 780
Gly Ile Pro Ala Val Gly Ile Pro Ala Val Gly Ile Pro Ala Val Gly
785                 790                 795                 800
Val Pro Ala Val Gly Ile Pro Ala Val Gly Ile Pro Ala Val Gly Ile
                805                 810                 815
Pro Ala Val Gly Ile Pro Ala Val Gly Ile Pro Ala Val Gly Ile Pro
            820                 825                 830
Ala Val Gly Ile Pro Ala Val Gly Ile Pro Ala Val Gly Ile Pro Ala
        835                 840                 845
Val Gly Val Pro Ala Val Gly Ile Pro Ala Val Gly Ile Pro Ala Val
    850                 855                 860
Gly Ile Pro Ala Val Gly Ile Pro Ala Val Gly Ile Pro Ala Val Gly
865                 870                 875                 880
Ile Pro Ala Val Gly Ile Pro Ala Val Gly Ile Pro Ala Val Gly Ile
                885                 890                 895
Pro Ala Val Gly Val Pro Ala Val Gly Ile Pro Ala Val Gly Ile Pro
            900                 905                 910
Ala Val Gly Ile Pro Ala Val Gly Ile Pro Ala Val Gly Ile Pro Ala
        915                 920                 925
Val Gly Ile Pro Ala Val Gly Ile Pro Ala Val Gly Ile Pro Ala Val
    930                 935                 940
Gly Ile Pro Ala Val Gly Val Pro Ala Val Gly Ile Pro Ala Val Gly
945                 950                 955                 960
Ile Pro Ala Val Gly Ile Pro Ala Val Gly Ile Pro Ala Val Gly Ile
                965                 970                 975
Pro Ala Val Gly Ile Pro Ala Val Gly Ile Pro Ala Val Gly Ile Pro
            980                 985                 990
Ala Val Gly Ile Pro Ala Val Gly Val Pro Ala Val Gly Ile Pro Ala
        995                 1000                1005
Val Gly Ile Pro Ala Val Gly Ile Pro Ala Val Gly Ile Pro Ala
    1010                1015                1020
Val Gly Ile Pro Ala Val Gly Ile Pro Ala Val Gly Ile Pro Ala
    1025                1030                1035
Val Gly Ile Pro Ala Val Gly Ile Pro Ala Val Gly Val Pro Ala
    1040                1045                1050
Val Gly Ile Pro Ala Val Gly Ile Pro Ala Val Gly Ile Pro Ala
    1055                1060                1065
Val Gly Ile Pro Ala Val Gly Ile Pro Ala Val Gly Ile Pro Ala
    1070                1075                1080

```
Val Gly Ile Pro Ala Val Gly Ile Pro Ala Val Gly Ile Pro Ala
    1085                1090                1095

Val Gly Val Pro Ala Val Gly Ile Pro Ala Val Gly Ile Pro Ala
    1100                1105                1110

Val Gly Ile Pro Ala Val Gly Ile Pro Ala Val Gly Ile Pro Ala
    1115                1120                1125

Val Gly Ile Pro Ala Val Gly Ile Pro Ala Val Gly Ile Pro Ala
    1130                1135                1140

Val Gly Ile Pro Ala Val Gly Val Pro Ala Val Gly Ile Pro Ala
    1145                1150                1155

Val Gly Ile Pro Ala Val Gly Ile Pro Ala Val Gly Ile Pro Ala
    1160                1165                1170

Val Gly Ile Pro Ala Val Gly Ile Pro Ala Val Gly Ile Pro Ala
    1175                1180                1185

Val Gly Ile Pro Ala Val Gly Ile Pro Ala Val Gly Val Pro Ala
    1190                1195                1200

Val Gly Ile Pro Ala Val Gly Ile Pro Ala Val Gly Ile Pro Ala
    1205                1210                1215

Val Gly Ile Pro Ala Val Gly Ile Pro Ala Val Gly Ile Pro Ala
    1220                1225                1230

Val Gly Ile Pro Ala Val Gly Ile Pro Ala Val Gly Ile Pro Ala
    1235                1240                1245

Val Gly Val Pro Ala Val Gly Ile Pro Ala Val Gly Ile Pro Ala
    1250                1255                1260

Val Gly Ile Pro Ala Val Gly Ile Pro Ala Val Gly Ile Pro Ala
    1265                1270                1275

Val Gly Ile Pro Ala Val Gly Ile Pro Ala Val Gly Ile Pro Ala
    1280                1285                1290

Val Gly Ile Pro Ala Val Gly Val Pro Ala Val Gly Ile Pro Ala
    1295                1300                1305

Val Gly Ile Pro Ala Val Gly Ile Pro Ala Val Gly Ile Pro Ala
    1310                1315                1320

Val Gly Ile Pro Ala Val Gly Ile Pro Ala Val Gly Ile Pro Ala
    1325                1330                1335

Val Gly Ile Pro Ala Val Gly Ile Pro Ala Val Gly Val Pro Ala
    1340                1345                1350

Val Gly Ile Pro Ala Val Gly Ile Pro Ala Val Gly Ile Pro Ala
    1355                1360                1365

Val Gly Ile Pro Ala Val Gly Ile Pro Ala Val Gly Ile Pro Ala
    1370                1375                1380

Val Gly Ile Pro Ala Val Gly Ile Pro Ala Val Gly Ile Pro Ala
    1385                1390                1395

Val Gly Val Pro Ala Val Gly Ile Pro Ala Val Gly Ile Pro Ala
    1400                1405                1410

Val Gly Ile Pro Ala Val Gly Ile Pro Ala Val Gly Ile Pro Ala
    1415                1420                1425

Val Gly Ile Pro Ala Val Gly Ile Pro Ala Val Gly Ile Pro Ala
    1430                1435                1440

Val Gly Ile Pro Ala Val Gly Val Pro Ala Val Gly Ile Pro Ala
    1445                1450                1455

Val Gly Ile Pro Ala Val Gly Ile Pro Ala Val Gly Ile Pro Ala
    1460                1465                1470

Val Gly Ile Pro Ala Val Gly Ile Pro Ala Val Gly Ile Pro Ala
```

```
                1475                1480                1485

Val Gly Ile Pro Ala Val Gly Ile Pro Ala Val Gly Val Pro Ala
    1490                1495                1500

Val Gly Ile Pro Ala Val Gly Ile Pro Ala Val Gly Ile Pro Ala
    1505                1510                1515

Val Gly Ile Pro Ala Val Gly Ile Pro Ala Val Gly Ile Pro Ala
    1520                1525                1530

Val Gly Ile Pro Ala Val Gly Ile Pro Ala Val Gly Ile Pro Ala
    1535                1540                1545

Val Gly Val Pro Ala Val Gly Ile Pro Ala Val Gly Ile Pro Ala
    1550                1555                1560

Val Gly Ile Pro Ala Val Gly Ile Pro Ala Val Gly Ile Pro Ala
    1565                1570                1575

Val Gly Ile Pro Ala Val Gly Ile Pro Ala Val Gly Ile Pro Ala
    1580                1585                1590

Val Gly Ile Pro Ala Val Gly Val Pro Ala Val Gly Ile Pro Ala
    1595                1600                1605

Val Gly Ile Pro Ala Val Gly Ile Pro Ala Val Gly Ile Pro Ala
    1610                1615                1620

Val Gly Ile Pro Ala Val Gly Ile Pro Ala Val Gly Ile Pro Ala
    1625                1630                1635

Val Gly Ile Pro Ala Val Gly Ile Pro Ala Val Gly Ile Pro Gly
    1640                1645                1650

Ala Gly Val Pro Gly Ala Gly Val Pro Gly Glu Gly Val Pro Gly
    1655                1660                1665

Ala Gly Val Pro Gly Ala Gly Val Pro Gly Ala Gly Val Pro Gly
    1670                1675                1680

Ala Gly Val Pro Gly Glu Gly Val Pro Gly Ala Gly Val Pro Gly
    1685                1690                1695

Ala Gly Val Pro Gly Ala Gly Val Pro Gly Ala Gly Val Pro Gly
    1700                1705                1710

Glu Gly Val Pro Gly Ala Gly Val Pro Gly Ala Gly Val Pro Gly
    1715                1720                1725

Ala Gly Val Pro Gly Ala Gly Val Pro Gly Glu Gly Val Pro Gly
    1730                1735                1740

Ala Gly Val Pro Gly Ala Gly Val Pro Gly Ala Gly Val Pro Gly
    1745                1750                1755

Ala Gly Val Pro Gly Glu Gly Val Pro Gly Ala Gly Val Pro Gly
    1760                1765                1770

Ala Gly Val Pro Gly Ala Gly Val Pro Gly Ala Gly Val Pro Gly
    1775                1780                1785

Glu Gly Val Pro Gly Ala Gly Val Pro Gly Ala Gly Val Pro Gly
    1790                1795                1800

Ala Gly Val Pro Gly Ala Gly Val Pro Gly Glu Gly Val Pro Gly
    1805                1810                1815

Ala Gly Val Pro Gly Ala Gly Val Pro Gly Ala Gly Val Pro Gly
    1820                1825                1830

Ala Gly Val Pro Gly Glu Gly Val Pro Gly Ala Gly Val Pro Gly
    1835                1840                1845

Ala Gly Val Pro Gly Ala Gly Val Pro Gly Ala Gly Val Pro Gly
    1850                1855                1860

Glu Gly Val Pro Gly Ala Gly Val Pro Gly Ala Gly Val Pro Gly
    1865                1870                1875
```

```
Ala Gly Val Pro Gly Ala Gly Val Pro Gly Glu Gly Val Pro Gly
    1880            1885            1890

Ala Gly Val Pro Gly Ala Gly Val Pro Gly Ala Gly Val Pro Gly
    1895            1900            1905

Ala Gly Val Pro Gly Glu Gly Val Pro Gly Ala Gly Val Pro Gly
    1910            1915            1920

Ala Gly Val Pro Gly Ala Gly Val Pro Gly Ala Gly Val Pro Gly
    1925            1930            1935

Glu Gly Val Pro Gly Ala Gly Val Pro Gly Ala Gly Val Pro Gly
    1940            1945            1950

Ala Gly Val Pro Gly Ala Gly Val Pro Gly Glu Gly Val Pro Gly
    1955            1960            1965

Ala Gly Val Pro Gly Ala Gly Val Pro Gly Ala Gly Val Pro Gly
    1970            1975            1980

Ala Gly Val Pro Gly Glu Gly Val Pro Gly Ala Gly Val Pro Gly
    1985            1990            1995

Ala Gly Val Pro Gly Ala Gly Val Pro Gly Ala Gly Val Pro Gly
    2000            2005            2010

Glu Gly Val Pro Gly Ala Gly Val Pro Gly Ala Gly Val Pro Gly
    2015            2020            2025

Ala Gly Val Pro Gly Ala Gly Val Pro Gly Glu Gly Val Pro Gly
    2030            2035            2040

Ala Gly Val Pro Gly Ala Gly Val Pro Gly Ala Gly Val Pro Gly
    2045            2050            2055

Ala Gly Val Pro Gly Glu Gly Val Pro Gly Ala Gly Val Pro Gly
    2060            2065            2070

Ala Gly Val Pro Gly Ala Gly Val Pro Gly Ala Gly Val Pro Gly
    2075            2080            2085

Glu Gly Val Pro Gly Ala Gly Val Pro Gly Ala Gly Val Pro Gly
    2090            2095            2100

Ala Gly Val Pro Gly Ala Gly Val Pro Gly Glu Gly Val Pro Gly
    2105            2110            2115

Ala Gly Val Pro Gly Ala Gly Val Pro Gly Ala Gly Val Pro Gly
    2120            2125            2130

Ala Gly Val Pro Gly Glu Gly Val Pro Gly Ala Gly Val Pro Gly
    2135            2140            2145

Ala Gly Val Pro Gly Ala Gly Val Pro Gly Ala Gly Val Pro Gly
    2150            2155            2160

Glu Gly Val Pro Gly Ala Gly Val Pro Gly Ala Gly Val Pro Ala
    2165            2170            2175

Val Gly Ile Pro Ala Val Gly Ile Pro Ala Val Gly Ile Pro Ala
    2180            2185            2190

Val Gly Ile Pro Ala Val Gly Ile Pro Ala Val Gly Ile Pro Ala
    2195            2200            2205

Val Gly Ile Pro Ala Val Gly Ile Pro Ala Val Gly Ile Pro Ala
    2210            2215            2220

Val Gly Val Pro Ala Val Gly Ile Pro Ala Val Gly Ile Pro Ala
    2225            2230            2235

Val Gly Ile Pro Ala Val Gly Ile Pro Ala Val Gly Ile Pro Ala
    2240            2245            2250

Val Gly Ile Pro Ala Val Gly Ile Pro Ala Val Gly Ile Pro Ala
    2255            2260            2265
```

```
Val Gly Ile Pro Ala Val Gly Val Pro Ala Val Gly Ile Pro Ala
    2270            2275            2280

Val Gly Ile Pro Ala Val Gly Ile Pro Ala Val Gly Ile Pro Ala
    2285            2290            2295

Val Gly Ile Pro Ala Val Gly Ile Pro Ala Val Gly Ile Pro Ala
    2300            2305            2310

Val Gly Ile Pro Ala Val Gly Ile Pro Ala Val Gly Val Pro Ala
    2315            2320            2325

Val Gly Ile Pro Ala Val Gly Ile Pro Ala Val Gly Ile Pro Ala
    2330            2335            2340

Val Gly Ile Pro Ala Val Gly Ile Pro Ala Val Gly Ile Pro Ala
    2345            2350            2355

Val Gly Ile Pro Ala Val Gly Ile Pro Ala Val Gly Ile Pro Ala
    2360            2365            2370

Val Gly Val Pro Ala Val Gly Ile Pro Ala Val Gly Ile Pro Ala
    2375            2380            2385

Val Gly Ile Pro Ala Val Gly Ile Pro Ala Val Gly Ile Pro Ala
    2390            2395            2400

Val Gly Ile Pro Ala Val Gly Ile Pro Ala Val Gly Ile Pro Ala
    2405            2410            2415

Val Gly Ile Pro Ala Val Gly Val Pro Ala Val Gly Ile Pro Ala
    2420            2425            2430

Val Gly Ile Pro Ala Val Gly Ile Pro Ala Val Gly Ile Pro Ala
    2435            2440            2445

Val Gly Ile Pro Ala Val Gly Ile Pro Ala Val Gly Ile Pro Ala
    2450            2455            2460

Val Gly Ile Pro Ala Val Gly Ile Pro Ala Val Gly Val Pro Ala
    2465            2470            2475

Val Gly Ile Pro Ala Val Gly Ile Pro Ala Val Gly Ile Pro Ala
    2480            2485            2490

Val Gly Ile Pro Ala Val Gly Ile Pro Ala Val Gly Ile Pro Ala
    2495            2500            2505

Val Gly Ile Pro Ala Val Gly Ile Pro Ala Val Gly Ile Pro Ala
    2510            2515            2520

Val Gly Val Pro Ala Val Gly Ile Pro Ala Val Gly Ile Pro Ala
    2525            2530            2535

Val Gly Ile Pro Ala Val Gly Ile Pro Ala Val Gly Ile Pro Ala
    2540            2545            2550

Val Gly Ile Pro Ala Val Gly Ile Pro Ala Val Gly Ile Pro Ala
    2555            2560            2565

Val Gly Ile Pro Ala Val Gly Val Pro Ala Val Gly Ile Pro Ala
    2570            2575            2580

Val Gly Ile Pro Ala Val Gly Ile Pro Ala Val Gly Ile Pro Ala
    2585            2590            2595

Val Gly Ile Pro Ala Val Gly Ile Pro Ala Val Gly Ile Pro Ala
    2600            2605            2610

Val Gly Ile Pro Ala Val Gly Ile Pro Ala Val Gly Val Pro Ala
    2615            2620            2625

Val Gly Ile Pro Ala Val Gly Ile Pro Ala Val Gly Ile Pro Ala
    2630            2635            2640

Val Gly Ile Pro Ala Val Gly Ile Pro Ala Val Gly Ile Pro Ala
    2645            2650            2655

Val Gly Ile Pro Ala Val Gly Ile Pro Ala Val Gly Ile Pro Ala
```

```
            2660                2665                2670

Val Gly Val Pro Ala Val Gly Ile Pro Ala Val Gly Ile Pro Ala
    2675                2680                2685

Val Gly Ile Pro Ala Val Gly Ile Pro Ala Val Gly Ile Pro Ala
    2690                2695                2700

Val Gly Ile Pro Ala Val Gly Ile Pro Ala Val Gly Ile Pro Ala
    2705                2710                2715

Val Gly Ile Pro Ala Val Gly Val Pro Ala Val Gly Ile Pro Ala
    2720                2725                2730

Val Gly Ile Pro Ala Val Gly Ile Pro Ala Val Gly Ile Pro Ala
    2735                2740                2745

Val Gly Ile Pro Ala Val Gly Ile Pro Ala Val Gly Ile Pro Ala
    2750                2755                2760

Val Gly Ile Pro Ala Val Gly Ile Pro Ala Val Gly Val Pro Ala
    2765                2770                2775

Val Gly Ile Pro Ala Val Gly Ile Pro Ala Val Gly Ile Pro Ala
    2780                2785                2790

Val Gly Ile Pro Ala Val Gly Ile Pro Ala Val Gly Ile Pro Ala
    2795                2800                2805

Val Gly Ile Pro Ala Val Gly Ile Pro Ala Val Gly Ile Pro Ala
    2810                2815                2820

Val Gly Val Pro Ala Val Gly Ile Pro Ala Val Gly Ile Pro Ala
    2825                2830                2835

Val Gly Ile Pro Ala Val Gly Ile Pro Ala Val Gly Ile Pro Ala
    2840                2845                2850

Val Gly Ile Pro Ala Val Gly Ile Pro Ala Val Gly Ile Pro Ala
    2855                2860                2865

Val Gly Ile Pro Ala Val Gly Val Pro Ala Val Gly Ile Pro Ala
    2870                2875                2880

Val Gly Ile Pro Ala Val Gly Ile Pro Ala Val Gly Ile Pro Ala
    2885                2890                2895

Val Gly Ile Pro Ala Val Gly Ile Pro Ala Val Gly Ile Pro Ala
    2900                2905                2910

Val Gly Ile Pro Ala Val Gly Ile Pro Ala Val Gly Val Pro Ala
    2915                2920                2925

Val Gly Ile Pro Ala Val Gly Ile Pro Ala Val Gly Ile Pro Ala
    2930                2935                2940

Val Gly Ile Pro Ala Val Gly Ile Pro Ala Val Gly Ile Pro Ala
    2945                2950                2955

Val Gly Ile Pro Ala Val Gly Ile Pro Ala Val Gly Ile Pro Ala
    2960                2965                2970

Val Gly Val Pro Ala Val Gly Ile Pro Ala Val Gly Ile Pro Ala
    2975                2980                2985

Val Gly Ile Pro Ala Val Gly Ile Pro Ala Val Gly Ile Pro Ala
    2990                2995                3000

Val Gly Ile Pro Ala Val Gly Ile Pro Ala Val Gly Ile Pro Ala
    3005                3010                3015

Val Gly Ile Pro Ala Val Gly Val Pro Ala Val Gly Ile Pro Ala
    3020                3025                3030

Val Gly Ile Pro Ala Val Gly Ile Pro Ala Val Gly Ile Pro Ala
    3035                3040                3045

Val Gly Ile Pro Ala Val Gly Ile Pro Ala Val Gly Ile Pro Ala
    3050                3055                3060
```

```
Val Gly Ile Pro Ala Val Gly Ile Pro Ala Val Gly Val Pro Ala
    3065                3070                3075

Val Gly Ile Pro Ala Val Gly Ile Pro Ala Val Gly Ile Pro Ala
    3080                3085                3090

Val Gly Ile Pro Ala Val Gly Ile Pro Ala Val Gly Ile Pro Ala
    3095                3100                3105

Val Gly Ile Pro Ala Val Gly Ile Pro Ala Val Gly Ile Pro Ala
    3110                3115                3120

Val Gly Val Pro Ala Val Gly Ile Pro Ala Val Gly Ile Pro Ala
    3125                3130                3135

Val Gly Ile Pro Ala Val Gly Ile Pro Ala Val Gly Ile Pro Ala
    3140                3145                3150

Val Gly Ile Pro Ala Val Gly Ile Pro Ala Val Gly Ile Pro Ala
    3155                3160                3165

Val Gly Ile Pro Ala Val Gly Val Pro Ala Val Gly Ile Pro Ala
    3170                3175                3180

Val Gly Ile Pro Ala Val Gly Ile Pro Ala Val Gly Ile Pro Ala
    3185                3190                3195

Val Gly Ile Pro Ala Val Gly Ile Pro Ala Val Gly Ile Pro Ala
    3200                3205                3210

Val Gly Ile Pro Ala Val Gly Ile Pro Ala Val Gly Val Pro Ala
    3215                3220                3225

Val Gly Ile Pro Ala Val Gly Ile Pro Ala Val Gly Ile Pro Ala
    3230                3235                3240

Val Gly Ile Pro Ala Val Gly Ile Pro Ala Val Gly Ile Pro Ala
    3245                3250                3255

Val Gly Ile Pro Ala Val Gly Ile Pro Ala Val Gly Ile Pro Ala
    3260                3265                3270

Val Gly Val Pro Ala Val Gly Ile Pro Ala Val Gly Ile Pro Ala
    3275                3280                3285

Val Gly Ile Pro Ala Val Gly Ile Pro Ala Val Gly Ile Pro Ala
    3290                3295                3300

Val Gly Ile Pro Ala Val Gly Ile Pro Ala Val Gly Ile Pro Ala
    3305                3310                3315

Val Gly Ile Pro Ala Val Gly Val Pro Ala Val Gly Ile Pro Ala
    3320                3325                3330

Val Gly Ile Pro Ala Val Gly Ile Pro Ala Val Gly Ile Pro Ala
    3335                3340                3345

Val Gly Ile Pro Ala Val Gly Ile Pro Ala Val Gly Ile Pro Ala
    3350                3355                3360

Val Gly Ile Pro Ala Val Gly Ile Pro Ala Val Gly Val Pro Ala
    3365                3370                3375

Val Gly Ile Pro Ala Val Gly Ile Pro Ala Val Gly Ile Pro Ala
    3380                3385                3390

Val Gly Ile Pro Ala Val Gly Ile Pro Ala Val Gly Ile Pro Ala
    3395                3400                3405

Val Gly Ile Pro Ala Val Gly Ile Pro Ala Val Gly Ile Pro Ala
    3410                3415                3420

Val Gly Val Pro Ala Val Gly Ile Pro Ala Val Gly Ile Pro Ala
    3425                3430                3435

Val Gly Ile Pro Ala Val Gly Ile Pro Ala Val Gly Ile Pro Ala
    3440                3445                3450
```

Val Gly Ile Pro Ala Val Gly Ile Pro Ala Val Gly Ile Pro Ala
3455                3460                3465

Val Gly Ile Pro Ala Val Gly Val Pro Ala Val Gly Ile Pro Ala
3470                3475                3480

Val Gly Ile Pro Ala Val Gly Ile Pro Ala Val Gly Ile Pro Ala
3485                3490                3495

Val Gly Ile Pro Ala Val Gly Ile Pro Ala Val Gly Ile Pro Ala
3500                3505                3510

Val Gly Ile Pro Ala Val Gly Ile Pro Ala Val Gly Val Pro Ala
3515                3520                3525

Val Gly Ile Pro Ala Val Gly Ile Pro Ala Val Gly Ile Pro Ala
3530                3535                3540

Val Gly Ile Pro Ala Val Gly Ile Pro Ala Val Gly Ile Pro Ala
3545                3550                3555

Val Gly Ile Pro Ala Val Gly Ile Pro Ala Val Gly Ile Pro Ala
3560                3565                3570

Val Gly Val Pro Ala Val Gly Ile Pro Ala Val Gly Ile Pro Ala
3575                3580                3585

Val Gly Ile Pro Ala Val Gly Ile Pro Ala Val Gly Ile Pro Ala
3590                3595                3600

Val Gly Ile Pro Ala Val Gly Ile Pro Ala Val Gly Ile Pro Ala
3605                3610                3615

Val Gly Ile Pro Ala Val Gly Val Pro Ala Val Gly Ile Pro Ala
3620                3625                3630

Val Gly Ile Pro Ala Val Gly Ile Pro Ala Val Gly Ile Pro Ala
3635                3640                3645

Val Gly Ile Pro Ala Val Gly Ile Pro Ala Val Gly Ile Pro Ala
3650                3655                3660

Val Gly Ile Pro Ala Val Gly Ile Pro Ala Val Gly Val Pro Ala
3665                3670                3675

Val Gly Ile Pro Ala Val Gly Ile Pro Ala Val Gly Ile Pro Ala
3680                3685                3690

Val Gly Ile Pro Ala Val Gly Ile Pro Ala Val Gly Ile Pro Ala
3695                3700                3705

Val Gly Ile Pro Ala Val Gly Ile Pro Ala Val Gly Ile Pro Ala
3710                3715                3720

Val Gly Val Pro Ala Val Gly Ile Pro Ala Val Gly Ile Pro Ala
3725                3730                3735

Val Gly Ile Pro Ala Val Gly Ile Pro Ala Val Gly Ile Pro Ala
3740                3745                3750

Val Gly Ile Pro Ala Val Gly Ile Pro Ala Val Gly Ile Pro Ala
3755                3760                3765

Val Gly Ile Pro Ala Val Gly Val Pro Ala Val Gly Ile Pro Ala
3770                3775                3780

Val Gly Ile Pro Ala Val Gly Ile Pro Ala Val Gly Ile Pro Ala
3785                3790                3795

Val Gly Ile Pro Ala Val Gly Ile Pro Ala Val Gly Ile Pro Ala
3800                3805                3810

Val Gly Ile Pro Ala Val Gly Ile Pro Ala Val Gly
3815                3820                3825

<210> SEQ ID NO 10
<211> LENGTH: 3830
<212> TYPE: PRT

<213> ORGANISM: Artificial Sequence
<220> FEATURE:
<223> OTHER INFORMATION: Synthetic construct

<400> SEQUENCE: 10

```
Val Pro Ala Val Gly Ile Pro Ala Val Gly Ile Pro Ala Val Gly Ile
 1               5                  10                  15

Pro Ala Val Gly Ile Pro Ala Val Gly Ile Pro Ala Val Gly Ile Pro
            20                  25                  30

Ala Val Gly Ile Pro Ala Val Gly Ile Pro Ala Val Gly Ile Pro Ala
        35                  40                  45

Val Gly Val Pro Ala Val Gly Ile Pro Ala Val Gly Ile Pro Ala Val
    50                  55                  60

Gly Ile Pro Ala Val Gly Ile Pro Ala Val Gly Ile Pro Ala Val Gly
65                  70                  75                  80

Ile Pro Ala Val Gly Ile Pro Ala Val Gly Ile Pro Ala Val Gly Ile
                85                  90                  95

Pro Ala Val Gly Val Pro Ala Val Gly Ile Pro Ala Val Gly Ile Pro
            100                 105                 110

Ala Val Gly Ile Pro Ala Val Gly Ile Pro Ala Val Gly Ile Pro Ala
        115                 120                 125

Val Gly Ile Pro Ala Val Gly Ile Pro Ala Val Gly Ile Pro Ala Val
    130                 135                 140

Gly Ile Pro Ala Val Gly Val Pro Ala Val Gly Ile Pro Ala Val Gly
145                 150                 155                 160

Ile Pro Ala Val Gly Ile Pro Ala Val Gly Ile Pro Ala Val Gly Ile
                165                 170                 175

Pro Ala Val Gly Ile Pro Ala Val Gly Ile Pro Ala Val Gly Ile Pro
            180                 185                 190

Ala Val Gly Ile Pro Ala Val Gly Val Pro Ala Val Gly Ile Pro Ala
        195                 200                 205

Val Gly Ile Pro Ala Val Gly Ile Pro Ala Val Gly Ile Pro Ala Val
    210                 215                 220

Gly Ile Pro Ala Val Gly Ile Pro Ala Val Gly Ile Pro Ala Val Gly
225                 230                 235                 240

Ile Pro Ala Val Gly Ile Pro Ala Val Gly Val Pro Ala Val Gly Ile
                245                 250                 255

Pro Ala Val Gly Ile Pro Ala Val Gly Ile Pro Ala Val Gly Ile Pro
            260                 265                 270

Ala Val Gly Ile Pro Ala Val Gly Ile Pro Ala Val Gly Ile Pro Ala
        275                 280                 285

Val Gly Ile Pro Ala Val Gly Ile Pro Ala Val Gly Val Pro Ala Val
    290                 295                 300

Gly Ile Pro Ala Val Gly Ile Pro Ala Val Gly Ile Pro Ala Val Gly
305                 310                 315                 320

Ile Pro Ala Val Gly Ile Pro Ala Val Gly Ile Pro Ala Val Gly Ile
                325                 330                 335

Pro Ala Val Gly Ile Pro Ala Val Gly Ile Pro Ala Val Gly Val Pro
            340                 345                 350

Ala Val Gly Ile Pro Ala Val Gly Ile Pro Ala Val Gly Ile Pro Ala
        355                 360                 365

Val Gly Ile Pro Ala Val Gly Ile Pro Ala Val Gly Ile Pro Ala Val
    370                 375                 380

Gly Ile Pro Ala Val Gly Ile Pro Ala Val Gly Ile Pro Ala Val Gly
```

```
                385                 390                 395                 400
Val Pro Ala Val Gly Ile Pro Ala Val Gly Ile Pro Ala Val Gly Ile
                    405                 410                 415

Pro Ala Val Gly Ile Pro Ala Val Gly Ile Pro Ala Val Gly Ile Pro
                420                 425                 430

Ala Val Gly Ile Pro Ala Val Gly Ile Pro Ala Val Gly Ile Pro Ala
            435                 440                 445

Val Gly Val Pro Ala Val Gly Ile Pro Ala Val Gly Ile Pro Ala Val
        450                 455                 460

Gly Ile Pro Ala Val Gly Ile Pro Ala Val Gly Ile Pro Ala Val Gly
465                 470                 475                 480

Ile Pro Ala Val Gly Ile Pro Ala Val Gly Ile Pro Ala Val Gly Ile
                485                 490                 495

Pro Ala Val Gly Val Pro Ala Val Gly Ile Pro Ala Val Gly Ile Pro
                500                 505                 510

Ala Val Gly Ile Pro Ala Val Gly Ile Pro Ala Val Gly Ile Pro Ala
            515                 520                 525

Val Gly Ile Pro Ala Val Gly Ile Pro Ala Val Gly Ile Pro Ala Val
        530                 535                 540

Gly Ile Pro Ala Val Gly Val Pro Ala Val Gly Ile Pro Ala Val Gly
545                 550                 555                 560

Ile Pro Ala Val Gly Ile Pro Ala Val Gly Ile Pro Ala Val Gly Ile
                565                 570                 575

Pro Ala Val Gly Ile Pro Ala Val Gly Ile Pro Ala Val Gly Ile Pro
                580                 585                 590

Ala Val Gly Ile Pro Ala Val Gly Val Pro Ala Val Gly Ile Pro Ala
            595                 600                 605

Val Gly Ile Pro Ala Val Gly Ile Pro Ala Val Gly Ile Pro Ala Val
        610                 615                 620

Gly Ile Pro Ala Val Gly Ile Pro Ala Val Gly Ile Pro Ala Val Gly
625                 630                 635                 640

Ile Pro Ala Val Gly Ile Pro Ala Val Gly Val Pro Ala Val Gly Ile
                645                 650                 655

Pro Ala Val Gly Ile Pro Ala Val Gly Ile Pro Ala Val Gly Ile Pro
                660                 665                 670

Ala Val Gly Ile Pro Ala Val Gly Ile Pro Ala Val Gly Ile Pro Ala
            675                 680                 685

Val Gly Ile Pro Ala Val Gly Ile Pro Ala Val Gly Val Pro Ala Val
        690                 695                 700

Gly Ile Pro Ala Val Gly Ile Pro Ala Val Gly Ile Pro Ala Val Gly
705                 710                 715                 720

Ile Pro Ala Val Gly Ile Pro Ala Val Gly Ile Pro Ala Val Gly Ile
                725                 730                 735

Pro Ala Val Gly Ile Pro Ala Val Gly Ile Pro Ala Val Gly Val Pro
                740                 745                 750

Ala Val Gly Ile Pro Ala Val Gly Ile Pro Ala Val Gly Ile Pro Ala
            755                 760                 765

Val Gly Ile Pro Ala Val Gly Ile Pro Ala Val Gly Ile Pro Ala Val
        770                 775                 780

Gly Ile Pro Ala Val Gly Ile Pro Ala Val Gly Ile Pro Ala Val Gly
785                 790                 795                 800

Val Pro Ala Val Gly Ile Pro Ala Val Gly Ile Pro Ala Val Gly Ile
                805                 810                 815
```

-continued

Pro Ala Val Gly Ile Pro Ala Val Gly Ile Pro Ala Val Gly Ile Pro
            820                 825                 830
Ala Val Gly Ile Pro Ala Val Gly Ile Pro Ala Val Gly Ile Pro Ala
        835                 840                 845
Val Gly Val Pro Ala Val Gly Ile Pro Ala Val Gly Ile Pro Ala Val
    850                 855                 860
Gly Ile Pro Ala Val Gly Ile Pro Ala Val Gly Ile Pro Ala Val Gly
865                 870                 875                 880
Ile Pro Ala Val Gly Ile Pro Ala Val Gly Ile Pro Ala Val Gly Ile
            885                 890                 895
Pro Ala Val Gly Val Pro Ala Val Gly Ile Pro Ala Val Gly Ile Pro
            900                 905                 910
Ala Val Gly Ile Pro Ala Val Gly Ile Pro Ala Val Gly Ile Pro Ala
        915                 920                 925
Val Gly Ile Pro Ala Val Gly Ile Pro Ala Val Gly Ile Pro Ala Val
    930                 935                 940
Gly Ile Pro Ala Val Gly Val Pro Ala Val Gly Ile Pro Ala Val Gly
945                 950                 955                 960
Ile Pro Ala Val Gly Ile Pro Ala Val Gly Ile Pro Ala Val Gly Ile
            965                 970                 975
Pro Ala Val Gly Ile Pro Ala Val Gly Ile Pro Ala Val Gly Ile Pro
            980                 985                 990
Ala Val Gly Ile Pro Ala Val Gly Val Pro Ala Val Gly Ile Pro Ala
        995                 1000                1005
Val Gly Ile Pro Ala Val Gly Ile Pro Ala Val Gly Ile Pro Ala
    1010                1015                1020
Val Gly Ile Pro Ala Val Gly Ile Pro Ala Val Gly Ile Pro Ala
    1025                1030                1035
Val Gly Ile Pro Ala Val Gly Ile Pro Ala Val Gly Val Pro Ala
    1040                1045                1050
Val Gly Ile Pro Ala Val Gly Ile Pro Ala Val Gly Ile Pro Ala
    1055                1060                1065
Val Gly Ile Pro Ala Val Gly Ile Pro Ala Val Gly Ile Pro Ala
    1070                1075                1080
Val Gly Ile Pro Ala Val Gly Ile Pro Ala Val Gly Ile Pro Ala
    1085                1090                1095
Val Gly Val Pro Ala Val Gly Ile Pro Ala Val Gly Ile Pro Ala
    1100                1105                1110
Val Gly Ile Pro Ala Val Gly Ile Pro Ala Val Gly Ile Pro Ala
    1115                1120                1125
Val Gly Ile Pro Ala Val Gly Ile Pro Ala Val Gly Ile Pro Ala
    1130                1135                1140
Val Gly Ile Pro Ala Val Gly Val Pro Ala Val Gly Ile Pro Ala
    1145                1150                1155
Val Gly Ile Pro Ala Val Gly Ile Pro Ala Val Gly Ile Pro Ala
    1160                1165                1170
Val Gly Ile Pro Ala Val Gly Ile Pro Ala Val Gly Ile Pro Ala
    1175                1180                1185
Val Gly Ile Pro Ala Val Gly Ile Pro Ala Val Gly Val Pro Ala
    1190                1195                1200
Val Gly Ile Pro Ala Val Gly Ile Pro Ala Val Gly Ile Pro Ala
    1205                1210                1215

-continued

Val Gly Ile Pro Ala Val Gly Ile Pro Ala Val Gly Ile Pro Ala
1220             1225             1230

Val Gly Ile Pro Ala Val Gly Ile Pro Ala Val Gly Ile Pro Ala
1235             1240             1245

Val Gly Val Pro Ala Val Gly Ile Pro Ala Val Gly Ile Pro Ala
1250             1255             1260

Val Gly Ile Pro Ala Val Gly Ile Pro Ala Val Gly Ile Pro Ala
1265             1270             1275

Val Gly Ile Pro Ala Val Gly Ile Pro Ala Val Gly Ile Pro Ala
1280             1285             1290

Val Gly Ile Pro Ala Val Gly Val Pro Ala Val Gly Ile Pro Ala
1295             1300             1305

Val Gly Ile Pro Ala Val Gly Ile Pro Ala Val Gly Ile Pro Ala
1310             1315             1320

Val Gly Ile Pro Ala Val Gly Ile Pro Ala Val Gly Ile Pro Ala
1325             1330             1335

Val Gly Ile Pro Ala Val Gly Ile Pro Ala Val Gly Val Pro Ala
1340             1345             1350

Val Gly Ile Pro Ala Val Gly Ile Pro Ala Val Gly Ile Pro Ala
1355             1360             1365

Val Gly Ile Pro Ala Val Gly Ile Pro Ala Val Gly Ile Pro Ala
1370             1375             1380

Val Gly Ile Pro Ala Val Gly Ile Pro Ala Val Gly Ile Pro Ala
1385             1390             1395

Val Gly Val Pro Ala Val Gly Ile Pro Ala Val Gly Ile Pro Ala
1400             1405             1410

Val Gly Ile Pro Ala Val Gly Ile Pro Ala Val Gly Ile Pro Ala
1415             1420             1425

Val Gly Ile Pro Ala Val Gly Ile Pro Ala Val Gly Ile Pro Ala
1430             1435             1440

Val Gly Ile Pro Ala Val Gly Val Pro Ala Val Gly Ile Pro Ala
1445             1450             1455

Val Gly Ile Pro Ala Val Gly Ile Pro Ala Val Gly Ile Pro Ala
1460             1465             1470

Val Gly Ile Pro Ala Val Gly Ile Pro Ala Val Gly Ile Pro Ala
1475             1480             1485

Val Gly Ile Pro Ala Val Gly Ile Pro Ala Val Gly Val Pro Ala
1490             1495             1500

Val Gly Ile Pro Ala Val Gly Ile Pro Ala Val Gly Ile Pro Ala
1505             1510             1515

Val Gly Ile Pro Ala Val Gly Ile Pro Ala Val Gly Ile Pro Ala
1520             1525             1530

Val Gly Ile Pro Ala Val Gly Ile Pro Ala Val Gly Ile Pro Ala
1535             1540             1545

Val Gly Val Pro Ala Val Gly Ile Pro Ala Val Gly Ile Pro Ala
1550             1555             1560

Val Gly Ile Pro Ala Val Gly Ile Pro Ala Val Gly Ile Pro Ala
1565             1570             1575

Val Gly Ile Pro Ala Val Gly Ile Pro Ala Val Gly Ile Pro Ala
1580             1585             1590

Val Gly Ile Pro Ala Val Gly Val Pro Ala Val Gly Ile Pro Ala
1595             1600             1605

Val Gly Ile Pro Ala Val Gly Ile Pro Ala Val Gly Ile Pro Ala

-continued

```
            1610                1615                1620
Val Gly Ile Pro Ala Val Gly Ile Pro Ala Val Gly Ile Pro Ala
    1625                1630                1635
Val Gly Ile Pro Ala Val Gly Ile Pro Ala Val Gly Ile Pro Gly
    1640                1645                1650
Ala Gly Val Pro Gly Ala Gly Val Pro Gly Glu Gly Val Pro Gly
    1655                1660                1665
Ala Gly Val Pro Gly Ala Gly Val Pro Gly Ala Gly Val Pro Gly
    1670                1675                1680
Ala Gly Val Pro Gly Glu Gly Val Pro Gly Ala Gly Val Pro Gly
    1685                1690                1695
Ala Gly Val Pro Gly Ala Gly Val Pro Gly Ala Gly Val Pro Gly
    1700                1705                1710
Glu Gly Val Pro Gly Ala Gly Val Pro Gly Ala Gly Val Pro Gly
    1715                1720                1725
Ala Gly Val Pro Gly Ala Gly Val Pro Gly Glu Gly Val Pro Gly
    1730                1735                1740
Ala Gly Val Pro Gly Ala Gly Val Pro Gly Ala Gly Val Pro Gly
    1745                1750                1755
Ala Gly Val Pro Gly Glu Gly Val Pro Gly Ala Gly Val Pro Gly
    1760                1765                1770
Ala Gly Val Pro Gly Ala Gly Val Pro Gly Ala Gly Val Pro Gly
    1775                1780                1785
Glu Gly Val Pro Gly Ala Gly Val Pro Gly Ala Gly Val Pro Gly
    1790                1795                1800
Ala Gly Val Pro Gly Ala Gly Val Pro Gly Glu Gly Val Pro Gly
    1805                1810                1815
Ala Gly Val Pro Gly Ala Gly Val Pro Gly Ala Gly Val Pro Gly
    1820                1825                1830
Ala Gly Val Pro Gly Glu Gly Val Pro Gly Ala Gly Val Pro Gly
    1835                1840                1845
Ala Gly Val Pro Gly Ala Gly Val Pro Gly Ala Gly Val Pro Gly
    1850                1855                1860
Glu Gly Val Pro Gly Ala Gly Val Pro Gly Ala Gly Val Pro Gly
    1865                1870                1875
Ala Gly Val Pro Gly Ala Gly Val Pro Gly Glu Gly Val Pro Gly
    1880                1885                1890
Ala Gly Val Pro Gly Ala Gly Val Pro Gly Ala Gly Val Pro Gly
    1895                1900                1905
Ala Gly Val Pro Gly Glu Gly Val Pro Gly Ala Gly Val Pro Gly
    1910                1915                1920
Ala Gly Val Pro Gly Ala Gly Val Pro Gly Ala Gly Val Pro Gly
    1925                1930                1935
Glu Gly Val Pro Gly Ala Gly Val Pro Gly Ala Gly Val Pro Gly
    1940                1945                1950
Ala Gly Val Pro Gly Ala Gly Val Pro Gly Glu Gly Val Pro Gly
    1955                1960                1965
Ala Gly Val Pro Gly Ala Gly Val Pro Gly Ala Gly Val Pro Gly
    1970                1975                1980
Ala Gly Val Pro Gly Glu Gly Val Pro Gly Ala Gly Val Pro Gly
    1985                1990                1995
Ala Gly Val Pro Gly Ala Gly Val Pro Gly Ala Gly Val Pro Gly
    2000                2005                2010
```

```
Glu Gly Val Pro Gly Ala Gly Val Pro Gly Ala Gly Val Pro Gly
    2015                2020                2025

Ala Gly Val Pro Gly Ala Gly Val Pro Gly Glu Gly Val Pro Gly
    2030                2035                2040

Ala Gly Val Pro Gly Ala Gly Val Pro Gly Ala Gly Val Pro Gly
    2045                2050                2055

Ala Gly Val Pro Gly Glu Gly Val Pro Gly Ala Gly Val Pro Gly
    2060                2065                2070

Ala Gly Val Pro Gly Ala Gly Val Pro Gly Ala Gly Val Pro Gly
    2075                2080                2085

Glu Gly Val Pro Gly Ala Gly Val Pro Gly Ala Gly Val Pro Gly
    2090                2095                2100

Ala Gly Val Pro Gly Ala Gly Val Pro Gly Glu Gly Val Pro Gly
    2105                2110                2115

Ala Gly Val Pro Gly Ala Gly Val Pro Gly Ala Gly Val Pro Gly
    2120                2125                2130

Ala Gly Val Pro Gly Glu Gly Val Pro Gly Ala Gly Val Pro Gly
    2135                2140                2145

Ala Gly Val Pro Gly Ala Gly Val Pro Gly Ala Gly Val Pro Gly
    2150                2155                2160

Glu Gly Val Pro Gly Ala Gly Val Pro Gly Ala Gly Val Pro Ala
    2165                2170                2175

Val Gly Ile Pro Ala Val Gly Ile Pro Ala Val Gly Ile Pro Ala
    2180                2185                2190

Val Gly Ile Pro Ala Val Gly Ile Pro Ala Val Gly Ile Pro Ala
    2195                2200                2205

Val Gly Ile Pro Ala Val Gly Ile Pro Ala Val Gly Ile Pro Ala
    2210                2215                2220

Val Gly Val Pro Ala Val Gly Ile Pro Ala Val Gly Ile Pro Ala
    2225                2230                2235

Val Gly Ile Pro Ala Val Gly Ile Pro Ala Val Gly Ile Pro Ala
    2240                2245                2250

Val Gly Ile Pro Ala Val Gly Ile Pro Ala Val Gly Ile Pro Ala
    2255                2260                2265

Val Gly Ile Pro Ala Val Gly Val Pro Ala Val Gly Ile Pro Ala
    2270                2275                2280

Val Gly Ile Pro Ala Val Gly Ile Pro Ala Val Gly Ile Pro Ala
    2285                2290                2295

Val Gly Ile Pro Ala Val Gly Ile Pro Ala Val Gly Ile Pro Ala
    2300                2305                2310

Val Gly Ile Pro Ala Val Gly Ile Pro Ala Val Gly Val Pro Ala
    2315                2320                2325

Val Gly Ile Pro Ala Val Gly Ile Pro Ala Val Gly Ile Pro Ala
    2330                2335                2340

Val Gly Ile Pro Ala Val Gly Ile Pro Ala Val Gly Ile Pro Ala
    2345                2350                2355

Val Gly Ile Pro Ala Val Gly Ile Pro Ala Val Gly Ile Pro Ala
    2360                2365                2370

Val Gly Val Pro Ala Val Gly Ile Pro Ala Val Gly Ile Pro Ala
    2375                2380                2385

Val Gly Ile Pro Ala Val Gly Ile Pro Ala Val Gly Ile Pro Ala
    2390                2395                2400
```

-continued

```
Val Gly Ile Pro Ala Val Gly Ile Pro Ala Val Gly Ile Pro Ala
2405                2410                2415

Val Gly Ile Pro Ala Val Gly Val Pro Ala Val Gly Ile Pro Ala
2420                2425                2430

Val Gly Ile Pro Ala Val Gly Ile Pro Ala Val Gly Ile Pro Ala
2435                2440                2445

Val Gly Ile Pro Ala Val Gly Ile Pro Ala Val Gly Ile Pro Ala
2450                2455                2460

Val Gly Ile Pro Ala Val Gly Ile Pro Ala Val Gly Val Pro Ala
2465                2470                2475

Val Gly Ile Pro Ala Val Gly Ile Pro Ala Val Gly Ile Pro Ala
2480                2485                2490

Val Gly Ile Pro Ala Val Gly Ile Pro Ala Val Gly Ile Pro Ala
2495                2500                2505

Val Gly Ile Pro Ala Val Gly Ile Pro Ala Val Gly Ile Pro Ala
2510                2515                2520

Val Gly Val Pro Ala Val Gly Ile Pro Ala Val Gly Ile Pro Ala
2525                2530                2535

Val Gly Ile Pro Ala Val Gly Ile Pro Ala Val Gly Ile Pro Ala
2540                2545                2550

Val Gly Ile Pro Ala Val Gly Ile Pro Ala Val Gly Ile Pro Ala
2555                2560                2565

Val Gly Ile Pro Ala Val Gly Val Pro Ala Val Gly Ile Pro Ala
2570                2575                2580

Val Gly Ile Pro Ala Val Gly Ile Pro Ala Val Gly Ile Pro Ala
2585                2590                2595

Val Gly Ile Pro Ala Val Gly Ile Pro Ala Val Gly Ile Pro Ala
2600                2605                2610

Val Gly Ile Pro Ala Val Gly Ile Pro Ala Val Gly Val Pro Ala
2615                2620                2625

Val Gly Ile Pro Ala Val Gly Ile Pro Ala Val Gly Ile Pro Ala
2630                2635                2640

Val Gly Ile Pro Ala Val Gly Ile Pro Ala Val Gly Ile Pro Ala
2645                2650                2655

Val Gly Ile Pro Ala Val Gly Ile Pro Ala Val Gly Ile Pro Ala
2660                2665                2670

Val Gly Val Pro Ala Val Gly Ile Pro Ala Val Gly Ile Pro Ala
2675                2680                2685

Val Gly Ile Pro Ala Val Gly Ile Pro Ala Val Gly Ile Pro Ala
2690                2695                2700

Val Gly Ile Pro Ala Val Gly Ile Pro Ala Val Gly Ile Pro Ala
2705                2710                2715

Val Gly Ile Pro Ala Val Gly Val Pro Ala Val Gly Ile Pro Ala
2720                2725                2730

Val Gly Ile Pro Ala Val Gly Ile Pro Ala Val Gly Ile Pro Ala
2735                2740                2745

Val Gly Ile Pro Ala Val Gly Ile Pro Ala Val Gly Ile Pro Ala
2750                2755                2760

Val Gly Ile Pro Ala Val Gly Ile Pro Ala Val Gly Val Pro Ala
2765                2770                2775

Val Gly Ile Pro Ala Val Gly Ile Pro Ala Val Gly Ile Pro Ala
2780                2785                2790

Val Gly Ile Pro Ala Val Gly Ile Pro Ala Val Gly Ile Pro Ala
```

-continued

```
            2795                2800                2805

Val Gly Ile Pro Ala Val Gly Ile Pro Ala Val Gly Ile Pro Ala
        2810                2815                2820

Val Gly Val Pro Ala Val Gly Ile Pro Ala Val Gly Ile Pro Ala
        2825                2830                2835

Val Gly Ile Pro Ala Val Gly Ile Pro Ala Val Gly Ile Pro Ala
        2840                2845                2850

Val Gly Ile Pro Ala Val Gly Ile Pro Ala Val Gly Ile Pro Ala
        2855                2860                2865

Val Gly Ile Pro Ala Val Gly Val Pro Ala Val Gly Ile Pro Ala
        2870                2875                2880

Val Gly Ile Pro Ala Val Gly Ile Pro Ala Val Gly Ile Pro Ala
        2885                2890                2895

Val Gly Ile Pro Ala Val Gly Ile Pro Ala Val Gly Ile Pro Ala
        2900                2905                2910

Val Gly Ile Pro Ala Val Gly Ile Pro Ala Val Gly Val Pro Ala
        2915                2920                2925

Val Gly Ile Pro Ala Val Gly Ile Pro Ala Val Gly Ile Pro Ala
        2930                2935                2940

Val Gly Ile Pro Ala Val Gly Ile Pro Ala Val Gly Ile Pro Ala
        2945                2950                2955

Val Gly Ile Pro Ala Val Gly Ile Pro Ala Val Gly Ile Pro Ala
        2960                2965                2970

Val Gly Val Pro Ala Val Gly Ile Pro Ala Val Gly Ile Pro Ala
        2975                2980                2985

Val Gly Ile Pro Ala Val Gly Ile Pro Ala Val Gly Ile Pro Ala
        2990                2995                3000

Val Gly Ile Pro Ala Val Gly Ile Pro Ala Val Gly Ile Pro Ala
        3005                3010                3015

Val Gly Ile Pro Ala Val Gly Val Pro Ala Val Gly Ile Pro Ala
        3020                3025                3030

Val Gly Ile Pro Ala Val Gly Ile Pro Ala Val Gly Ile Pro Ala
        3035                3040                3045

Val Gly Ile Pro Ala Val Gly Ile Pro Ala Val Gly Ile Pro Ala
        3050                3055                3060

Val Gly Ile Pro Ala Val Gly Ile Pro Ala Val Gly Val Pro Ala
        3065                3070                3075

Val Gly Ile Pro Ala Val Gly Ile Pro Ala Val Gly Ile Pro Ala
        3080                3085                3090

Val Gly Ile Pro Ala Val Gly Ile Pro Ala Val Gly Ile Pro Ala
        3095                3100                3105

Val Gly Ile Pro Ala Val Gly Ile Pro Ala Val Gly Ile Pro Ala
        3110                3115                3120

Val Gly Val Pro Ala Val Gly Ile Pro Ala Val Gly Ile Pro Ala
        3125                3130                3135

Val Gly Ile Pro Ala Val Gly Ile Pro Ala Val Gly Ile Pro Ala
        3140                3145                3150

Val Gly Ile Pro Ala Val Gly Ile Pro Ala Val Gly Ile Pro Ala
        3155                3160                3165

Val Gly Ile Pro Ala Val Gly Val Pro Ala Val Gly Ile Pro Ala
        3170                3175                3180

Val Gly Ile Pro Ala Val Gly Ile Pro Ala Val Gly Ile Pro Ala
        3185                3190                3195
```

```
Val Gly Ile Pro Ala Val Gly Ile Pro Ala Val Gly Ile Pro Ala
    3200            3205            3210

Val Gly Ile Pro Ala Val Gly Ile Pro Ala Val Gly Val Pro Ala
    3215            3220            3225

Val Gly Ile Pro Ala Val Gly Ile Pro Ala Val Gly Ile Pro Ala
    3230            3235            3240

Val Gly Ile Pro Ala Val Gly Ile Pro Ala Val Gly Ile Pro Ala
    3245            3250            3255

Val Gly Ile Pro Ala Val Gly Ile Pro Ala Val Gly Ile Pro Ala
    3260            3265            3270

Val Gly Val Pro Ala Val Gly Ile Pro Ala Val Gly Ile Pro Ala
    3275            3280            3285

Val Gly Ile Pro Ala Val Gly Ile Pro Ala Val Gly Ile Pro Ala
    3290            3295            3300

Val Gly Ile Pro Ala Val Gly Ile Pro Ala Val Gly Ile Pro Ala
    3305            3310            3315

Val Gly Ile Pro Ala Val Gly Val Pro Ala Val Gly Ile Pro Ala
    3320            3325            3330

Val Gly Ile Pro Ala Val Gly Ile Pro Ala Val Gly Ile Pro Ala
    3335            3340            3345

Val Gly Ile Pro Ala Val Gly Ile Pro Ala Val Gly Ile Pro Ala
    3350            3355            3360

Val Gly Ile Pro Ala Val Gly Ile Pro Ala Val Gly Val Pro Ala
    3365            3370            3375

Val Gly Ile Pro Ala Val Gly Ile Pro Ala Val Gly Ile Pro Ala
    3380            3385            3390

Val Gly Ile Pro Ala Val Gly Ile Pro Ala Val Gly Ile Pro Ala
    3395            3400            3405

Val Gly Ile Pro Ala Val Gly Ile Pro Ala Val Gly Ile Pro Ala
    3410            3415            3420

Val Gly Val Pro Ala Val Gly Ile Pro Ala Val Gly Ile Pro Ala
    3425            3430            3435

Val Gly Ile Pro Ala Val Gly Ile Pro Ala Val Gly Ile Pro Ala
    3440            3445            3450

Val Gly Ile Pro Ala Val Gly Ile Pro Ala Val Gly Ile Pro Ala
    3455            3460            3465

Val Gly Ile Pro Ala Val Gly Val Pro Ala Val Gly Ile Pro Ala
    3470            3475            3480

Val Gly Ile Pro Ala Val Gly Ile Pro Ala Val Gly Ile Pro Ala
    3485            3490            3495

Val Gly Ile Pro Ala Val Gly Ile Pro Ala Val Gly Ile Pro Ala
    3500            3505            3510

Val Gly Ile Pro Ala Val Gly Ile Pro Ala Val Gly Val Pro Ala
    3515            3520            3525

Val Gly Ile Pro Ala Val Gly Ile Pro Ala Val Gly Ile Pro Ala
    3530            3535            3540

Val Gly Ile Pro Ala Val Gly Ile Pro Ala Val Gly Ile Pro Ala
    3545            3550            3555

Val Gly Ile Pro Ala Val Gly Ile Pro Ala Val Gly Ile Pro Ala
    3560            3565            3570

Val Gly Val Pro Ala Val Gly Ile Pro Ala Val Gly Ile Pro Ala
    3575            3580            3585
```

Val Gly Ile Pro Ala Val Gly Ile Pro Ala Val Gly Ile Pro Ala
    3590                3595                3600

Val Gly Ile Pro Ala Val Gly Ile Pro Ala Val Gly Ile Pro Ala
    3605                3610                3615

Val Gly Ile Pro Ala Val Gly Val Pro Ala Val Gly Ile Pro Ala
    3620                3625                3630

Val Gly Ile Pro Ala Val Gly Ile Pro Ala Val Gly Ile Pro Ala
    3635                3640                3645

Val Gly Ile Pro Ala Val Gly Ile Pro Ala Val Gly Ile Pro Ala
    3650                3655                3660

Val Gly Ile Pro Ala Val Gly Ile Pro Ala Val Gly Val Pro Ala
    3665                3670                3675

Val Gly Ile Pro Ala Val Gly Ile Pro Ala Val Gly Ile Pro Ala
    3680                3685                3690

Val Gly Ile Pro Ala Val Gly Ile Pro Ala Val Gly Ile Pro Ala
    3695                3700                3705

Val Gly Ile Pro Ala Val Gly Ile Pro Ala Val Gly Ile Pro Ala
    3710                3715                3720

Val Gly Val Pro Ala Val Gly Ile Pro Ala Val Gly Ile Pro Ala
    3725                3730                3735

Val Gly Ile Pro Ala Val Gly Ile Pro Ala Val Gly Ile Pro Ala
    3740                3745                3750

Val Gly Ile Pro Ala Val Gly Ile Pro Ala Val Gly Ile Pro Ala
    3755                3760                3765

Val Gly Ile Pro Ala Val Gly Val Pro Ala Val Gly Ile Pro Ala
    3770                3775                3780

Val Gly Ile Pro Ala Val Gly Ile Pro Ala Val Gly Ile Pro Ala
    3785                3790                3795

Val Gly Ile Pro Ala Val Gly Ile Pro Ala Val Gly Ile Pro Ala
    3800                3805                3810

Val Gly Ile Pro Ala Val Gly Ile Pro Ala Val Gly Val Pro Gly
    3815                3820                3825

Val Gly
    3830

<210> SEQ ID NO 11
<211> LENGTH: 15
<212> TYPE: DNA
<213> ORGANISM: Artificial Sequence
<220> FEATURE:
<223> OTHER INFORMATION: Synthetic construct

<400> SEQUENCE: 11
attccaggtg caggc                                                      15

<210> SEQ ID NO 12
<211> LENGTH: 15
<212> TYPE: DNA
<213> ORGANISM: Artificial Sequence
<220> FEATURE:
<223> OTHER INFORMATION: synthetic construct

<400> SEQUENCE: 12
gtaccgggtg ctggc                                                      15

<210> SEQ ID NO 13
<211> LENGTH: 15
<212> TYPE: DNA

<213> ORGANISM: Artificial Sequence
<220> FEATURE:
<223> OTHER INFORMATION: synthetic construct

<400> SEQUENCE: 13
gttccgggtg aaggt                                                            15

<210> SEQ ID NO 14
<211> LENGTH: 15
<212> TYPE: DNA
<213> ORGANISM: Artificial Sequence
<220> FEATURE:
<223> OTHER INFORMATION: synthetic construct

<400> SEQUENCE: 14
gttcctgctg ttggt                                                            15

<210> SEQ ID NO 15
<211> LENGTH: 15
<212> TYPE: DNA
<213> ORGANISM: Artificial Sequence
<220> FEATURE:
<223> OTHER INFORMATION: synthetic construct

<400> SEQUENCE: 15
attccggctg ttggt                                                            15

<210> SEQ ID NO 16
<211> LENGTH: 2550
<212> TYPE: DNA
<213> ORGANISM: Artificial Sequence
<220> FEATURE:
<223> OTHER INFORMATION: synthetic construct

<400> SEQUENCE: 16
gttcctgctg ttggtattcc ggctgttggt atcccagctg ttggtatccc agctgttggc     60
attccggctg taggtattcc tgctgttggt attccggctg ttggtatccc agctgttggt    120
atcccagctg ttggcattcc ggctgtaggt attcctgctg ttggtattcc ggctgttggt    180
atcccagctg ttggtatccc agctgttggc attccggctg taggtattcc tgctgttggt    240
attccggctg ttggtatccc agctgttggt atcccagctg ttggcattcc ggctgtaggt    300
attcctgctg ttggtattcc ggctgttggt atcccagctg ttggtatccc agctgttggc    360
attccggctg taggtattcc tgctgttggt attccggctg ttggtatccc agctgttggt    420
atcccagctg ttggcattcc ggctgtaggt attcctgctg ttggtattcc ggctgttggt    480
atcccagctg ttggtatccc agctgttggc attccggctg taggtattcc tgctgttggt    540
attccggctg ttggtatccc agctgttggt atcccagctg ttggcattcc ggctgtaggt    600
attcctgctg ttggtattcc ggctgttggt atcccagctg ttggtatccc agctgttggc    660
attccggctg taggtattcc tgctgttggt attccggctg ttggtatccc agctgttggt    720
atcccagctg ttggcattcc ggctgtaggt attcctgctg ttggtattcc ggctgttggt    780
atcccagctg ttggtatccc agctgttggc attccggctg taggtattcc tgctgttggt    840
attccggctg ttggtatccc agctgttggt atcccagctg ttggcattcc ggctgtaggt    900
attcctgctg ttggtattcc ggctgttggt atcccagctg ttggtatccc agctgttggc    960
attccggctg taggtattcc tgctgttggt attccggctg ttggtatccc agctgttggt   1020
atcccagctg ttggcattcc ggctgtaggt attcctgctg ttggtattcc ggctgttggt   1080
atcccagctg ttggtatccc agctgttggc attccggctg taggtattcc tgctgttggt   1140

-continued

```
attccggctg ttggtatccc agctgttggt atcccagctg ttggcattcc ggctgtaggt    1200
attcctgctg ttggtattcc ggctgttggt atcccagctg ttggtatccc agctgttggc    1260
attccggctg taggtattcc tgctgttggt attccggctg ttggtatccc agctgttggt    1320
atcccagctg ttggcattcc ggctgtaggt attcctgctg ttggtattcc ggctgttggt    1380
atcccagctg ttggtatccc agctgttggc attccggctg taggtattcc tgctgttggt    1440
attccggctg ttggtatccc agctgttggt atcccagctg ttggcattcc ggctgtaggt    1500
attcctgctg ttggtattcc ggctgttggt atcccagctg ttggtatccc agctgttggc    1560
attccggctg taggtattcc tgctgttggt attccggctg ttggtatccc agctgttggt    1620
atcccagctg ttggcattcc ggctgtaggt attcctgctg ttggtattcc ggctgttggt    1680
atcccagctg ttggtatccc agctgttggc attccggctg taggtattcc tgctgttggt    1740
attccggctg ttggtatccc agctgttggt atcccagctg ttggcattcc ggctgtaggt    1800
attcctgctg ttggtattcc ggctgttggt atcccagctg ttggtatccc agctgttggc    1860
attccggctg taggtattcc tgctgttggt attccggctg ttggtatccc agctgttggt    1920
atcccagctg ttggcattcc ggctgtaggt attcctgctg ttggtattcc ggctgttggt    1980
atcccagctg ttggtatccc agctgttggc attccggctg taggtattcc tgctgttggt    2040
attccggctg ttggtatccc agctgttggt atcccagctg ttggcattcc ggctgtaggt    2100
attcctgctg ttggtattcc ggctgttggt atcccagctg ttggtatccc agctgttggc    2160
attccggctg taggtattcc tgctgttggt attccggctg ttggtatccc agctgttggt    2220
atcccagctg ttggcattcc ggctgtaggt attcctgctg ttggtattcc ggctgttggt    2280
atcccagctg ttggtatccc agctgttggc attccggctg taggtattcc tgctgttggt    2340
attccggctg ttggtatccc agctgttggt atcccagctg ttggcattcc ggctgtaggt    2400
attcctgctg ttggtattcc ggctgttggt atcccagctg ttggtatccc agctgttggc    2460
attccggctg taggtattcc tgctgttggt attccggctg ttggtatccc agctgttggt    2520
atcccagctg ttggcattcc ggctgtaggt                                      2550
```

<210> SEQ ID NO 17
<211> LENGTH: 2565
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(2565)

<400> SEQUENCE: 17

```
gtt cct gct gtt ggt att ccg gct gtt ggt atc cca gct gtt ggt atc       48
Val Pro Ala Val Gly Ile Pro Ala Val Gly Ile Pro Ala Val Gly Ile
1               5                   10                  15 cca gct gtt ggc att ccg gct gta ggt att cct gct gtt ggt att ccg       96
Pro Ala Val Gly Ile Pro Ala Val Gly Ile Pro Ala Val Gly Ile Pro
            20                  25                  30 gct gtt ggt atc cca gct gtt ggt atc cca gct gtt ggc att ccg gct      144
Ala Val Gly Ile Pro Ala Val Gly Ile Pro Ala Val Gly Ile Pro Ala
        35                  40                  45 gta ggt att cct gct gtt ggt att ccg gct gtt ggt atc cca gct gtt      192
Val Gly Ile Pro Ala Val Gly Ile Pro Ala Val Gly Ile Pro Ala Val
    50                  55                  60 ggt atc cca gct gtt ggc att ccg gct gta ggt att cct gct gtt ggt      240
```

-continued

| | | |
|---|---|---|
| Gly Ile Pro Ala Val Gly Ile Pro Ala Val Gly Ile Pro Ala Val Gly<br>65                  70                  75                  80 | | |
| att ccg gct gtt ggt atc cca gct gtt ggt atc cca gct gtt ggc att<br>Ile Pro Ala Val Gly Ile Pro Ala Val Gly Ile Pro Ala Val Gly Ile<br>                  85                  90                  95 | 288 | |
| ccg gct gta ggt att cct gct gtt ggt att ccg gct gtt ggt atc cca<br>Pro Ala Val Gly Ile Pro Ala Val Gly Ile Pro Ala Val Gly Ile Pro<br>          100                105                110 | 336 | |
| gct gtt ggt atc cca gct gtt ggc att ccg gct gta ggt att cct gct<br>Ala Val Gly Ile Pro Ala Val Gly Ile Pro Ala Val Gly Ile Pro Ala<br>          115                120                125 | 384 | |
| gtt ggt att ccg gct gtt ggt atc cca gct gtt ggt atc cca gct gtt<br>Val Gly Ile Pro Ala Val Gly Ile Pro Ala Val Gly Ile Pro Ala Val<br>130                  135                140 | 432 | |
| ggc att ccg gct gta ggt att cct gct gtt ggt att ccg gct gtt ggt<br>Gly Ile Pro Ala Val Gly Ile Pro Ala Val Gly Ile Pro Ala Val Gly<br>145                  150                155                160 | 480 | |
| atc cca gct gtt ggt atc cca gct gtt ggc att ccg gct gta ggt att<br>Ile Pro Ala Val Gly Ile Pro Ala Val Gly Ile Pro Ala Val Gly Ile<br>          165                170                175 | 528 | |
| cct gct gtt ggt att ccg gct gtt ggt atc cca gct gtt ggt atc cca<br>Pro Ala Val Gly Ile Pro Ala Val Gly Ile Pro Ala Val Gly Ile Pro<br>          180                185                190 | 576 | |
| gct gtt ggc att ccg gct gta ggt att cct gct gtt ggt att ccg gct<br>Ala Val Gly Ile Pro Ala Val Gly Ile Pro Ala Val Gly Ile Pro Ala<br>          195                200                205 | 624 | |
| gtt ggt atc cca gct gtt ggt atc cca gct gtt ggc att ccg gct gta<br>Val Gly Ile Pro Ala Val Gly Ile Pro Ala Val Gly Ile Pro Ala Val<br>210                  215                220 | 672 | |
| ggt att cct gct gtt ggt att ccg gct gtt ggt atc cca gct gtt ggt<br>Gly Ile Pro Ala Val Gly Ile Pro Ala Val Gly Ile Pro Ala Val Gly<br>225                  230                235                240 | 720 | |
| atc cca gct gtt ggc att ccg gct gta ggt att cct gct gtt ggt att<br>Ile Pro Ala Val Gly Ile Pro Ala Val Gly Ile Pro Ala Val Gly Ile<br>          245                250                255 | 768 | |
| ccg gct gtt ggt atc cca gct gtt ggt atc cca gct gtt ggc att ccg<br>Pro Ala Val Gly Ile Pro Ala Val Gly Ile Pro Ala Val Gly Ile Pro<br>          260                265                270 | 816 | |
| gct gta ggt att cct gct gtt ggt att ccg gct gtt ggt atc cca gct<br>Ala Val Gly Ile Pro Ala Val Gly Ile Pro Ala Val Gly Ile Pro Ala<br>          275                280                285 | 864 | |
| gtt ggt atc cca gct gtt ggc att ccg gct gta ggt att cct gct gtt<br>Val Gly Ile Pro Ala Val Gly Ile Pro Ala Val Gly Ile Pro Ala Val<br>290                  295                300 | 912 | |
| ggt att ccg gct gtt ggt atc cca gct gtt ggt atc cca gct gtt ggc<br>Gly Ile Pro Ala Val Gly Ile Pro Ala Val Gly Ile Pro Ala Val Gly<br>305                  310                315                320 | 960 | |
| att ccg gct gta ggt att cct gct gtt ggt att ccg gct gtt ggt atc<br>Ile Pro Ala Val Gly Ile Pro Ala Val Gly Ile Pro Ala Val Gly Ile<br>          325                330                335 | 1008 | |
| cca gct gtt ggt atc cca gct gtt ggc att ccg gct gta ggt att cct<br>Pro Ala Val Gly Ile Pro Ala Val Gly Ile Pro Ala Val Gly Ile Pro<br>          340                345                350 | 1056 | |
| gct gtt ggt att ccg gct gtt ggt atc cca gct gtt ggt atc cca gct<br>Ala Val Gly Ile Pro Ala Val Gly Ile Pro Ala Val Gly Ile Pro Ala<br>          355                360                365 | 1104 | |
| gtt ggc att ccg gct gta ggt att cct gct gtt ggt att ccg gct gtt<br>Val Gly Ile Pro Ala Val Gly Ile Pro Ala Val Gly Ile Pro Ala Val<br>370                  375                380 | 1152 | |

```
                                      -continued ggt atc cca gct gtt ggt atc cca gct gtt ggc att ccg gct gta ggt    1200
Gly Ile Pro Ala Val Gly Ile Pro Ala Val Gly Ile Pro Ala Val Gly
385                 390                 395                 400 att cct gct gtt ggt att ccg gct gtt ggt atc cca gct gtt ggt atc    1248
Ile Pro Ala Val Gly Ile Pro Ala Val Gly Ile Pro Ala Val Gly Ile
            405                 410                 415 cca gct gtt ggc att ccg gct gta ggt att cct gct gtt ggt att ccg    1296
Pro Ala Val Gly Ile Pro Ala Val Gly Ile Pro Ala Val Gly Ile Pro
        420                 425                 430 gct gtt ggt atc cca gct gtt ggt atc cca gct gtt ggc att ccg gct    1344
Ala Val Gly Ile Pro Ala Val Gly Ile Pro Ala Val Gly Ile Pro Ala
    435                 440                 445 gta ggt att cct gct gtt ggt att ccg gct gtt ggt atc cca gct gtt    1392
Val Gly Ile Pro Ala Val Gly Ile Pro Ala Val Gly Ile Pro Ala Val
450                 455                 460 ggt atc cca gct gtt ggc att ccg gct gta ggt att cct gct gtt ggt    1440
Gly Ile Pro Ala Val Gly Ile Pro Ala Val Gly Ile Pro Ala Val Gly
465                 470                 475                 480 att ccg gct gtt ggt atc cca gct gtt ggt atc cca gct gtt ggc att    1488
Ile Pro Ala Val Gly Ile Pro Ala Val Gly Ile Pro Ala Val Gly Ile
            485                 490                 495 ccg gct gta ggt att cct gct gtt ggt att ccg gct gtt ggt atc cca    1536
Pro Ala Val Gly Ile Pro Ala Val Gly Ile Pro Ala Val Gly Ile Pro
        500                 505                 510 gct gtt ggt atc cca gct gtt ggc att ccg gct gta ggt att cct gct    1584
Ala Val Gly Ile Pro Ala Val Gly Ile Pro Ala Val Gly Ile Pro Ala
    515                 520                 525 gtt ggt att ccg gct gtt ggt atc cca gct gtt ggt atc cca gct gtt    1632
Val Gly Ile Pro Ala Val Gly Ile Pro Ala Val Gly Ile Pro Ala Val
530                 535                 540 ggc att ccg gct gta ggt att cct gct gtt ggt att ccg gct gtt ggt    1680
Gly Ile Pro Ala Val Gly Ile Pro Ala Val Gly Ile Pro Ala Val Gly
545                 550                 555                 560 atc cca gct gtt ggt atc cca gct gtt ggc att ccg gct gta ggt att    1728
Ile Pro Ala Val Gly Ile Pro Ala Val Gly Ile Pro Ala Val Gly Ile
            565                 570                 575 cct gct gtt ggt att ccg gct gtt ggt atc cca gct gtt ggt atc cca    1776
Pro Ala Val Gly Ile Pro Ala Val Gly Ile Pro Ala Val Gly Ile Pro
        580                 585                 590 gct gtt ggc att ccg gct gta ggt att cct gct gtt ggt att ccg gct    1824
Ala Val Gly Ile Pro Ala Val Gly Ile Pro Ala Val Gly Ile Pro Ala
    595                 600                 605 gtt ggt atc cca gct gtt ggt atc cca gct gtt ggc att ccg gct gta    1872
Val Gly Ile Pro Ala Val Gly Ile Pro Ala Val Gly Ile Pro Ala Val
610                 615                 620 ggt att cct gct gtt ggt att ccg gct gtt ggt atc cca gct gtt ggt    1920
Gly Ile Pro Ala Val Gly Ile Pro Ala Val Gly Ile Pro Ala Val Gly
625                 630                 635                 640 atc cca gct gtt ggc att ccg gct gta ggt att cct gct gtt ggt att    1968
Ile Pro Ala Val Gly Ile Pro Ala Val Gly Ile Pro Ala Val Gly Ile
            645                 650                 655 ccg gct gtt ggt atc cca gct gtt ggt atc cca gct gtt ggc att ccg    2016
Pro Ala Val Gly Ile Pro Ala Val Gly Ile Pro Ala Val Gly Ile Pro
        660                 665                 670 gct gta ggt att cct gct gtt ggt att ccg gct gtt ggt atc cca gct    2064
Ala Val Gly Ile Pro Ala Val Gly Ile Pro Ala Val Gly Ile Pro Ala
    675                 680                 685 gtt ggt atc cca gct gtt ggc att ccg gct gta ggt att cct gct gtt    2112
Val Gly Ile Pro Ala Val Gly Ile Pro Ala Val Gly Ile Pro Ala Val
690                 695                 700
```

-continued

```
ggt att ccg gct gtt ggt atc cca gct gtt ggc            2160
Gly Ile Pro Ala Val Gly Ile Pro Ala Val Gly
705                 710                 715                 720 att ccg gct gta ggt att cct gct gtt ggt att ccg gct gtt ggt atc    2208
Ile Pro Ala Val Gly Ile Pro Ala Val Gly Ile Pro Ala Val Gly Ile
                725                 730                 735 cca gct gtt ggt atc cca gct gtt ggc att ccg gct gta ggt att cct    2256
Pro Ala Val Gly Ile Pro Ala Val Gly Ile Pro Ala Val Gly Ile Pro
            740                 745                 750 gct gtt ggt att ccg gct gtt ggt atc cca gct gtt ggt atc cca gct    2304
Ala Val Gly Ile Pro Ala Val Gly Ile Pro Ala Val Gly Ile Pro Ala
        755                 760                 765 gtt ggc att ccg gct gta ggt att cct gct gtt ggt att ccg gct gtt    2352
Val Gly Ile Pro Ala Val Gly Ile Pro Ala Val Gly Ile Pro Ala Val
    770                 775                 780 ggt atc cca gct gtt ggt atc cca gct gtt ggc att ccg gct gta ggt    2400
Gly Ile Pro Ala Val Gly Ile Pro Ala Val Gly Ile Pro Ala Val Gly
785                 790                 795                 800 att cct gct gtt ggt att ccg gct gtt ggt atc cca gct gtt ggt atc    2448
Ile Pro Ala Val Gly Ile Pro Ala Val Gly Ile Pro Ala Val Gly Ile
                805                 810                 815 cca gct gtt ggc att ccg gct gta ggt att cct gct gtt ggt att ccg    2496
Pro Ala Val Gly Ile Pro Ala Val Gly Ile Pro Ala Val Gly Ile Pro
            820                 825                 830 gct gtt ggt atc cca gct gtt ggt atc cca gct gtt ggc att ccg gct    2544
Ala Val Gly Ile Pro Ala Val Gly Ile Pro Ala Val Gly Ile Pro Ala
        835                 840                 845 gta ggt gta cca ggt gta ggc                                        2565
Val Gly Val Pro Gly Val Gly
    850                 855
```

<210> SEQ ID NO 18
<211> LENGTH: 855
<212> TYPE: PRT
<213> ORGANISM: Artificial Sequence
<220> FEATURE:
<223> OTHER INFORMATION: Synthetic Construct

<400> SEQUENCE: 18

```
Val Pro Ala Val Gly Ile Pro Ala Val Gly Ile Pro Ala Val Gly Ile
1               5                   10                  15

Pro Ala Val Gly Ile Pro Ala Val Gly Ile Pro Ala Val Gly Ile Pro
            20                  25                  30

Ala Val Gly Ile Pro Ala Val Gly Ile Pro Ala Val Gly Ile Pro Ala
        35                  40                  45

Val Gly Ile Pro Ala Val Gly Ile Pro Ala Val Gly Ile Pro Ala Val
    50                  55                  60

Gly Ile Pro Ala Val Gly Ile Pro Ala Val Gly Ile Pro Ala Val Gly
65                  70                  75                  80

Ile Pro Ala Val Gly Ile Pro Ala Val Gly Ile Pro Ala Val Gly Ile
                85                  90                  95

Pro Ala Val Gly Ile Pro Ala Val Gly Ile Pro Ala Val Gly Ile Pro
            100                 105                 110

Ala Val Gly Ile Pro Ala Val Gly Ile Pro Ala Val Gly Ile Pro Ala
        115                 120                 125

Val Gly Ile Pro Ala Val Gly Ile Pro Ala Val Gly Ile Pro Ala Val
    130                 135                 140

Gly Ile Pro Ala Val Gly Ile Pro Ala Val Gly Ile Pro Ala Val Gly
```

```
            145                 150                 155                 160
Ile Pro Ala Val Gly Ile Pro Ala Val Gly Ile Pro Ala Val Gly Ile
                165                 170                 175
Pro Ala Val Gly Ile Pro Ala Val Gly Ile Pro Ala Val Gly Ile Pro
                180                 185                 190
Ala Val Gly Ile Pro Ala Val Gly Ile Pro Ala Val Gly Ile Pro Ala
                195                 200                 205
Val Gly Ile Pro Ala Val Gly Ile Pro Ala Val Gly Ile Pro Ala Val
            210                 215                 220
Gly Ile Pro Ala Val Gly Ile Pro Ala Val Gly Ile Pro Ala Val Gly
225                 230                 235                 240
Ile Pro Ala Val Gly Ile Pro Ala Val Gly Ile Pro Ala Val Gly Ile
                245                 250                 255
Pro Ala Val Gly Ile Pro Ala Val Gly Ile Pro Ala Val Gly Ile Pro
                260                 265                 270
Ala Val Gly Ile Pro Ala Val Gly Ile Pro Ala Val Gly Ile Pro Ala
                275                 280                 285
Val Gly Ile Pro Ala Val Gly Ile Pro Ala Val Gly Ile Pro Ala Val
            290                 295                 300
Gly Ile Pro Ala Val Gly Ile Pro Ala Val Gly Ile Pro Ala Val Gly
305                 310                 315                 320
Ile Pro Ala Val Gly Ile Pro Ala Val Gly Ile Pro Ala Val Gly Ile
                325                 330                 335
Pro Ala Val Gly Ile Pro Ala Val Gly Ile Pro Ala Val Gly Ile Pro
                340                 345                 350
Ala Val Gly Ile Pro Ala Val Gly Ile Pro Ala Val Gly Ile Pro Ala
                355                 360                 365
Val Gly Ile Pro Ala Val Gly Ile Pro Ala Val Gly Ile Pro Ala Val
            370                 375                 380
Gly Ile Pro Ala Val Gly Ile Pro Ala Val Gly Ile Pro Ala Val Gly
385                 390                 395                 400
Ile Pro Ala Val Gly Ile Pro Ala Val Gly Ile Pro Ala Val Gly Ile
                405                 410                 415
Pro Ala Val Gly Ile Pro Ala Val Gly Ile Pro Ala Val Gly Ile Pro
                420                 425                 430
Ala Val Gly Ile Pro Ala Val Gly Ile Pro Ala Val Gly Ile Pro Ala
                435                 440                 445
Val Gly Ile Pro Ala Val Gly Ile Pro Ala Val Gly Ile Pro Ala Val
            450                 455                 460
Gly Ile Pro Ala Val Gly Ile Pro Ala Val Gly Ile Pro Ala Val Gly
465                 470                 475                 480
Ile Pro Ala Val Gly Ile Pro Ala Val Gly Ile Pro Ala Val Gly Ile
                485                 490                 495
Pro Ala Val Gly Ile Pro Ala Val Gly Ile Pro Ala Val Gly Ile Pro
                500                 505                 510
Ala Val Gly Ile Pro Ala Val Gly Ile Pro Ala Val Gly Ile Pro Ala
                515                 520                 525
Val Gly Ile Pro Ala Val Gly Ile Pro Ala Val Gly Ile Pro Ala Val
            530                 535                 540
Gly Ile Pro Ala Val Gly Ile Pro Ala Val Gly Ile Pro Ala Val Gly
545                 550                 555                 560
Ile Pro Ala Val Gly Ile Pro Ala Val Gly Ile Pro Ala Val Gly Ile
                565                 570                 575
```

```
Pro Ala Val Gly Ile Pro Ala Val Gly Ile Pro Ala Val Gly Ile Pro
            580                 585                 590

Ala Val Gly Ile Pro Ala Val Gly Ile Pro Ala Val Gly Ile Pro Ala
        595                 600                 605

Val Gly Ile Pro Ala Val Gly Ile Pro Ala Val Gly Ile Pro Ala Val
    610                 615                 620

Gly Ile Pro Ala Val Gly Ile Pro Ala Val Gly Ile Pro Ala Val Gly
625                 630                 635                 640

Ile Pro Ala Val Gly Ile Pro Ala Val Gly Ile Pro Ala Val Gly Ile
                645                 650                 655

Pro Ala Val Gly Ile Pro Ala Val Gly Ile Pro Ala Val Gly Ile Pro
            660                 665                 670

Ala Val Gly Ile Pro Ala Val Gly Ile Pro Ala Val Gly Ile Pro Ala
        675                 680                 685

Val Gly Ile Pro Ala Val Gly Ile Pro Ala Val Gly Ile Pro Ala Val
    690                 695                 700

Gly Ile Pro Ala Val Gly Ile Pro Ala Val Gly Ile Pro Ala Val Gly
705                 710                 715                 720

Ile Pro Ala Val Gly Ile Pro Ala Val Gly Ile Pro Ala Val Gly Ile
                725                 730                 735

Pro Ala Val Gly Ile Pro Ala Val Gly Ile Pro Ala Val Gly Ile Pro
            740                 745                 750

Ala Val Gly Ile Pro Ala Val Gly Ile Pro Ala Val Gly Ile Pro Ala
        755                 760                 765

Val Gly Ile Pro Ala Val Gly Ile Pro Ala Val Gly Ile Pro Ala Val
    770                 775                 780

Gly Ile Pro Ala Val Gly Ile Pro Ala Val Gly Ile Pro Ala Val Gly
785                 790                 795                 800

Ile Pro Ala Val Gly Ile Pro Ala Val Gly Ile Pro Ala Val Gly Ile
                805                 810                 815

Pro Ala Val Gly Ile Pro Ala Val Gly Ile Pro Ala Val Gly Ile Pro
            820                 825                 830

Ala Val Gly Ile Pro Ala Val Gly Ile Pro Ala Val Gly Ile Pro Ala
        835                 840                 845

Val Gly Val Pro Gly Val Gly
    850                 855

<210> SEQ ID NO 19
<211> LENGTH: 1575
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(1575)

<400> SEQUENCE: 19 att cca ggt gca ggc gta ccg ggt gct ggc gtt ccg ggt gaa ggt gtt      48
Ile Pro Gly Ala Gly Val Pro Gly Ala Gly Val Pro Gly Glu Gly Val
1               5                   10                  15 cca ggc gca ggt gta ccg ggt gcg ggt gtt cca ggt gca ggc gta ccg      96
Pro Gly Ala Gly Val Pro Gly Ala Gly Pro Gly Ala Gly Val Pro
            20                  25                  30 ggt gct ggc gtt ccg ggt gaa ggt gtt cca ggc gca ggt gta ccg ggt     144
Gly Ala Gly Val Pro Gly Glu Gly Val Pro Gly Ala Gly Val Pro Gly
        35                  40                  45
```

| | | |
|---|---|---|
| gcg ggt ggt cca ggt gca ggc gta ccg ggt gct ggc gtt ccg ggt gaa<br>Ala Gly Gly Pro Gly Ala Gly Val Pro Gly Ala Gly Val Pro Gly Glu<br>50          55          60 | 192 | |
| ggt gtt cca ggc gca ggt gta ccg ggt gcg ggt ggt cca ggt gca ggc<br>Gly Val Pro Gly Ala Gly Val Pro Gly Ala Gly Gly Pro Gly Ala Gly<br>65          70          75          80 | 240 | |
| gta ccg ggt gct ggc gtt ccg ggt gaa ggt gtt cca ggc gca ggt gta<br>Val Pro Gly Ala Gly Val Pro Gly Glu Gly Val Pro Gly Ala Gly Val<br>85          90          95 | 288 | |
| ccg ggt gcg ggt ggt cca ggt gca ggc gta ccg ggt gct ggc gtt ccg<br>Pro Gly Ala Gly Gly Pro Gly Ala Gly Val Pro Gly Ala Gly Val Pro<br>100         105         110 | 336 | |
| ggt gaa ggt gtt cca ggc gca ggt gta ccg ggt gcg ggt ggt cca ggt<br>Gly Glu Gly Val Pro Gly Ala Gly Val Pro Gly Ala Gly Gly Pro Gly<br>115         120         125 | 384 | |
| gca ggc gta ccg ggt gct ggc gtt ccg ggt gaa ggt gtt cca ggc gca<br>Ala Gly Val Pro Gly Ala Gly Val Pro Gly Glu Gly Val Pro Gly Ala<br>130         135         140 | 432 | |
| ggt gta ccg ggt gcg ggt ggt cca ggt gca ggc gta ccg ggt gct ggc<br>Gly Val Pro Gly Ala Gly Gly Pro Gly Ala Gly Val Pro Gly Ala Gly<br>145         150         155         160 | 480 | |
| gtt ccg ggt gaa ggt gtt cca ggc gca ggt gta ccg ggt gcg ggt ggt<br>Val Pro Gly Glu Gly Val Pro Gly Ala Gly Val Pro Gly Ala Gly Gly<br>165         170         175 | 528 | |
| cca ggt gca ggc gta ccg ggt gct ggc gtt ccg ggt gaa ggt gtt cca<br>Pro Gly Ala Gly Val Pro Gly Ala Gly Val Pro Gly Glu Gly Val Pro<br>180         185         190 | 576 | |
| ggc gca ggt gta ccg ggt gcg ggt ggt cca ggt gca ggc gta ccg ggt<br>Gly Ala Gly Val Pro Gly Ala Gly Gly Pro Gly Ala Gly Val Pro Gly<br>195         200         205 | 624 | |
| gct ggc gtt ccg ggt gaa ggt gtt cca ggc gca ggt gta ccg ggt gcg<br>Ala Gly Val Pro Gly Glu Gly Val Pro Gly Ala Gly Val Pro Gly Ala<br>210         215         220 | 672 | |
| ggt ggt cca ggt gca ggc gta ccg ggt gct ggc gtt ccg ggt gaa ggt<br>Gly Gly Pro Gly Ala Gly Val Pro Gly Ala Gly Val Pro Gly Glu Gly<br>225         230         235         240 | 720 | |
| gtt cca ggc gca ggt gta ccg ggt gcg ggt ggt cca ggt gca ggc gta<br>Val Pro Gly Ala Gly Val Pro Gly Ala Gly Gly Pro Gly Ala Gly Val<br>245         250         255 | 768 | |
| ccg ggt gct ggc gtt ccg ggt gaa ggt gtt cca ggc gca ggt gta ccg<br>Pro Gly Ala Gly Val Pro Gly Glu Gly Val Pro Gly Ala Gly Val Pro<br>260         265         270 | 816 | |
| ggt gcg ggt ggt cca ggt gca ggc gta ccg ggt gct ggc gtt ccg ggt<br>Gly Ala Gly Gly Pro Gly Ala Gly Val Pro Gly Ala Gly Val Pro Gly<br>275         280         285 | 864 | |
| gaa ggt gtt cca ggc gca ggt gta ccg ggt gcg ggt ggt cca ggt gca<br>Glu Gly Val Pro Gly Ala Gly Val Pro Gly Ala Gly Gly Pro Gly Ala<br>290         295         300 | 912 | |
| ggc gta ccg ggt gct ggc gtt ccg ggt gaa ggt gtt cca ggc gca ggt<br>Gly Val Pro Gly Ala Gly Val Pro Gly Glu Gly Val Pro Gly Ala Gly<br>305         310         315         320 | 960 | |
| gta ccg ggt gcg ggt ggt cca ggt gca ggc gta ccg ggt gct ggc gtt<br>Val Pro Gly Ala Gly Gly Pro Gly Ala Gly Val Pro Gly Ala Gly Val<br>325         330         335 | 1008 | |
| ccg ggt gaa ggt gtt cca ggc gca ggt gta ccg ggt gcg ggt ggt cca<br>Pro Gly Glu Gly Val Pro Gly Ala Gly Val Pro Gly Ala Gly Gly Pro<br>340         345         350 | 1056 | |
| ggt gca ggc gta ccg ggt gct ggc gtt ccg ggt gaa ggt gtt cca ggc<br>Gly Ala Gly Val Pro Gly Ala Gly Val Pro Gly Glu Gly Val Pro Gly | 1104 | |

```
gca ggt gta ccg ggt gcg ggt ggt cca ggt gca ggt gta ccg ggt gct    1152
Ala Gly Val Pro Gly Ala Gly Gly Pro Gly Ala Gly Val Pro Gly Ala
370                 375                 380 ggc gtt ccg ggt gaa ggt gtt cca ggc gca ggt gta ccg ggt gcg ggt    1200
Gly Val Pro Gly Glu Gly Val Pro Gly Ala Gly Val Pro Gly Ala Gly
385                 390                 395                 400 ggt cca ggt gca ggc gta ccg ggt gct ggc gtt ccg ggt gaa ggt gtt    1248
Gly Pro Gly Ala Gly Val Pro Gly Ala Gly Val Pro Gly Glu Gly Val
            405                 410                 415 cca ggc gca ggt gta ccg ggt gcg ggt ggt cca ggt gca ggc gta ccg    1296
Pro Gly Ala Gly Val Pro Gly Ala Gly Gly Pro Gly Ala Gly Val Pro
        420                 425                 430 ggt gct ggc gtt ccg ggt gaa ggt gtt cca ggc gca ggt gta ccg ggt    1344
Gly Ala Gly Val Pro Gly Glu Gly Val Pro Gly Ala Gly Val Pro Gly
    435                 440                 445 gcg ggt ggt cca ggt gca ggc gta ccg ggt gct ggc gtt ccg ggt gaa    1392
Ala Gly Gly Pro Gly Ala Gly Val Pro Gly Ala Gly Val Pro Gly Glu
450                 455                 460 ggt gtt cca ggc gca ggt gta ccg ggt gcg ggt ggt cca ggt gca ggc    1440
Gly Val Pro Gly Ala Gly Val Pro Gly Ala Gly Gly Pro Gly Ala Gly
465                 470                 475                 480 gta ccg ggt gct ggc gtt ccg ggt gaa ggt gtt cca ggc gca ggt gta    1488
Val Pro Gly Ala Gly Val Pro Gly Glu Gly Val Pro Gly Ala Gly Val
            485                 490                 495 ccg ggt gcg ggt ggt cca ggt gca ggc gta ccg ggt gct ggc gtt ccg    1536
Pro Gly Ala Gly Gly Pro Gly Ala Gly Val Pro Gly Ala Gly Val Pro
        500                 505                 510 ggt gaa ggt gtt cca ggc gca ggt gta ccg ggt gcg ggt                1575
Gly Glu Gly Val Pro Gly Ala Gly Val Pro Gly Ala Gly
    515                 520                 525
```

<210> SEQ ID NO 20
<211> LENGTH: 525
<212> TYPE: PRT
<213> ORGANISM: Artificial Sequence
<220> FEATURE:
<223> OTHER INFORMATION: Synthetic Construct

<400> SEQUENCE: 20

```
Ile Pro Gly Ala Gly Val Pro Gly Ala Gly Val Pro Gly Glu Gly Val
1               5                   10                  15

Pro Gly Ala Gly Val Pro Gly Ala Gly Gly Pro Gly Ala Gly Val Pro
            20                  25                  30

Gly Ala Gly Val Pro Gly Glu Gly Val Pro Gly Ala Gly Val Pro Gly
        35                  40                  45

Ala Gly Gly Pro Gly Ala Gly Val Pro Gly Ala Gly Val Pro Gly Glu
    50                  55                  60

Gly Val Pro Gly Ala Gly Val Pro Gly Ala Gly Gly Pro Gly Ala Gly
65                  70                  75                  80

Val Pro Gly Ala Gly Val Pro Gly Glu Gly Val Pro Gly Ala Gly Val
                85                  90                  95

Pro Gly Ala Gly Gly Pro Gly Ala Gly Val Pro Gly Ala Gly Val Pro
            100                 105                 110

Gly Glu Gly Val Pro Gly Ala Gly Val Pro Gly Ala Gly Gly Pro Gly
        115                 120                 125

Ala Gly Val Pro Gly Ala Gly Val Pro Gly Glu Gly Val Pro Gly Ala
    130                 135                 140
```

```
Gly Val Pro Gly Ala Gly Gly Pro Gly Ala Gly Val Pro Gly Ala Gly
145                 150                 155                 160
Val Pro Gly Glu Gly Val Pro Gly Ala Gly Val Pro Gly Ala Gly Gly
                165                 170                 175
Pro Gly Ala Gly Val Pro Gly Ala Gly Val Pro Gly Glu Gly Val Pro
            180                 185                 190
Gly Ala Gly Val Pro Gly Ala Gly Pro Gly Ala Gly Val Pro Gly
        195                 200                 205
Ala Gly Val Pro Gly Glu Gly Val Pro Gly Ala Gly Val Pro Gly Ala
    210                 215                 220
Gly Gly Pro Gly Ala Gly Val Pro Gly Ala Gly Val Pro Gly Glu Gly
225                 230                 235                 240
Val Pro Gly Ala Gly Val Pro Gly Ala Gly Gly Pro Gly Ala Gly Val
                245                 250                 255
Pro Gly Ala Gly Val Pro Gly Glu Gly Val Pro Gly Ala Gly Val Pro
            260                 265                 270
Gly Ala Gly Gly Pro Gly Ala Gly Val Pro Gly Ala Gly Val Pro Gly
        275                 280                 285
Glu Gly Val Pro Gly Ala Gly Val Pro Gly Ala Gly Gly Pro Gly Ala
    290                 295                 300
Gly Val Pro Gly Ala Gly Val Pro Gly Glu Gly Val Pro Gly Ala Gly
305                 310                 315                 320
Val Pro Gly Ala Gly Gly Pro Gly Ala Gly Val Pro Gly Ala Gly Val
                325                 330                 335
Pro Gly Glu Gly Val Pro Gly Ala Gly Val Pro Gly Ala Gly Gly Pro
            340                 345                 350
Gly Ala Gly Val Pro Gly Ala Gly Val Pro Gly Glu Gly Val Pro Gly
        355                 360                 365
Ala Gly Val Pro Gly Ala Gly Gly Pro Gly Ala Gly Val Pro Gly Ala
    370                 375                 380
Gly Val Pro Gly Glu Gly Val Pro Gly Ala Gly Val Pro Gly Ala Gly
385                 390                 395                 400
Gly Pro Gly Ala Gly Val Pro Gly Ala Gly Val Pro Gly Glu Gly Val
                405                 410                 415
Pro Gly Ala Gly Val Pro Gly Ala Gly Gly Pro Gly Ala Gly Val Pro
            420                 425                 430
Gly Ala Gly Val Pro Gly Glu Gly Val Pro Gly Ala Gly Val Pro Gly
        435                 440                 445
Ala Gly Gly Pro Gly Ala Gly Val Pro Gly Ala Gly Val Pro Gly Glu
    450                 455                 460
Gly Val Pro Gly Ala Gly Val Pro Gly Ala Gly Gly Pro Gly Ala Gly
465                 470                 475                 480
Val Pro Gly Ala Gly Val Pro Gly Glu Gly Val Pro Gly Ala Gly Val
                485                 490                 495
Pro Gly Ala Gly Gly Pro Gly Ala Gly Val Pro Gly Ala Gly Val Pro
            500                 505                 510
Gly Glu Gly Val Pro Gly Ala Gly Val Pro Gly Ala Gly
        515                 520                 525

<210> SEQ ID NO 21
<211> LENGTH: 6675
<212> TYPE: DNA
<213> ORGANISM: Artificial Sequence
<220> FEATURE:
<223> OTHER INFORMATION: synthetic construct
```

<400> SEQUENCE: 21

```
gttcctgctg ttggtattcc ggctgttggt atcccagctg ttggtatccc agctgttggc     60
attccggctg taggtattcc tgctgttggt attccggctg ttggtatccc agctgttggt    120
atcccagctg ttggcattcc ggctgtaggt attcctgctg ttggtattcc ggctgttggt    180
atcccagctg ttggtatccc agctgttggc attccggctg taggtattcc tgctgttggt    240
attccggctg ttggtatccc agctgttggt atcccagctg ttggcattcc ggctgtaggt    300
attcctgctg ttggtattcc ggctgttggt atcccagctg ttggtatccc agctgttggc    360
attccggctg taggtattcc tgctgttggt attccggctg ttggtatccc agctgttggt    420
atcccagctg ttggcattcc ggctgtaggt attcctgctg ttggtattcc ggctgttggt    480
atcccagctg ttggtatccc agctgttggc attccggctg taggtattcc tgctgttggt    540
attccggctg ttggtatccc agctgttggt atcccagctg ttggcattcc ggctgtaggt    600
attcctgctg ttggtattcc ggctgttggt atcccagctg ttggtatccc agctgttggc    660
attccggctg taggtattcc tgctgttggt attccggctg ttggtatccc agctgttggt    720
atcccagctg ttggcattcc ggctgtaggt attcctgctg ttggtattcc ggctgttggt    780
atcccagctg ttggtatccc agctgttggc attccggctg taggtattcc tgctgttggt    840
attccggctg ttggtatccc agctgttggt atcccagctg ttggcattcc ggctgtaggt    900
attcctgctg ttggtattcc ggctgttggt atcccagctg ttggtatccc agctgttggc    960
attccggctg taggtattcc tgctgttggt attccggctg ttggtatccc agctgttggt   1020
atcccagctg ttggcattcc ggctgtaggt attcctgctg ttggtattcc ggctgttggt   1080
atcccagctg ttggtatccc agctgttggc attccggctg taggtattcc tgctgttggt   1140
attccggctg ttggtatccc agctgttggt atcccagctg ttggcattcc ggctgtaggt   1200
attcctgctg ttggtattcc ggctgttggt atcccagctg ttggtatccc agctgttggc   1260
attccggctg taggtattcc tgctgttggt attccggctg ttggtatccc agctgttggt   1320
atcccagctg ttggcattcc ggctgtaggt attcctgctg ttggtattcc ggctgttggt   1380
atcccagctg ttggtatccc agctgttggc attccggctg taggtattcc tgctgttggt   1440
attccggctg ttggtatccc agctgttggt atcccagctg ttggcattcc ggctgtaggt   1500
attcctgctg ttggtattcc ggctgttggt atcccagctg ttggtatccc agctgttggc   1560
attccggctg taggtattcc tgctgttggt attccggctg ttggtatccc agctgttggt   1620
atcccagctg ttggcattcc ggctgtaggt attcctgctg ttggtattcc ggctgttggt   1680
atcccagctg ttggtatccc agctgttggc attccggctg taggtattcc tgctgttggt   1740
attccggctg ttggtatccc agctgttggt atcccagctg ttggcattcc ggctgtaggt   1800
attcctgctg ttggtattcc ggctgttggt atcccagctg ttggtatccc agctgttggc   1860
attccggctg taggtattcc tgctgttggt attccggctg ttggtatccc agctgttggt   1920
atcccagctg ttggcattcc ggctgtaggt attcctgctg ttggtattcc ggctgttggt   1980
atcccagctg ttggtatccc agctgttggc attccggctg taggtattcc tgctgttggt   2040
attccggctg ttggtatccc agctgttggt atcccagctg ttggcattcc ggctgtaggt   2100
attcctgctg ttggtattcc ggctgttggt atcccagctg ttggtatccc agctgttggc   2160
attccggctg taggtattcc tgctgttggt attccggctg ttggtatccc agctgttggt   2220
atcccagctg ttggcattcc ggctgtaggt attcctgctg ttggtattcc ggctgttggt   2280
```

```
atcccagctg ttggtatccc agctgttggc attccggctg taggtattcc tgctgttggt      2340
attccggctg ttggtatccc agctgttggt atcccagctg ttggcattcc ggctgtaggt      2400
attcctgctg ttggtattcc ggctgttggt atcccagctg ttggtatccc agctgttggc      2460
attccggctg taggtattcc tgctgttggt attccggctg ttggtatccc agctgttggt      2520
atcccagctg ttggcattcc ggctgtaggt attccaggtg caggcgtacc gggtgctggc      2580
gttccgggtg aaggtgttcc aggcgcaggt gtaccgggtg cgggtggtcc aggtgcaggc      2640
gtaccgggtg ctggcgttcc gggtgaaggt gttccaggcg caggtgtacc gggtgcgggt      2700
ggtccaggtg caggcgtacc gggtgctggc gttccgggtg aaggtgttcc aggcgcaggt      2760
gtaccgggtg cgggtggtcc aggtgcaggc gtaccgggtg ctggcgttcc gggtgaaggt      2820
gttccaggcg caggtgtacc gggtgcgggt ggtccaggtg caggcgtacc gggtgctggc      2880
gttccgggtg aaggtgttcc aggcgcaggt gtaccgggtg cgggtggtcc aggtgcaggc      2940
gtaccgggtg ctggcgttcc gggtgaaggt gttccaggcg caggtgtacc gggtgcgggt      3000
ggtccaggtg caggcgtacc gggtgctggc gttccgggtg aaggtgttcc aggcgcaggt      3060
gtaccgggtg cgggtggtcc aggtgcaggc gtaccgggtg ctggcgttcc gggtgaaggt      3120
gttccaggcg caggtgtacc gggtgcgggt ggtccaggtg caggcgtacc gggtgctggc      3180
gttccgggtg aaggtgttcc aggcgcaggt gtaccgggtg cgggtggtcc aggtgcaggc      3240
gtaccgggtg ctggcgttcc gggtgaaggt gttccaggcg caggtgtacc gggtgcgggt      3300
ggtccaggtg caggcgtacc gggtgctggc gttccgggtg aaggtgttcc aggcgcaggt      3360
gtaccgggtg cgggtggtcc aggtgcaggc gtaccgggtg ctggcgttcc gggtgaaggt      3420
gttccaggcg caggtgtacc gggtgcgggt ggtccaggtg caggcgtacc gggtgctggc      3480
gttccgggtg aaggtgttcc aggcgcaggt gtaccgggtg cgggtggtcc aggtgcaggc      3540
gtaccgggtg ctggcgttcc gggtgaaggt gttccaggcg caggtgtacc gggtgcgggt      3600
ggtccaggtg caggcgtacc gggtgctggc gttccgggtg aaggtgttcc aggcgcaggt      3660
gtaccgggtg cgggtggtcc aggtgcaggc gtaccgggtg ctggcgttcc gggtgaaggt      3720
gttccaggcg caggtgtacc gggtgcgggt ggtccaggtg caggcgtacc gggtgctggc      3780
gttccgggtg aaggtgttcc aggcgcaggt gtaccgggtg cgggtggtcc aggtgcaggc      3840
gtaccgggtg ctggcgttcc gggtgaaggt gttccaggcg caggtgtacc gggtgcgggt      3900
ggtccaggtg caggcgtacc gggtgctggc gttccgggtg aaggtgttcc aggcgcaggt      3960
gtaccgggtg cgggtggtcc aggtgcaggc gtaccgggtg ctggcgttcc gggtgaaggt      4020
gttccaggcg caggtgtacc gggtgcgggt ggtccaggtg caggcgtacc gggtgctggc      4080
gttccgggtg aaggtgttcc aggcgcaggt gtaccgggtg cgggtgttcc tgctgttggt      4140
attccggctg ttggtatccc agctgttggt atcccagctg ttggcattcc ggctgtaggt      4200
attcctgctg ttggtattcc ggctgttggt atcccagctg ttggtatccc agctgttggc      4260
attccggctg taggtattcc tgctgttggt attccggctg ttggtatccc agctgttggt      4320
atcccagctg ttggcattcc ggctgtaggt attcctgctg ttggtattcc ggctgttggt      4380
atcccagctg ttggtatccc agctgttggc attccggctg taggtattcc tgctgttggt      4440
attccggctg ttggtatccc agctgttggt atcccagctg ttggcattcc ggctgtaggt      4500
attcctgctg ttggtattcc ggctgttggt atcccagctg ttggtatccc agctgttggc      4560
attccggctg taggtattcc tgctgttggt attccggctg ttggtatccc agctgttggt      4620
atcccagctg ttggcattcc ggctgtaggt attcctgctg ttggtattcc ggctgttggt      4680
```

```
atcccagctg ttggtatccc agctgttggc attccggctg taggtattcc tgctgttggt    4740
attccggctg ttggtatccc agctgttggt atcccagctg ttggcattcc ggctgtaggt    4800
attcctgctg ttggtattcc ggctgttggt atcccagctg ttggtatccc agctgttggc    4860
attccggctg taggtattcc tgctgttggt attccggctg ttggtatccc agctgttggt    4920
atcccagctg ttggcattcc ggctgtaggt attcctgctg ttggtattcc ggctgttggt    4980
atcccagctg ttggtatccc agctgttggc attccggctg taggtattcc tgctgttggt    5040
attccggctg ttggtatccc agctgttggt atcccagctg ttggcattcc ggctgtaggt    5100
attcctgctg ttggtattcc ggctgttggt atcccagctg ttggtatccc agctgttggc    5160
attccggctg taggtattcc tgctgttggt attccggctg ttggtatccc agctgttggt    5220
atcccagctg ttggcattcc ggctgtaggt attcctgctg ttggtattcc ggctgttggt    5280
atcccagctg ttggtatccc agctgttggc attccggctg taggtattcc tgctgttggt    5340
attccggctg ttggtatccc agctgttggt atcccagctg ttggcattcc ggctgtaggt    5400
attcctgctg ttggtattcc ggctgttggt atcccagctg ttggtatccc agctgttggc    5460
attccggctg taggtattcc tgctgttggt attccggctg ttggtatccc agctgttggt    5520
atcccagctg ttggcattcc ggctgtaggt attcctgctg ttggtattcc ggctgttggt    5580
atcccagctg ttggtatccc agctgttggc attccggctg taggtattcc tgctgttggt    5640
attccggctg ttggtatccc agctgttggt atcccagctg ttggcattcc ggctgtaggt    5700
attcctgctg ttggtattcc ggctgttggt atcccagctg ttggtatccc agctgttggc    5760
attccggctg taggtattcc tgctgttggt attccggctg ttggtatccc agctgttggt    5820
atcccagctg ttggcattcc ggctgtaggt attcctgctg ttggtattcc ggctgttggt    5880
atcccagctg ttggtatccc agctgttggc attccggctg taggtattcc tgctgttggt    5940
attccggctg ttggtatccc agctgttggt atcccagctg ttggcattcc ggctgtaggt    6000
attcctgctg ttggtattcc ggctgttggt atcccagctg ttggtatccc agctgttggc    6060
attccggctg taggtattcc tgctgttggt attccggctg ttggtatccc agctgttggt    6120
atcccagctg ttggcattcc ggctgtaggt attcctgctg ttggtattcc ggctgttggt    6180
atcccagctg ttggtatccc agctgttggc attccggctg taggtattcc tgctgttggt    6240
attccggctg ttggtatccc agctgttggt atcccagctg ttggcattcc ggctgtaggt    6300
attcctgctg ttggtattcc ggctgttggt atcccagctg ttggtatccc agctgttggc    6360
attccggctg taggtattcc tgctgttggt attccggctg ttggtatccc agctgttggt    6420
atcccagctg ttggcattcc ggctgtaggt attcctgctg ttggtattcc ggctgttggt    6480
atcccagctg ttggtatccc agctgttggc attccggctg taggtattcc tgctgttggt    6540
attccggctg ttggtatccc agctgttggt atcccagctg ttggcattcc ggctgtaggt    6600
attcctgctg ttggtattcc ggctgttggt atcccagctg ttggtatccc agctgttggc    6660
attccggctg taggt                                                     6675

<210> SEQ ID NO 22
<211> LENGTH: 6690
<212> TYPE: DNA
<213> ORGANISM: Artificial Sequence
<220> FEATURE:
<223> OTHER INFORMATION: synthetic construct

<400> SEQUENCE: 22
```

```
gttcctgctg ttggtattcc ggctgttggt atcccagctg ttggtatccc agctgttggc      60
attccggctg taggtattcc tgctgttggt attccggctg ttggtatccc agctgttggt     120
atcccagctg ttggcattcc ggctgtaggt attcctgctg ttggtattcc ggctgttggt     180
atcccagctg ttggtatccc agctgttggc attccggctg taggtattcc tgctgttggt     240
attccggctg ttggtatccc agctgttggt atcccagctg ttggcattcc ggctgtaggt     300
attcctgctg ttggtattcc ggctgttggt atcccagctg ttggtatccc agctgttggc     360
attccggctg taggtattcc tgctgttggt attccggctg ttggtatccc agctgttggt     420
atcccagctg ttggcattcc ggctgtaggt attcctgctg ttggtattcc ggctgttggt     480
atcccagctg ttggtatccc agctgttggc attccggctg taggtattcc tgctgttggt     540
attccggctg ttggtatccc agctgttggt atcccagctg ttggcattcc ggctgtaggt     600
attcctgctg ttggtattcc ggctgttggt atcccagctg ttggtatccc agctgttggc     660
attccggctg taggtattcc tgctgttggt attccggctg ttggtatccc agctgttggt     720
atcccagctg ttggcattcc ggctgtaggt attcctgctg ttggtattcc ggctgttggt     780
atcccagctg ttggtatccc agctgttggc attccggctg taggtattcc tgctgttggt     840
attccggctg ttggtatccc agctgttggt atcccagctg ttggcattcc ggctgtaggt     900
attcctgctg ttggtattcc ggctgttggt atcccagctg ttggtatccc agctgttggc     960
attccggctg taggtattcc tgctgttggt attccggctg ttggtatccc agctgttggt    1020
atcccagctg ttggcattcc ggctgtaggt attcctgctg ttggtattcc ggctgttggt    1080
atcccagctg ttggtatccc agctgttggc attccggctg taggtattcc tgctgttggt    1140
attccggctg ttggtatccc agctgttggt atcccagctg ttggcattcc ggctgtaggt    1200
attcctgctg ttggtattcc ggctgttggt atcccagctg ttggtatccc agctgttggc    1260
attccggctg taggtattcc tgctgttggt attccggctg ttggtatccc agctgttggt    1320
atcccagctg ttggcattcc ggctgtaggt attcctgctg ttggtattcc ggctgttggt    1380
atcccagctg ttggtatccc agctgttggc attccggctg taggtattcc tgctgttggt    1440
attccggctg ttggtatccc agctgttggt atcccagctg ttggcattcc ggctgtaggt    1500
attcctgctg ttggtattcc ggctgttggt atcccagctg ttggtatccc agctgttggc    1560
attccggctg taggtattcc tgctgttggt attccggctg ttggtatccc agctgttggt    1620
atcccagctg ttggcattcc ggctgtaggt attcctgctg ttggtattcc ggctgttggt    1680
atcccagctg ttggtatccc agctgttggc attccggctg taggtattcc tgctgttggt    1740
attccggctg ttggtatccc agctgttggt atcccagctg ttggcattcc ggctgtaggt    1800
attcctgctg ttggtattcc ggctgttggt atcccagctg ttggtatccc agctgttggc    1860
attccggctg taggtattcc tgctgttggt attccggctg ttggtatccc agctgttggt    1920
atcccagctg ttggcattcc ggctgtaggt attcctgctg ttggtattcc ggctgttggt    1980
atcccagctg ttggtatccc agctgttggc attccggctg taggtattcc tgctgttggt    2040
attccggctg ttggtatccc agctgttggt atcccagctg ttggcattcc ggctgtaggt    2100
attcctgctg ttggtattcc ggctgttggt atcccagctg ttggtatccc agctgttggc    2160
attccggctg taggtattcc tgctgttggt attccggctg ttggtatccc agctgttggt    2220
atcccagctg ttggcattcc ggctgtaggt attcctgctg ttggtattcc ggctgttggt    2280
atcccagctg ttggtatccc agctgttggc attccggctg taggtattcc tgctgttggt    2340
attccggctg ttggtatccc agctgttggt atcccagctg ttggcattcc ggctgtaggt    2400
```

```
attcctgctg ttggtattcc ggctgttggt atcccagctg ttggtatccc agctgttggc    2460
attccggctg taggtattcc tgctgttggt attccggctg ttggtatccc agctgttggt    2520
atcccagctg ttggcattcc ggctgtaggt attccaggtg caggcgtacc gggtgctggc    2580 gttccggg tg aaggtgttcc aggcgcaggt gtaccgggtg cgggtggtcc agg tgcaggc    2640 gtaccgggtg ctggcgttcc gggtgaaggt gttccaggcg caggtgtacc gggtgcgggt    2700
ggtccaggtg caggcgtacc gggtgctggc gttccggg tg aaggtgttcc aggcgcaggt    2760
gtaccgggtg cgggtggtcc aggtgcaggc gtaccgggtg ctggcgttcc gggtgaaggt    2820
gttccaggcg caggtgtacc gggtgcgggt ggtccaggtg caggcgtacc gggtgctggc    2880
gttccgggtg aaggtgttcc aggcgcaggt gtaccgggtg cgggtggtcc aggtgcaggc    2940
gtaccgggtg ctggcgttcc gggtgaaggt gttccaggcg caggtgtacc gggtgcgggt    3000
ggtccaggtg caggcgtacc gggtgctggc gttccggg tg aaggtgttcc aggcgcaggt    3060
gtaccgggtg cgggtggtcc aggtgcaggc gtaccgggtg ctggcgttcc gggtgaaggt    3120
gttccaggcg caggtgtacc gggtgcgggt ggtccaggtg caggcgtacc gggtgctggc    3180
gttccgggtg aaggtgttcc aggcgcaggt gtaccgggtg cgggtggtcc aggtgcaggc    3240
gtaccgggtg ctggcgttcc gggtgaaggt gttccaggcg caggtgtacc gggtgcgggt    3300
ggtccaggtg caggcgtacc gggtgctggc gttccggg tg aaggtgttcc aggcgcaggt    3360
gtaccgggtg cgggtggtcc aggtgcaggc gtaccgggtg ctggcgttcc gggtgaaggt    3420
gttccaggcg caggtgtacc gggtgcgggt ggtccaggtg caggcgtacc gggtgctggc    3480
gttccgggtg aaggtgttcc aggcgcaggt gtaccgggtg cgggtggtcc aggtgcaggc    3540
gtaccgggtg ctggcgttcc gggtgaaggt gttccaggcg caggtgtacc gggtgcgggt    3600
ggtccaggtg caggcgtacc gggtgctggc gttccggg tg aaggtgttcc aggcgcaggt    3660
gtaccgggtg cgggtggtcc aggtgcaggc gtaccgggtg ctggcgttcc gggtgaaggt    3720
gttccaggcg caggtgtacc gggtgcgggt ggtccaggtg caggcgtacc gggtgctggc    3780
gttccgggtg aaggtgttcc aggcgcaggt gtaccgggtg cgggtggtcc aggtgcaggc    3840
gtaccgggtg ctggcgttcc gggtgaaggt gttccaggcg caggtgtacc gggtgcgggt    3900
ggtccaggtg caggcgtacc gggtgctggc gttccggg tg aaggtgttcc aggcgcaggt    3960
gtaccgggtg cgggtggtcc aggtgcaggc gtaccgggtg ctggcgttcc gggtgaaggt    4020
gttccaggcg caggtgtacc gggtgcgggt ggtccaggtg caggcgtacc gggtgctggc    4080
gttccgggtg aaggtgttcc aggcgcaggt gtaccgggtg cgggtgttcc tgctgttggt    4140
attccggctg ttggtatccc agctgttggt atcccagctg ttggcattcc ggctgtaggt    4200
attcctgctg ttggtattcc ggctgttggt atcccagctg ttggtatccc agctgttggc    4260
attccggctg taggtattcc tgctgttggt attccggctg ttggtatccc agctgttggt    4320
atcccagctg ttggcattcc ggctgtaggt attcctgctg ttggtattcc ggctgttggt    4380
atcccagctg ttggtatccc agctgttggc attccggctg taggtattcc tgctgttggt    4440
attccggctg ttggtatccc agctgttggt atcccagctg ttggcattcc ggctgtaggt    4500
attcctgctg ttggtattcc ggctgttggt atcccagctg ttggtatccc agctgttggc    4560
attccggctg taggtattcc tgctgttggt attccggctg ttggtatccc agctgttggt    4620
atcccagctg ttggcattcc ggctgtaggt attcctgctg ttggtattcc ggctgttggt    4680
atcccagctg ttggtatccc agctgttggc attccggctg taggtattcc tgctgttggt    4740
```

```
attccggctg ttggtatccc agctgttggt atcccagctg ttggcattcc ggctgtaggt    4800
attcctgctg ttggtattcc ggctgttggt atcccagctg ttggtatccc agctgttggc    4860
attccggctg taggtattcc tgctgttggt atccggctg ttggtatccc agctgttggt     4920
atcccagctg ttggcattcc ggctgtaggt attcctgctg ttggtattcc ggctgttggt    4980
atcccagctg ttggtatccc agctgttggc attccggctg taggtattcc tgctgttggt    5040
attccggctg ttggtatccc agctgttggt atcccagctg ttggcattcc ggctgtaggt    5100
attcctgctg ttggtattcc ggctgttggt atcccagctg ttggtatccc agctgttggc    5160
attccggctg taggtattcc tgctgttggt attccggctg ttggtatccc agctgttggt    5220
atcccagctg ttggcattcc ggctgtaggt attcctgctg ttggtattcc ggctgttggt    5280
atcccagctg ttggtatccc agctgttggc attccggctg taggtattcc tgctgttggt    5340
attccggctg ttggtatccc agctgttggt atcccagctg ttggcattcc ggctgtaggt    5400
attcctgctg ttggtattcc ggctgttggt atcccagctg ttggtatccc agctgttggc    5460
attccggctg taggtattcc tgctgttggt attccggctg ttggtatccc agctgttggt    5520
atcccagctg ttggcattcc ggctgtaggt attcctgctg ttggtattcc ggctgttggt    5580
atcccagctg ttggtatccc agctgttggc attccggctg taggtattcc tgctgttggt    5640
attccggctg ttggtatccc agctgttggt atcccagctg ttggcattcc ggctgtaggt    5700
attcctgctg ttggtattcc ggctgttggt atcccagctg ttggtatccc agctgttggc    5760
attccggctg taggtattcc tgctgttggt attccggctg ttggtatccc agctgttggt    5820
atcccagctg ttggcattcc ggctgtaggt attcctgctg ttggtattcc ggctgttggt    5880
atcccagctg ttggtatccc agctgttggc attccggctg taggtattcc tgctgttggt    5940
attccggctg ttggtatccc agctgttggt atcccagctg ttggcattcc ggctgtaggt    6000
attcctgctg ttggtattcc ggctgttggt atcccagctg ttggtatccc agctgttggc    6060
attccggctg taggtattcc tgctgttggt attccggctg ttggtatccc agctgttggt    6120
atcccagctg ttggcattcc ggctgtaggt attcctgctg ttggtattcc ggctgttggt    6180
atcccagctg ttggtatccc agctgttggc attccggctg taggtattcc tgctgttggt    6240
attccggctg ttggtatccc agctgttggt atcccagctg ttggcattcc ggctgtaggt    6300
attcctgctg ttggtattcc ggctgttggt atcccagctg ttggtatccc agctgttggc    6360
attccggctg taggtattcc tgctgttggt attccggctg ttggtatccc agctgttggt    6420
atcccagctg ttggcattcc ggctgtaggt attcctgctg ttggtattcc ggctgttggt    6480
atcccagctg ttggtatccc agctgttggc attccggctg taggtattcc tgctgttggt    6540
attccggctg ttggtatccc agctgttggt atcccagctg ttggcattcc ggctgtaggt    6600
attcctgctg ttggtattcc ggctgttggt atcccagctg ttggtatccc agctgttggc    6660
attccggctg taggtgtacc aggtgtaggc                                     6690
```

<210> SEQ ID NO 23
<211> LENGTH: 856
<212> TYPE: PRT
<213> ORGANISM: Artificial Sequence
<220> FEATURE:
<223> OTHER INFORMATION: synthetic construct

<400> SEQUENCE: 23

Val Pro Ala Val Gly Lys Val Pro Ala Val Gly Ile Pro Ala Val Gly
1               5                   10                  15

-continued

```
Ile Pro Ala Val Gly Ile Pro Ala Val Gly Ile Pro Ala Val Gly Ile
             20                  25                  30
Pro Ala Val Gly Ile Pro Ala Val Gly Ile Pro Ala Val Gly Ile Pro
         35                  40                  45
Ala Val Gly Ile Pro Ala Val Gly Ile Pro Ala Val Gly Ile Pro Ala
     50                  55                  60
Val Gly Ile Pro Ala Val Gly Ile Pro Ala Val Gly Ile Pro Ala Val
 65                  70                  75                  80
Gly Ile Pro Ala Val Gly Ile Pro Ala Val Gly Ile Pro Ala Val Gly
                 85                  90                  95
Ile Pro Ala Val Gly Ile Pro Ala Val Gly Ile Pro Ala Val Gly Ile
            100                 105                 110
Pro Ala Val Gly Ile Pro Ala Val Gly Ile Pro Ala Val Gly Ile Pro
        115                 120                 125
Ala Val Gly Ile Pro Ala Val Gly Ile Pro Ala Val Gly Ile Pro Ala
    130                 135                 140
Val Gly Ile Pro Ala Val Gly Ile Pro Ala Val Gly Ile Pro Ala Val
145                 150                 155                 160
Gly Ile Pro Ala Val Gly Ile Pro Ala Val Gly Ile Pro Ala Val Gly
                165                 170                 175
Ile Pro Ala Val Gly Ile Pro Ala Val Gly Ile Pro Ala Val Gly Ile
            180                 185                 190
Pro Ala Val Gly Ile Pro Ala Val Gly Ile Pro Ala Val Gly Ile Pro
        195                 200                 205
Ala Val Gly Ile Pro Ala Val Gly Ile Pro Ala Val Gly Ile Pro Ala
    210                 215                 220
Val Gly Ile Pro Ala Val Gly Ile Pro Ala Val Gly Ile Pro Ala Val
225                 230                 235                 240
Gly Ile Pro Ala Val Gly Ile Pro Ala Val Gly Ile Pro Ala Val Gly
                245                 250                 255
Ile Pro Ala Val Gly Ile Pro Ala Val Gly Ile Pro Ala Val Gly Ile
            260                 265                 270
Pro Ala Val Gly Ile Pro Ala Val Gly Ile Pro Ala Val Gly Ile Pro
        275                 280                 285
Ala Val Gly Ile Pro Ala Val Gly Ile Pro Ala Val Gly Ile Pro Ala
    290                 295                 300
Val Gly Ile Pro Ala Val Gly Ile Pro Ala Val Gly Ile Pro Ala Val
305                 310                 315                 320
Gly Ile Pro Ala Val Gly Ile Pro Ala Val Gly Ile Pro Ala Val Gly
                325                 330                 335
Ile Pro Ala Val Gly Ile Pro Ala Val Gly Ile Pro Ala Val Gly Ile
            340                 345                 350
Pro Ala Val Gly Ile Pro Ala Val Gly Ile Pro Ala Val Gly Ile Pro
        355                 360                 365
Ala Val Gly Ile Pro Ala Val Gly Ile Pro Ala Val Gly Ile Pro Ala
    370                 375                 380
Val Gly Ile Pro Ala Val Gly Ile Pro Ala Val Gly Ile Pro Ala Val
385                 390                 395                 400
Gly Ile Pro Ala Val Gly Ile Pro Ala Val Gly Ile Pro Ala Val Gly
                405                 410                 415
Ile Pro Ala Val Gly Ile Pro Ala Val Gly Ile Pro Ala Val Gly Ile
            420                 425                 430
Pro Ala Val Gly Ile Pro Ala Val Gly Ile Pro Ala Val Gly Ile Pro
```

```
            435                 440                 445
Ala Val Gly Ile Pro Ala Val Gly Ile Pro Ala Val Gly Ile Pro Ala
450                 455                 460
Val Gly Ile Pro Ala Val Gly Ile Pro Ala Val Gly Ile Pro Ala Val
465                 470                 475                 480
Gly Ile Pro Ala Val Gly Ile Pro Ala Val Gly Ile Pro Ala Val Gly
                485                 490                 495
Ile Pro Ala Val Gly Ile Pro Ala Val Gly Ile Pro Ala Val Gly Ile
            500                 505                 510
Pro Ala Val Gly Ile Pro Ala Val Gly Ile Pro Ala Val Gly Ile Pro
        515                 520                 525
Ala Val Gly Ile Pro Ala Val Gly Ile Pro Ala Val Gly Ile Pro Ala
    530                 535                 540
Val Gly Ile Pro Ala Val Gly Ile Pro Ala Val Gly Ile Pro Ala Val
545                 550                 555                 560
Gly Ile Pro Ala Val Gly Ile Pro Ala Val Gly Ile Pro Ala Val Gly
                565                 570                 575
Ile Pro Ala Val Gly Ile Pro Ala Val Gly Ile Pro Ala Val Gly Ile
            580                 585                 590
Pro Ala Val Gly Ile Pro Ala Val Gly Ile Pro Ala Val Gly Ile Pro
        595                 600                 605
Ala Val Gly Ile Pro Ala Val Gly Ile Pro Ala Val Gly Ile Pro Ala
    610                 615                 620
Val Gly Ile Pro Ala Val Gly Ile Pro Ala Val Gly Ile Pro Ala Val
625                 630                 635                 640
Gly Ile Pro Ala Val Gly Ile Pro Ala Val Gly Ile Pro Ala Val Gly
                645                 650                 655
Ile Pro Ala Val Gly Ile Pro Ala Val Gly Ile Pro Ala Val Gly Ile
            660                 665                 670
Pro Ala Val Gly Ile Pro Ala Val Gly Ile Pro Ala Val Gly Ile Pro
        675                 680                 685
Ala Val Gly Ile Pro Ala Val Gly Ile Pro Ala Val Gly Ile Pro Ala
    690                 695                 700
Val Gly Ile Pro Ala Val Gly Ile Pro Ala Val Gly Ile Pro Ala Val
705                 710                 715                 720
Gly Ile Pro Ala Val Gly Ile Pro Ala Val Gly Ile Pro Ala Val Gly
                725                 730                 735
Ile Pro Ala Val Gly Ile Pro Ala Val Gly Ile Pro Ala Val Gly Ile
            740                 745                 750
Pro Ala Val Gly Ile Pro Ala Val Gly Ile Pro Ala Val Gly Ile Pro
        755                 760                 765
Ala Val Gly Ile Pro Ala Val Gly Ile Pro Ala Val Gly Ile Pro Ala
    770                 775                 780
Val Gly Ile Pro Ala Val Gly Ile Pro Ala Val Gly Ile Pro Ala Val
785                 790                 795                 800
Gly Ile Pro Ala Val Gly Ile Pro Ala Val Gly Ile Pro Ala Val Gly
                805                 810                 815
Ile Pro Ala Val Gly Ile Pro Ala Val Gly Ile Pro Ala Val Gly Ile
            820                 825                 830
Pro Ala Val Gly Ile Pro Ala Val Gly Ile Pro Ala Val Gly Ile Pro
        835                 840                 845
Ala Val Gly Ile Pro Ala Val Gly
    850                 855
```

-continued

<210> SEQ ID NO 24
<211> LENGTH: 874
<212> TYPE: PRT
<213> ORGANISM: Artificial Sequence
<220> FEATURE:
<223> OTHER INFORMATION: synthetic construct

<400> SEQUENCE: 24

```
Val Pro Ala Val Gly Lys Ala Ala Lys Val Pro Gly Ala Gly Val Pro
1               5                   10                  15

Ala Val Gly Ile Pro Ala Val Gly Ile Pro Ala Val Gly Ile Pro Ala
            20                  25                  30

Val Gly Ile Pro Ala Val Gly Ile Pro Ala Val Gly Ile Pro Ala Val
        35                  40                  45

Gly Ile Pro Ala Val Gly Ile Pro Ala Val Gly Ile Pro Ala Val Gly
    50                  55                  60

Ile Pro Ala Val Gly Ile Pro Ala Val Gly Ile Pro Ala Val Gly Ile
65                  70                  75                  80

Pro Ala Val Gly Ile Pro Ala Val Gly Ile Pro Ala Val Gly Ile Pro
                85                  90                  95

Ala Val Gly Ile Pro Ala Val Gly Ile Pro Ala Val Gly Ile Pro Ala
            100                 105                 110

Val Gly Ile Pro Ala Val Gly Ile Pro Ala Val Gly Ile Pro Ala Val
        115                 120                 125

Gly Ile Pro Ala Val Gly Ile Pro Ala Val Gly Ile Pro Ala Val Gly
    130                 135                 140

Ile Pro Ala Val Gly Ile Pro Ala Val Gly Ile Pro Ala Val Gly Ile
145                 150                 155                 160

Pro Ala Val Gly Ile Pro Ala Val Gly Ile Pro Ala Val Gly Ile Pro
                165                 170                 175

Ala Val Gly Ile Pro Ala Val Gly Ile Pro Ala Val Gly Ile Pro Ala
            180                 185                 190

Val Gly Ile Pro Ala Val Gly Ile Pro Ala Val Gly Ile Pro Ala Val
        195                 200                 205

Gly Ile Pro Ala Val Gly Ile Pro Ala Val Gly Ile Pro Ala Val Gly
    210                 215                 220

Ile Pro Ala Val Gly Ile Pro Ala Val Gly Ile Pro Ala Val Gly Ile
225                 230                 235                 240

Pro Ala Val Gly Ile Pro Ala Val Gly Ile Pro Ala Val Gly Ile Pro
                245                 250                 255

Ala Val Gly Ile Pro Ala Val Gly Ile Pro Ala Val Gly Ile Pro Ala
            260                 265                 270

Val Gly Ile Pro Ala Val Gly Ile Pro Ala Val Gly Ile Pro Ala Val
        275                 280                 285

Gly Ile Pro Ala Val Gly Ile Pro Ala Val Gly Ile Pro Ala Val Gly
    290                 295                 300

Ile Pro Ala Val Gly Ile Pro Ala Val Gly Ile Pro Ala Val Gly Ile
305                 310                 315                 320

Pro Ala Val Gly Ile Pro Ala Val Gly Ile Pro Ala Val Gly Ile Pro
                325                 330                 335

Ala Val Gly Ile Pro Ala Val Gly Ile Pro Ala Val Gly Ile Pro Ala
            340                 345                 350

Val Gly Ile Pro Ala Val Gly Ile Pro Ala Val Gly Ile Pro Ala Val
        355                 360                 365
```

-continued

Gly Ile Pro Ala Val Gly Ile Pro Ala Val Gly Ile Pro Ala Val Gly
    370                 375                 380
Ile Pro Ala Val Gly Ile Pro Ala Val Gly Ile Pro Ala Val Gly Ile
385                 390                 395                 400
Pro Ala Val Gly Ile Pro Ala Val Gly Ile Pro Ala Val Gly Ile Pro
                405                 410                 415
Ala Val Gly Ile Pro Ala Val Gly Ile Pro Ala Val Gly Ile Pro Ala
            420                 425                 430
Val Gly Ile Pro Ala Val Gly Ile Pro Ala Val Gly Ile Pro Ala Val
        435                 440                 445
Gly Ile Pro Ala Val Gly Ile Pro Ala Val Gly Ile Pro Ala Val Gly
    450                 455                 460
Ile Pro Ala Val Gly Ile Pro Ala Val Gly Ile Pro Ala Val Gly Ile
465                 470                 475                 480
Pro Ala Val Gly Ile Pro Ala Val Gly Ile Pro Ala Val Gly Ile Pro
                485                 490                 495
Ala Val Gly Ile Pro Ala Val Gly Ile Pro Ala Val Gly Ile Pro Ala
            500                 505                 510
Val Gly Ile Pro Ala Val Gly Ile Pro Ala Val Gly Ile Pro Ala Val
        515                 520                 525
Gly Ile Pro Ala Val Gly Ile Pro Ala Val Gly Ile Pro Ala Val Gly
    530                 535                 540
Ile Pro Ala Val Gly Ile Pro Ala Val Gly Ile Pro Ala Val Gly Ile
545                 550                 555                 560
Pro Ala Val Gly Ile Pro Ala Val Gly Ile Pro Ala Val Gly Ile Pro
                565                 570                 575
Ala Val Gly Ile Pro Ala Val Gly Ile Pro Ala Val Gly Ile Pro Ala
            580                 585                 590
Val Gly Ile Pro Ala Val Gly Ile Pro Ala Val Gly Ile Pro Ala Val
        595                 600                 605
Gly Ile Pro Ala Val Gly Ile Pro Ala Val Gly Ile Pro Ala Val Gly
    610                 615                 620
Ile Pro Ala Val Gly Ile Pro Ala Val Gly Ile Pro Ala Val Gly Ile
625                 630                 635                 640
Pro Ala Val Gly Ile Pro Ala Val Gly Ile Pro Ala Val Gly Ile Pro
                645                 650                 655
Ala Val Gly Ile Pro Ala Val Gly Ile Pro Ala Val Gly Ile Pro Ala
            660                 665                 670
Val Gly Ile Pro Ala Val Gly Ile Pro Ala Val Gly Ile Pro Ala Val
        675                 680                 685
Gly Ile Pro Ala Val Gly Ile Pro Ala Val Gly Ile Pro Ala Val Gly
    690                 695                 700
Ile Pro Ala Val Gly Ile Pro Ala Val Gly Ile Pro Ala Val Gly Ile
705                 710                 715                 720
Pro Ala Val Gly Ile Pro Ala Val Gly Ile Pro Ala Val Gly Ile Pro
                725                 730                 735
Ala Val Gly Ile Pro Ala Val Gly Ile Pro Ala Val Gly Ile Pro Ala
            740                 745                 750
Val Gly Ile Pro Ala Val Gly Ile Pro Ala Val Gly Ile Pro Ala Val
        755                 760                 765
Gly Ile Pro Ala Val Gly Ile Pro Ala Val Gly Ile Pro Ala Val Gly
    770                 775                 780

-continued

```
Ile Pro Ala Val Gly Ile Pro Ala Val Gly Ile Pro Ala Val Gly Ile
785                 790                 795                 800

Pro Ala Val Gly Ile Pro Ala Val Gly Ile Pro Ala Val Gly Ile Pro
                805                 810                 815

Ala Val Gly Ile Pro Ala Val Gly Ile Pro Ala Val Gly Ile Pro Ala
            820                 825                 830

Val Gly Ile Pro Ala Val Gly Ile Pro Ala Val Gly Ile Pro Ala Val
        835                 840                 845

Gly Ile Pro Ala Val Gly Ile Pro Ala Val Gly Ile Pro Ala Val Gly
    850                 855                 860

Ile Pro Ala Val Gly Lys Ala Ala Lys Ala
865                 870

<210> SEQ ID NO 25
<211> LENGTH: 39
<212> TYPE: PRT
<213> ORGANISM: Artificial Sequence
<220> FEATURE:
<223> OTHER INFORMATION: synthetic construct

<400> SEQUENCE: 25

Ile Pro Ala Val Gly Lys Ala Ala Lys Val Pro Gly Ala Gly Val Pro
1               5                   10                  15

Gly Ala Gly Val Pro Gly Ala Gly Val Pro Gly Glu Gly Val Pro Gly
            20                  25                  30

Ala Gly Val Pro Gly Ala Gly
        35

<210> SEQ ID NO 26
<211> LENGTH: 2812
<212> TYPE: PRT
<213> ORGANISM: Artificial Sequence
<220> FEATURE:
<223> OTHER INFORMATION: synthetic construct

<400> SEQUENCE: 26

Val Pro Ala Val Gly Lys Val Pro Ala Val Gly Ile Pro Ala Val Gly
1               5                   10                  15

Ile Pro Ala Val Gly Ile Pro Ala Val Gly Ile Pro Ala Val Gly Ile
            20                  25                  30

Pro Ala Val Gly Ile Pro Ala Val Gly Ile Pro Ala Val Gly Ile Pro
        35                  40                  45

Ala Val Gly Ile Pro Ala Val Gly Ile Pro Ala Val Gly Ile Pro Ala
    50                  55                  60

Val Gly Ile Pro Ala Val Gly Ile Pro Ala Val Gly Ile Pro Ala Val
65                  70                  75                  80

Gly Ile Pro Ala Val Gly Ile Pro Ala Val Gly Ile Pro Ala Val Gly
                85                  90                  95

Ile Pro Ala Val Gly Ile Pro Ala Val Gly Ile Pro Ala Val Gly Ile
            100                 105                 110

Pro Ala Val Gly Ile Pro Ala Val Gly Ile Pro Ala Val Gly Ile Pro
        115                 120                 125

Ala Val Gly Ile Pro Ala Val Gly Ile Pro Ala Val Gly Ile Pro Ala
    130                 135                 140

Val Gly Ile Pro Ala Val Gly Ile Pro Ala Val Gly Ile Pro Ala Val
145                 150                 155                 160

Gly Ile Pro Ala Val Gly Ile Pro Ala Val Gly Ile Pro Ala Val Gly
                165                 170                 175
```

-continued

```
Ile Pro Ala Val Gly Ile Pro Ala Val Gly Ile Pro Ala Val Gly Ile
            180                 185                 190
Pro Ala Val Gly Ile Pro Ala Val Gly Ile Pro Ala Val Gly Ile Pro
            195                 200                 205
Ala Val Gly Ile Pro Ala Val Gly Ile Pro Ala Val Gly Ile Pro Ala
210                 215                 220
Val Gly Ile Pro Ala Val Gly Ile Pro Ala Val Gly Ile Pro Ala Val
225                 230                 235                 240
Gly Ile Pro Ala Val Gly Ile Pro Ala Val Gly Ile Pro Ala Val Gly
            245                 250                 255
Ile Pro Ala Val Gly Ile Pro Ala Val Gly Ile Pro Ala Val Gly Ile
            260                 265                 270
Pro Ala Val Gly Ile Pro Ala Val Gly Ile Pro Ala Val Gly Ile Pro
            275                 280                 285
Ala Val Gly Ile Pro Ala Val Gly Ile Pro Ala Val Gly Ile Pro Ala
            290                 295                 300
Val Gly Ile Pro Ala Val Gly Ile Pro Ala Val Gly Ile Pro Ala Val
305                 310                 315                 320
Gly Ile Pro Ala Val Gly Ile Pro Ala Val Gly Ile Pro Ala Val Gly
            325                 330                 335
Ile Pro Ala Val Gly Ile Pro Ala Val Gly Ile Pro Ala Val Gly Ile
            340                 345                 350
Pro Ala Val Gly Ile Pro Ala Val Gly Ile Pro Ala Val Gly Ile Pro
            355                 360                 365
Ala Val Gly Ile Pro Ala Val Gly Ile Pro Ala Val Gly Ile Pro Ala
            370                 375                 380
Val Gly Ile Pro Ala Val Gly Ile Pro Ala Val Gly Ile Pro Ala Val
385                 390                 395                 400
Gly Ile Pro Ala Val Gly Ile Pro Ala Val Gly Ile Pro Ala Val Gly
            405                 410                 415
Ile Pro Ala Val Gly Ile Pro Ala Val Gly Ile Pro Ala Val Gly Ile
            420                 425                 430
Pro Ala Val Gly Ile Pro Ala Val Gly Ile Pro Ala Val Gly Ile Pro
            435                 440                 445
Ala Val Gly Ile Pro Ala Val Gly Ile Pro Ala Val Gly Ile Pro Ala
            450                 455                 460
Val Gly Ile Pro Ala Val Gly Ile Pro Ala Val Gly Ile Pro Ala Val
465                 470                 475                 480
Gly Ile Pro Ala Val Gly Ile Pro Ala Val Gly Ile Pro Ala Val Gly
            485                 490                 495
Ile Pro Ala Val Gly Ile Pro Ala Val Gly Ile Pro Ala Val Gly Ile
            500                 505                 510
Pro Ala Val Gly Ile Pro Ala Val Gly Ile Pro Ala Val Gly Ile Pro
            515                 520                 525
Ala Val Gly Ile Pro Ala Val Gly Ile Pro Ala Val Gly Ile Pro Ala
            530                 535                 540
Val Gly Ile Pro Ala Val Gly Ile Pro Ala Val Gly Ile Pro Ala Val
545                 550                 555                 560
Gly Ile Pro Ala Val Gly Ile Pro Ala Val Gly Ile Pro Ala Val Gly
            565                 570                 575
Ile Pro Ala Val Gly Ile Pro Ala Val Gly Ile Pro Ala Val Gly Ile
            580                 585                 590
```

-continued

Pro Ala Val Gly Ile Pro Ala Val Gly Ile Pro Ala Val Gly Ile Pro
            595                 600                 605

Ala Val Gly Ile Pro Ala Val Gly Ile Pro Ala Val Gly Ile Pro Ala
        610                 615                 620

Val Gly Ile Pro Ala Val Gly Ile Pro Ala Val Gly Ile Pro Ala Val
625                 630                 635                 640

Gly Ile Pro Ala Val Gly Ile Pro Ala Val Gly Ile Pro Ala Val Gly
            645                 650                 655

Ile Pro Ala Val Gly Ile Pro Ala Val Gly Ile Pro Ala Val Gly Ile
            660                 665                 670

Pro Ala Val Gly Ile Pro Ala Val Gly Ile Pro Ala Val Gly Ile Pro
            675                 680                 685

Ala Val Gly Ile Pro Ala Val Gly Ile Pro Ala Val Gly Ile Pro Ala
        690                 695                 700

Val Gly Ile Pro Ala Val Gly Ile Pro Ala Val Gly Ile Pro Ala Val
705                 710                 715                 720

Gly Ile Pro Ala Val Gly Ile Pro Ala Val Gly Ile Pro Ala Val Gly
            725                 730                 735

Ile Pro Ala Val Gly Ile Pro Ala Val Gly Ile Pro Ala Val Gly Ile
            740                 745                 750

Pro Ala Val Gly Ile Pro Ala Val Gly Ile Pro Ala Val Gly Ile Pro
            755                 760                 765

Ala Val Gly Ile Pro Ala Val Gly Ile Pro Ala Val Gly Ile Pro Ala
        770                 775                 780

Val Gly Ile Pro Ala Val Gly Ile Pro Ala Val Gly Ile Pro Ala Val
785                 790                 795                 800

Gly Ile Pro Ala Val Gly Ile Pro Ala Val Gly Ile Pro Ala Val Gly
            805                 810                 815

Ile Pro Ala Val Gly Ile Pro Ala Val Gly Ile Pro Ala Val Gly Ile
            820                 825                 830

Pro Ala Val Gly Ile Pro Ala Val Gly Ile Pro Ala Val Gly Ile Pro
            835                 840                 845

Ala Val Gly Ile Pro Ala Val Gly Ile Pro Ala Val Gly Lys Ala Ala
        850                 855                 860

Lys Val Pro Gly Ala Gly Val Pro Gly Ala Gly Val Pro Gly Ala Gly
865                 870                 875                 880

Val Pro Gly Glu Gly Val Pro Gly Ala Gly Val Pro Gly Ala Gly Ile
            885                 890                 895

Pro Ala Val Gly Lys Ala Ala Lys Val Pro Gly Ala Gly Val Pro Gly
            900                 905                 910

Ala Gly Val Pro Gly Ala Gly Val Pro Gly Glu Gly Val Pro Gly Ala
        915                 920                 925

Gly Val Pro Gly Ala Gly Ile Pro Ala Val Gly Lys Ala Ala Lys Val
930                 935                 940

Pro Gly Ala Gly Val Pro Gly Ala Gly Val Pro Gly Ala Gly Val Pro
945                 950                 955                 960

Gly Glu Gly Val Pro Gly Ala Gly Val Pro Gly Ala Gly Ile Pro Ala
            965                 970                 975

Val Gly Lys Ala Ala Lys Val Pro Gly Ala Gly Val Pro Gly Ala Gly
            980                 985                 990

Val Pro Gly Ala Gly Val Pro Gly Glu Gly Val Pro Gly Ala Gly Val
        995                 1000                1005

Pro Gly Ala Gly Ile Pro Ala Val Gly Lys Ala Ala Lys Val Pro

```
               1010                1015                1020

Gly Ala Gly Val Pro Gly Ala Gly Val Pro Gly Ala Gly Val Pro
               1025                1030                1035

Gly Glu Gly Val Pro Gly Ala Gly Val Pro Gly Ala Gly Ile Pro
               1040                1045                1050

Ala Val Gly Lys Ala Ala Lys Val Pro Gly Ala Gly Val Pro Gly
               1055                1060                1065

Ala Gly Val Pro Gly Ala Gly Val Pro Gly Glu Gly Val Pro Gly
               1070                1075                1080

Ala Gly Val Pro Gly Ala Gly Ile Pro Ala Val Gly Lys Ala Ala
               1085                1090                1095

Lys Val Pro Gly Ala Gly Val Pro Gly Ala Gly Val Pro Gly Ala
               1100                1105                1110

Gly Val Pro Gly Glu Gly Val Pro Gly Ala Gly Val Pro Gly Ala
               1115                1120                1125

Gly Ile Pro Ala Val Gly Lys Ala Ala Lys Val Pro Gly Ala Gly
               1130                1135                1140

Val Pro Gly Ala Gly Val Pro Gly Ala Gly Val Pro Gly Glu Gly
               1145                1150                1155

Val Pro Gly Ala Gly Val Pro Gly Ala Gly Ile Pro Ala Val Gly
               1160                1165                1170

Lys Ala Ala Lys Val Pro Gly Ala Gly Val Pro Gly Ala Gly Val
               1175                1180                1185

Pro Gly Ala Gly Val Pro Gly Glu Gly Val Pro Gly Ala Gly Val
               1190                1195                1200

Pro Gly Ala Gly Ile Pro Ala Val Gly Lys Ala Ala Lys Val Pro
               1205                1210                1215

Gly Ala Gly Val Pro Gly Ala Gly Val Pro Gly Ala Gly Val Pro
               1220                1225                1230

Gly Glu Gly Val Pro Gly Ala Gly Val Pro Gly Ala Gly Ile Pro
               1235                1240                1245

Ala Val Gly Lys Ala Ala Lys Val Pro Gly Ala Gly Val Pro Gly
               1250                1255                1260

Ala Gly Val Pro Gly Ala Gly Val Pro Gly Glu Gly Val Pro Gly
               1265                1270                1275

Ala Gly Val Pro Gly Ala Gly Ile Pro Ala Val Gly Lys Ala Ala
               1280                1285                1290

Lys Val Pro Gly Ala Gly Val Pro Gly Ala Gly Val Pro Gly Ala
               1295                1300                1305

Gly Val Pro Gly Glu Gly Val Pro Gly Ala Gly Val Pro Gly Ala
               1310                1315                1320

Gly Ile Pro Ala Val Gly Lys Ala Ala Lys Val Pro Gly Ala Gly
               1325                1330                1335

Val Pro Gly Ala Gly Val Pro Gly Ala Gly Val Pro Gly Glu Gly
               1340                1345                1350

Val Pro Gly Ala Gly Val Pro Gly Ala Gly Ile Pro Ala Val Gly
               1355                1360                1365

Lys Ala Ala Lys Val Pro Gly Ala Gly Val Pro Gly Ala Gly Val
               1370                1375                1380

Pro Gly Ala Gly Val Pro Gly Glu Gly Val Pro Gly Ala Gly Val
               1385                1390                1395

Pro Gly Ala Gly Ile Pro Ala Val Gly Lys Ala Ala Lys Val Pro
               1400                1405                1410
```

```
Gly Ala Gly Val Pro Gly Ala Gly Val Pro Gly Ala Gly Val Pro
    1415                1420                1425

Gly Glu Gly Val Pro Gly Ala Gly Val Pro Gly Ala Gly Ile Pro
    1430                1435                1440

Ala Val Gly Lys Ala Ala Lys Val Pro Gly Ala Gly Val Pro Gly
    1445                1450                1455

Ala Gly Val Pro Gly Ala Gly Val Pro Gly Glu Gly Val Pro Gly
    1460                1465                1470

Ala Gly Val Pro Gly Ala Gly Ile Pro Ala Val Gly Lys Ala Ala
    1475                1480                1485

Lys Val Pro Gly Ala Gly Val Pro Gly Ala Gly Val Pro Gly Ala
    1490                1495                1500

Gly Val Pro Gly Glu Gly Val Pro Gly Ala Gly Val Pro Gly Ala
    1505                1510                1515

Gly Ile Pro Ala Val Gly Lys Ala Ala Lys Val Pro Gly Ala Gly
    1520                1525                1530

Val Pro Gly Ala Gly Val Pro Gly Ala Gly Val Pro Gly Glu Gly
    1535                1540                1545

Val Pro Gly Ala Gly Val Pro Gly Ala Gly Ile Pro Ala Val Gly
    1550                1555                1560

Lys Ala Ala Lys Val Pro Gly Ala Gly Val Pro Gly Ala Gly Val
    1565                1570                1575

Pro Gly Ala Gly Val Pro Gly Glu Gly Val Pro Gly Ala Gly Val
    1580                1585                1590

Pro Gly Ala Gly Ile Pro Ala Val Gly Lys Ala Ala Lys Val Pro
    1595                1600                1605

Gly Ala Gly Val Pro Gly Ala Gly Val Pro Gly Ala Gly Val Pro
    1610                1615                1620

Gly Glu Gly Val Pro Gly Ala Gly Val Pro Gly Ala Gly Ile Pro
    1625                1630                1635

Ala Val Gly Lys Ala Ala Lys Val Pro Gly Ala Gly Val Pro Gly
    1640                1645                1650

Ala Gly Val Pro Gly Ala Gly Val Pro Gly Glu Gly Val Pro Gly
    1655                1660                1665

Ala Gly Val Pro Gly Ala Gly Ile Pro Ala Val Gly Lys Ala Ala
    1670                1675                1680

Lys Val Pro Gly Ala Gly Val Pro Gly Ala Gly Val Pro Gly Ala
    1685                1690                1695

Gly Val Pro Gly Glu Gly Val Pro Gly Ala Gly Val Pro Gly Ala
    1700                1705                1710

Gly Ile Pro Ala Val Gly Lys Ala Ala Lys Val Pro Gly Ala Gly
    1715                1720                1725

Val Pro Gly Ala Gly Val Pro Gly Ala Gly Val Pro Gly Glu Gly
    1730                1735                1740

Val Pro Gly Ala Gly Val Pro Gly Ala Gly Ile Pro Ala Val Gly
    1745                1750                1755

Lys Ala Ala Lys Val Pro Gly Ala Gly Val Pro Gly Ala Gly Val
    1760                1765                1770

Pro Gly Ala Gly Val Pro Gly Glu Gly Val Pro Gly Ala Gly Val
    1775                1780                1785

Pro Gly Ala Gly Ile Pro Ala Val Gly Lys Ala Ala Lys Val Pro
    1790                1795                1800
```

Gly Ala Gly Val Pro Gly Ala Gly Val Pro Gly Ala Gly Val Pro
1805                1810                1815

Gly Glu Gly Val Pro Gly Ala Gly Val Pro Gly Ala Gly Ile Pro
1820                1825                1830

Ala Val Gly Lys Ala Ala Lys Val Pro Gly Ala Gly Val Pro Gly
1835                1840                1845

Ala Gly Val Pro Gly Ala Gly Val Pro Gly Glu Gly Val Pro Gly
1850                1855                1860

Ala Gly Val Pro Gly Ala Gly Ile Pro Ala Val Gly Lys Ala Ala
1865                1870                1875

Lys Val Pro Gly Ala Gly Val Pro Gly Ala Gly Val Pro Gly Ala
1880                1885                1890

Gly Val Pro Gly Glu Gly Val Pro Gly Ala Gly Val Pro Gly Ala
1895                1900                1905

Gly Ile Pro Ala Val Gly Lys Ala Ala Lys Val Pro Gly Ala Gly
1910                1915                1920

Val Pro Gly Ala Gly Val Pro Gly Ala Gly Val Pro Gly Glu Gly
1925                1930                1935

Val Pro Gly Ala Gly Val Pro Gly Ala Gly Val Pro Ala Val Gly
1940                1945                1950

Lys Ala Ala Lys Val Pro Gly Ala Gly Val Pro Ala Val Gly Ile
1955                1960                1965

Pro Ala Val Gly Ile Pro Ala Val Gly Ile Pro Ala Val Gly Ile
1970                1975                1980

Pro Ala Val Gly Ile Pro Ala Val Gly Ile Pro Ala Val Gly Ile
1985                1990                1995

Pro Ala Val Gly Ile Pro Ala Val Gly Ile Pro Ala Val Gly Ile
2000                2005                2010

Pro Ala Val Gly Ile Pro Ala Val Gly Ile Pro Ala Val Gly Ile
2015                2020                2025

Pro Ala Val Gly Ile Pro Ala Val Gly Ile Pro Ala Val Gly Ile
2030                2035                2040

Pro Ala Val Gly Ile Pro Ala Val Gly Ile Pro Ala Val Gly Ile
2045                2050                2055

Pro Ala Val Gly Ile Pro Ala Val Gly Ile Pro Ala Val Gly Ile
2060                2065                2070

Pro Ala Val Gly Ile Pro Ala Val Gly Ile Pro Ala Val Gly Ile
2075                2080                2085

Pro Ala Val Gly Ile Pro Ala Val Gly Ile Pro Ala Val Gly Ile
2090                2095                2100

Pro Ala Val Gly Ile Pro Ala Val Gly Ile Pro Ala Val Gly Ile
2105                2110                2115

Pro Ala Val Gly Ile Pro Ala Val Gly Ile Pro Ala Val Gly Ile
2120                2125                2130

Pro Ala Val Gly Ile Pro Ala Val Gly Ile Pro Ala Val Gly Ile
2135                2140                2145

Pro Ala Val Gly Ile Pro Ala Val Gly Ile Pro Ala Val Gly Ile
2150                2155                2160

Pro Ala Val Gly Ile Pro Ala Val Gly Ile Pro Ala Val Gly Ile
2165                2170                2175

Pro Ala Val Gly Ile Pro Ala Val Gly Ile Pro Ala Val Gly Ile
2180                2185                2190

Pro Ala Val Gly Ile Pro Ala Val Gly Ile Pro Ala Val Gly Ile

-continued

```
                2195                2200                2205

Pro Ala Val Gly Ile Pro Ala Val Gly Ile Pro Ala Val Gly Ile
    2210                2215                2220

Pro Ala Val Gly Ile Pro Ala Val Gly Ile Pro Ala Val Gly Ile
    2225                2230                2235

Pro Ala Val Gly Ile Pro Ala Val Gly Ile Pro Ala Val Gly Ile
    2240                2245                2250

Pro Ala Val Gly Ile Pro Ala Val Gly Ile Pro Ala Val Gly Ile
    2255                2260                2265

Pro Ala Val Gly Ile Pro Ala Val Gly Ile Pro Ala Val Gly Ile
    2270                2275                2280

Pro Ala Val Gly Ile Pro Ala Val Gly Ile Pro Ala Val Gly Ile
    2285                2290                2295

Pro Ala Val Gly Ile Pro Ala Val Gly Ile Pro Ala Val Gly Ile
    2300                2305                2310

Pro Ala Val Gly Ile Pro Ala Val Gly Ile Pro Ala Val Gly Ile
    2315                2320                2325

Pro Ala Val Gly Ile Pro Ala Val Gly Ile Pro Ala Val Gly Ile
    2330                2335                2340

Pro Ala Val Gly Ile Pro Ala Val Gly Ile Pro Ala Val Gly Ile
    2345                2350                2355

Pro Ala Val Gly Ile Pro Ala Val Gly Ile Pro Ala Val Gly Ile
    2360                2365                2370

Pro Ala Val Gly Ile Pro Ala Val Gly Ile Pro Ala Val Gly Ile
    2375                2380                2385

Pro Ala Val Gly Ile Pro Ala Val Gly Ile Pro Ala Val Gly Ile
    2390                2395                2400

Pro Ala Val Gly Ile Pro Ala Val Gly Ile Pro Ala Val Gly Ile
    2405                2410                2415

Pro Ala Val Gly Ile Pro Ala Val Gly Ile Pro Ala Val Gly Ile
    2420                2425                2430

Pro Ala Val Gly Ile Pro Ala Val Gly Ile Pro Ala Val Gly Ile
    2435                2440                2445

Pro Ala Val Gly Ile Pro Ala Val Gly Ile Pro Ala Val Gly Ile
    2450                2455                2460

Pro Ala Val Gly Ile Pro Ala Val Gly Ile Pro Ala Val Gly Ile
    2465                2470                2475

Pro Ala Val Gly Ile Pro Ala Val Gly Ile Pro Ala Val Gly Ile
    2480                2485                2490

Pro Ala Val Gly Ile Pro Ala Val Gly Ile Pro Ala Val Gly Ile
    2495                2500                2505

Pro Ala Val Gly Ile Pro Ala Val Gly Ile Pro Ala Val Gly Ile
    2510                2515                2520

Pro Ala Val Gly Ile Pro Ala Val Gly Ile Pro Ala Val Gly Ile
    2525                2530                2535

Pro Ala Val Gly Ile Pro Ala Val Gly Ile Pro Ala Val Gly Ile
    2540                2545                2550

Pro Ala Val Gly Ile Pro Ala Val Gly Ile Pro Ala Val Gly Ile
    2555                2560                2565

Pro Ala Val Gly Ile Pro Ala Val Gly Ile Pro Ala Val Gly Ile
    2570                2575                2580

Pro Ala Val Gly Ile Pro Ala Val Gly Ile Pro Ala Val Gly Ile
    2585                2590                2595
```

-continued

| Pro | Ala | Val | Gly | Ile | Pro | Ala | Val | Gly | Ile | Pro | Ala | Val | Gly | Ile |
|     |     |     | 2600|     |     |     |     | 2605|     |     |     |     | 2610|     |

| Pro | Ala | Val | Gly | Ile | Pro | Ala | Val | Gly | Ile | Pro | Ala | Val | Gly | Ile |
|     |     |     | 2615|     |     |     |     | 2620|     |     |     |     | 2625|     |

| Pro | Ala | Val | Gly | Ile | Pro | Ala | Val | Gly | Ile | Pro | Ala | Val | Gly | Ile |
|     |     |     | 2630|     |     |     |     | 2635|     |     |     |     | 2640|     |

| Pro | Ala | Val | Gly | Ile | Pro | Ala | Val | Gly | Ile | Pro | Ala | Val | Gly | Ile |
|     |     |     | 2645|     |     |     |     | 2650|     |     |     |     | 2655|     |

| Pro | Ala | Val | Gly | Ile | Pro | Ala | Val | Gly | Ile | Pro | Ala | Val | Gly | Ile |
|     |     |     | 2660|     |     |     |     | 2665|     |     |     |     | 2670|     |

| Pro | Ala | Val | Gly | Ile | Pro | Ala | Val | Gly | Ile | Pro | Ala | Val | Gly | Ile |
|     |     |     | 2675|     |     |     |     | 2680|     |     |     |     | 2685|     |

| Pro | Ala | Val | Gly | Ile | Pro | Ala | Val | Gly | Ile | Pro | Ala | Val | Gly | Ile |
|     |     |     | 2690|     |     |     |     | 2695|     |     |     |     | 2700|     |

| Pro | Ala | Val | Gly | Ile | Pro | Ala | Val | Gly | Ile | Pro | Ala | Val | Gly | Ile |
|     |     |     | 2705|     |     |     |     | 2710|     |     |     |     | 2715|     |

| Pro | Ala | Val | Gly | Ile | Pro | Ala | Val | Gly | Ile | Pro | Ala | Val | Gly | Ile |
|     |     |     | 2720|     |     |     |     | 2725|     |     |     |     | 2730|     |

| Pro | Ala | Val | Gly | Ile | Pro | Ala | Val | Gly | Ile | Pro | Ala | Val | Gly | Ile |
|     |     |     | 2735|     |     |     |     | 2740|     |     |     |     | 2745|     |

| Pro | Ala | Val | Gly | Ile | Pro | Ala | Val | Gly | Ile | Pro | Ala | Val | Gly | Ile |
|     |     |     | 2750|     |     |     |     | 2755|     |     |     |     | 2760|     |

| Pro | Ala | Val | Gly | Ile | Pro | Ala | Val | Gly | Ile | Pro | Ala | Val | Gly | Ile |
|     |     |     | 2765|     |     |     |     | 2770|     |     |     |     | 2775|     |

| Pro | Ala | Val | Gly | Ile | Pro | Ala | Val | Gly | Ile | Pro | Ala | Val | Gly | Ile |
|     |     |     | 2780|     |     |     |     | 2785|     |     |     |     | 2790|     |

| Pro | Ala | Val | Gly | Ile | Pro | Ala | Val | Gly | Ile | Pro | Ala | Val | Gly | Ile |
|     |     |     | 2795|     |     |     |     | 2800|     |     |     |     | 2805|     |

Pro Ala Val Gly
    2810

<210> SEQ ID NO 27
<211> LENGTH: 2568
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(2568)

<400> SEQUENCE: 27

```
gtt cca gct gtt ggt aag gtt cca gct gtt ggt atc cca gct gtt ggt       48
Val Pro Ala Val Gly Lys Val Pro Ala Val Gly Ile Pro Ala Val Gly
1               5                   10                  15 atc cca gct gtt ggc att ccg gct gta ggt atc ccg gca gtg ggc att       96
Ile Pro Ala Val Gly Ile Pro Ala Val Gly Ile Pro Ala Val Gly Ile
            20                  25                  30 ccg gct gtt ggt atc cca gct gtt ggt atc cca gct gtt ggc att ccg      144
Pro Ala Val Gly Ile Pro Ala Val Gly Ile Pro Ala Val Gly Ile Pro
        35                  40                  45 gct gta ggt atc ccg gca gtg ggc att ccg gct gtt ggt atc cca gct      192
Ala Val Gly Ile Pro Ala Val Gly Ile Pro Ala Val Gly Ile Pro Ala
    50                  55                  60 gtt ggt atc cca gct gtt ggc att ccg gct gta ggt atc ccg gca gtg      240
Val Gly Ile Pro Ala Val Gly Ile Pro Ala Val Gly Ile Pro Ala Val
65                  70                  75                  80
```

-continued

| | | |
|---|---|---|
| ggc att ccg gct gtt ggt atc cca gct gtt ggt atc cca gct gtt ggc<br>Gly Ile Pro Ala Val Gly Ile Pro Ala Val Gly Ile Pro Ala Val Gly<br>85                      90                      95 | 288 |
| att ccg gct gta ggt atc ccg gca gtg ggc att ccg gct gtt ggt atc<br>Ile Pro Ala Val Gly Ile Pro Ala Val Gly Ile Pro Ala Val Gly Ile<br>100                      105                    110 | 336 |
| cca gct gtt ggt atc cca gct gtt ggc att ccg gct gta ggt atc ccg<br>Pro Ala Val Gly Ile Pro Ala Val Gly Ile Pro Ala Val Gly Ile Pro<br>115                      120                    125 | 384 |
| gca gtg ggc att ccg gct gtt ggt atc cca gct gtt ggt atc cca gct<br>Ala Val Gly Ile Pro Ala Val Gly Ile Pro Ala Val Gly Ile Pro Ala<br>130                      135                    140 | 432 |
| gtt ggc att ccg gct gta ggt atc ccg gca gtg ggc att ccg gct gtt<br>Val Gly Ile Pro Ala Val Gly Ile Pro Ala Val Gly Ile Pro Ala Val<br>145                      150                    155                    160 | 480 |
| ggt atc cca gct gtt ggt atc cca gct gtt ggc att ccg gct gta ggt<br>Gly Ile Pro Ala Val Gly Ile Pro Ala Val Gly Ile Pro Ala Val Gly<br>                  165                    170                    175 | 528 |
| atc ccg gca gtg ggc att ccg gct gtt ggt atc cca gct gtt ggt atc<br>Ile Pro Ala Val Gly Ile Pro Ala Val Gly Ile Pro Ala Val Gly Ile<br>                  180                    185                    190 | 576 |
| cca gct gtt ggc att ccg gct gta ggt atc ccg gca gtg ggc att ccg<br>Pro Ala Val Gly Ile Pro Ala Val Gly Ile Pro Ala Val Gly Ile Pro<br>195                      200                    205 | 624 |
| gct gtt ggt atc cca gct gtt ggt atc cca gct gtt ggc att ccg gct<br>Ala Val Gly Ile Pro Ala Val Gly Ile Pro Ala Val Gly Ile Pro Ala<br>210                      215                    220 | 672 |
| gta ggt atc ccg gca gtg ggc att ccg gct gtt ggt atc cca gct gtt<br>Val Gly Ile Pro Ala Val Gly Ile Pro Ala Val Gly Ile Pro Ala Val<br>225                      230                    235                    240 | 720 |
| ggt atc cca gct gtt ggc att ccg gct gta ggt atc ccg gca gtg ggc<br>Gly Ile Pro Ala Val Gly Ile Pro Ala Val Gly Ile Pro Ala Val Gly<br>                  245                    250                    255 | 768 |
| att ccg gct gtt ggt atc cca gct gtt ggt atc cca gct gtt ggc att<br>Ile Pro Ala Val Gly Ile Pro Ala Val Gly Ile Pro Ala Val Gly Ile<br>260                      265                    270 | 816 |
| ccg gct gta ggt atc ccg gca gtg ggc att ccg gct gtt ggt atc cca<br>Pro Ala Val Gly Ile Pro Ala Val Gly Ile Pro Ala Val Gly Ile Pro<br>275                      280                    285 | 864 |
| gct gtt ggt atc cca gct gtt ggc att ccg gct gta ggt atc ccg gca<br>Ala Val Gly Ile Pro Ala Val Gly Ile Pro Ala Val Gly Ile Pro Ala<br>290                      295                    300 | 912 |
| gtg ggc att ccg gct gtt ggt atc cca gct gtt ggt atc cca gct gtt<br>Val Gly Ile Pro Ala Val Gly Ile Pro Ala Val Gly Ile Pro Ala Val<br>305                      310                    315                    320 | 960 |
| ggc att ccg gct gta ggt atc ccg gca gtg ggc att ccg gct gtt ggt<br>Gly Ile Pro Ala Val Gly Ile Pro Ala Val Gly Ile Pro Ala Val Gly<br>                  325                    330                    335 | 1008 |
| atc cca gct gtt ggt atc cca gct gtt ggc att ccg gct gta ggt atc<br>Ile Pro Ala Val Gly Ile Pro Ala Val Gly Ile Pro Ala Val Gly Ile<br>                  340                    345                    350 | 1056 |
| ccg gca gtg ggc att ccg gct gtt ggt atc cca gct gtt ggt atc cca<br>Pro Ala Val Gly Ile Pro Ala Val Gly Ile Pro Ala Val Gly Ile Pro<br>355                      360                    365 | 1104 |
| gct gtt ggc att ccg gct gta ggt atc ccg gca gtg ggc att ccg gct<br>Ala Val Gly Ile Pro Ala Val Gly Ile Pro Ala Val Gly Ile Pro Ala<br>370                      375                    380 | 1152 |
| gtt ggt atc cca gct gtt ggt atc cca gct gtt ggc att ccg gct gta<br>Val Gly Ile Pro Ala Val Gly Ile Pro Ala Val Gly Ile Pro Ala Val<br>385                      390                    395                    400 | 1200 |

```
ggt atc ccg gca gtg ggc att ccg gct gtt ggt atc cca gct gtt ggt         1248
Gly Ile Pro Ala Val Gly Ile Pro Ala Val Gly Ile Pro Ala Val Gly
            405                 410                 415 atc cca gct gtt ggc att ccg gct gta ggt atc ccg gca gtg ggc att         1296
Ile Pro Ala Val Gly Ile Pro Ala Val Gly Ile Pro Ala Val Gly Ile
                420                 425                 430 ccg gct gtt ggt atc cca gct gtt ggt atc cca gct gtt ggc att ccg         1344
Pro Ala Val Gly Ile Pro Ala Val Gly Ile Pro Ala Val Gly Ile Pro
                    435                 440                 445 gct gta ggt atc ccg gca gtg ggc att ccg gct gtt ggt atc cca gct         1392
Ala Val Gly Ile Pro Ala Val Gly Ile Pro Ala Val Gly Ile Pro Ala
        450                 455                 460 gtt ggt atc cca gct gtt ggc att ccg gct gta ggt atc ccg gca gtg         1440
Val Gly Ile Pro Ala Val Gly Ile Pro Ala Val Gly Ile Pro Ala Val
465                 470                 475                 480 ggc att ccg gct gtt ggt atc cca gct gtt ggt atc cca gct gtt ggc         1488
Gly Ile Pro Ala Val Gly Ile Pro Ala Val Gly Ile Pro Ala Val Gly
                485                 490                 495 att ccg gct gta ggt atc ccg gca gtg ggc att ccg gct gtt ggt atc         1536
Ile Pro Ala Val Gly Ile Pro Ala Val Gly Ile Pro Ala Val Gly Ile
                    500                 505                 510 cca gct gtt ggt atc cca gct gtt ggc att ccg gct gta ggt atc ccg         1584
Pro Ala Val Gly Ile Pro Ala Val Gly Ile Pro Ala Val Gly Ile Pro
                        515                 520                 525 gca gtg ggc att ccg gct gtt ggt atc cca gct gtt ggt atc cca gct         1632
Ala Val Gly Ile Pro Ala Val Gly Ile Pro Ala Val Gly Ile Pro Ala
        530                 535                 540 gtt ggc att ccg gct gta ggt atc ccg gca gtg ggc att ccg gct gtt         1680
Val Gly Ile Pro Ala Val Gly Ile Pro Ala Val Gly Ile Pro Ala Val
545                 550                 555                 560 ggt atc cca gct gtt ggt atc cca gct gtt ggc att ccg gct gta ggt         1728
Gly Ile Pro Ala Val Gly Ile Pro Ala Val Gly Ile Pro Ala Val Gly
                565                 570                 575 atc ccg gca gtg ggc att ccg gct gtt ggt atc cca gct gtt ggt atc         1776
Ile Pro Ala Val Gly Ile Pro Ala Val Gly Ile Pro Ala Val Gly Ile
                    580                 585                 590 cca gct gtt ggc att ccg gct gta ggt atc ccg gca gtg ggc att ccg         1824
Pro Ala Val Gly Ile Pro Ala Val Gly Ile Pro Ala Val Gly Ile Pro
                        595                 600                 605 gct gtt ggt atc cca gct gtt ggt atc cca gct gtt ggc att ccg gct         1872
Ala Val Gly Ile Pro Ala Val Gly Ile Pro Ala Val Gly Ile Pro Ala
        610                 615                 620 gta ggt atc ccg gca gtg ggc att ccg gct gtt ggt atc cca gct gtt         1920
Val Gly Ile Pro Ala Val Gly Ile Pro Ala Val Gly Ile Pro Ala Val
625                 630                 635                 640 ggt atc cca gct gtt ggc att ccg gct gta ggt atc ccg gca gtg ggc         1968
Gly Ile Pro Ala Val Gly Ile Pro Ala Val Gly Ile Pro Ala Val Gly
                645                 650                 655 att ccg gct gtt ggt atc cca gct gtt ggt atc cca gct gtt ggc att         2016
Ile Pro Ala Val Gly Ile Pro Ala Val Gly Ile Pro Ala Val Gly Ile
                    660                 665                 670 ccg gct gta ggt atc ccg gca gtg ggc att ccg gct gtt ggt atc cca         2064
Pro Ala Val Gly Ile Pro Ala Val Gly Ile Pro Ala Val Gly Ile Pro
                        675                 680                 685 gct gtt ggt atc cca gct gtt ggc att ccg gct gta ggt atc ccg gca         2112
Ala Val Gly Ile Pro Ala Val Gly Ile Pro Ala Val Gly Ile Pro Ala
        690                 695                 700 gtg ggc att ccg gct gtt ggt atc cca gct gtt ggt atc cca gct gtt         2160
Val Gly Ile Pro Ala Val Gly Ile Pro Ala Val Gly Ile Pro Ala Val
```

```
                705                 710                 715                 720
ggc att ccg gct gta ggt atc ccg gca gtg ggc att ccg gct gtt ggt      2208
Gly Ile Pro Ala Val Gly Ile Pro Ala Val Gly Ile Pro Ala Val Gly
            725                 730                 735 atc cca gct gtt ggt atc cca gct gtt ggc att ccg gct gta ggt atc      2256
Ile Pro Ala Val Gly Ile Pro Ala Val Gly Ile Pro Ala Val Gly Ile
        740                 745                 750 ccg gca gtg ggc att ccg gct gtt ggt atc cca gct gtt ggt atc cca      2304
Pro Ala Val Gly Ile Pro Ala Val Gly Ile Pro Ala Val Gly Ile Pro
    755                 760                 765 gct gtt ggc att ccg gct gta ggt atc ccg gca gtg ggc att ccg gct      2352
Ala Val Gly Ile Pro Ala Val Gly Ile Pro Ala Val Gly Ile Pro Ala
770                 775                 780 gtt ggt atc cca gct gtt ggt atc cca gct gtt ggc att ccg gct gta      2400
Val Gly Ile Pro Ala Val Gly Ile Pro Ala Val Gly Ile Pro Ala Val
785                 790                 795                 800 ggt atc ccg gca gtg ggc att ccg gct gtt ggt atc cca gct gtt ggt      2448
Gly Ile Pro Ala Val Gly Ile Pro Ala Val Gly Ile Pro Ala Val Gly
            805                 810                 815 atc cca gct gtt ggc att ccg gct gta ggt atc ccg gca gtg ggc att      2496
Ile Pro Ala Val Gly Ile Pro Ala Val Gly Ile Pro Ala Val Gly Ile
        820                 825                 830 ccg gct gtt ggt atc cca gct gtt ggt atc cca gct gtt ggc att ccg      2544
Pro Ala Val Gly Ile Pro Ala Val Gly Ile Pro Ala Val Gly Ile Pro
    835                 840                 845 gct gta ggt atc ccg gca gtg ggc                                      2568
Ala Val Gly Ile Pro Ala Val Gly
        850                 855

<210> SEQ ID NO 28
<211> LENGTH: 856
<212> TYPE: PRT
<213> ORGANISM: Artificial Sequence
<220> FEATURE:
<223> OTHER INFORMATION: Synthetic Construct

<400> SEQUENCE: 28

Val Pro Ala Val Gly Lys Val Pro Ala Val Gly Ile Pro Ala Val Gly
1               5                   10                  15

Ile Pro Ala Val Gly Ile Pro Ala Val Gly Ile Pro Ala Val Gly Ile
            20                  25                  30

Pro Ala Val Gly Ile Pro Ala Val Gly Ile Pro Ala Val Gly Ile Pro
        35                  40                  45

Ala Val Gly Ile Pro Ala Val Gly Ile Pro Ala Val Gly Ile Pro Ala
    50                  55                  60

Val Gly Ile Pro Ala Val Gly Ile Pro Ala Val Gly Ile Pro Ala Val
65                  70                  75                  80

Gly Ile Pro Ala Val Gly Ile Pro Ala Val Gly Ile Pro Ala Val Gly
                85                  90                  95

Ile Pro Ala Val Gly Ile Pro Ala Val Gly Ile Pro Ala Val Gly Ile
            100                 105                 110

Pro Ala Val Gly Ile Pro Ala Val Gly Ile Pro Ala Val Gly Ile Pro
        115                 120                 125

Ala Val Gly Ile Pro Ala Val Gly Ile Pro Ala Val Gly Ile Pro Ala
    130                 135                 140

Val Gly Ile Pro Ala Val Gly Ile Pro Ala Val Gly Ile Pro Ala Val
145                 150                 155                 160

Gly Ile Pro Ala Val Gly Ile Pro Ala Val Gly Ile Pro Ala Val Gly
```

-continued

```
                165                 170                 175
Ile Pro Ala Val Gly Ile Pro Ala Val Gly Ile Pro Ala Val Gly Ile
            180                 185                 190
Pro Ala Val Gly Ile Pro Ala Val Gly Ile Pro Ala Val Gly Ile Pro
        195                 200                 205
Ala Val Gly Ile Pro Ala Val Gly Ile Pro Ala Val Gly Ile Pro Ala
    210                 215                 220
Val Gly Ile Pro Ala Val Gly Ile Pro Ala Val Gly Ile Pro Ala Val
225                 230                 235                 240
Gly Ile Pro Ala Val Gly Ile Pro Ala Val Gly Ile Pro Ala Val Gly
            245                 250                 255
Ile Pro Ala Val Gly Ile Pro Ala Val Gly Ile Pro Ala Val Gly Ile
            260                 265                 270
Pro Ala Val Gly Ile Pro Ala Val Gly Ile Pro Ala Val Gly Ile Pro
        275                 280                 285
Ala Val Gly Ile Pro Ala Val Gly Ile Pro Ala Val Gly Ile Pro Ala
    290                 295                 300
Val Gly Ile Pro Ala Val Gly Ile Pro Ala Val Gly Ile Pro Ala Val
305                 310                 315                 320
Gly Ile Pro Ala Val Gly Ile Pro Ala Val Gly Ile Pro Ala Val Gly
            325                 330                 335
Ile Pro Ala Val Gly Ile Pro Ala Val Gly Ile Pro Ala Val Gly Ile
            340                 345                 350
Pro Ala Val Gly Ile Pro Ala Val Gly Ile Pro Ala Val Gly Ile Pro
        355                 360                 365
Ala Val Gly Ile Pro Ala Val Gly Ile Pro Ala Val Gly Ile Pro Ala
    370                 375                 380
Val Gly Ile Pro Ala Val Gly Ile Pro Ala Val Gly Ile Pro Ala Val
385                 390                 395                 400
Gly Ile Pro Ala Val Gly Ile Pro Ala Val Gly Ile Pro Ala Val Gly
            405                 410                 415
Ile Pro Ala Val Gly Ile Pro Ala Val Gly Ile Pro Ala Val Gly Ile
            420                 425                 430
Pro Ala Val Gly Ile Pro Ala Val Gly Ile Pro Ala Val Gly Ile Pro
        435                 440                 445
Ala Val Gly Ile Pro Ala Val Gly Ile Pro Ala Val Gly Ile Pro Ala
    450                 455                 460
Val Gly Ile Pro Ala Val Gly Ile Pro Ala Val Gly Ile Pro Ala Val
465                 470                 475                 480
Gly Ile Pro Ala Val Gly Ile Pro Ala Val Gly Ile Pro Ala Val Gly
            485                 490                 495
Ile Pro Ala Val Gly Ile Pro Ala Val Gly Ile Pro Ala Val Gly Ile
            500                 505                 510
Pro Ala Val Gly Ile Pro Ala Val Gly Ile Pro Ala Val Gly Ile Pro
        515                 520                 525
Ala Val Gly Ile Pro Ala Val Gly Ile Pro Ala Val Gly Ile Pro Ala
    530                 535                 540
Val Gly Ile Pro Ala Val Gly Ile Pro Ala Val Gly Ile Pro Ala Val
545                 550                 555                 560
Gly Ile Pro Ala Val Gly Ile Pro Ala Val Gly Ile Pro Ala Val Gly
            565                 570                 575
Ile Pro Ala Val Gly Ile Pro Ala Val Gly Ile Pro Ala Val Gly Ile
            580                 585                 590
```

```
Pro Ala Val Gly Ile Pro Ala Val Gly Ile Pro Ala Val Gly Ile Pro
        595                 600                 605
Ala Val Gly Ile Pro Ala Val Gly Ile Pro Ala Val Gly Ile Pro Ala
    610                 615                 620
Val Gly Ile Pro Ala Val Gly Ile Pro Ala Val Gly Ile Pro Ala Val
625                 630                 635                 640
Gly Ile Pro Ala Val Gly Ile Pro Ala Val Gly Ile Pro Ala Val Gly
            645                 650                 655
Ile Pro Ala Val Gly Ile Pro Ala Val Gly Ile Pro Ala Val Gly Ile
        660                 665                 670
Pro Ala Val Gly Ile Pro Ala Val Gly Ile Pro Ala Val Gly Ile Pro
        675                 680                 685
Ala Val Gly Ile Pro Ala Val Gly Ile Pro Ala Val Gly Ile Pro Ala
    690                 695                 700
Val Gly Ile Pro Ala Val Gly Ile Pro Ala Val Gly Ile Pro Ala Val
705                 710                 715                 720
Gly Ile Pro Ala Val Gly Ile Pro Ala Val Gly Ile Pro Ala Val Gly
            725                 730                 735
Ile Pro Ala Val Gly Ile Pro Ala Val Gly Ile Pro Ala Val Gly Ile
        740                 745                 750
Pro Ala Val Gly Ile Pro Ala Val Gly Ile Pro Ala Val Gly Ile Pro
        755                 760                 765
Ala Val Gly Ile Pro Ala Val Gly Ile Pro Ala Val Gly Ile Pro Ala
    770                 775                 780
Val Gly Ile Pro Ala Val Gly Ile Pro Ala Val Gly Ile Pro Ala Val
785                 790                 795                 800
Gly Ile Pro Ala Val Gly Ile Pro Ala Val Gly Ile Pro Ala Val Gly
            805                 810                 815
Ile Pro Ala Val Gly Ile Pro Ala Val Gly Ile Pro Ala Val Gly Ile
        820                 825                 830
Pro Ala Val Gly Ile Pro Ala Val Gly Ile Pro Ala Val Gly Ile Pro
        835                 840                 845
Ala Val Gly Ile Pro Ala Val Gly
    850                 855

<210> SEQ ID NO 29
<211> LENGTH: 2622
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(2622)

<400> SEQUENCE: 29 gtt cca gct gtt ggt aag gcg gcc aag gtt cca ggt gca ggc gtt cca      48
Val Pro Ala Val Gly Lys Ala Ala Lys Val Pro Gly Ala Gly Val Pro
1               5                   10                  15 gct gtt ggt atc cca gct gtt ggt atc cca gct gtt ggc att ccg gct      96
Ala Val Gly Ile Pro Ala Val Gly Ile Pro Ala Val Gly Ile Pro Ala
            20                  25                  30 gta ggt atc ccg gca gtg ggc att ccg gct gtt ggt atc cca gct gtt     144
Val Gly Ile Pro Ala Val Gly Ile Pro Ala Val Gly Ile Pro Ala Val
        35                  40                  45 ggt atc cca gct gtt ggc att ccg gct gta ggt atc ccg gca gtg ggc     192
Gly Ile Pro Ala Val Gly Ile Pro Ala Val Gly Ile Pro Ala Val Gly
```

-continued

```
                50                  55                  60
att ccg gct gtt ggt atc cca gct gtt ggt atc cca gct gtt ggc att     240
Ile Pro Ala Val Gly Ile Pro Ala Val Gly Ile Pro Ala Val Gly Ile
65              70                  75                  80 ccg gct gta ggt atc ccg gca gtg ggc att ccg gct gtt ggt atc cca     288
Pro Ala Val Gly Ile Pro Ala Val Gly Ile Pro Ala Val Gly Ile Pro
            85                  90                  95 gct gtt ggt atc cca gct gtt ggc att ccg gct gta ggt atc ccg gca     336
Ala Val Gly Ile Pro Ala Val Gly Ile Pro Ala Val Gly Ile Pro Ala
        100                 105                 110 gtg ggc att ccg gct gtt ggt atc cca gct gtt ggt atc cca gct gtt     384
Val Gly Ile Pro Ala Val Gly Ile Pro Ala Val Gly Ile Pro Ala Val
    115                 120                 125 ggc att ccg gct gta ggt atc ccg gca gtg ggc att ccg gct gtt ggt     432
Gly Ile Pro Ala Val Gly Ile Pro Ala Val Gly Ile Pro Ala Val Gly
130                 135                 140 atc cca gct gtt ggt atc cca gct gtt ggc att ccg gct gta ggt atc     480
Ile Pro Ala Val Gly Ile Pro Ala Val Gly Ile Pro Ala Val Gly Ile
145                 150                 155                 160 ccg gca gtg ggc att ccg gct gtt ggt atc cca gct gtt ggt atc cca     528
Pro Ala Val Gly Ile Pro Ala Val Gly Ile Pro Ala Val Gly Ile Pro
            165                 170                 175 gct gtt ggc att ccg gct gta ggt atc ccg gca gtg ggc att ccg gct     576
Ala Val Gly Ile Pro Ala Val Gly Ile Pro Ala Val Gly Ile Pro Ala
        180                 185                 190 gtt ggt atc cca gct gtt ggt atc cca gct gtt ggc att ccg gct gta     624
Val Gly Ile Pro Ala Val Gly Ile Pro Ala Val Gly Ile Pro Ala Val
    195                 200                 205 ggt atc ccg gca gtg ggc att ccg gct gtt ggt atc cca gct gtt ggt     672
Gly Ile Pro Ala Val Gly Ile Pro Ala Val Gly Ile Pro Ala Val Gly
210                 215                 220 atc cca gct gtt ggc att ccg gct gta ggt atc ccg gca gtg ggc att     720
Ile Pro Ala Val Gly Ile Pro Ala Val Gly Ile Pro Ala Val Gly Ile
225                 230                 235                 240 ccg gct gtt ggt atc cca gct gtt ggt atc cca gct gtt ggc att ccg     768
Pro Ala Val Gly Ile Pro Ala Val Gly Ile Pro Ala Val Gly Ile Pro
            245                 250                 255 gct gta ggt atc ccg gca gtg ggc att ccg gct gtt ggt atc cca gct     816
Ala Val Gly Ile Pro Ala Val Gly Ile Pro Ala Val Gly Ile Pro Ala
        260                 265                 270 gtt ggt atc cca gct gtt ggc att ccg gct gta ggt atc ccg gca gtg     864
Val Gly Ile Pro Ala Val Gly Ile Pro Ala Val Gly Ile Pro Ala Val
    275                 280                 285 ggc att ccg gct gtt ggt atc cca gct gtt ggt atc cca gct gtt ggc     912
Gly Ile Pro Ala Val Gly Ile Pro Ala Val Gly Ile Pro Ala Val Gly
290                 295                 300 att ccg gct gta ggt atc ccg gca gtg ggc att ccg gct gtt ggt atc     960
Ile Pro Ala Val Gly Ile Pro Ala Val Gly Ile Pro Ala Val Gly Ile
305                 310                 315                 320 cca gct gtt ggt atc cca gct gtt ggc att ccg gct gta ggt atc ccg    1008
Pro Ala Val Gly Ile Pro Ala Val Gly Ile Pro Ala Val Gly Ile Pro
            325                 330                 335 gca gtg ggc att ccg gct gtt ggt atc cca gct gtt ggt atc cca gct    1056
Ala Val Gly Ile Pro Ala Val Gly Ile Pro Ala Val Gly Ile Pro Ala
        340                 345                 350 gtt ggc att ccg gct gta ggt atc ccg gca gtg ggc att ccg gct gtt    1104
Val Gly Ile Pro Ala Val Gly Ile Pro Ala Val Gly Ile Pro Ala Val
    355                 360                 365 ggt atc cca gct gtt ggt atc cca gct gtt ggc att ccg gct gta ggt    1152
```

-continued

| | | |
|---|---|---|
| Gly Ile Pro Ala Val Gly Ile Pro Ala Val Gly Ile Pro Ala Val Gly<br>370                       375                      380 | | |
| atc ccg gca gtg ggc att ccg gct gtt ggt atc cca gct gtt ggt atc<br>Ile Pro Ala Val Gly Ile Pro Ala Val Gly Ile Pro Ala Val Gly Ile<br>385                       390                      395                      400 | 1200 |
| cca gct gtt ggc att ccg gct gta ggt atc ccg gca gtg ggc att ccg<br>Pro Ala Val Gly Ile Pro Ala Val Gly Ile Pro Ala Val Gly Ile Pro<br>                      405                      410                      415 | 1248 |
| gct gtt ggt atc cca gct gtt ggt atc cca gct gtt ggc att ccg gct<br>Ala Val Gly Ile Pro Ala Val Gly Ile Pro Ala Val Gly Ile Pro Ala<br>                  420                      425                      430 | 1296 |
| gta ggt atc ccg gca gtg ggc att ccg gct gtt ggt atc cca gct gtt<br>Val Gly Ile Pro Ala Val Gly Ile Pro Ala Val Gly Ile Pro Ala Val<br>              435                      440                      445 | 1344 |
| ggt atc cca gct gtt ggc att ccg gct gta ggt atc ccg gca gtg ggc<br>Gly Ile Pro Ala Val Gly Ile Pro Ala Val Gly Ile Pro Ala Val Gly<br>450                       455                      460 | 1392 |
| att ccg gct gtt ggt atc cca gct gtt ggt atc cca gct gtt ggc att<br>Ile Pro Ala Val Gly Ile Pro Ala Val Gly Ile Pro Ala Val Gly Ile<br>465                       470                      475                      480 | 1440 |
| ccg gct gta ggt atc ccg gca gtg ggc att ccg gct gtt ggt atc cca<br>Pro Ala Val Gly Ile Pro Ala Val Gly Ile Pro Ala Val Gly Ile Pro<br>                  485                      490                      495 | 1488 |
| gct gtt ggt atc cca gct gtt ggc att ccg gct gta ggt atc ccg gca<br>Ala Val Gly Ile Pro Ala Val Gly Ile Pro Ala Val Gly Ile Pro Ala<br>             500                      505                      510 | 1536 |
| gtg ggc att ccg gct gtt ggt atc cca gct gtt ggt atc cca gct gtt<br>Val Gly Ile Pro Ala Val Gly Ile Pro Ala Val Gly Ile Pro Ala Val<br>             515                      520                      525 | 1584 |
| ggc att ccg gct gta ggt atc ccg gca gtg ggc att ccg gct gtt ggt<br>Gly Ile Pro Ala Val Gly Ile Pro Ala Val Gly Ile Pro Ala Val Gly<br>530                       535                      540 | 1632 |
| atc cca gct gtt ggt atc cca gct gtt ggc att ccg gct gta ggt atc<br>Ile Pro Ala Val Gly Ile Pro Ala Val Gly Ile Pro Ala Val Gly Ile<br>545                       550                      555                      560 | 1680 |
| ccg gca gtg ggc att ccg gct gtt ggt atc cca gct gtt ggt atc cca<br>Pro Ala Val Gly Ile Pro Ala Val Gly Ile Pro Ala Val Gly Ile Pro<br>                  565                      570                      575 | 1728 |
| gct gtt ggc att ccg gct gta ggt atc ccg gca gtg ggc att ccg gct<br>Ala Val Gly Ile Pro Ala Val Gly Ile Pro Ala Val Gly Ile Pro Ala<br>             580                      585                      590 | 1776 |
| gtt ggt atc cca gct gtt ggt atc cca gct gtt ggc att ccg gct gta<br>Val Gly Ile Pro Ala Val Gly Ile Pro Ala Val Gly Ile Pro Ala Val<br>             595                      600                      605 | 1824 |
| ggt atc ccg gca gtg ggc att ccg gct gtt ggt atc cca gct gtt ggt<br>Gly Ile Pro Ala Val Gly Ile Pro Ala Val Gly Ile Pro Ala Val Gly<br>610                       615                      620 | 1872 |
| atc cca gct gtt ggc att ccg gct gta ggt atc ccg gca gtg ggc att<br>Ile Pro Ala Val Gly Ile Pro Ala Val Gly Ile Pro Ala Val Gly Ile<br>625                       630                      635                      640 | 1920 |
| ccg gct gtt ggt atc cca gct gtt ggt atc cca gct gtt ggc att ccg<br>Pro Ala Val Gly Ile Pro Ala Val Gly Ile Pro Ala Val Gly Ile Pro<br>                  645                      650                      655 | 1968 |
| gct gta ggt atc ccg gca gtg ggc att ccg gct gtt ggt atc cca gct<br>Ala Val Gly Ile Pro Ala Val Gly Ile Pro Ala Val Gly Ile Pro Ala<br>             660                      665                      670 | 2016 |
| gtt ggt atc cca gct gtt ggc att ccg gct gta ggt atc ccg gca gtg<br>Val Gly Ile Pro Ala Val Gly Ile Pro Ala Val Gly Ile Pro Ala Val<br>             675                      680                      685 | 2064 |

```
ggc att ccg gct gtt ggt atc cca gct gtt ggt atc cca gct gtt ggc      2112
Gly Ile Pro Ala Val Gly Ile Pro Ala Val Gly Ile Pro Ala Val Gly
690                 695                 700 att ccg gct gta ggt atc ccg gca gtg ggc att ccg gct gtt ggt atc      2160
Ile Pro Ala Val Gly Ile Pro Ala Val Gly Ile Pro Ala Val Gly Ile
705                 710                 715                 720 cca gct gtt ggt atc cca gct gtt ggc att ccg gct gta ggt atc ccg      2208
Pro Ala Val Gly Ile Pro Ala Val Gly Ile Pro Ala Val Gly Ile Pro
                725                 730                 735 gca gtg ggc att ccg gct gtt ggt atc cca gct gtt ggt atc cca gct      2256
Ala Val Gly Ile Pro Ala Val Gly Ile Pro Ala Val Gly Ile Pro Ala
            740                 745                 750 gtt ggc att ccg gct gta ggt atc ccg gca gtg ggc att ccg gct gtt      2304
Val Gly Ile Pro Ala Val Gly Ile Pro Ala Val Gly Ile Pro Ala Val
        755                 760                 765 ggt atc cca gct gtt ggt atc cca gct gtt ggc att ccg gct gta ggt      2352
Gly Ile Pro Ala Val Gly Ile Pro Ala Val Gly Ile Pro Ala Val Gly
    770                 775                 780 atc ccg gca gtg ggc att ccg gct gtt ggt atc cca gct gtt ggt atc      2400
Ile Pro Ala Val Gly Ile Pro Ala Val Gly Ile Pro Ala Val Gly Ile
785                 790                 795                 800 cca gct gtt ggc att ccg gct gta ggt atc ccg gca gtg ggc att ccg      2448
Pro Ala Val Gly Ile Pro Ala Val Gly Ile Pro Ala Val Gly Ile Pro
                805                 810                 815 gct gtt ggt atc cca gct gtt ggt atc cca gct gtt ggc att ccg gct      2496
Ala Val Gly Ile Pro Ala Val Gly Ile Pro Ala Val Gly Ile Pro Ala
            820                 825                 830 gta ggt atc ccg gca gtg ggc att ccg gct gtt ggt atc cca gct gtt      2544
Val Gly Ile Pro Ala Val Gly Ile Pro Ala Val Gly Ile Pro Ala Val
        835                 840                 845 ggt atc cca gct gtt ggc att ccg gct gta ggt atc ccg gca gtg ggc      2592
Gly Ile Pro Ala Val Gly Ile Pro Ala Val Gly Ile Pro Ala Val Gly
    850                 855                 860 att cca gct gtt ggt aag gcg gcc aag gcg                              2622
Ile Pro Ala Val Gly Lys Ala Ala Lys Ala
865                 870
```

<210> SEQ ID NO 30
<211> LENGTH: 874
<212> TYPE: PRT
<213> ORGANISM: Artificial Sequence
<220> FEATURE:
<223> OTHER INFORMATION: Synthetic Construct

<400> SEQUENCE: 30

```
Val Pro Ala Val Gly Lys Ala Ala Lys Val Pro Gly Ala Gly Val Pro
1               5                   10                  15

Ala Val Gly Ile Pro Ala Val Gly Ile Pro Ala Val Gly Ile Pro Ala
            20                  25                  30

Val Gly Ile Pro Ala Val Gly Ile Pro Ala Val Gly Ile Pro Ala Val
        35                  40                  45

Gly Ile Pro Ala Val Gly Ile Pro Ala Val Gly Ile Pro Ala Val Gly
    50                  55                  60

Ile Pro Ala Val Gly Ile Pro Ala Val Gly Ile Pro Ala Val Gly Ile
65                  70                  75                  80

Pro Ala Val Gly Ile Pro Ala Val Gly Ile Pro Ala Val Gly Ile Pro
                85                  90                  95

Ala Val Gly Ile Pro Ala Val Gly Ile Pro Ala Val Gly Ile Pro Ala
            100                 105                 110
```

Val Gly Ile Pro Ala Val Gly Ile Pro Ala Val Gly Ile Pro Ala Val
            115                 120                 125

Gly Ile Pro Ala Val Gly Ile Pro Ala Val Gly Ile Pro Ala Val Gly
130                 135                 140

Ile Pro Ala Val Gly Ile Pro Ala Val Gly Ile Pro Ala Val Gly Ile
145                 150                 155                 160

Pro Ala Val Gly Ile Pro Ala Val Gly Ile Pro Ala Val Gly Ile Pro
                165                 170                 175

Ala Val Gly Ile Pro Ala Val Gly Ile Pro Ala Val Gly Ile Pro Ala
            180                 185                 190

Val Gly Ile Pro Ala Val Gly Ile Pro Ala Val Gly Ile Pro Ala Val
        195                 200                 205

Gly Ile Pro Ala Val Gly Ile Pro Ala Val Gly Ile Pro Ala Val Gly
210                 215                 220

Ile Pro Ala Val Gly Ile Pro Ala Val Gly Ile Pro Ala Val Gly Ile
225                 230                 235                 240

Pro Ala Val Gly Ile Pro Ala Val Gly Ile Pro Ala Val Gly Ile Pro
                245                 250                 255

Ala Val Gly Ile Pro Ala Val Gly Ile Pro Ala Val Gly Ile Pro Ala
            260                 265                 270

Val Gly Ile Pro Ala Val Gly Ile Pro Ala Val Gly Ile Pro Ala Val
        275                 280                 285

Gly Ile Pro Ala Val Gly Ile Pro Ala Val Gly Ile Pro Ala Val Gly
290                 295                 300

Ile Pro Ala Val Gly Ile Pro Ala Val Gly Ile Pro Ala Val Gly Ile
305                 310                 315                 320

Pro Ala Val Gly Ile Pro Ala Val Gly Ile Pro Ala Val Gly Ile Pro
                325                 330                 335

Ala Val Gly Ile Pro Ala Val Gly Ile Pro Ala Val Gly Ile Pro Ala
            340                 345                 350

Val Gly Ile Pro Ala Val Gly Ile Pro Ala Val Gly Ile Pro Ala Val
        355                 360                 365

Gly Ile Pro Ala Val Gly Ile Pro Ala Val Gly Ile Pro Ala Val Gly
370                 375                 380

Ile Pro Ala Val Gly Ile Pro Ala Val Gly Ile Pro Ala Val Gly Ile
385                 390                 395                 400

Pro Ala Val Gly Ile Pro Ala Val Gly Ile Pro Ala Val Gly Ile Pro
                405                 410                 415

Ala Val Gly Ile Pro Ala Val Gly Ile Pro Ala Val Gly Ile Pro Ala
            420                 425                 430

Val Gly Ile Pro Ala Val Gly Ile Pro Ala Val Gly Ile Pro Ala Val
        435                 440                 445

Gly Ile Pro Ala Val Gly Ile Pro Ala Val Gly Ile Pro Ala Val Gly
450                 455                 460

Ile Pro Ala Val Gly Ile Pro Ala Val Gly Ile Pro Ala Val Gly Ile
465                 470                 475                 480

Pro Ala Val Gly Ile Pro Ala Val Gly Ile Pro Ala Val Gly Ile Pro
                485                 490                 495

Ala Val Gly Ile Pro Ala Val Gly Ile Pro Ala Val Gly Ile Pro Ala
            500                 505                 510

Val Gly Ile Pro Ala Val Gly Ile Pro Ala Val Gly Ile Pro Ala Val
        515                 520                 525

Gly Ile Pro Ala Val Gly Ile Pro Ala Val Gly Ile Pro Ala Val Gly

Ile Pro Ala Val Gly Ile Pro Ala Val Gly Ile Pro Ala Val Gly Ile
545                 550                 555                 560

Pro Ala Val Gly Ile Pro Ala Val Gly Ile Pro Ala Val Gly Ile Pro
            565                 570                 575

Ala Val Gly Ile Pro Ala Val Gly Ile Pro Ala Val Gly Ile Pro Ala
        580                 585                 590

Val Gly Ile Pro Ala Val Gly Ile Pro Ala Val Gly Ile Pro Ala Val
    595                 600                 605

Gly Ile Pro Ala Val Gly Ile Pro Ala Val Gly Ile Pro Ala Val Gly
610                 615                 620

Ile Pro Ala Val Gly Ile Pro Ala Val Gly Ile Pro Ala Val Gly Ile
625                 630                 635                 640

Pro Ala Val Gly Ile Pro Ala Val Gly Ile Pro Ala Val Gly Ile Pro
            645                 650                 655

Ala Val Gly Ile Pro Ala Val Gly Ile Pro Ala Val Gly Ile Pro Ala
        660                 665                 670

Val Gly Ile Pro Ala Val Gly Ile Pro Ala Val Gly Ile Pro Ala Val
    675                 680                 685

Gly Ile Pro Ala Val Gly Ile Pro Ala Val Gly Ile Pro Ala Val Gly
690                 695                 700

Ile Pro Ala Val Gly Ile Pro Ala Val Gly Ile Pro Ala Val Gly Ile
705                 710                 715                 720

Pro Ala Val Gly Ile Pro Ala Val Gly Ile Pro Ala Val Gly Ile Pro
            725                 730                 735

Ala Val Gly Ile Pro Ala Val Gly Ile Pro Ala Val Gly Ile Pro Ala
        740                 745                 750

Val Gly Ile Pro Ala Val Gly Ile Pro Ala Val Gly Ile Pro Ala Val
    755                 760                 765

Gly Ile Pro Ala Val Gly Ile Pro Ala Val Gly Ile Pro Ala Val Gly
770                 775                 780

Ile Pro Ala Val Gly Ile Pro Ala Val Gly Ile Pro Ala Val Gly Ile
785                 790                 795                 800

Pro Ala Val Gly Ile Pro Ala Val Gly Ile Pro Ala Val Gly Ile Pro
            805                 810                 815

Ala Val Gly Ile Pro Ala Val Gly Ile Pro Ala Val Gly Ile Pro Ala
        820                 825                 830

Val Gly Ile Pro Ala Val Gly Ile Pro Ala Val Gly Ile Pro Ala Val
    835                 840                 845

Gly Ile Pro Ala Val Gly Ile Pro Ala Val Gly Ile Pro Ala Val Gly
850                 855                 860

Ile Pro Ala Val Gly Lys Ala Ala Lys Ala
865                 870

<210> SEQ ID NO 31
<211> LENGTH: 2064
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(2064)

<400> SEQUENCE: 31 att cca gct gtt ggt aag gcg gcc aag gtt cca ggt gca ggc gtt cca        48

```
Ile Pro Ala Val Gly Lys Ala Ala Lys Val Pro Gly Ala Gly Val Pro
1               5                   10                  15 ggt gca ggc gta ccg ggt gct ggc gtt ccg ggt gaa ggt gtt cca ggc         96
Gly Ala Gly Val Pro Gly Ala Gly Val Pro Gly Glu Gly Val Pro Gly
            20                  25                  30 gca ggt gta ccg ggt gcg ggt gtt cca ggt gca ggc gta ccg ggt gct        144
Ala Gly Val Pro Gly Ala Gly Val Pro Gly Ala Gly Val Pro Gly Ala
                35                  40                  45 ggc gtt ccg ggt gaa ggt gtt cca ggc gca ggt gta ccg ggt gcg ggt        192
Gly Val Pro Gly Glu Gly Val Pro Gly Ala Gly Val Pro Gly Ala Gly
    50                  55                  60 cca ggt gca ggc gta ccg ggt gct ggc gtt ccg ggt gaa ggt gtt cca        240
Pro Gly Ala Gly Val Pro Gly Ala Gly Val Pro Gly Glu Gly Val Pro
65                  70                  75                  80 ggc gca ggt gta ccg ggt gcg ggt cca ggt gca ggc gta ccg ggt gct        288
Gly Ala Gly Val Pro Gly Ala Gly Pro Gly Ala Gly Val Pro Gly Ala
                85                  90                  95 ggc gtt ccg ggt gaa ggt gtt cca ggc gca ggt gta ccg ggt gcg ggt        336
Gly Val Pro Gly Glu Gly Val Pro Gly Ala Gly Val Pro Gly Ala Gly
            100                 105                 110 cca ggt gca ggc gta ccg ggt gct ggc gtt ccg ggt gaa ggt gtt cca        384
Pro Gly Ala Gly Val Pro Gly Ala Gly Val Pro Gly Glu Gly Val Pro
        115                 120                 125 ggc gca ggt gta ccg ggt gcg ggt cca ggt gca ggc gta ccg ggt gct        432
Gly Ala Gly Val Pro Gly Ala Gly Pro Gly Ala Gly Val Pro Gly Ala
    130                 135                 140 ggc gtt ccg ggt gaa ggt gtt cca ggc gca ggt gta ccg ggt gcg ggt        480
Gly Val Pro Gly Glu Gly Val Pro Gly Ala Gly Val Pro Gly Ala Gly
145                 150                 155                 160 cca ggt gca ggc gta ccg ggt gct ggc gtt ccg ggt gaa ggt gtt cca        528
Pro Gly Ala Gly Val Pro Gly Ala Gly Val Pro Gly Glu Gly Val Pro
                165                 170                 175 ggc gca ggt gta ccg ggt gcg ggt cca ggt gca ggc gta ccg ggt gct        576
Gly Ala Gly Val Pro Gly Ala Gly Pro Gly Ala Gly Val Pro Gly Ala
            180                 185                 190 ggc gtt ccg ggt gaa ggt gtt cca ggc gca ggt gta ccg ggt gcg ggt        624
Gly Val Pro Gly Glu Gly Val Pro Gly Ala Gly Val Pro Gly Ala Gly
        195                 200                 205 cca ggt gca ggc gta ccg ggt gct ggc gtt ccg ggt gaa ggt gtt cca        672
Pro Gly Ala Gly Val Pro Gly Ala Gly Val Pro Gly Glu Gly Val Pro
    210                 215                 220 ggc gca ggt gta ccg ggt gcg ggt cca ggt gca ggc gta ccg ggt gct        720
Gly Ala Gly Val Pro Gly Ala Gly Pro Gly Ala Gly Val Pro Gly Ala
225                 230                 235                 240 ggc gtt ccg ggt gaa ggt gtt cca ggc gca ggt gta ccg ggt gcg ggt        768
Gly Val Pro Gly Glu Gly Val Pro Gly Ala Gly Val Pro Gly Ala Gly
                245                 250                 255 cca ggt gca ggc gta ccg ggt gct ggc gtt ccg ggt gaa ggt gtt cca        816
Pro Gly Ala Gly Val Pro Gly Ala Gly Val Pro Gly Glu Gly Val Pro
            260                 265                 270 ggc gca ggt gta ccg ggt gcg ggt cca ggt gca ggc gta ccg ggt gct        864
Gly Ala Gly Val Pro Gly Ala Gly Pro Gly Ala Gly Val Pro Gly Ala
        275                 280                 285 ggc gtt ccg ggt gaa ggt gtt cca ggc gca ggt gta ccg ggt gcg ggt        912
Gly Val Pro Gly Glu Gly Val Pro Gly Ala Gly Val Pro Gly Ala Gly
    290                 295                 300 cca ggt gca ggc gta ccg ggt gct ggc gtt ccg ggt gaa ggt gtt cca        960
Pro Gly Ala Gly Val Pro Gly Ala Gly Val Pro Gly Glu Gly Val Pro
305                 310                 315                 320
```

```
ggc gca ggt gta ccg ggt gcg ggt cca ggt gca ggc gta ccg ggt gct     1008
Gly Ala Gly Val Pro Gly Ala Gly Pro Gly Ala Gly Val Pro Gly Ala
            325                 330                 335 ggc gtt ccg ggt gaa ggt gtt cca ggc gca ggt gta ccg ggt gcg ggt     1056
Gly Val Pro Gly Glu Gly Val Pro Gly Ala Gly Val Pro Gly Ala Gly
            340                 345                 350 cca ggt gca ggc gta ccg ggt gct ggc gtt ccg ggt gaa ggt gtt cca     1104
Pro Gly Ala Gly Val Pro Gly Ala Gly Val Pro Gly Glu Gly Val Pro
            355                 360                 365 ggc gca ggt gta ccg ggt gcg ggt cca ggt gca ggc gta ccg ggt gct     1152
Gly Ala Gly Val Pro Gly Ala Gly Pro Gly Ala Gly Val Pro Gly Ala
            370                 375                 380 ggc gtt ccg ggt gaa ggt gtt cca ggc gca ggt gta ccg ggt gcg ggt     1200
Gly Val Pro Gly Glu Gly Val Pro Gly Ala Gly Val Pro Gly Ala Gly
385                 390                 395                 400 cca ggt gca ggc gta ccg ggt gct ggc gtt ccg ggt gaa ggt gtt cca     1248
Pro Gly Ala Gly Val Pro Gly Ala Gly Val Pro Gly Glu Gly Val Pro
            405                 410                 415 ggc gca ggt gta ccg ggt gcg ggt cca ggt gca ggc gta ccg ggt gct     1296
Gly Ala Gly Val Pro Gly Ala Gly Pro Gly Ala Gly Val Pro Gly Ala
            420                 425                 430 ggc gtt ccg ggt gaa ggt gtt cca ggc gca ggt gta ccg ggt gcg ggt     1344
Gly Val Pro Gly Glu Gly Val Pro Gly Ala Gly Val Pro Gly Ala Gly
            435                 440                 445 cca ggt gca ggc gta ccg ggt gct ggc gtt ccg ggt gaa ggt gtt cca     1392
Pro Gly Ala Gly Val Pro Gly Ala Gly Val Pro Gly Glu Gly Val Pro
            450                 455                 460 ggc gca ggt gta ccg ggt gcg ggt cca ggt gca ggc gta ccg ggt gct     1440
Gly Ala Gly Val Pro Gly Ala Gly Pro Gly Ala Gly Val Pro Gly Ala
465                 470                 475                 480 ggc gtt ccg ggt gaa ggt gtt cca ggc gca ggt gta ccg ggt gcg ggt     1488
Gly Val Pro Gly Glu Gly Val Pro Gly Ala Gly Val Pro Gly Ala Gly
            485                 490                 495 cca ggt gca ggc gta ccg ggt gct ggc gtt ccg ggt gaa ggt gtt cca     1536
Pro Gly Ala Gly Val Pro Gly Ala Gly Val Pro Gly Glu Gly Val Pro
            500                 505                 510 ggc gca ggt gta ccg ggt gcg ggt cca ggt gca ggc gta ccg ggt gct     1584
Gly Ala Gly Val Pro Gly Ala Gly Pro Gly Ala Gly Val Pro Gly Ala
            515                 520                 525 ggc gtt ccg ggt gaa ggt gtt cca ggc gca ggt gta ccg ggt gcg ggt     1632
Gly Val Pro Gly Glu Gly Val Pro Gly Ala Gly Val Pro Gly Ala Gly
            530                 535                 540 cca ggt gca ggc gta ccg ggt gct ggc gtt ccg ggt gaa ggt gtt cca     1680
Pro Gly Ala Gly Val Pro Gly Ala Gly Val Pro Gly Glu Gly Val Pro
545                 550                 555                 560 ggc gca ggt gta ccg ggt gcg ggt cca ggt gca ggc gta ccg ggt gct     1728
Gly Ala Gly Val Pro Gly Ala Gly Pro Gly Ala Gly Val Pro Gly Ala
            565                 570                 575 ggc gtt ccg ggt gaa ggt gtt cca ggc gca ggt gta ccg ggt gcg ggt     1776
Gly Val Pro Gly Glu Gly Val Pro Gly Ala Gly Val Pro Gly Ala Gly
            580                 585                 590 cca ggt gca ggc gta ccg ggt gct ggc gtt ccg ggt gaa ggt gtt cca     1824
Pro Gly Ala Gly Val Pro Gly Ala Gly Val Pro Gly Glu Gly Val Pro
            595                 600                 605 ggc gca ggt gta ccg ggt gcg ggt cca ggt gca ggc gta ccg ggt gct     1872
Gly Ala Gly Val Pro Gly Ala Gly Pro Gly Ala Gly Val Pro Gly Ala
            610                 615                 620 ggc gtt ccg ggt gaa ggt gtt cca ggc gca ggt gta ccg ggt gcg ggt     1920
Gly Val Pro Gly Glu Gly Val Pro Gly Ala Gly Val Pro Gly Ala Gly
625                 630                 635                 640
```

-continued

```
cca ggt gca ggc gta ccg ggt gct ggc gtt ccg ggt gaa ggt gtt cca    1968
Pro Gly Ala Gly Val Pro Gly Ala Gly Val Pro Gly Glu Gly Val Pro
            645                 650                 655 ggc gca ggt gta ccg ggt gcg ggt cca ggt gca ggc gta ccg ggt gct    2016
Gly Ala Gly Val Pro Gly Ala Gly Pro Gly Ala Gly Val Pro Gly Ala
        660                 665                 670 ggc gtt ccg ggt gaa ggt gtt cca ggc gca ggt gta ccg ggt gcg ggt    2064
Gly Val Pro Gly Glu Gly Val Pro Gly Ala Gly Val Pro Gly Ala Gly
    675                 680                 685
```

<210> SEQ ID NO 32
<211> LENGTH: 688
<212> TYPE: PRT
<213> ORGANISM: Artificial Sequence
<220> FEATURE:
<223> OTHER INFORMATION: Synthetic Construct

<400> SEQUENCE: 32

```
Ile Pro Ala Val Gly Lys Ala Ala Lys Val Pro Gly Ala Gly Val Pro
1               5                   10                  15

Gly Ala Gly Val Pro Gly Ala Gly Val Pro Gly Glu Gly Val Pro Gly
            20                  25                  30

Ala Gly Val Pro Gly Ala Gly Val Pro Gly Ala Gly Val Pro Gly Ala
        35                  40                  45

Gly Val Pro Gly Glu Gly Val Pro Gly Ala Gly Val Pro Gly Ala Gly
    50                  55                  60

Pro Gly Ala Gly Val Pro Gly Ala Gly Val Pro Gly Glu Gly Val Pro
65                  70                  75                  80

Gly Ala Gly Val Pro Gly Ala Gly Pro Gly Ala Gly Val Pro Gly Ala
            85                  90                  95

Gly Val Pro Gly Glu Gly Val Pro Gly Ala Gly Val Pro Gly Ala Gly
            100                 105                 110

Pro Gly Ala Gly Val Pro Gly Ala Gly Val Pro Gly Glu Gly Val Pro
        115                 120                 125

Gly Ala Gly Val Pro Gly Ala Gly Pro Gly Ala Gly Val Pro Gly Ala
    130                 135                 140

Gly Val Pro Gly Glu Gly Val Pro Gly Ala Gly Val Pro Gly Ala Gly
145                 150                 155                 160

Pro Gly Ala Gly Val Pro Gly Ala Gly Val Pro Gly Glu Gly Val Pro
            165                 170                 175

Gly Ala Gly Val Pro Gly Ala Gly Pro Gly Ala Gly Val Pro Gly Ala
        180                 185                 190

Gly Val Pro Gly Glu Gly Val Pro Gly Ala Gly Val Pro Gly Ala Gly
    195                 200                 205

Pro Gly Ala Gly Val Pro Gly Ala Gly Val Pro Gly Glu Gly Val Pro
    210                 215                 220

Gly Ala Gly Val Pro Gly Ala Gly Pro Gly Ala Gly Val Pro Gly Ala
225                 230                 235                 240

Gly Val Pro Gly Glu Gly Val Pro Gly Ala Gly Val Pro Gly Ala Gly
            245                 250                 255

Pro Gly Ala Gly Val Pro Gly Ala Gly Val Pro Gly Glu Gly Val Pro
        260                 265                 270

Gly Ala Gly Val Pro Gly Ala Gly Pro Gly Ala Gly Val Pro Gly Ala
    275                 280                 285

Gly Val Pro Gly Glu Gly Val Pro Gly Ala Gly Val Pro Gly Ala Gly
    290                 295                 300
```

Pro Gly Ala Gly Val Pro Gly Ala Gly Val Pro Gly Glu Gly Val Pro
305                 310                 315                 320

Gly Ala Gly Val Pro Gly Ala Gly Pro Gly Ala Gly Val Pro Gly Ala
                325                 330                 335

Gly Val Pro Gly Glu Gly Val Pro Gly Ala Gly Val Pro Gly Ala Gly
            340                 345                 350

Pro Gly Ala Gly Val Pro Gly Ala Gly Val Pro Gly Glu Gly Val Pro
        355                 360                 365

Gly Ala Gly Val Pro Gly Ala Gly Pro Gly Ala Gly Val Pro Gly Ala
                370                 375                 380

Gly Val Pro Gly Glu Gly Val Pro Gly Ala Gly Val Pro Gly Ala Gly
385                 390                 395                 400

Pro Gly Ala Gly Val Pro Gly Ala Gly Val Pro Gly Glu Gly Val Pro
                405                 410                 415

Gly Ala Gly Val Pro Gly Ala Gly Pro Gly Ala Gly Val Pro Gly Ala
            420                 425                 430

Gly Val Pro Gly Glu Gly Val Pro Gly Ala Gly Val Pro Gly Ala Gly
        435                 440                 445

Pro Gly Ala Gly Val Pro Gly Ala Gly Val Pro Gly Glu Gly Val Pro
    450                 455                 460

Gly Ala Gly Val Pro Gly Ala Gly Pro Gly Ala Gly Val Pro Gly Ala
465                 470                 475                 480

Gly Val Pro Gly Glu Gly Val Pro Gly Ala Gly Val Pro Gly Ala Gly
                485                 490                 495

Pro Gly Ala Gly Val Pro Gly Ala Gly Val Pro Gly Glu Gly Val Pro
            500                 505                 510

Gly Ala Gly Val Pro Gly Ala Gly Pro Gly Ala Gly Val Pro Gly Ala
        515                 520                 525

Gly Val Pro Gly Glu Gly Val Pro Gly Ala Gly Val Pro Gly Ala Gly
    530                 535                 540

Pro Gly Ala Gly Val Pro Gly Ala Gly Val Pro Gly Glu Gly Val Pro
545                 550                 555                 560

Gly Ala Gly Val Pro Gly Ala Gly Pro Gly Ala Gly Val Pro Gly Ala
                565                 570                 575

Gly Val Pro Gly Glu Gly Val Pro Gly Ala Gly Val Pro Gly Ala Gly
            580                 585                 590

Pro Gly Ala Gly Val Pro Gly Ala Gly Val Pro Gly Glu Gly Val Pro
        595                 600                 605

Gly Ala Gly Val Pro Gly Ala Gly Pro Gly Ala Gly Val Pro Gly Ala
    610                 615                 620

Gly Val Pro Gly Glu Gly Val Pro Gly Ala Gly Val Pro Gly Ala Gly
625                 630                 635                 640

Pro Gly Ala Gly Val Pro Gly Ala Gly Val Pro Gly Glu Gly Val Pro
                645                 650                 655

Gly Ala Gly Val Pro Gly Ala Gly Pro Gly Ala Gly Val Pro Gly Ala
            660                 665                 670

Gly Val Pro Gly Glu Gly Val Pro Gly Ala Gly Val Pro Gly Ala Gly
        675                 680                 685

<210> SEQ ID NO 33
<211> LENGTH: 1957
<212> TYPE: PRT
<213> ORGANISM: Artificial Sequence
<220> FEATURE:

<223> OTHER INFORMATION: synthetic construct

<400> SEQUENCE: 33

```
Lys Ile Pro Ala Val Gly Ile Pro Ala Val Gly Ile Pro Ala Val Gly
1               5                   10                  15

Ile Pro Ala Val Gly Ile Pro Ala Val Gly Ile Pro Ala Val Gly Ile
            20                  25                  30

Pro Ala Val Gly Ile Pro Ala Val Gly Ile Pro Ala Val Gly Ile Pro
        35                  40                  45

Ala Val Gly Ile Pro Ala Val Gly Ile Pro Ala Val Gly Ile Pro Ala
    50                  55                  60

Val Gly Ile Pro Ala Val Gly Ile Pro Ala Val Gly Ile Pro Ala Val
65                  70                  75                  80

Gly Ile Pro Ala Val Gly Ile Pro Ala Val Gly Ile Pro Ala Val Gly
                85                  90                  95

Ile Pro Ala Val Gly Ile Pro Ala Val Gly Ile Pro Ala Val Gly Ile
            100                 105                 110

Pro Ala Val Gly Ile Pro Ala Val Gly Ile Pro Ala Val Gly Ile Pro
        115                 120                 125

Ala Val Gly Ile Pro Ala Val Gly Ile Pro Ala Val Gly Ile Pro Ala
    130                 135                 140

Val Gly Ile Pro Ala Val Gly Ile Pro Ala Val Gly Ile Pro Ala Val
145                 150                 155                 160

Gly Ile Pro Ala Val Gly Ile Pro Ala Val Gly Ile Pro Ala Val Gly
                165                 170                 175

Ile Pro Ala Val Gly Ile Pro Ala Val Gly Ile Pro Ala Val Gly Ile
            180                 185                 190

Pro Ala Val Gly Ile Pro Ala Val Gly Ile Pro Ala Val Gly Ile Pro
        195                 200                 205

Ala Val Gly Ile Pro Ala Val Gly Ile Pro Ala Val Gly Ile Pro Ala
    210                 215                 220

Val Gly Ile Pro Ala Val Gly Ile Pro Ala Val Gly Ile Pro Ala Val
225                 230                 235                 240

Gly Ile Pro Ala Val Gly Ile Pro Ala Val Gly Ile Pro Ala Val Gly
                245                 250                 255

Ile Pro Ala Val Gly Ile Pro Ala Val Gly Ile Pro Ala Val Gly Ile
            260                 265                 270

Pro Ala Val Gly Ile Pro Ala Val Gly Ile Pro Ala Val Gly Ile Pro
        275                 280                 285

Ala Val Gly Ile Pro Ala Val Gly Ile Pro Ala Val Gly Ile Pro Ala
    290                 295                 300

Val Gly Ile Pro Ala Val Gly Ile Pro Ala Val Gly Ile Pro Ala Val
305                 310                 315                 320

Gly Ile Pro Ala Val Gly Ile Pro Ala Val Gly Ile Pro Ala Val Gly
                325                 330                 335

Ile Pro Ala Val Gly Ile Pro Ala Val Gly Ile Pro Ala Val Gly Ile
            340                 345                 350

Pro Ala Val Gly Ile Pro Ala Val Gly Ile Pro Ala Val Gly Ile Pro
        355                 360                 365

Ala Val Gly Ile Pro Ala Val Gly Ile Pro Ala Val Gly Ile Pro Ala
    370                 375                 380

Val Gly Ile Pro Ala Val Gly Ile Pro Ala Val Gly Ile Pro Ala Val
385                 390                 395                 400
```

-continued

Gly Ile Pro Ala Val Gly Ile Pro Ala Val Gly Ile Pro Ala Val Gly
                    405                 410                 415
Ile Pro Ala Val Gly Ile Pro Ala Val Gly Ile Pro Ala Val Gly Ile
                420                 425                 430
Pro Ala Val Gly Ile Pro Ala Val Gly Ile Pro Ala Val Gly Ile Pro
            435                 440                 445
Ala Val Gly Ile Pro Ala Val Gly Ile Pro Ala Val Gly Ile Pro Ala
        450                 455                 460
Val Gly Ile Pro Ala Val Gly Ile Pro Ala Val Gly Ile Pro Ala Val
465                 470                 475                 480
Gly Ile Pro Ala Val Gly Ile Pro Ala Val Gly Ile Pro Ala Val Gly
                485                 490                 495
Ile Pro Ala Val Gly Ile Pro Ala Val Gly Ile Pro Ala Val Gly Ile
            500                 505                 510
Pro Ala Val Gly Ile Pro Ala Val Gly Ile Pro Ala Val Gly Ile Pro
        515                 520                 525
Ala Val Gly Ile Pro Ala Val Gly Ile Pro Ala Val Gly Ile Pro Ala
    530                 535                 540
Val Gly Ile Pro Ala Val Gly Ile Pro Ala Val Gly Ile Pro Ala Val
545                 550                 555                 560
Gly Ile Pro Ala Val Gly Ile Pro Ala Val Gly Ile Pro Ala Val Gly
                565                 570                 575
Ile Pro Ala Val Gly Ile Pro Ala Val Gly Ile Pro Ala Val Gly Ile
            580                 585                 590
Pro Ala Val Gly Ile Pro Ala Val Gly Ile Pro Ala Val Gly Ile Pro
        595                 600                 605
Ala Val Gly Ile Pro Ala Val Gly Ile Pro Ala Val Gly Ile Pro Ala
    610                 615                 620
Val Gly Ile Pro Ala Val Gly Ile Pro Ala Val Gly Ile Pro Ala Val
625                 630                 635                 640
Gly Ile Pro Ala Val Gly Ile Pro Ala Val Gly Lys Lys Val Pro Gly
                645                 650                 655
Ala Gly Val Pro Gly Ala Gly Val Pro Gly Ala Gly Val Pro Gly Ala
            660                 665                 670
Gly Val Pro Gly Glu Gly Val Pro Gly Ala Gly Val Pro Gly Ala Gly
        675                 680                 685
Val Pro Gly Ala Gly Val Pro Gly Ala Gly Val Pro Gly Glu Gly Val
    690                 695                 700
Pro Gly Ala Gly Val Pro Gly Ala Gly Val Pro Gly Ala Gly Val Pro
705                 710                 715                 720
Gly Ala Gly Val Pro Gly Glu Gly Val Pro Gly Ala Gly Val Pro Gly
                725                 730                 735
Ala Gly Val Pro Gly Ala Gly Val Pro Gly Ala Gly Val Pro Gly Glu
            740                 745                 750
Gly Val Pro Gly Ala Gly Val Pro Gly Ala Gly Val Pro Gly Ala Gly
        755                 760                 765
Val Pro Gly Ala Gly Val Pro Gly Glu Gly Val Pro Gly Ala Gly Val
    770                 775                 780
Pro Gly Ala Gly Val Pro Gly Ala Gly Val Pro Gly Ala Gly Val Pro
785                 790                 795                 800
Gly Glu Gly Val Pro Gly Ala Gly Val Pro Gly Ala Gly Val Pro Gly
                805                 810                 815
Ala Gly Val Pro Gly Ala Gly Val Pro Gly Glu Gly Val Pro Gly Ala

-continued

```
                820             825             830
Gly Val Pro Gly Ala Gly Val Pro Gly Ala Gly Val Pro Gly Ala Gly
            835             840             845
Val Pro Gly Glu Gly Val Pro Gly Ala Gly Val Pro Gly Ala Gly Val
850                 855             860
Pro Gly Ala Gly Val Pro Gly Ala Gly Val Pro Gly Glu Gly Val Pro
865             870             875             880
Gly Ala Gly Val Pro Gly Ala Gly Val Pro Gly Ala Gly Val Pro Gly
                885             890             895
Ala Gly Val Pro Gly Glu Gly Val Pro Gly Ala Gly Val Pro Gly Ala
            900             905             910
Gly Val Pro Gly Ala Gly Val Pro Gly Ala Gly Val Pro Gly Glu Gly
            915             920             925
Val Pro Gly Ala Gly Val Pro Gly Ala Gly Val Pro Gly Ala Gly Val
        930             935             940
Pro Gly Ala Gly Val Pro Gly Glu Gly Val Pro Gly Ala Gly Val Pro
945             950             955             960
Gly Ala Gly Val Pro Gly Ala Gly Val Pro Gly Ala Gly Val Pro Gly
                965             970             975
Glu Gly Val Pro Gly Ala Gly Val Pro Gly Ala Gly Val Pro Gly Ala
            980             985             990
Gly Val Pro Gly Ala Gly Val Pro  Gly Glu Gly Val Pro  Gly Ala Gly
            995             1000            1005
Val Pro  Gly Ala Gly Val Pro  Gly Ala Gly Val Pro  Gly Ala Gly
    1010            1015            1020
Val Pro  Gly Glu Gly Val Pro  Gly Ala Gly Val Pro  Gly Ala Gly
    1025            1030            1035
Val Pro  Gly Ala Gly Val Pro  Gly Ala Gly Val Pro  Gly Glu Gly
    1040            1045            1050
Val Pro  Gly Ala Gly Val Pro  Gly Ala Gly Val Pro  Gly Ala Gly
    1055            1060            1065
Val Pro  Gly Ala Gly Val Pro  Gly Glu Gly Val Pro  Gly Ala Gly
    1070            1075            1080
Val Pro  Gly Ala Gly Val Pro  Gly Ala Gly Val Pro  Gly Ala Gly
    1085            1090            1095
Val Pro  Gly Glu Gly Val Pro  Gly Ala Gly Val Pro  Gly Ala Gly
    1100            1105            1110
Val Pro  Gly Ala Gly Val Pro  Gly Ala Gly Val Pro  Gly Glu Gly
    1115            1120            1125
Val Pro  Gly Ala Gly Val Pro  Gly Ala Gly Val Pro  Gly Ala Gly
    1130            1135            1140
Val Pro  Gly Ala Gly Val Pro  Gly Glu Gly Val Pro  Gly Ala Gly
    1145            1150            1155
Val Pro  Gly Ala Gly Val Pro  Gly Ala Gly Val Pro  Gly Ala Gly
    1160            1165            1170
Val Pro  Gly Glu Gly Val Pro  Gly Ala Gly Val Pro  Gly Ala Gly
    1175            1180            1185
Val Pro  Gly Ala Gly Val Pro  Gly Ala Gly Val Pro  Gly Glu Gly
    1190            1195            1200
Val Pro  Gly Ala Gly Val Pro  Gly Ala Gly Val Pro  Gly Ala Gly
    1205            1210            1215
Val Pro  Gly Ala Gly Val Pro  Gly Glu Gly Val Pro  Gly Ala Gly
    1220            1225            1230
```

```
Val Pro Gly Ala Gly Val Pro Gly Ala Gly Val Pro Gly Ala Gly
    1235                1240                1245

Val Pro Gly Glu Gly Val Pro Gly Ala Gly Val Pro Gly Ala Gly
    1250                1255                1260

Val Pro Gly Ala Gly Val Pro Gly Ala Gly Val Pro Gly Glu Gly
    1265                1270                1275

Val Pro Gly Ala Gly Val Pro Gly Ala Gly Val Pro Gly Ala Gly
    1280                1285                1290

Val Pro Gly Ala Gly Val Pro Gly Glu Gly Lys Lys Ile Pro Ala
    1295                1300                1305

Val Gly Ile Pro Ala Val Gly Ile Pro Ala Val Gly Ile Pro Ala
    1310                1315                1320

Val Gly Ile Pro Ala Val Gly Ile Pro Ala Val Gly Ile Pro Ala
    1325                1330                1335

Val Gly Ile Pro Ala Val Gly Ile Pro Ala Val Gly Ile Pro Ala
    1340                1345                1350

Val Gly Ile Pro Ala Val Gly Ile Pro Ala Val Gly Ile Pro Ala
    1355                1360                1365

Val Gly Ile Pro Ala Val Gly Ile Pro Ala Val Gly Ile Pro Ala
    1370                1375                1380

Val Gly Ile Pro Ala Val Gly Ile Pro Ala Val Gly Ile Pro Ala
    1385                1390                1395

Val Gly Ile Pro Ala Val Gly Ile Pro Ala Val Gly Ile Pro Ala
    1400                1405                1410

Val Gly Ile Pro Ala Val Gly Ile Pro Ala Val Gly Ile Pro Ala
    1415                1420                1425

Val Gly Ile Pro Ala Val Gly Ile Pro Ala Val Gly Ile Pro Ala
    1430                1435                1440

Val Gly Ile Pro Ala Val Gly Ile Pro Ala Val Gly Ile Pro Ala
    1445                1450                1455

Val Gly Ile Pro Ala Val Gly Ile Pro Ala Val Gly Ile Pro Ala
    1460                1465                1470

Val Gly Ile Pro Ala Val Gly Ile Pro Ala Val Gly Ile Pro Ala
    1475                1480                1485

Val Gly Ile Pro Ala Val Gly Ile Pro Ala Val Gly Ile Pro Ala
    1490                1495                1500

Val Gly Ile Pro Ala Val Gly Ile Pro Ala Val Gly Ile Pro Ala
    1505                1510                1515

Val Gly Ile Pro Ala Val Gly Ile Pro Ala Val Gly Ile Pro Ala
    1520                1525                1530

Val Gly Ile Pro Ala Val Gly Ile Pro Ala Val Gly Ile Pro Ala
    1535                1540                1545

Val Gly Ile Pro Ala Val Gly Ile Pro Ala Val Gly Ile Pro Ala
    1550                1555                1560

Val Gly Ile Pro Ala Val Gly Ile Pro Ala Val Gly Ile Pro Ala
    1565                1570                1575

Val Gly Ile Pro Ala Val Gly Ile Pro Ala Val Gly Ile Pro Ala
    1580                1585                1590

Val Gly Ile Pro Ala Val Gly Ile Pro Ala Val Gly Ile Pro Ala
    1595                1600                1605

Val Gly Ile Pro Ala Val Gly Ile Pro Ala Val Gly Ile Pro Ala
    1610                1615                1620
```

Val Gly Ile Pro Ala Val Gly Ile Pro Ala Val Gly Ile Pro Ala
    1625                1630                1635

Val Gly Ile Pro Ala Val Gly Ile Pro Ala Val Gly Ile Pro Ala
    1640                1645                1650

Val Gly Ile Pro Ala Val Gly Ile Pro Ala Val Gly Ile Pro Ala
    1655                1660                1665

Val Gly Ile Pro Ala Val Gly Ile Pro Ala Val Gly Ile Pro Ala
    1670                1675                1680

Val Gly Ile Pro Ala Val Gly Ile Pro Ala Val Gly Ile Pro Ala
    1685                1690                1695

Val Gly Ile Pro Ala Val Gly Ile Pro Ala Val Gly Ile Pro Ala
    1700                1705                1710

Val Gly Ile Pro Ala Val Gly Ile Pro Ala Val Gly Ile Pro Ala
    1715                1720                1725

Val Gly Ile Pro Ala Val Gly Ile Pro Ala Val Gly Ile Pro Ala
    1730                1735                1740

Val Gly Ile Pro Ala Val Gly Ile Pro Ala Val Gly Ile Pro Ala
    1745                1750                1755

Val Gly Ile Pro Ala Val Gly Ile Pro Ala Val Gly Ile Pro Ala
    1760                1765                1770

Val Gly Ile Pro Ala Val Gly Ile Pro Ala Val Gly Ile Pro Ala
    1775                1780                1785

Val Gly Ile Pro Ala Val Gly Ile Pro Ala Val Gly Ile Pro Ala
    1790                1795                1800

Val Gly Ile Pro Ala Val Gly Ile Pro Ala Val Gly Ile Pro Ala
    1805                1810                1815

Val Gly Ile Pro Ala Val Gly Ile Pro Ala Val Gly Ile Pro Ala
    1820                1825                1830

Val Gly Ile Pro Ala Val Gly Ile Pro Ala Val Gly Ile Pro Ala
    1835                1840                1845

Val Gly Ile Pro Ala Val Gly Ile Pro Ala Val Gly Ile Pro Ala
    1850                1855                1860

Val Gly Ile Pro Ala Val Gly Ile Pro Ala Val Gly Ile Pro Ala
    1865                1870                1875

Val Gly Ile Pro Ala Val Gly Ile Pro Ala Val Gly Ile Pro Ala
    1880                1885                1890

Val Gly Ile Pro Ala Val Gly Ile Pro Ala Val Gly Ile Pro Ala
    1895                1900                1905

Val Gly Ile Pro Ala Val Gly Ile Pro Ala Val Gly Ile Pro Ala
    1910                1915                1920

Val Gly Ile Pro Ala Val Gly Ile Pro Ala Val Gly Ile Pro Ala
    1925                1930                1935

Val Gly Ile Pro Ala Val Gly Ile Pro Ala Val Gly Ile Pro Ala
    1940                1945                1950

Val Gly Lys Lys
    1955

<210> SEQ ID NO 34
<211> LENGTH: 1249
<212> TYPE: PRT
<213> ORGANISM: Artificial Sequence
<220> FEATURE:
<223> OTHER INFORMATION: synthetic construct

<400> SEQUENCE: 34

-continued

```
Val Pro Ala Val Gly Lys Val Pro Ala Val Gly Ile Pro Ala Val Gly
 1               5                  10                  15

Ile Pro Ala Val Gly Ile Pro Ala Val Gly Ile Pro Ala Val Gly Ile
             20                  25                  30

Pro Ala Val Gly Ile Pro Ala Val Gly Ile Pro Ala Val Gly Ile Pro
         35                  40                  45

Ala Val Gly Ile Pro Ala Val Gly Ile Pro Ala Val Gly Ile Pro Ala
     50                  55                  60

Val Gly Ile Pro Ala Val Gly Ile Pro Ala Val Gly Ile Pro Ala Val
 65                  70                  75                  80

Gly Ile Pro Ala Val Gly Ile Pro Ala Val Gly Ile Pro Ala Val Gly
                 85                  90                  95

Ile Pro Ala Val Gly Ile Pro Ala Val Gly Ile Pro Ala Val Gly Ile
            100                 105                 110

Pro Ala Val Gly Ile Pro Ala Val Gly Ile Pro Ala Val Gly Ile Pro
        115                 120                 125

Ala Val Gly Ile Pro Ala Val Gly Ile Pro Ala Val Gly Ile Pro Ala
    130                 135                 140

Val Gly Ile Pro Ala Val Gly Ile Pro Ala Val Gly Ile Pro Ala Val
145                 150                 155                 160

Gly Ile Pro Ala Val Gly Ile Pro Ala Val Gly Ile Pro Ala Val Gly
                165                 170                 175

Ile Pro Ala Val Gly Ile Pro Ala Val Gly Ile Pro Ala Val Gly Ile
            180                 185                 190

Pro Ala Val Gly Ile Pro Ala Val Gly Ile Pro Ala Val Gly Ile Pro
        195                 200                 205

Ala Val Gly Ile Pro Ala Val Gly Ile Pro Ala Val Gly Ile Pro Ala
    210                 215                 220

Val Gly Ile Pro Ala Val Gly Ile Pro Ala Val Gly Ile Pro Ala Val
225                 230                 235                 240

Gly Ile Pro Ala Val Gly Ile Pro Ala Val Gly Ile Pro Ala Val Gly
                245                 250                 255

Ile Pro Ala Val Gly Ile Pro Ala Val Gly Ile Pro Ala Val Gly Ile
            260                 265                 270

Pro Ala Val Gly Ile Pro Ala Val Gly Ile Pro Ala Val Gly Ile Pro
        275                 280                 285

Ala Val Gly Ile Pro Ala Val Gly Ile Pro Ala Val Gly Ile Pro Ala
    290                 295                 300

Val Gly Ile Pro Ala Val Gly Ile Pro Ala Val Gly Ile Pro Ala Val
305                 310                 315                 320

Gly Ile Pro Ala Val Gly Ile Pro Ala Val Gly Ile Pro Ala Val Gly
                325                 330                 335

Ile Pro Ala Val Gly Ile Pro Ala Val Gly Ile Pro Ala Val Gly Ile
            340                 345                 350

Pro Ala Val Gly Ile Pro Ala Val Gly Ile Pro Ala Val Gly Ile Pro
        355                 360                 365

Ala Val Gly Ile Pro Ala Val Gly Ile Pro Ala Val Gly Ile Pro Ala
    370                 375                 380

Val Gly Ile Pro Ala Val Gly Ile Pro Ala Val Gly Ile Pro Ala Val
385                 390                 395                 400

Gly Ile Pro Ala Val Gly Ile Pro Ala Val Gly Ile Pro Ala Val Gly
                405                 410                 415

Ile Pro Ala Val Gly Lys Ala Ala Lys Val Pro Gly Ala Gly Val Pro
```

```
                420                 425                 430
Gly Ile Gly Val Pro Gly Ile Gly Val Pro Gly Ile Gly Val Pro Gly
            435                 440                 445
Ile Gly Val Pro Gly Ile Gly Val Pro Gly Ile Gly Val Pro Gly Ile
            450                 455                 460
Gly Val Pro Gly Ile Gly Val Pro Gly Ile Gly Val Pro Gly Ile Gly
465                 470                 475                 480
Val Pro Gly Ile Gly Val Pro Gly Ile Gly Val Pro Gly Ile Gly Val
                485                 490                 495
Pro Gly Ile Gly Val Pro Gly Ile Gly Val Pro Gly Ile Gly Val Pro
            500                 505                 510
Gly Ile Gly Val Pro Gly Ile Gly Val Pro Gly Ile Gly Val Pro Gly
            515                 520                 525
Ile Gly Val Pro Gly Ile Gly Val Pro Gly Ile Gly Val Pro Gly Ile
            530                 535                 540
Gly Val Pro Gly Ile Gly Val Pro Gly Ile Gly Val Pro Gly Ile Gly
545                 550                 555                 560
Val Pro Gly Ile Gly Val Pro Gly Ile Gly Val Pro Gly Ile Gly Val
                565                 570                 575
Pro Gly Ile Gly Val Pro Gly Ile Gly Val Pro Gly Ile Gly Val Pro
            580                 585                 590
Gly Ile Gly Val Pro Gly Ile Gly Val Pro Gly Ile Gly Val Pro Gly
            595                 600                 605
Ile Gly Val Pro Gly Ile Gly Val Pro Gly Ile Gly Val Pro Gly Ile
            610                 615                 620
Gly Val Pro Gly Ile Gly Val Pro Gly Ile Gly Val Pro Gly Ile Gly
625                 630                 635                 640
Val Pro Gly Ile Gly Val Pro Gly Ile Gly Val Pro Gly Ile Gly Val
                645                 650                 655
Pro Gly Ile Gly Val Pro Gly Ile Gly Val Pro Gly Ile Gly Val Pro
            660                 665                 670
Gly Ile Gly Val Pro Gly Ile Gly Val Pro Gly Ile Gly Val Pro Gly
            675                 680                 685
Ile Gly Val Pro Gly Ile Gly Val Pro Gly Ile Gly Val Pro Gly Ile
            690                 695                 700
Gly Val Pro Gly Ile Gly Val Pro Gly Ile Gly Val Pro Gly Ile Gly
705                 710                 715                 720
Val Pro Gly Ile Gly Val Pro Gly Ile Gly Val Pro Gly Ile Gly Val
                725                 730                 735
Pro Gly Ile Gly Val Pro Gly Ile Gly Val Pro Gly Ile Gly Val Pro
            740                 745                 750
Gly Ile Gly Val Pro Gly Ile Gly Val Pro Gly Ile Gly Val Pro Gly
            755                 760                 765
Ile Gly Val Pro Gly Ile Gly Val Pro Gly Ile Gly Val Pro Gly Ile
            770                 775                 780
Gly Val Pro Gly Ile Gly Val Pro Gly Ile Gly Val Pro Gly Ile Gly
785                 790                 795                 800
Val Pro Gly Ile Gly Val Pro Gly Ile Gly Val Pro Gly Ile Gly Val
                805                 810                 815
Pro Ala Val Gly Lys Ala Ala Lys Val Pro Gly Ala Gly Val Pro Ala
            820                 825                 830
Val Gly Ile Pro Ala Val Gly Ile Pro Ala Val Gly Ile Pro Ala Val
            835                 840                 845
```

Gly Ile Pro Ala Val Gly Ile Pro Ala Val Gly Ile Pro Ala Val Gly
         850                 855                 860

Ile Pro Ala Val Gly Ile Pro Ala Val Gly Ile Pro Ala Val Gly Ile
865                 870                 875                 880

Pro Ala Val Gly Ile Pro Ala Val Gly Ile Pro Ala Val Gly Ile Pro
             885                 890                 895

Ala Val Gly Ile Pro Ala Val Gly Ile Pro Ala Val Gly Ile Pro Ala
         900                 905                 910

Val Gly Ile Pro Ala Val Gly Ile Pro Ala Val Gly Ile Pro Ala Val
         915                 920                 925

Gly Ile Pro Ala Val Gly Ile Pro Ala Val Gly Ile Pro Ala Val Gly
         930                 935                 940

Ile Pro Ala Val Gly Ile Pro Ala Val Gly Ile Pro Ala Val Gly Ile
945                 950                 955                 960

Pro Ala Val Gly Ile Pro Ala Val Gly Ile Pro Ala Val Gly Ile Pro
             965                 970                 975

Ala Val Gly Ile Pro Ala Val Gly Ile Pro Ala Val Gly Ile Pro Ala
         980                 985                 990

Val Gly Ile Pro Ala Val Gly Ile  Pro Ala Val Gly Ile  Pro Ala Val
         995                 1000                1005

Gly Ile  Pro Ala Val Gly Ile  Pro Ala Val Gly Ile  Pro Ala Val
         1010                1015                1020

Gly Ile  Pro Ala Val Gly Ile  Pro Ala Val Gly Ile  Pro Ala Val
1025                1030                1035

Gly Ile  Pro Ala Val Gly Ile  Pro Ala Val Gly Ile  Pro Ala Val
1040                1045                1050

Gly Ile  Pro Ala Val Gly Ile  Pro Ala Val Gly Ile  Pro Ala Val
1055                1060                1065

Gly Ile  Pro Ala Val Gly Ile  Pro Ala Val Gly Ile  Pro Ala Val
1070                1075                1080

Gly Ile  Pro Ala Val Gly Ile  Pro Ala Val Gly Ile  Pro Ala Val
1085                1090                1095

Gly Ile  Pro Ala Val Gly Ile  Pro Ala Val Gly Ile  Pro Ala Val
1100                1105                1110

Gly Ile  Pro Ala Val Gly Ile  Pro Ala Val Gly Ile  Pro Ala Val
1115                1120                1125

Gly Ile  Pro Ala Val Gly Ile  Pro Ala Val Gly Ile  Pro Ala Val
1130                1135                1140

Gly Ile  Pro Ala Val Gly Ile  Pro Ala Val Gly Ile  Pro Ala Val
1145                1150                1155

Gly Ile  Pro Ala Val Gly Ile  Pro Ala Val Gly Ile  Pro Ala Val
1160                1165                1170

Gly Ile  Pro Ala Val Gly Ile  Pro Ala Val Gly Ile  Pro Ala Val
1175                1180                1185

Gly Ile  Pro Ala Val Gly Ile  Pro Ala Val Gly Ile  Pro Ala Val
1190                1195                1200

Gly Ile  Pro Ala Val Gly Ile  Pro Ala Val Gly Ile  Pro Ala Val
1205                1210                1215

Gly Ile  Pro Ala Val Gly Ile  Pro Ala Val Gly Ile  Pro Ala Val
1220                1225                1230

Gly Ile  Pro Ala Val Gly Val  Pro Ala Val Gly Lys  Ala Ala Lys
1235                1240                1245

Ala

<210> SEQ ID NO 35
<211> LENGTH: 411
<212> TYPE: PRT
<213> ORGANISM: Artificial Sequence
<220> FEATURE:
<223> OTHER INFORMATION: synthetic construct

<400> SEQUENCE: 35

```
Val Pro Ala Val Gly Lys Val Pro Ala Val Gly Ile Pro Ala Val Gly
1               5                   10                  15

Ile Pro Ala Val Gly Ile Pro Ala Val Gly Ile Pro Ala Val Gly Ile
            20                  25                  30

Pro Ala Val Gly Ile Pro Ala Val Gly Ile Pro Ala Val Gly Ile Pro
        35                  40                  45

Ala Val Gly Ile Pro Ala Val Gly Ile Pro Ala Val Gly Ile Pro Ala
    50                  55                  60

Val Gly Ile Pro Ala Val Gly Ile Pro Ala Val Gly Ile Pro Ala Val
65                  70                  75                  80

Gly Ile Pro Ala Val Gly Ile Pro Ala Val Gly Ile Pro Ala Val Gly
                85                  90                  95

Ile Pro Ala Val Gly Ile Pro Ala Val Gly Ile Pro Ala Val Gly Ile
            100                 105                 110

Pro Ala Val Gly Ile Pro Ala Val Gly Ile Pro Ala Val Gly Ile Pro
        115                 120                 125

Ala Val Gly Ile Pro Ala Val Gly Ile Pro Ala Val Gly Ile Pro Ala
    130                 135                 140

Val Gly Ile Pro Ala Val Gly Ile Pro Ala Val Gly Ile Pro Ala Val
145                 150                 155                 160

Gly Ile Pro Ala Val Gly Ile Pro Ala Val Gly Ile Pro Ala Val Gly
                165                 170                 175

Ile Pro Ala Val Gly Ile Pro Ala Val Gly Ile Pro Ala Val Gly Ile
            180                 185                 190

Pro Ala Val Gly Ile Pro Ala Val Gly Ile Pro Ala Val Gly Ile Pro
        195                 200                 205

Ala Val Gly Ile Pro Ala Val Gly Ile Pro Ala Val Gly Ile Pro Ala
    210                 215                 220

Val Gly Ile Pro Ala Val Gly Ile Pro Ala Val Gly Ile Pro Ala Val
225                 230                 235                 240

Gly Ile Pro Ala Val Gly Ile Pro Ala Val Gly Ile Pro Ala Val Gly
                245                 250                 255

Ile Pro Ala Val Gly Ile Pro Ala Val Gly Ile Pro Ala Val Gly Ile
            260                 265                 270

Pro Ala Val Gly Ile Pro Ala Val Gly Ile Pro Ala Val Gly Ile Pro
        275                 280                 285

Ala Val Gly Ile Pro Ala Val Gly Ile Pro Ala Val Gly Ile Pro Ala
    290                 295                 300

Val Gly Ile Pro Ala Val Gly Ile Pro Ala Val Gly Ile Pro Ala Val
305                 310                 315                 320

Gly Ile Pro Ala Val Gly Ile Pro Ala Val Gly Ile Pro Ala Val Gly
                325                 330                 335

Ile Pro Ala Val Gly Ile Pro Ala Val Gly Ile Pro Ala Val Gly Ile
            340                 345                 350

Pro Ala Val Gly Ile Pro Ala Val Gly Ile Pro Ala Val Gly Ile Pro
```

-continued

```
                355                 360                 365
Ala Val Gly Ile Pro Ala Val Gly Ile Pro Ala Val Gly Ile Pro Ala
            370                 375                 380
Val Gly Ile Pro Ala Val Gly Ile Pro Ala Val Gly Ile Pro Ala Val
385                 390                 395                 400
Gly Ile Pro Ala Val Gly Ile Pro Ala Val Gly
                405                 410

<210> SEQ ID NO 36
<211> LENGTH: 399
<212> TYPE: PRT
<213> ORGANISM: Artificial Sequence
<220> FEATURE:
<223> OTHER INFORMATION: synthetic construct

<400> SEQUENCE: 36

Ile Pro Ala Val Gly Ile Pro Ala Val Gly Lys Ala Ala Lys Val Pro
1               5                   10                  15
Gly Ala Gly Val Pro Gly Ile Gly Val Pro Gly Ile Gly Val Pro Gly
            20                  25                  30
Ile Gly Val Pro Gly Ile Gly Val Pro Gly Ile Gly Val Pro Gly Ile
        35                  40                  45
Gly Val Pro Gly Ile Gly Val Pro Gly Ile Gly Val Pro Gly Ile Gly
    50                  55                  60
Val Pro Gly Ile Gly Val Pro Gly Ile Gly Val Pro Gly Ile Gly Val
65                  70                  75                  80
Pro Gly Ile Gly Val Pro Gly Ile Gly Val Pro Gly Ile Gly Val Pro
                85                  90                  95
Gly Ile Gly Val Pro Gly Ile Gly Val Pro Gly Ile Gly Val Pro Gly
            100                 105                 110
Ile Gly Val Pro Gly Ile Gly Val Pro Gly Ile Gly Val Pro Gly Ile
        115                 120                 125
Gly Val Pro Gly Ile Gly Val Pro Gly Ile Gly Val Pro Gly Ile Gly
    130                 135                 140
Val Pro Gly Ile Gly Val Pro Gly Ile Gly Val Pro Gly Ile Gly Val
145                 150                 155                 160
Pro Gly Ile Gly Val Pro Gly Ile Gly Val Pro Gly Ile Gly Val Pro
                165                 170                 175
Gly Ile Gly Val Pro Gly Ile Gly Val Pro Gly Ile Gly Val Pro Gly
            180                 185                 190
Ile Gly Val Pro Gly Ile Gly Val Pro Gly Ile Gly Val Pro Gly Ile
        195                 200                 205
Gly Val Pro Gly Ile Gly Val Pro Gly Ile Gly Val Pro Gly Ile Gly
    210                 215                 220
Val Pro Gly Ile Gly Val Pro Gly Ile Gly Val Pro Gly Ile Gly Val
225                 230                 235                 240
Pro Gly Ile Gly Val Pro Gly Ile Gly Val Pro Gly Ile Gly Val Pro
                245                 250                 255
Gly Ile Gly Val Pro Gly Ile Gly Val Pro Gly Ile Gly Val Pro Gly
            260                 265                 270
Ile Gly Val Pro Gly Ile Gly Val Pro Gly Ile Gly Val Pro Gly Ile
        275                 280                 285
Gly Val Pro Gly Ile Gly Val Pro Gly Ile Gly Val Pro Gly Ile Gly
    290                 295                 300
Val Pro Gly Ile Gly Val Pro Gly Ile Gly Val Pro Gly Ile Gly Val
```

```
                305                 310                 315                 320
Pro Gly Ile Gly Val Pro Gly Ile Gly Val Pro Gly Ile Gly Val Pro
                325                 330                 335
Gly Ile Gly Val Pro Gly Ile Gly Val Pro Gly Ile Gly Val Pro Gly
                340                 345                 350
Ile Gly Val Pro Gly Ile Gly Val Pro Gly Ile Gly Val Pro Gly Ile
                355                 360                 365
Gly Val Pro Gly Ile Gly Val Pro Gly Ile Gly Val Pro Gly Ile Gly
                370                 375                 380
Val Pro Gly Ile Gly Val Pro Gly Ile Gly Val Pro Gly Ile Gly
385                 390                 395

<210> SEQ ID NO 37
<211> LENGTH: 10
<212> TYPE: PRT
<213> ORGANISM: Artificial Sequence
<220> FEATURE:
<223> OTHER INFORMATION: synthetic construct

<400> SEQUENCE: 37

Val Pro Gly Ile Gly Val Pro Ala Val Gly
1               5                   10

<210> SEQ ID NO 38
<211> LENGTH: 4
<212> TYPE: PRT
<213> ORGANISM: Artificial Sequence
<220> FEATURE:
<223> OTHER INFORMATION: synthetic construct

<400> SEQUENCE: 38

Lys Ala Ala Lys
1

<210> SEQ ID NO 39
<211> LENGTH: 10
<212> TYPE: PRT
<213> ORGANISM: Artificial Sequence
<220> FEATURE:
<223> OTHER INFORMATION: synthetic construct

<400> SEQUENCE: 39

Val Pro Gly Ala Gly Val Pro Ala Val Gly
1               5                   10

<210> SEQ ID NO 40
<211> LENGTH: 400
<212> TYPE: PRT
<213> ORGANISM: Artificial Sequence
<220> FEATURE:
<223> OTHER INFORMATION: synthetic construct

<400> SEQUENCE: 40

Ile Pro Ala Val Gly Ile Pro Ala Val Gly Ile Pro Ala Val Gly Ile
1               5                   10                  15
Pro Ala Val Gly Ile Pro Ala Val Gly Ile Pro Ala Val Gly Ile Pro
                20                  25                  30
Ala Val Gly Ile Pro Ala Val Gly Ile Pro Ala Val Gly Ile Pro Ala
                35                  40                  45
Val Gly Ile Pro Ala Val Gly Ile Pro Ala Val Gly Ile Pro Ala Val
                50                  55                  60
Gly Ile Pro Ala Val Gly Ile Pro Ala Val Gly Ile Pro Ala Val Gly
```

```
                65                  70                  75                  80
Ile Pro Ala Val Gly Ile Pro Ala Val Gly Ile Pro Ala Val Gly Ile
                    85                  90                  95
Pro Ala Val Gly Ile Pro Ala Val Gly Ile Pro Ala Val Gly Ile Pro
                100                 105                 110
Ala Val Gly Ile Pro Ala Val Gly Ile Pro Ala Val Gly Ile Pro Ala
                115                 120                 125
Val Gly Ile Pro Ala Val Gly Ile Pro Ala Val Gly Ile Pro Ala Val
            130                 135                 140
Gly Ile Pro Ala Val Gly Ile Pro Ala Val Gly Ile Pro Ala Val Gly
145                 150                 155                 160
Ile Pro Ala Val Gly Ile Pro Ala Val Gly Ile Pro Ala Val Gly Ile
                165                 170                 175
Pro Ala Val Gly Ile Pro Ala Val Gly Ile Pro Ala Val Gly Ile Pro
                180                 185                 190
Ala Val Gly Ile Pro Ala Val Gly Ile Pro Ala Val Gly Ile Pro Ala
                195                 200                 205
Val Gly Ile Pro Ala Val Gly Ile Pro Ala Val Gly Ile Pro Ala Val
            210                 215                 220
Gly Ile Pro Ala Val Gly Ile Pro Ala Val Gly Ile Pro Ala Val Gly
225                 230                 235                 240
Ile Pro Ala Val Gly Ile Pro Ala Val Gly Ile Pro Ala Val Gly Ile
                245                 250                 255
Pro Ala Val Gly Ile Pro Ala Val Gly Ile Pro Ala Val Gly Ile Pro
                260                 265                 270
Ala Val Gly Ile Pro Ala Val Gly Ile Pro Ala Val Gly Ile Pro Ala
                275                 280                 285
Val Gly Ile Pro Ala Val Gly Ile Pro Ala Val Gly Ile Pro Ala Val
            290                 295                 300
Gly Ile Pro Ala Val Gly Ile Pro Ala Val Gly Ile Pro Ala Val Gly
305                 310                 315                 320
Ile Pro Ala Val Gly Ile Pro Ala Val Gly Ile Pro Ala Val Gly Ile
                325                 330                 335
Pro Ala Val Gly Ile Pro Ala Val Gly Ile Pro Ala Val Gly Ile Pro
                340                 345                 350
Ala Val Gly Ile Pro Ala Val Gly Ile Pro Ala Val Gly Ile Pro Ala
                355                 360                 365
Val Gly Ile Pro Ala Val Gly Ile Pro Ala Val Gly Ile Pro Ala Val
            370                 375                 380
Gly Ile Pro Ala Val Gly Ile Pro Ala Val Gly Ile Pro Ala Val Gly
385                 390                 395                 400

<210> SEQ ID NO 41
<211> LENGTH: 15
<212> TYPE: PRT
<213> ORGANISM: Artificial Sequence
<220> FEATURE:
<223> OTHER INFORMATION: synthetic construct

<400> SEQUENCE: 41

Ile Pro Ala Val Gly Val Pro Ala Val Gly Lys Ala Ala Lys Ala
1               5                   10                  15

<210> SEQ ID NO 42
<211> LENGTH: 3747
<212> TYPE: DNA
```

<213> ORGANISM: Artificial Sequence
<220> FEATURE:
<223> OTHER INFORMATION: synthetic construct

<400> SEQUENCE: 42

```
gttccagctg ttggtaaggt tccagctgtt ggtattccgg ctgttggtat cccagctgtt    60
ggtatcccag ctgttggcat tccggctgta ggtatcccgg cagtgggcat tccggctgtt   120
ggtatcccag ctgttggtat cccagctgtt ggcattccgg ctgtaggtat cccggcagtg   180
ggcattccgg ctgttggtat cccagctgtt ggtatcccag ctgttggcat tccggctgta   240
ggtatcccgg cagtgggcat tccggctgtt ggtatcccag ctgttggtat cccagctgtt   300
ggcattccgg ctgtaggtat cccggcagtg ggcattccgg ctgttggtat cccagctgtt   360
ggtatcccag ctgttggcat tccggctgta ggtatcccgg cagtgggcat tccggctgtt   420
ggtatcccag ctgttggtat cccagctgtt ggcattccgg ctgtaggtat cccggcagtg   480
ggcattccgg ctgttggtat cccagctgtt ggtatcccag ctgttggcat tccggctgta   540
ggtatcccgg cagtgggcat tccggctgtt ggtatcccag ctgttggtat cccagctgtt   600
ggcattccgg ctgtaggtat cccggcagtg ggcattccgg ctgttggtat cccagctgtt   660
ggtatcccag ctgttggcat tccggctgta ggtatcccgg cagtgggcat tccggctgtt   720
ggtatcccag ctgttggtat cccagctgtt ggcattccgg ctgtaggtat cccggcagtg   780
ggcattccgg ctgttggtat cccagctgtt ggtatcccag ctgttggcat tccggctgta   840
ggtatcccgg cagtgggcat tccggctgtt ggtatcccag ctgttggtat cccagctgtt   900
ggcattccgg ctgtaggtat cccggcagtg ggcattccgg ctgttggtat cccagctgtt   960
ggtatcccag ctgttggcat tccggctgta ggtatcccgg cagtgggcat tccggctgtt  1020
ggtatcccag ctgttggtat cccagctgtt ggcattccgg ctgtaggtat cccggcagtg  1080
ggcattccgg ctgttggtat cccagctgtt ggtatcccag ctgttggcat tccggctgta  1140
ggtatcccgg cagtgggcat tccggctgtt ggtatcccag ctgttggtat cccagctgtt  1200
ggcattccgg ctgtaggtat cccggcagtg ggcattccgg ctgttggtat tccagctgtt  1260
ggtaaggcgg ccaaggttcc aggtgcaggc gttccaggta ttggtgtacc tggtattggc  1320
gttccgggta tcggtgtgcc aggcatcggt gtaccgggta ttggcgttcc aggcattggc  1380
gtacctggta ttggcgttcc gggtatcggt gtgccaggca tcggtgtacc gggtattggc  1440
gttccaggca ttggcgtacc tggtattggc gttccgggta tcggtgtgcc aggcatcggt  1500
gtaccgggta ttggcgttcc aggcattggc gtacctggta ttggcgttcc gggtatcggt  1560
gtgccaggca tcggtgtacc gggtattggc gttccaggca ttggcgtacc tggtattggc  1620
gttccgggta tcggtgtgcc aggcatcggt gtaccgggta ttggcgttcc aggcattggc  1680
gtacctggta ttggcgttcc gggtatcggt gtgccaggca tcggtgtacc gggtattggc  1740
gttccaggca ttggcgtacc tggtattggc gttccgggta tcggtgtgcc aggcatcggt  1800
gtaccgggta ttggcgttcc aggcattggc gtacctggta ttggcgttcc gggtatcggt  1860
gtgccaggca tcggtgtacc gggtattggc gttccaggca ttggcgtacc tggtattggc  1920
gttccgggta tcggtgtgcc aggcatcggt gtaccgggta ttggcgttcc aggcattggc  1980
gtacctggta ttggcgttcc gggtatcggt gtgccaggca tcggtgtacc gggtattggc  2040
gttccaggca ttggcgtacc tggtattggc gttccgggta tcggtgtgcc aggcatcggt  2100
gtaccgggta ttggcgttcc aggcattggc gtacctggta ttggcgttcc gggtatcggt  2160
gtgccaggca tcggtgtacc gggtattggc gttccaggca ttggcgtacc tggtattggc  2220
```

```
gttccgggta tcggtgtgcc aggcatcggt gtaccgggta ttggcgttcc aggcattggc    2280
gtacctggta ttggcgttcc gggtatcggt gtgccaggca tcggtgtacc gggtattggc    2340
gttccaggca ttggcgtacc tggtattggc gttccgggta tcggtgtgcc aggcatcggt    2400
gtaccgggta ttggcgttcc aggcattggc gtacctggta ttggtgttcc agctgttggt    2460
aaggcggcca aggttccagg tgcaggcgtt ccagctgttg gtattccggc tgttggtatc    2520
ccagctgttg gtatcccagc tgttggcatt ccggctgtag gtatcccggc agtgggcatt    2580
ccggctgttg gtatcccagc tgttggtatc ccagctgttg gcattccggc tgtaggtatc    2640
ccggcagtgg gcattccggc tgttggtatc ccagctgttg gtatcccagc tgttggcatt    2700
ccggctgtag gtatcccggc agtgggcatt ccggctgttg gtatcccagc tgttggtatc    2760
ccagctgttg gcattccggc tgtaggtatc ccggcagtgg gcattccggc tgttggtatc    2820
ccagctgttg gtatcccagc tgttggcatt ccggctgtag gtatcccggc agtgggcatt    2880
ccggctgttg gtatcccagc tgttggtatc ccagctgttg gcattccggc tgtaggtatc    2940
ccggcagtgg gcattccggc tgttggtatc ccagctgttg gtatcccagc tgttggcatt    3000
ccggctgtag gtatcccggc agtgggcatt ccggctgttg gtatcccagc tgttggtatc    3060
ccagctgttg gcattccggc tgtaggtatc ccggcagtgg gcattccggc tgttggtatc    3120
ccagctgttg gtatcccagc tgttggcatt ccggctgtag gtatcccggc agtgggcatt    3180
ccggctgttg gtatcccagc tgttggtatc ccagctgttg gcattccggc tgtaggtatc    3240
ccggcagtgg gcattccggc tgttggtatc ccagctgttg gtatcccagc tgttggcatt    3300
ccggctgtag gtatcccggc agtgggcatt ccggctgttg gtatcccagc tgttggtatc    3360
ccagctgttg gcattccggc tgtaggtatc ccggcagtgg gcattccggc tgttggtatc    3420
ccagctgttg gtatcccagc tgttggcatt ccggctgtag gtatcccggc agtgggcatt    3480
ccggctgttg gtatcccagc tgttggtatc ccagctgttg gcattccggc tgtaggtatc    3540
ccggcagtgg gcattccggc tgttggtatc ccagctgttg gtatcccagc tgttggcatt    3600
ccggctgtag gtatcccggc agtgggcatt ccggctgttg gtatcccagc tgttggtatc    3660
ccagctgttg gcattccggc tgtaggtatc ccggcagtgg gcattccggc tgttggtatt    3720
ccagctgttg gtaaggcggc caaggcg                                        3747
```

```
<210> SEQ ID NO 43
<211> LENGTH: 5
<212> TYPE: PRT
<213> ORGANISM: Artificial Sequence
<220> FEATURE:
<223> OTHER INFORMATION: synthetic construct

<400> SEQUENCE: 43

Val Pro Gly Ile Gly
1               5

<210> SEQ ID NO 44
<211> LENGTH: 378
<212> TYPE: PRT
<213> ORGANISM: Artificial Sequence
<220> FEATURE:
<223> OTHER INFORMATION: synthetic construct

<400> SEQUENCE: 44

Lys Val Pro Gly Ile Gly Val Pro Gly Ile Gly Val Pro Gly Ile Gly
1               5                   10                  15
```

Val Pro Gly Ile Gly Val Pro Gly Ile Gly Val Pro Gly Ile Gly Val
            20                  25                  30

Pro Gly Ile Gly Val Pro Gly Ile Gly Val Pro Gly Ile Gly Val Pro
        35                  40                  45

Gly Ile Gly Val Pro Gly Ile Gly Val Pro Gly Ile Gly Val Pro Gly
    50                  55                  60

Ile Gly Val Pro Gly Ile Gly Val Pro Gly Ile Gly Val Pro Gly Ile
65                  70                  75                  80

Gly Val Pro Gly Ile Gly Val Pro Gly Ile Gly Val Pro Gly Ile Gly
                85                  90                  95

Val Pro Gly Ile Gly Val Pro Gly Ile Gly Val Pro Gly Ile Gly Val
            100                 105                 110

Pro Gly Ile Gly Val Pro Gly Ile Gly Val Pro Gly Ile Gly Val Pro
        115                 120                 125

Gly Ile Gly Val Pro Gly Ile Gly Val Pro Gly Ile Gly Val Pro Gly
    130                 135                 140

Ile Gly Val Pro Gly Ile Gly Val Pro Gly Ile Gly Val Pro Gly Ile
145                 150                 155                 160

Gly Val Pro Gly Ile Gly Val Pro Gly Ile Gly Val Pro Gly Ile Gly
                165                 170                 175

Val Pro Gly Ile Gly Val Pro Gly Ile Gly Val Pro Gly Ile Gly Val
            180                 185                 190

Pro Gly Ile Gly Val Pro Gly Ile Gly Val Pro Gly Ile Gly Val Pro
        195                 200                 205

Gly Ile Gly Val Pro Gly Ile Gly Val Pro Gly Ile Gly Val Pro Gly
    210                 215                 220

Ile Gly Val Pro Gly Ile Gly Val Pro Gly Ile Gly Val Pro Gly Ile
225                 230                 235                 240

Gly Val Pro Gly Ile Gly Val Pro Gly Ile Gly Val Pro Gly Ile Gly
                245                 250                 255

Val Pro Gly Ile Gly Val Pro Gly Ile Gly Val Pro Gly Ile Gly Val
            260                 265                 270

Pro Gly Ile Gly Val Pro Gly Ile Gly Val Pro Gly Ile Gly Val Pro
        275                 280                 285

Gly Ile Gly Val Pro Gly Ile Gly Val Pro Gly Ile Gly Val Pro Gly
    290                 295                 300

Ile Gly Val Pro Gly Ile Gly Val Pro Gly Ile Gly Val Pro Gly Ile
305                 310                 315                 320

Gly Val Pro Gly Ile Gly Val Pro Gly Ile Gly Val Pro Gly Ile Gly
                325                 330                 335

Val Pro Gly Ile Gly Val Pro Gly Ile Gly Val Pro Gly Ile Gly Val
            340                 345                 350

Pro Gly Ile Gly Val Pro Gly Ile Gly Val Pro Gly Ile Gly Val Pro
        355                 360                 365

Gly Ile Gly Val Pro Gly Ile Gly Lys Lys
    370                 375

<210> SEQ ID NO 45
<211> LENGTH: 5
<212> TYPE: PRT
<213> ORGANISM: Artificial Sequence
<220> FEATURE:
<223> OTHER INFORMATION: synthetic construct

<400> SEQUENCE: 45

Ile Pro Ala Val Gly
1               5

<210> SEQ ID NO 46
<211> LENGTH: 403
<212> TYPE: PRT
<213> ORGANISM: Artificial Sequence
<220> FEATURE:
<223> OTHER INFORMATION: synthetic construct

<400> SEQUENCE: 46

Lys Ile Pro Ala Val Gly Ile Pro Ala Val Gly Ile Pro Ala Val Gly
1               5                   10                  15

Ile Pro Ala Val Gly Ile Pro Ala Val Gly Ile Pro Ala Val Gly Ile
            20                  25                  30

Pro Ala Val Gly Ile Pro Ala Val Gly Ile Pro Ala Val Gly Ile Pro
        35                  40                  45

Ala Val Gly Ile Pro Ala Val Gly Ile Pro Ala Val Gly Ile Pro Ala
    50                  55                  60

Val Gly Ile Pro Ala Val Gly Ile Pro Ala Val Gly Ile Pro Ala Val
65                  70                  75                  80

Gly Ile Pro Ala Val Gly Ile Pro Ala Val Gly Ile Pro Ala Val Gly
                85                  90                  95

Ile Pro Ala Val Gly Ile Pro Ala Val Gly Ile Pro Ala Val Gly Ile
            100                 105                 110

Pro Ala Val Gly Ile Pro Ala Val Gly Ile Pro Ala Val Gly Ile Pro
        115                 120                 125

Ala Val Gly Ile Pro Ala Val Gly Ile Pro Ala Val Gly Ile Pro Ala
    130                 135                 140

Val Gly Ile Pro Ala Val Gly Ile Pro Ala Val Gly Ile Pro Ala Val
145                 150                 155                 160

Gly Ile Pro Ala Val Gly Ile Pro Ala Val Gly Ile Pro Ala Val Gly
                165                 170                 175

Ile Pro Ala Val Gly Ile Pro Ala Val Gly Ile Pro Ala Val Gly Ile
            180                 185                 190

Pro Ala Val Gly Ile Pro Ala Val Gly Ile Pro Ala Val Gly Ile Pro
        195                 200                 205

Ala Val Gly Ile Pro Ala Val Gly Ile Pro Ala Val Gly Ile Pro Ala
    210                 215                 220

Val Gly Ile Pro Ala Val Gly Ile Pro Ala Val Gly Ile Pro Ala Val
225                 230                 235                 240

Gly Ile Pro Ala Val Gly Ile Pro Ala Val Gly Ile Pro Ala Val Gly
                245                 250                 255

Ile Pro Ala Val Gly Ile Pro Ala Val Gly Ile Pro Ala Val Gly Ile
            260                 265                 270

Pro Ala Val Gly Ile Pro Ala Val Gly Ile Pro Ala Val Gly Ile Pro
        275                 280                 285

Ala Val Gly Ile Pro Ala Val Gly Ile Pro Ala Val Gly Ile Pro Ala
    290                 295                 300

Val Gly Ile Pro Ala Val Gly Ile Pro Ala Val Gly Ile Pro Ala Val
305                 310                 315                 320

Gly Ile Pro Ala Val Gly Ile Pro Ala Val Gly Ile Pro Ala Val Gly
                325                 330                 335

Ile Pro Ala Val Gly Ile Pro Ala Val Gly Ile Pro Ala Val Gly Ile
            340                 345                 350

```
Pro Ala Val Gly Ile Pro Ala Val Gly Ile Pro
        355                 360                 365

Ala Val Gly Ile Pro Ala Val Gly Ile Pro Ala Val Gly Ile Pro Ala
        370                 375                 380

Val Gly Ile Pro Ala Val Gly Ile Pro Ala Val Gly Ile Pro Ala Val
385                 390                 395                 400

Gly Lys Lys

<210> SEQ ID NO 47
<211> LENGTH: 1181
<212> TYPE: PRT
<213> ORGANISM: Artificial Sequence
<220> FEATURE:
<223> OTHER INFORMATION: synthetic construct

<400> SEQUENCE: 47

Ile Pro Ala Val Gly Ile Pro Ala Val Gly Ile Pro Ala Val Gly Ile
1               5                   10                  15

Pro Ala Val Gly Ile Pro Ala Val Gly Ile Pro Ala Val Gly Ile Pro
            20                  25                  30

Ala Val Gly Ile Pro Ala Val Gly Ile Pro Ala Val Gly Ile Pro Ala
        35                  40                  45

Val Gly Ile Pro Ala Val Gly Ile Pro Ala Val Gly Ile Pro Ala Val
    50                  55                  60

Gly Ile Pro Ala Val Gly Ile Pro Ala Val Gly Ile Pro Ala Val Gly
65                  70                  75                  80

Ile Pro Ala Val Gly Ile Pro Ala Val Gly Ile Pro Ala Val Gly Ile
                85                  90                  95

Pro Ala Val Gly Ile Pro Ala Val Gly Ile Pro Ala Val Gly Ile Pro
            100                 105                 110

Ala Val Gly Ile Pro Ala Val Gly Ile Pro Ala Val Gly Ile Pro Ala
        115                 120                 125

Val Gly Ile Pro Ala Val Gly Ile Pro Ala Val Gly Ile Pro Ala Val
    130                 135                 140

Gly Ile Pro Ala Val Gly Ile Pro Ala Val Gly Ile Pro Ala Val Gly
145                 150                 155                 160

Ile Pro Ala Val Gly Ile Pro Ala Val Gly Ile Pro Ala Val Gly Ile
                165                 170                 175

Pro Ala Val Gly Ile Pro Ala Val Gly Ile Pro Ala Val Gly Ile Pro
            180                 185                 190

Ala Val Gly Ile Pro Ala Val Gly Ile Pro Ala Val Gly Ile Pro Ala
        195                 200                 205

Val Gly Ile Pro Ala Val Gly Ile Pro Ala Val Gly Ile Pro Ala Val
    210                 215                 220

Gly Ile Pro Ala Val Gly Ile Pro Ala Val Gly Ile Pro Ala Val Gly
225                 230                 235                 240

Ile Pro Ala Val Gly Ile Pro Ala Val Gly Ile Pro Ala Val Gly Ile
                245                 250                 255

Pro Ala Val Gly Ile Pro Ala Val Gly Ile Pro Ala Val Gly Ile Pro
            260                 265                 270

Ala Val Gly Ile Pro Ala Val Gly Ile Pro Ala Val Gly Ile Pro Ala
        275                 280                 285

Val Gly Ile Pro Ala Val Gly Ile Pro Ala Val Gly Ile Pro Ala Val
    290                 295                 300

Gly Ile Pro Ala Val Gly Ile Pro Ala Val Gly Ile Pro Ala Val Gly
```

```
                 305                 310                 315                 320
        Ile Pro Ala Val Gly Ile Pro Ala Val Gly Ile Pro Ala Val Gly Ile
                         325                 330                 335

Pro Ala Val Gly Ile Pro Ala Val Gly Ile Pro Ala Val Gly Ile Pro
                         340                 345                 350

Ala Val Gly Ile Pro Ala Val Gly Ile Pro Ala Val Gly Ile Pro Ala
                         355                 360                 365

Val Gly Ile Pro Ala Val Gly Ile Pro Ala Val Gly Ile Pro Ala Val
                370                 375                 380

Gly Ile Pro Ala Val Gly Ile Pro Ala Val Gly Ile Pro Ala Val Gly
        385                 390                 395                 400

Lys Lys Val Pro Gly Ile Gly Val Pro Gly Ile Gly Val Pro Gly Ile
                         405                 410                 415

Gly Val Pro Gly Ile Gly Val Pro Gly Ile Gly Val Pro Gly Ile Gly
                         420                 425                 430

Val Pro Gly Ile Gly Val Pro Gly Ile Gly Val Pro Gly Ile Gly Val
                435                 440                 445

Pro Gly Ile Gly Val Pro Gly Ile Gly Val Pro Gly Ile Gly Val Pro
                450                 455                 460

Gly Ile Gly Val Pro Gly Ile Gly Val Pro Gly Ile Gly Val Pro Gly
        465                 470                 475                 480

Ile Gly Val Pro Gly Ile Gly Val Pro Gly Ile Gly Val Pro Gly Ile
                         485                 490                 495

Gly Val Pro Gly Ile Gly Val Pro Gly Ile Gly Val Pro Gly Ile Gly
                         500                 505                 510

Val Pro Gly Ile Gly Val Pro Gly Ile Gly Val Pro Gly Ile Gly Val
                         515                 520                 525

Pro Gly Ile Gly Val Pro Gly Ile Gly Val Pro Gly Ile Gly Val Pro
                530                 535                 540

Gly Ile Gly Val Pro Gly Ile Gly Val Pro Gly Ile Gly Val Pro Gly
        545                 550                 555                 560

Ile Gly Val Pro Gly Ile Gly Val Pro Gly Ile Gly Val Pro Gly Ile
                         565                 570                 575

Gly Val Pro Gly Ile Gly Val Pro Gly Ile Gly Val Pro Gly Ile Gly
                         580                 585                 590

Val Pro Gly Ile Gly Val Pro Gly Ile Gly Val Pro Gly Ile Gly Val
                         595                 600                 605

Pro Gly Ile Gly Val Pro Gly Ile Gly Val Pro Gly Ile Gly Val Pro
                610                 615                 620

Gly Ile Gly Val Pro Gly Ile Gly Val Pro Gly Ile Gly Val Pro Gly
        625                 630                 635                 640

Ile Gly Val Pro Gly Ile Gly Val Pro Gly Ile Gly Val Pro Gly Ile
                         645                 650                 655

Gly Val Pro Gly Ile Gly Val Pro Gly Ile Gly Val Pro Gly Ile Gly
                         660                 665                 670

Val Pro Gly Ile Gly Val Pro Gly Ile Gly Val Pro Gly Ile Gly Val
                         675                 680                 685

Pro Gly Ile Gly Val Pro Gly Ile Gly Val Pro Gly Ile Gly Val Pro
                690                 695                 700

Gly Ile Gly Val Pro Gly Ile Gly Val Pro Gly Ile Gly Val Pro Gly
        705                 710                 715                 720

Ile Gly Val Pro Gly Ile Gly Val Pro Gly Ile Gly Val Pro Gly Ile
                         725                 730                 735
```

-continued

Gly Val Pro Gly Ile Gly Val Pro Gly Ile Gly Val Pro Gly Ile Gly
             740                 745                 750

Val Pro Gly Ile Gly Val Pro Gly Ile Gly Val Pro Gly Ile Gly Val
             755                 760                 765

Pro Gly Ile Gly Val Pro Gly Ile Gly Lys Lys Ile Pro Ala Val Gly
             770                 775                 780

Ile Pro Ala Val Gly Pro Ala Val Gly Pro Ala Val Gly Pro Ala Val Gly Ile
785                 790                 795                 800

Pro Ala Val Gly Ile Pro Ala Val Gly Ile Pro Ala Val Gly Ile Pro
             805                 810                 815

Ala Val Gly Ile Pro Ala Val Gly Ile Pro Ala Val Gly Ile Pro Ala
             820                 825                 830

Val Gly Ile Pro Ala Val Gly Ile Pro Ala Val Gly Ile Pro Ala Val
             835                 840                 845

Gly Ile Pro Ala Val Gly Ile Pro Ala Val Gly Ile Pro Ala Val Gly
             850                 855                 860

Ile Pro Ala Val Gly Ile Pro Ala Val Gly Ile Pro Ala Val Gly Ile
865                 870                 875                 880

Pro Ala Val Gly Ile Pro Ala Val Gly Ile Pro Ala Val Gly Ile Pro
             885                 890                 895

Ala Val Gly Ile Pro Ala Val Gly Ile Pro Ala Val Gly Ile Pro Ala
             900                 905                 910

Val Gly Ile Pro Ala Val Gly Ile Pro Ala Val Gly Ile Pro Ala Val
             915                 920                 925

Gly Ile Pro Ala Val Gly Ile Pro Ala Val Gly Ile Pro Ala Val Gly
             930                 935                 940

Ile Pro Ala Val Gly Ile Pro Ala Val Gly Ile Pro Ala Val Gly Ile
945                 950                 955                 960

Pro Ala Val Gly Ile Pro Ala Val Gly Ile Pro Ala Val Gly Ile Pro
             965                 970                 975

Ala Val Gly Ile Pro Ala Val Gly Ile Pro Ala Val Gly Ile Pro Ala
             980                 985                 990

Val Gly Ile Pro Ala Val Gly Ile Pro Ala Val Gly Ile Pro Ala Val
             995                1000                1005

Gly Ile Pro Ala Val Gly Ile Pro Ala Val Gly Ile Pro Ala Val
            1010                1015                1020

Gly Ile Pro Ala Val Gly Ile Pro Ala Val Gly Ile Pro Ala Val
            1025                1030                1035

Gly Ile Pro Ala Val Gly Ile Pro Ala Val Gly Ile Pro Ala Val
            1040                1045                1050

Gly Ile Pro Ala Val Gly Ile Pro Ala Val Gly Ile Pro Ala Val
            1055                1060                1065

Gly Ile Pro Ala Val Gly Ile Pro Ala Val Gly Ile Pro Ala Val
            1070                1075                1080

Gly Ile Pro Ala Val Gly Ile Pro Ala Val Gly Ile Pro Ala Val
            1085                1090                1095

Gly Ile Pro Ala Val Gly Ile Pro Ala Val Gly Ile Pro Ala Val
            1100                1105                1110

Gly Ile Pro Ala Val Gly Ile Pro Ala Val Gly Ile Pro Ala Val
            1115                1120                1125

Gly Ile Pro Ala Val Gly Ile Pro Ala Val Gly Ile Pro Ala Val
            1130                1135                1140

```
Gly Ile  Pro Ala Val Gly Ile  Pro Ala Val Gly Ile  Pro Ala Val
    1145                 1150                 1155

Gly Ile  Pro Ala Val Gly Ile  Pro Ala Val Gly Ile  Pro Ala Val
    1160                 1165                 1170

Gly Ile  Pro Ala Val Gly Lys  Lys
    1175                 1180

<210> SEQ ID NO 48
<211> LENGTH: 781
<212> TYPE: PRT
<213> ORGANISM: Artificial Sequence
<220> FEATURE:
<223> OTHER INFORMATION: synthetic construct

<400> SEQUENCE: 48

Lys Ile  Pro Ala Val Gly Ile  Pro Ala Val Gly Ile  Pro Ala Val Gly
1                 5                  10                  15

Ile Pro  Ala Val Gly Ile  Pro Ala Val Gly Ile  Pro Ala Val Gly Ile
             20                  25                  30

Pro Ala  Val Gly Ile  Pro Ala Val Gly Ile  Pro Ala Val Gly Ile  Pro
         35                  40                  45

Ala Val  Gly Ile Pro Ala  Val Gly Ile Pro Ala  Val Gly Ile Pro Ala
     50                   55                   60

Val Gly Ile Pro Ala Val Gly Ile Pro Ala Val Gly Ile Pro Ala Val
65                   70                   75                   80

Gly Ile  Pro Ala Val Gly Ile  Pro Ala Val Gly Ile  Pro Ala Val Gly
                 85                   90                   95

Ile Pro  Ala Val Gly Ile  Pro Ala Val Gly Ile  Pro Ala Val Gly Ile
             100                 105                 110

Pro Ala  Val Gly Ile  Pro Ala Val Gly Ile  Pro Ala Val Gly Ile  Pro
         115                 120                 125

Ala Val  Gly Ile Pro Ala  Val Gly Ile Pro Ala  Val Gly Ile Pro Ala
     130                  135                  140

Val Gly Ile Pro Ala Val Gly Ile Pro Ala Val Gly Ile Pro Ala Val
145                 150                 155                 160

Gly Ile  Pro Ala Val Gly Ile  Pro Ala Val Gly Ile  Pro Ala Val Gly
                 165                 170                 175

Ile Pro  Ala Val Gly Ile  Pro Ala Val Gly Ile  Pro Ala Val Gly Ile
             180                 185                 190

Pro Ala  Val Gly Ile  Pro Ala Val Gly Ile  Pro Ala Val Gly Ile  Pro
         195                 200                 205

Ala Val  Gly Ile Pro Ala  Val Gly Ile Pro Ala  Val Gly Ile Pro Ala
     210                  215                  220

Val Gly Ile Pro Ala Val Gly Ile Pro Ala Val Gly Ile Pro Ala Val
225                 230                 235                 240

Gly Ile  Pro Ala Val Gly Ile  Pro Ala Val Gly Ile  Pro Ala Val Gly
                 245                 250                 255

Ile Pro  Ala Val Gly Ile  Pro Ala Val Gly Ile  Pro Ala Val Gly Ile
             260                 265                 270

Pro Ala  Val Gly Ile  Pro Ala Val Gly Ile  Pro Ala Val Gly Ile  Pro
         275                 280                 285

Ala Val  Gly Ile Pro Ala  Val Gly Ile Pro Ala  Val Gly Ile Pro Ala
     290                  295                  300

Val Gly Ile Pro Ala Val Gly Ile Pro Ala Val Gly Ile Pro Ala Val
305                 310                 315                 320
```

```
Gly Ile Pro Ala Val Gly Ile Pro Ala Val Gly Ile Pro Ala Val Gly
                325                 330                 335

Ile Pro Ala Val Gly Ile Pro Ala Val Gly Ile Pro Ala Val Gly Ile
            340                 345                 350

Pro Ala Val Gly Ile Pro Ala Val Gly Ile Pro Ala Val Gly Ile Pro
        355                 360                 365

Ala Val Gly Ile Pro Ala Val Gly Ile Pro Ala Val Gly Ile Pro Ala
    370                 375                 380

Val Gly Ile Pro Ala Val Gly Ile Pro Ala Val Gly Ile Pro Ala Val
385                 390                 395                 400

Gly Lys Lys Val Pro Gly Ile Gly Val Pro Gly Ile Gly Val Pro
                405                 410                 415

Gly Ile Gly Val Pro Gly Ile Gly Val Pro Gly Ile Gly Val Pro Gly
            420                 425                 430

Ile Gly Val Pro Gly Ile Gly Val Pro Gly Ile Gly Val Pro Gly Ile
        435                 440                 445

Gly Val Pro Gly Ile Gly Val Pro Gly Ile Gly Val Pro Gly Ile Gly
    450                 455                 460

Val Pro Gly Ile Gly Val Pro Gly Ile Gly Val Pro Gly Ile Gly Val
465                 470                 475                 480

Pro Gly Ile Gly Val Pro Gly Ile Gly Val Pro Gly Ile Gly Val Pro
                485                 490                 495

Gly Ile Gly Val Pro Gly Ile Gly Val Pro Gly Ile Gly Val Pro Gly
            500                 505                 510

Ile Gly Val Pro Gly Ile Gly Val Pro Gly Ile Gly Val Pro Gly Ile
        515                 520                 525

Gly Val Pro Gly Ile Gly Val Pro Gly Ile Gly Val Pro Gly Ile Gly
    530                 535                 540

Val Pro Gly Ile Gly Val Pro Gly Ile Gly Val Pro Gly Ile Gly Val
545                 550                 555                 560

Pro Gly Ile Gly Val Pro Gly Ile Gly Val Pro Gly Ile Gly Val Pro
                565                 570                 575

Gly Ile Gly Val Pro Gly Ile Gly Val Pro Gly Ile Gly Val Pro Gly
            580                 585                 590

Ile Gly Val Pro Gly Ile Gly Val Pro Gly Ile Gly Val Pro Gly Ile
        595                 600                 605

Gly Val Pro Gly Ile Gly Val Pro Gly Ile Gly Val Pro Gly Ile Gly
    610                 615                 620

Val Pro Gly Ile Gly Val Pro Gly Ile Gly Val Pro Gly Ile Gly Val
625                 630                 635                 640

Pro Gly Ile Gly Val Pro Gly Ile Gly Val Pro Gly Ile Gly Val Pro
                645                 650                 655

Gly Ile Gly Val Pro Gly Ile Gly Val Pro Gly Ile Gly Val Pro Gly
            660                 665                 670

Ile Gly Val Pro Gly Ile Gly Val Pro Gly Ile Gly Val Pro Gly Ile
        675                 680                 685

Gly Val Pro Gly Ile Gly Val Pro Gly Ile Gly Val Pro Gly Ile Gly
    690                 695                 700

Val Pro Gly Ile Gly Val Pro Gly Ile Gly Val Pro Gly Ile Gly Val
705                 710                 715                 720

Pro Gly Ile Gly Val Pro Gly Ile Gly Val Pro Gly Ile Gly Val Pro
                725                 730                 735

Gly Ile Gly Val Pro Gly Ile Gly Val Pro Gly Ile Gly Val Pro Gly
```

```
                    740                 745                 750
Ile Gly Val Pro Gly Ile Gly Val Pro Gly Ile Gly Val Pro Gly Ile
            755                 760                 765
Gly Val Pro Gly Ile Gly Val Pro Gly Ile Gly Lys Lys
        770                 775                 780

<210> SEQ ID NO 49
<211> LENGTH: 1584
<212> TYPE: PRT
<213> ORGANISM: Artificial Sequence
<220> FEATURE:
<223> OTHER INFORMATION: synthetic construct

<400> SEQUENCE: 49

Lys Ile Pro Ala Val Gly Ile Pro Ala Val Gly Ile Pro Ala Val Gly
1               5                   10                  15

Ile Pro Ala Val Gly Ile Pro Ala Val Gly Ile Pro Ala Val Gly Ile
            20                  25                  30

Pro Ala Val Gly Ile Pro Ala Val Gly Ile Pro Ala Val Gly Ile Pro
        35                  40                  45

Ala Val Gly Ile Pro Ala Val Gly Ile Pro Ala Val Gly Ile Pro Ala
    50                  55                  60

Val Gly Ile Pro Ala Val Gly Ile Pro Ala Val Gly Ile Pro Ala Val
65                  70                  75                  80

Gly Ile Pro Ala Val Gly Ile Pro Ala Val Gly Ile Pro Ala Val Gly
                85                  90                  95

Ile Pro Ala Val Gly Ile Pro Ala Val Gly Ile Pro Ala Val Gly Ile
            100                 105                 110

Pro Ala Val Gly Ile Pro Ala Val Gly Ile Pro Ala Val Gly Ile Pro
        115                 120                 125

Ala Val Gly Ile Pro Ala Val Gly Ile Pro Ala Val Gly Ile Pro Ala
    130                 135                 140

Val Gly Ile Pro Ala Val Gly Ile Pro Ala Val Gly Ile Pro Ala Val
145                 150                 155                 160

Gly Ile Pro Ala Val Gly Ile Pro Ala Val Gly Ile Pro Ala Val Gly
                165                 170                 175

Ile Pro Ala Val Gly Ile Pro Ala Val Gly Ile Pro Ala Val Gly Ile
            180                 185                 190

Pro Ala Val Gly Ile Pro Ala Val Gly Ile Pro Ala Val Gly Ile Pro
        195                 200                 205

Ala Val Gly Ile Pro Ala Val Gly Ile Pro Ala Val Gly Ile Pro Ala
    210                 215                 220

Val Gly Ile Pro Ala Val Gly Ile Pro Ala Val Gly Ile Pro Ala Val
225                 230                 235                 240

Gly Ile Pro Ala Val Gly Ile Pro Ala Val Gly Ile Pro Ala Val Gly
                245                 250                 255

Ile Pro Ala Val Gly Ile Pro Ala Val Gly Ile Pro Ala Val Gly Ile
            260                 265                 270

Pro Ala Val Gly Ile Pro Ala Val Gly Ile Pro Ala Val Gly Ile Pro
        275                 280                 285

Ala Val Gly Ile Pro Ala Val Gly Ile Pro Ala Val Gly Ile Pro Ala
    290                 295                 300

Val Gly Ile Pro Ala Val Gly Ile Pro Ala Val Gly Ile Pro Ala Val
305                 310                 315                 320

Gly Ile Pro Ala Val Gly Ile Pro Ala Val Gly Ile Pro Ala Val Gly
```

```
                   325                 330                 335
Ile Pro Ala Val Gly Ile Pro Ala Val Gly Ile Pro Ala Val Gly Ile
                340                 345                 350
Pro Ala Val Gly Ile Pro Ala Val Gly Ile Pro Ala Val Gly Ile Pro
                355                 360                 365
Ala Val Gly Ile Pro Ala Val Gly Ile Pro Ala Val Gly Ile Pro Ala
            370                 375                 380
Val Gly Ile Pro Ala Val Gly Ile Pro Ala Val Gly Ile Pro Ala Val
385                 390                 395                 400
Gly Lys Lys Ile Pro Ala Val Gly Ile Pro Ala Val Gly Ile Pro Ala
                405                 410                 415
Val Gly Ile Pro Ala Val Gly Ile Pro Ala Val Gly Ile Pro Ala Val
                420                 425                 430
Gly Ile Pro Ala Val Gly Ile Pro Ala Val Gly Ile Pro Ala Val Gly
            435                 440                 445
Ile Pro Ala Val Gly Ile Pro Ala Val Gly Ile Pro Ala Val Gly Ile
            450                 455                 460
Pro Ala Val Gly Ile Pro Ala Val Gly Ile Pro Ala Val Gly Ile Pro
465                 470                 475                 480
Ala Val Gly Ile Pro Ala Val Gly Ile Pro Ala Val Gly Ile Pro Ala
                485                 490                 495
Val Gly Ile Pro Ala Val Gly Ile Pro Ala Val Gly Ile Pro Ala Val
                500                 505                 510
Gly Ile Pro Ala Val Gly Ile Pro Ala Val Gly Ile Pro Ala Val Gly
            515                 520                 525
Ile Pro Ala Val Gly Ile Pro Ala Val Gly Ile Pro Ala Val Gly Ile
            530                 535                 540
Pro Ala Val Gly Ile Pro Ala Val Gly Ile Pro Ala Val Gly Ile Pro
545                 550                 555                 560
Ala Val Gly Ile Pro Ala Val Gly Ile Pro Ala Val Gly Ile Pro Ala
                565                 570                 575
Val Gly Ile Pro Ala Val Gly Ile Pro Ala Val Gly Ile Pro Ala Val
                580                 585                 590
Gly Ile Pro Ala Val Gly Ile Pro Ala Val Gly Ile Pro Ala Val Gly
            595                 600                 605
Ile Pro Ala Val Gly Ile Pro Ala Val Gly Ile Pro Ala Val Gly Ile
            610                 615                 620
Pro Ala Val Gly Ile Pro Ala Val Gly Ile Pro Ala Val Gly Ile Pro
625                 630                 635                 640
Ala Val Gly Ile Pro Ala Val Gly Ile Pro Ala Val Gly Ile Pro Ala
                645                 650                 655
Val Gly Ile Pro Ala Val Gly Ile Pro Ala Val Gly Ile Pro Ala Val
                660                 665                 670
Gly Ile Pro Ala Val Gly Ile Pro Ala Val Gly Ile Pro Ala Val Gly
            675                 680                 685
Ile Pro Ala Val Gly Ile Pro Ala Val Gly Ile Pro Ala Val Gly Ile
            690                 695                 700
Pro Ala Val Gly Ile Pro Ala Val Gly Ile Pro Ala Val Gly Ile Pro
705                 710                 715                 720
Ala Val Gly Ile Pro Ala Val Gly Ile Pro Ala Val Gly Ile Pro Ala
                725                 730                 735
Val Gly Ile Pro Ala Val Gly Ile Pro Ala Val Gly Ile Pro Ala Val
                740                 745                 750
```

-continued

```
Gly Ile Pro Ala Val Gly Ile Pro Ala Val Gly
        755                 760                 765

Ile Pro Ala Val Gly Ile Pro Ala Val Gly Ile
        770                 775                 780

Pro Ala Val Gly Ile Pro Ala Val Gly Ile Pro
785                 790                 795                 800

Ala Val Gly Lys Lys Val Pro Gly Ile Gly Val
        805                 810                 815

Pro Gly Ile Gly Val Pro Gly Ile Gly Val Pro
        820                 825                 830

Gly Ile Gly Val Pro Gly Ile Gly Val Pro Gly
        835                 840                 845

Ile Gly Val Pro Gly Ile Gly Val Pro Gly Ile
        850                 855                 860

Gly Val Pro Gly Ile Gly Val Pro Gly Ile Gly
865                 870                 875                 880

Val Pro Gly Ile Gly Val Pro Gly Ile Gly Val
                885                 890                 895

Pro Gly Ile Gly Val Pro Gly Ile Gly Val Pro
        900                 905                 910

Gly Ile Gly Val Pro Gly Ile Gly Val Pro Gly
        915                 920                 925

Ile Gly Val Pro Gly Ile Gly Val Pro Gly Ile
        930                 935                 940

Gly Val Pro Gly Ile Gly Val Pro Gly Ile Gly
945                 950                 955                 960

Val Pro Gly Ile Gly Val Pro Gly Ile Gly Val
                965                 970                 975

Pro Gly Ile Gly Val Pro Gly Ile Gly Val Pro
        980                 985                 990

Gly Ile Gly Val Pro Gly Ile Gly  Val Pro Gly Ile Gly  Val Pro Gly
        995                 1000                 1005

Ile Gly  Val Pro Gly Ile Gly  Val Pro Gly Ile Gly  Val Pro Gly
        1010                 1015                 1020

Ile Gly  Val Pro Gly Ile Gly  Val Pro Gly Ile Gly  Val Pro Gly
        1025                 1030                 1035

Ile Gly  Val Pro Gly Ile Gly  Val Pro Gly Ile Gly  Val Pro Gly
        1040                 1045                 1050

Ile Gly  Val Pro Gly Ile Gly  Val Pro Gly Ile Gly  Val Pro Gly
        1055                 1060                 1065

Ile Gly  Val Pro Gly Ile Gly  Val Pro Gly Ile Gly  Val Pro Gly
        1070                 1075                 1080

Ile Gly  Val Pro Gly Ile Gly  Val Pro Gly Ile Gly  Val Pro Gly
        1085                 1090                 1095

Ile Gly  Val Pro Gly Ile Gly  Val Pro Gly Ile Gly  Val Pro Gly
        1100                 1105                 1110

Ile Gly  Val Pro Gly Ile Gly  Val Pro Gly Ile Gly  Val Pro Gly
        1115                 1120                 1125

Ile Gly  Val Pro Gly Ile Gly  Val Pro Gly Ile Gly  Val Pro Gly
        1130                 1135                 1140

Ile Gly  Val Pro Gly Ile Gly  Val Pro Gly Ile Gly  Val Pro Gly
        1145                 1150                 1155
```

```
Ile Gly Val Pro Gly Ile Gly Val Pro Gly Ile Gly Val Pro Gly
    1160                1165                1170

Ile Gly Val Pro Gly Ile Gly Lys Lys Ile Pro Ala Val Gly Ile
    1175                1180                1185

Pro Ala Val Gly Ile Pro Ala Val Gly Ile Pro Ala Val Gly Ile
    1190                1195                1200

Pro Ala Val Gly Ile Pro Ala Val Gly Ile Pro Ala Val Gly Ile
    1205                1210                1215

Pro Ala Val Gly Ile Pro Ala Val Gly Ile Pro Ala Val Gly Ile
    1220                1225                1230

Pro Ala Val Gly Ile Pro Ala Val Gly Ile Pro Ala Val Gly Ile
    1235                1240                1245

Pro Ala Val Gly Ile Pro Ala Val Gly Ile Pro Ala Val Gly Ile
    1250                1255                1260

Pro Ala Val Gly Ile Pro Ala Val Gly Ile Pro Ala Val Gly Ile
    1265                1270                1275

Pro Ala Val Gly Ile Pro Ala Val Gly Ile Pro Ala Val Gly Ile
    1280                1285                1290

Pro Ala Val Gly Ile Pro Ala Val Gly Ile Pro Ala Val Gly Ile
    1295                1300                1305

Pro Ala Val Gly Ile Pro Ala Val Gly Ile Pro Ala Val Gly Ile
    1310                1315                1320

Pro Ala Val Gly Ile Pro Ala Val Gly Ile Pro Ala Val Gly Ile
    1325                1330                1335

Pro Ala Val Gly Ile Pro Ala Val Gly Ile Pro Ala Val Gly Ile
    1340                1345                1350

Pro Ala Val Gly Ile Pro Ala Val Gly Ile Pro Ala Val Gly Ile
    1355                1360                1365

Pro Ala Val Gly Ile Pro Ala Val Gly Ile Pro Ala Val Gly Ile
    1370                1375                1380

Pro Ala Val Gly Ile Pro Ala Val Gly Ile Pro Ala Val Gly Ile
    1385                1390                1395

Pro Ala Val Gly Ile Pro Ala Val Gly Ile Pro Ala Val Gly Ile
    1400                1405                1410

Pro Ala Val Gly Ile Pro Ala Val Gly Ile Pro Ala Val Gly Ile
    1415                1420                1425

Pro Ala Val Gly Ile Pro Ala Val Gly Ile Pro Ala Val Gly Ile
    1430                1435                1440

Pro Ala Val Gly Ile Pro Ala Val Gly Ile Pro Ala Val Gly Ile
    1445                1450                1455

Pro Ala Val Gly Ile Pro Ala Val Gly Ile Pro Ala Val Gly Ile
    1460                1465                1470

Pro Ala Val Gly Ile Pro Ala Val Gly Ile Pro Ala Val Gly Ile
    1475                1480                1485

Pro Ala Val Gly Ile Pro Ala Val Gly Ile Pro Ala Val Gly Ile
    1490                1495                1500

Pro Ala Val Gly Ile Pro Ala Val Gly Ile Pro Ala Val Gly Ile
    1505                1510                1515

Pro Ala Val Gly Ile Pro Ala Val Gly Ile Pro Ala Val Gly Ile
    1520                1525                1530

Pro Ala Val Gly Ile Pro Ala Val Gly Ile Pro Ala Val Gly Ile
    1535                1540                1545

Pro Ala Val Gly Ile Pro Ala Val Gly Ile Pro Ala Val Gly Ile
```

-continued

```
                1550                1555                1560

Pro Ala  Val Gly Ile Pro Ala  Val Gly Ile Pro Ala  Val Gly Ile
            1565                1570                1575

Pro Ala  Val Gly Lys Lys
            1580

<210> SEQ ID NO 50
<211> LENGTH: 2030
<212> TYPE: PRT
<213> ORGANISM: Artificial Sequence
<220> FEATURE:
<223> OTHER INFORMATION: synthetic construct

<400> SEQUENCE: 50

Val Pro Ala Val Gly Ile Pro Ala Val Gly Ile Pro Ala Val Gly Ile
1               5                   10                  15

Pro Ala Val Gly Ile Pro Ala Val Gly Val Pro Ala Val Gly Ile Pro
                20                  25                  30

Ala Val Gly Ile Pro Ala Val Gly Ile Pro Ala Val Gly Ile Pro Ala
            35                  40                  45

Val Gly Val Pro Ala Val Gly Ile Pro Ala Val Gly Ile Pro Ala Val
50                  55                  60

Gly Ile Pro Ala Val Gly Ile Pro Ala Val Gly Val Pro Ala Val Gly
65                  70                  75                  80

Ile Pro Ala Val Gly Ile Pro Ala Val Gly Ile Pro Ala Val Gly Ile
                85                  90                  95

Pro Ala Val Gly Val Pro Ala Val Gly Ile Pro Ala Val Gly Ile Pro
                100                 105                 110

Ala Val Gly Ile Pro Ala Val Gly Ile Pro Ala Val Gly Val Pro Ala
            115                 120                 125

Val Gly Ile Pro Ala Val Gly Ile Pro Ala Val Gly Ile Pro Ala Val
        130                 135                 140

Gly Ile Pro Ala Val Gly Val Pro Ala Val Gly Ile Pro Ala Val Gly
145                 150                 155                 160

Ile Pro Ala Val Gly Ile Pro Ala Val Gly Ile Pro Ala Val Gly Val
                165                 170                 175

Pro Ala Val Gly Ile Pro Ala Val Gly Ile Pro Ala Val Gly Ile Pro
                180                 185                 190

Ala Val Gly Ile Pro Ala Val Gly Val Pro Ala Val Gly Ile Pro Ala
            195                 200                 205

Val Gly Ile Pro Ala Val Gly Ile Pro Ala Val Gly Ile Pro Ala Val
        210                 215                 220

Gly Val Pro Ala Val Gly Ile Pro Ala Val Gly Ile Pro Ala Val Gly
225                 230                 235                 240

Ile Pro Ala Val Gly Ile Pro Ala Val Gly Val Pro Ala Val Gly Ile
                245                 250                 255

Pro Ala Val Gly Ile Pro Ala Val Gly Ile Pro Ala Val Gly Ile Pro
                260                 265                 270

Ala Val Gly Val Pro Ala Val Gly Ile Pro Ala Val Gly Ile Pro Ala
            275                 280                 285

Val Gly Ile Pro Ala Val Gly Ile Pro Ala Val Gly Val Pro Ala Val
        290                 295                 300

Gly Ile Pro Ala Val Gly Ile Pro Ala Val Gly Ile Pro Ala Val Gly
305                 310                 315                 320

Ile Pro Ala Val Gly Val Pro Ala Val Gly Ile Pro Ala Val Gly Ile
```

```
                    325                 330                 335
Pro Ala Val Gly Ile Pro Ala Val Gly Ile Pro Ala Val Gly Val Pro
                340                 345                 350
Ala Val Gly Ile Pro Ala Val Gly Ile Pro Ala Val Gly Ile Pro Ala
                355                 360                 365
Val Gly Ile Pro Ala Val Gly Val Pro Ala Val Gly Ile Pro Ala Val
                370                 375                 380
Gly Ile Pro Ala Val Gly Ile Pro Ala Val Gly Ile Pro Ala Val Gly
385                 390                 395                 400
Val Pro Ala Val Gly Ile Pro Ala Val Gly Val Pro Gly Val Gly Val
                405                 410                 415
Pro Gly Val Gly Val Pro Gly Val Gly Val Pro Gly Glu Gly Val Pro
                420                 425                 430
Gly Val Gly Val Pro Gly Val Gly Val Pro Gly Val Gly Val Pro Gly
                435                 440                 445
Val Gly Val Pro Gly Glu Gly Val Pro Gly Val Gly Val Pro Gly Val
                450                 455                 460
Gly Val Pro Gly Val Gly Val Pro Gly Val Gly Val Pro Gly Glu Gly
465                 470                 475                 480
Val Pro Gly Val Gly Val Pro Gly Val Gly Val Pro Gly Val Gly Val
                485                 490                 495
Pro Gly Val Gly Val Pro Gly Glu Gly Val Pro Gly Val Gly Val Pro
                500                 505                 510
Gly Val Gly Val Pro Gly Val Gly Val Pro Gly Val Gly Val Pro Gly
                515                 520                 525
Glu Gly Val Pro Gly Val Gly Val Pro Gly Val Gly Val Pro Gly Val
                530                 535                 540
Gly Val Pro Gly Val Gly Val Pro Gly Glu Gly Val Pro Gly Val Gly
545                 550                 555                 560
Val Pro Gly Val Gly Val Pro Gly Val Gly Val Pro Gly Val Gly Val
                565                 570                 575
Pro Gly Glu Gly Val Pro Gly Val Gly Val Pro Gly Val Gly Val Pro
                580                 585                 590
Gly Val Gly Val Pro Gly Val Gly Val Pro Gly Glu Gly Val Pro Gly
                595                 600                 605
Val Gly Val Pro Gly Val Gly Val Pro Gly Val Gly Val Pro Gly Val
                610                 615                 620
Gly Val Pro Gly Glu Gly Val Pro Gly Val Gly Val Pro Gly Val Gly
625                 630                 635                 640
Val Pro Gly Val Gly Val Pro Gly Val Gly Val Pro Gly Glu Gly Val
                645                 650                 655
Pro Gly Val Gly Val Pro Gly Val Gly Val Pro Gly Val Gly Val Pro
                660                 665                 670
Gly Val Gly Val Pro Gly Glu Gly Val Pro Gly Val Gly Val Pro Gly
                675                 680                 685
Val Gly Val Pro Gly Val Gly Val Pro Gly Val Gly Val Pro Gly Glu
                690                 695                 700
Gly Val Pro Gly Val Gly Val Pro Gly Val Gly Val Pro Gly Val Gly
705                 710                 715                 720
Val Pro Gly Val Gly Val Pro Gly Glu Gly Val Pro Gly Val Gly Val
                725                 730                 735
Pro Gly Val Gly Val Pro Gly Val Gly Val Pro Gly Val Gly Val Pro
                740                 745                 750
```

```
Gly Glu Gly Val Pro Gly Val Gly Val Pro Gly Val Gly Pro Gly
            755                 760                 765
Val Gly Val Pro Gly Val Gly Val Pro Gly Glu Gly Val Pro Gly Val
        770                 775                 780
Gly Val Pro Gly Val Gly Val Pro Gly Val Gly Val Pro Gly Val Gly
785                 790                 795                 800
Val Pro Gly Glu Gly Val Pro Gly Val Gly Val Pro Gly Val Gly Val
            805                 810                 815
Pro Gly Val Gly Val Pro Gly Val Gly Val Pro Gly Glu Gly Val Pro
        820                 825                 830
Gly Val Gly Val Pro Gly Val Gly Val Pro Gly Val Gly Val Pro Gly
835                 840                 845
Val Gly Val Pro Gly Glu Gly Val Pro Gly Val Gly Val Pro Gly Val
        850                 855                 860
Gly Val Pro Gly Val Gly Val Pro Gly Val Gly Val Pro Gly Glu Gly
865                 870                 875                 880
Val Pro Gly Val Gly Val Pro Gly Val Gly Val Pro Gly Val Gly Val
            885                 890                 895
Pro Gly Val Gly Val Pro Gly Glu Gly Val Pro Gly Val Gly Val Pro
        900                 905                 910
Gly Val Gly Val Pro Gly Val Gly Val Pro Gly Val Gly Val Pro Gly
915                 920                 925
Glu Gly Val Pro Gly Val Gly Val Pro Gly Val Gly Val Pro Gly Val
        930                 935                 940
Gly Val Pro Gly Val Gly Val Pro Gly Glu Gly Val Pro Gly Val Gly
945                 950                 955                 960
Val Pro Gly Val Gly Val Pro Gly Val Gly Val Pro Gly Val Gly Val
            965                 970                 975
Pro Gly Glu Gly Val Pro Gly Val Gly Val Pro Gly Val Gly Val Pro
        980                 985                 990
Gly Val Gly Val Pro Gly Val Gly Val Pro Gly Glu Gly Val Pro Gly
            995                1000                1005
Val Gly Val Pro Gly Val Gly Val Pro Gly Val Gly Val Pro Gly
        1010                1015                1020
Val Gly Val Pro Gly Glu Gly Val Pro Gly Val Gly Val Pro Gly
        1025                1030                1035
Val Gly Val Pro Gly Val Gly Val Pro Gly Val Gly Val Pro Gly
        1040                1045                1050
Glu Gly Val Pro Gly Val Gly Val Pro Gly Val Gly Val Pro Gly
        1055                1060                1065
Val Gly Val Pro Gly Val Gly Val Pro Gly Glu Gly Val Pro Gly
        1070                1075                1080
Val Gly Val Pro Gly Val Gly Val Pro Gly Val Gly Val Pro Gly
        1085                1090                1095
Val Gly Val Pro Gly Glu Gly Val Pro Gly Val Gly Val Pro Gly
        1100                1105                1110
Val Gly Val Pro Gly Val Gly Val Pro Gly Val Gly Val Pro Gly
        1115                1120                1125
Glu Gly Val Pro Gly Val Gly Val Pro Gly Val Gly Val Pro Gly
        1130                1135                1140
Val Gly Val Pro Gly Val Gly Val Pro Gly Glu Gly Val Pro Gly
        1145                1150                1155
```

```
Val Gly Val Pro Gly Val Gly Val Pro Gly Val Gly Val Pro Gly
    1160                1165                1170

Val Gly Val Pro Gly Glu Gly Val Pro Gly Val Gly Val Pro Gly
    1175                1180                1185

Val Gly Val Pro Gly Val Gly Val Pro Gly Val Gly Val Pro Gly
    1190                1195                1200

Glu Gly Val Pro Gly Val Gly Val Pro Gly Val Gly Val Pro Gly
    1205                1210                1215

Val Gly Val Pro Gly Val Gly Val Pro Gly Glu Gly Val Pro Gly
    1220                1225                1230

Val Gly Val Pro Gly Val Gly Val Pro Gly Val Gly Val Pro Gly
    1235                1240                1245

Val Gly Val Pro Gly Glu Gly Val Pro Gly Val Gly Val Pro Gly
    1250                1255                1260

Val Gly Val Pro Gly Val Gly Val Pro Gly Val Gly Val Pro Gly
    1265                1270                1275

Glu Gly Val Pro Gly Val Gly Val Pro Gly Val Gly Val Pro Gly
    1280                1285                1290

Val Gly Val Pro Gly Val Gly Val Pro Gly Glu Gly Val Pro Gly
    1295                1300                1305

Val Gly Val Pro Gly Val Gly Val Pro Gly Val Gly Val Pro Gly
    1310                1315                1320

Val Gly Val Pro Gly Glu Gly Val Pro Gly Val Gly Val Pro Gly
    1325                1330                1335

Val Gly Val Pro Gly Val Gly Val Pro Gly Val Gly Val Pro Gly
    1340                1345                1350

Glu Gly Val Pro Gly Val Gly Val Pro Gly Val Gly Val Pro Gly
    1355                1360                1365

Val Gly Val Pro Gly Val Gly Val Pro Gly Glu Gly Val Pro Gly
    1370                1375                1380

Val Gly Val Pro Gly Val Gly Val Pro Gly Val Gly Val Pro Gly
    1385                1390                1395

Val Gly Val Pro Gly Glu Gly Val Pro Gly Val Gly Val Pro Gly
    1400                1405                1410

Val Gly Val Pro Gly Val Gly Val Pro Gly Val Gly Val Pro Gly
    1415                1420                1425

Glu Gly Val Pro Gly Val Gly Val Pro Gly Val Gly Val Pro Gly
    1430                1435                1440

Val Gly Val Pro Gly Val Gly Val Pro Gly Glu Gly Val Pro Gly
    1445                1450                1455

Val Gly Val Pro Gly Val Gly Val Pro Gly Val Gly Val Pro Gly
    1460                1465                1470

Val Gly Val Pro Gly Glu Gly Val Pro Gly Val Gly Val Pro Gly
    1475                1480                1485

Val Gly Val Pro Gly Val Gly Val Pro Gly Val Gly Val Pro Gly
    1490                1495                1500

Glu Gly Val Pro Gly Val Gly Val Pro Gly Val Gly Val Pro Gly
    1505                1510                1515

Val Gly Val Pro Gly Val Gly Val Pro Gly Glu Gly Val Pro Gly
    1520                1525                1530

Val Gly Val Pro Gly Val Gly Val Pro Gly Val Gly Val Pro Gly
    1535                1540                1545

Val Gly Val Pro Gly Glu Gly Val Pro Gly Val Gly Val Pro Gly
```

-continued

```
                1550                1555                1560
Val Gly Val Pro Gly Val Gly Val Pro Gly Val Gly Val Pro Gly
            1565                1570                1575
Glu Gly Val Pro Gly Val Gly Val Pro Gly Val Gly Val Pro Gly
            1580                1585                1590
Val Gly Val Pro Gly Val Gly Val Pro Gly Glu Gly Val Pro Gly
            1595                1600                1605
Val Gly Val Pro Gly Val Gly Val Pro Gly Val Gly Val Pro Ala
            1610                1615                1620
Val Gly Ile Pro Ala Val Gly Ile Pro Ala Val Gly Ile Pro Ala
            1625                1630                1635
Val Gly Ile Pro Ala Val Gly Val Pro Ala Val Gly Ile Pro Ala
            1640                1645                1650
Val Gly Ile Pro Ala Val Gly Ile Pro Ala Val Gly Ile Pro Ala
            1655                1660                1665
Val Gly Val Pro Ala Val Gly Ile Pro Ala Val Gly Ile Pro Ala
            1670                1675                1680
Val Gly Ile Pro Ala Val Gly Ile Pro Ala Val Gly Val Pro Ala
            1685                1690                1695
Val Gly Ile Pro Ala Val Gly Ile Pro Ala Val Gly Ile Pro Ala
            1700                1705                1710
Val Gly Ile Pro Ala Val Gly Val Pro Ala Val Gly Ile Pro Ala
            1715                1720                1725
Val Gly Ile Pro Ala Val Gly Ile Pro Ala Val Gly Ile Pro Ala
            1730                1735                1740
Val Gly Val Pro Ala Val Gly Ile Pro Ala Val Gly Ile Pro Ala
            1745                1750                1755
Val Gly Ile Pro Ala Val Gly Ile Pro Ala Val Gly Val Pro Ala
            1760                1765                1770
Val Gly Ile Pro Ala Val Gly Ile Pro Ala Val Gly Ile Pro Ala
            1775                1780                1785
Val Gly Ile Pro Ala Val Gly Val Pro Ala Val Gly Ile Pro Ala
            1790                1795                1800
Val Gly Ile Pro Ala Val Gly Ile Pro Ala Val Gly Ile Pro Ala
            1805                1810                1815
Val Gly Val Pro Ala Val Gly Ile Pro Ala Val Gly Ile Pro Ala
            1820                1825                1830
Val Gly Ile Pro Ala Val Gly Ile Pro Ala Val Gly Val Pro Ala
            1835                1840                1845
Val Gly Ile Pro Ala Val Gly Ile Pro Ala Val Gly Ile Pro Ala
            1850                1855                1860
Val Gly Ile Pro Ala Val Gly Val Pro Ala Val Gly Ile Pro Ala
            1865                1870                1875
Val Gly Ile Pro Ala Val Gly Ile Pro Ala Val Gly Ile Pro Ala
            1880                1885                1890
Val Gly Val Pro Ala Val Gly Ile Pro Ala Val Gly Ile Pro Ala
            1895                1900                1905
Val Gly Ile Pro Ala Val Gly Ile Pro Ala Val Gly Val Pro Ala
            1910                1915                1920
Val Gly Ile Pro Ala Val Gly Ile Pro Ala Val Gly Ile Pro Ala
            1925                1930                1935
Val Gly Ile Pro Ala Val Gly Val Pro Ala Val Gly Ile Pro Ala
            1940                1945                1950
```

Val Gly Ile Pro Ala Val Gly Ile Pro Ala Val Gly Ile Pro Ala
    1955                1960                1965

Val Gly Val Pro Ala Val Gly Ile Pro Ala Val Gly Ile Pro Ala
    1970                1975                1980

Val Gly Ile Pro Ala Val Gly Ile Pro Ala Val Gly Val Pro Ala
    1985                1990                1995

Val Gly Ile Pro Ala Val Gly Ile Pro Ala Val Gly Ile Pro Ala
    2000                2005                2010

Val Gly Ile Pro Ala Val Gly Val Pro Ala Val Gly Ile Pro Ala
    2015                2020                2025

Val Gly
    2030

<210> SEQ ID NO 51
<211> LENGTH: 410
<212> TYPE: PRT
<213> ORGANISM: Artificial Sequence
<220> FEATURE:
<223> OTHER INFORMATION: synthetic construct

<400> SEQUENCE: 51

Val Pro Ala Val Gly Ile Pro Ala Val Gly Ile Pro Ala Val Gly Ile
1               5                   10                  15

Pro Ala Val Gly Ile Pro Ala Val Gly Val Pro Ala Val Gly Ile Pro
            20                  25                  30

Ala Val Gly Ile Pro Ala Val Gly Ile Pro Ala Val Gly Ile Pro Ala
        35                  40                  45

Val Gly Val Pro Ala Val Gly Ile Pro Ala Val Gly Ile Pro Ala Val
    50                  55                  60

Gly Ile Pro Ala Val Gly Ile Pro Ala Val Gly Val Pro Ala Val Gly
65                  70                  75                  80

Ile Pro Ala Val Gly Ile Pro Ala Val Gly Ile Pro Ala Val Gly Ile
                85                  90                  95

Pro Ala Val Gly Val Pro Ala Val Gly Ile Pro Ala Val Gly Ile Pro
            100                 105                 110

Ala Val Gly Ile Pro Ala Val Gly Ile Pro Ala Val Gly Val Pro Ala
        115                 120                 125

Val Gly Ile Pro Ala Val Gly Ile Pro Ala Val Gly Ile Pro Ala Val
    130                 135                 140

Gly Ile Pro Ala Val Gly Val Pro Ala Val Gly Ile Pro Ala Val Gly
145                 150                 155                 160

Ile Pro Ala Val Gly Ile Pro Ala Val Gly Ile Pro Ala Val Gly Val
                165                 170                 175

Pro Ala Val Gly Ile Pro Ala Val Gly Ile Pro Ala Val Gly Ile Pro
            180                 185                 190

Ala Val Gly Ile Pro Ala Val Gly Val Pro Ala Val Gly Ile Pro Ala
        195                 200                 205

Val Gly Ile Pro Ala Val Gly Ile Pro Ala Val Gly Ile Pro Ala Val
    210                 215                 220

Gly Val Pro Ala Val Gly Ile Pro Ala Val Gly Ile Pro Ala Val Gly
225                 230                 235                 240

Ile Pro Ala Val Gly Ile Pro Ala Val Gly Val Pro Ala Val Gly Ile
                245                 250                 255

Pro Ala Val Gly Ile Pro Ala Val Gly Ile Pro Ala Val Gly Ile Pro
            260                 265                 270

```
Ala Val Gly Val Pro Ala Val Gly Ile Pro Ala Val Gly Ile Pro Ala
            275                 280                 285
Val Gly Ile Pro Ala Val Gly Ile Pro Ala Val Gly Val Pro Ala Val
        290                 295                 300
Gly Ile Pro Ala Val Gly Ile Pro Ala Val Gly Ile Pro Ala Val Gly
305                 310                 315                 320
Ile Pro Ala Val Gly Val Pro Ala Val Gly Ile Pro Ala Val Gly Ile
                325                 330                 335
Pro Ala Val Gly Ile Pro Ala Val Gly Ile Pro Ala Val Gly Val Pro
            340                 345                 350
Ala Val Gly Ile Pro Ala Val Gly Ile Pro Ala Val Gly Ile Pro Ala
        355                 360                 365
Val Gly Ile Pro Ala Val Gly Val Pro Ala Val Gly Ile Pro Ala Val
    370                 375                 380
Gly Ile Pro Ala Val Gly Ile Pro Ala Val Gly Ile Pro Ala Val Gly
385                 390                 395                 400
Val Pro Ala Val Gly Ile Pro Ala Val Gly
                405                 410

<210> SEQ ID NO 52
<211> LENGTH: 1200
<212> TYPE: PRT
<213> ORGANISM: Artificial Sequence
<220> FEATURE:
<223> OTHER INFORMATION: synthetic construct

<400> SEQUENCE: 52

Val Pro Gly Val Gly Val Pro Gly Val Gly Val Pro Gly Glu Gly Val
1               5                   10                  15
Pro Gly Val Gly Val Pro Gly Val Gly Val Pro Gly Val Gly Val Pro
            20                  25                  30
Gly Val Gly Val Pro Gly Glu Gly Val Pro Gly Val Gly Val Pro Gly
        35                  40                  45
Val Gly Val Pro Gly Val Gly Val Pro Gly Val Gly Val Pro Gly Glu
    50                  55                  60
Gly Val Pro Gly Val Gly Val Pro Gly Val Gly Val Pro Gly Val Gly
65                  70                  75                  80
Val Pro Gly Val Gly Val Pro Gly Glu Gly Val Pro Gly Val Gly Val
                85                  90                  95
Pro Gly Val Gly Val Pro Gly Val Gly Val Pro Gly Val Gly Val Pro
            100                 105                 110
Gly Glu Gly Val Pro Gly Val Gly Val Pro Gly Val Gly Val Pro Gly
        115                 120                 125
Val Gly Val Pro Gly Val Gly Val Pro Gly Glu Gly Val Pro Gly Val
    130                 135                 140
Gly Val Pro Gly Val Gly Val Pro Gly Val Gly Val Pro Gly Val Gly
145                 150                 155                 160
Val Pro Gly Glu Gly Val Pro Gly Val Gly Val Pro Gly Val Gly Val
                165                 170                 175
Pro Gly Val Gly Val Pro Gly Val Gly Val Pro Gly Glu Gly Val Pro
            180                 185                 190
Gly Val Gly Val Pro Gly Val Gly Val Pro Gly Val Gly Val Pro Gly
        195                 200                 205
Val Gly Val Pro Gly Glu Gly Val Pro Gly Val Gly Val Pro Gly Val
    210                 215                 220
```

```
Gly Val Pro Gly Val Gly Val Pro Gly Val Gly Val Pro Gly Glu Gly
225                 230                 235                 240
Val Pro Gly Val Gly Val Pro Gly Val Gly Val Pro Gly Val Gly Val
                245                 250                 255
Pro Gly Val Gly Val Pro Gly Glu Gly Val Pro Gly Val Gly Val Pro
            260                 265                 270
Gly Val Gly Val Pro Gly Val Gly Val Pro Gly Val Gly Val Pro Gly
        275                 280                 285
Glu Gly Val Pro Gly Val Gly Val Pro Gly Val Gly Val Pro Gly Val
    290                 295                 300
Gly Val Pro Gly Val Gly Val Pro Gly Glu Gly Val Pro Gly Val Gly
305                 310                 315                 320
Val Pro Gly Val Gly Val Pro Gly Val Gly Val Pro Gly Val Gly Val
                325                 330                 335
Pro Gly Glu Gly Val Pro Gly Val Gly Val Pro Gly Val Gly Val Pro
            340                 345                 350
Gly Val Gly Val Pro Gly Val Gly Val Pro Gly Glu Gly Val Pro Gly
        355                 360                 365
Val Gly Val Pro Gly Val Gly Val Pro Gly Val Gly Val Pro Gly Val
    370                 375                 380
Gly Val Pro Gly Glu Gly Val Pro Gly Val Gly Val Pro Gly Val Gly
385                 390                 395                 400
Val Pro Gly Val Gly Val Pro Gly Val Gly Val Pro Gly Glu Gly Val
                405                 410                 415
Pro Gly Val Gly Val Pro Gly Val Gly Val Pro Gly Val Gly Val Pro
            420                 425                 430
Gly Val Gly Val Pro Gly Glu Gly Val Pro Gly Val Gly Val Pro Gly
        435                 440                 445
Val Gly Val Pro Gly Val Gly Val Pro Gly Val Gly Val Pro Gly Glu
    450                 455                 460
Gly Val Pro Gly Val Gly Val Pro Gly Val Gly Val Pro Gly Val Gly
465                 470                 475                 480
Val Pro Gly Val Gly Val Pro Gly Glu Gly Val Pro Gly Val Gly Val
                485                 490                 495
Pro Gly Val Gly Val Pro Gly Val Gly Val Pro Gly Val Gly Val Pro
            500                 505                 510
Gly Glu Gly Val Pro Gly Val Gly Val Pro Gly Val Gly Val Pro Gly
        515                 520                 525
Val Gly Val Pro Gly Val Gly Val Pro Gly Glu Gly Val Pro Gly Val
    530                 535                 540
Gly Val Pro Gly Val Gly Val Pro Gly Val Gly Val Pro Gly Val Gly
545                 550                 555                 560
Val Pro Gly Glu Gly Val Pro Gly Val Gly Val Pro Gly Val Gly Val
                565                 570                 575
Pro Gly Val Gly Val Pro Gly Val Gly Val Pro Gly Glu Gly Val Pro
            580                 585                 590
Gly Val Gly Val Pro Gly Val Gly Val Pro Gly Val Gly Val Pro Gly
        595                 600                 605
Val Gly Val Pro Gly Glu Gly Val Pro Gly Val Gly Val Pro Gly Val
    610                 615                 620
Gly Val Pro Gly Val Gly Val Pro Gly Val Gly Val Pro Gly Glu Gly
625                 630                 635                 640
```

```
Val Pro Gly Val Gly Val Pro Gly Val Gly Val
            645                 650                 655

Pro Gly Val Gly Val Pro Gly Glu Gly Val Pro Gly Val Gly Val Pro
            660                 665                 670

Gly Val Gly Val Pro Gly Val Gly Val Pro Gly Val Gly Val Pro Gly
            675                 680                 685

Glu Gly Val Pro Gly Val Gly Val Pro Gly Val Gly Val Pro Gly Val
            690                 695                 700

Gly Val Pro Gly Val Gly Val Pro Gly Glu Gly Val Pro Gly Val Gly
705                 710                 715                 720

Val Pro Gly Val Gly Val Pro Gly Val Gly Val Pro Gly Val Gly Val
            725                 730                 735

Pro Gly Glu Gly Val Pro Gly Val Gly Val Pro Gly Val Gly Val Pro
            740                 745                 750

Gly Val Gly Val Pro Gly Val Gly Val Pro Gly Glu Gly Val Pro Gly
            755                 760                 765

Val Gly Val Pro Gly Val Gly Val Pro Gly Val Gly Val Pro Gly Val
            770                 775                 780

Gly Val Pro Gly Glu Gly Val Pro Gly Val Gly Val Pro Gly Val Gly
785                 790                 795                 800

Val Pro Gly Val Gly Val Pro Gly Val Gly Val Pro Gly Glu Gly Val
            805                 810                 815

Pro Gly Val Gly Val Pro Gly Val Gly Val Pro Gly Val Gly Val Pro
            820                 825                 830

Gly Val Gly Val Pro Gly Glu Gly Val Pro Gly Val Gly Val Pro Gly
            835                 840                 845

Val Gly Val Pro Gly Val Gly Val Pro Gly Val Gly Val Pro Gly Glu
850                 855                 860

Gly Val Pro Gly Val Gly Val Pro Gly Val Gly Val Pro Gly Val Gly
865                 870                 875                 880

Val Pro Gly Val Gly Val Pro Gly Glu Gly Val Pro Gly Val Gly Val
            885                 890                 895

Pro Gly Val Gly Val Pro Gly Val Gly Val Pro Gly Val Gly Val Pro
            900                 905                 910

Gly Glu Gly Val Pro Gly Val Gly Val Pro Gly Val Gly Val Pro Gly
            915                 920                 925

Val Gly Val Pro Gly Val Gly Val Pro Gly Glu Gly Val Pro Gly Val
            930                 935                 940

Gly Val Pro Gly Val Gly Val Pro Gly Val Gly Val Pro Gly Val Gly
945                 950                 955                 960

Val Pro Gly Glu Gly Val Pro Gly Val Gly Val Pro Gly Val Gly Val
            965                 970                 975

Pro Gly Val Gly Val Pro Gly Val Gly Val Pro Gly Glu Gly Val Pro
            980                 985                 990

Gly Val Gly Val Pro Gly Val Gly Val Pro Gly Val Gly Val Pro Gly
            995                 1000                1005

Val Gly Val Pro Gly Glu Gly Val Pro Gly Val Gly Val Pro Gly
            1010                1015                1020

Val Gly Val Pro Gly Val Gly Val Pro Gly Val Gly Val Pro Gly
            1025                1030                1035

Glu Gly Val Pro Gly Val Gly Val Pro Gly Val Gly Val Pro Gly
            1040                1045                1050

Val Gly Val Pro Gly Val Gly Val Pro Gly Glu Gly Val Pro Gly
```

```
                1055                1060                1065

Val Gly Val Pro Gly Val Gly Val Pro Gly Val Gly Val Pro Gly
        1070                1075                1080

Val Gly Val Pro Gly Glu Gly Val Pro Gly Val Gly Val Pro Gly
        1085                1090                1095

Val Gly Val Pro Gly Val Gly Val Pro Gly Val Gly Val Pro Gly
        1100                1105                1110

Glu Gly Val Pro Gly Val Gly Val Pro Gly Val Gly Val Pro Gly
        1115                1120                1125

Val Gly Val Pro Gly Val Gly Val Pro Gly Glu Gly Val Pro Gly
        1130                1135                1140

Val Gly Val Pro Gly Val Gly Val Pro Gly Val Gly Val Pro Gly
        1145                1150                1155

Val Gly Val Pro Gly Glu Gly Val Pro Gly Val Gly Val Pro Gly
        1160                1165                1170

Val Gly Val Pro Gly Val Gly Val Pro Gly Val Gly Val Pro Gly
        1175                1180                1185

Glu Gly Val Pro Gly Val Gly Val Pro Gly Val Gly
        1190                1195                1200

<210> SEQ ID NO 53
<211> LENGTH: 25
<212> TYPE: PRT
<213> ORGANISM: Artificial Sequence
<220> FEATURE:
<223> OTHER INFORMATION: synthetic construct

<400> SEQUENCE: 53

Val Pro Gly Val Gly Val Pro Gly Val Gly Val Pro Gly Glu Gly Val
1               5                   10                  15

Pro Gly Val Gly Val Pro Gly Val Gly
            20                  25

<210> SEQ ID NO 54
<211> LENGTH: 75
<212> TYPE: DNA
<213> ORGANISM: Artificial Sequence
<220> FEATURE:
<223> OTHER INFORMATION: synthetic construct

<400> SEQUENCE: 54
gttccaggag tcggagttcc tggtgttgga gtaccaggtg aaggtgttcc tggtgtagga      60
gtccctggtg taggt                                                      75

<210> SEQ ID NO 55
<211> LENGTH: 42
<212> TYPE: DNA
<213> ORGANISM: Artificial Sequence
<220> FEATURE:
<223> OTHER INFORMATION: synthetic construct

<400> SEQUENCE: 55
tccagctgtt gttaaggccg cgaaggttcc aggtgcaggc gt                         42

<210> SEQ ID NO 56
<211> LENGTH: 48
<212> TYPE: DNA
<213> ORGANISM: Artificial Sequence
<220> FEATURE:
<223> OTHER INFORMATION: synthetic construct
```

-continued

<400> SEQUENCE: 56

```
gatccaaggt tccaagagac ggtacccgtc tcttccaaag ccgcgaa          48
```

<210> SEQ ID NO 57
<211> LENGTH: 75
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(75)

<400> SEQUENCE: 57

```
gta cct ggt att ggc gtt ccg ggt atc ggt gtg cca ggc atc ggt gta    48
Val Pro Gly Ile Gly Val Pro Gly Ile Gly Val Pro Gly Ile Gly Val
1               5                   10                  15 ccg ggt att ggc gtt cca ggc att ggc                                75
Pro Gly Ile Gly Val Pro Gly Ile Gly
            20                  25
```

<210> SEQ ID NO 58
<211> LENGTH: 25
<212> TYPE: PRT
<213> ORGANISM: Artificial Sequence
<220> FEATURE:
<223> OTHER INFORMATION: Synthetic Construct

<400> SEQUENCE: 58

```
Val Pro Gly Ile Gly Val Pro Gly Ile Gly Val Pro Gly Ile Gly Val
1               5                   10                  15

Pro Gly Ile Gly Val Pro Gly Ile Gly
            20                  25
```

<210> SEQ ID NO 59
<211> LENGTH: 75
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(75)

<400> SEQUENCE: 59

```
gtt cca ggt att ggt gtc cca gga atc ggt gtt cct gga att gga gtc    48
Val Pro Gly Ile Gly Val Pro Gly Ile Gly Val Pro Gly Ile Gly Val
1               5                   10                  15 cca ggt att gga gtt cca ggt ata ggt                                75
Pro Gly Ile Gly Val Pro Gly Ile Gly
            20                  25
```

<210> SEQ ID NO 60
<211> LENGTH: 25
<212> TYPE: PRT
<213> ORGANISM: Artificial Sequence
<220> FEATURE:
<223> OTHER INFORMATION: Synthetic Construct

<400> SEQUENCE: 60

```
Val Pro Gly Ile Gly Val Pro Gly Ile Gly Val Pro Gly Ile Gly Val
1               5                   10                  15

Pro Gly Ile Gly Val Pro Gly Ile Gly
            20                  25
```

```
<210> SEQ ID NO 61
<211> LENGTH: 75
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(75)

<400> SEQUENCE: 61 att ccg gct gtt ggt atc cca gct gtt ggt atc cca gct gtt ggc att      48
Ile Pro Ala Val Gly Ile Pro Ala Val Gly Ile Pro Ala Val Gly Ile
1               5                   10                  15 ccg gct gta ggt atc ccg gca gtg ggc                                  75
Pro Ala Val Gly Ile Pro Ala Val Gly
            20                  25

<210> SEQ ID NO 62
<211> LENGTH: 25
<212> TYPE: PRT
<213> ORGANISM: Artificial Sequence
<220> FEATURE:
<223> OTHER INFORMATION: Synthetic Construct

<400> SEQUENCE: 62

Ile Pro Ala Val Gly Ile Pro Ala Val Gly Ile Pro Ala Val Gly Ile
1               5                   10                  15

Pro Ala Val Gly Ile Pro Ala Val Gly
            20                  25

<210> SEQ ID NO 63
<211> LENGTH: 75
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(75)

<400> SEQUENCE: 63 att cca gct gtt ggt atc cct gcc gtc ggt att cct gct gtt gga atc      48
Ile Pro Ala Val Gly Ile Pro Ala Val Gly Ile Pro Ala Val Gly Ile
1               5                   10                  15 cca gca gtc ggt att cca gcc gtt gga                                  75
Pro Ala Val Gly Ile Pro Ala Val Gly
            20                  25

<210> SEQ ID NO 64
<211> LENGTH: 25
<212> TYPE: PRT
<213> ORGANISM: Artificial Sequence
<220> FEATURE:
<223> OTHER INFORMATION: Synthetic Construct

<400> SEQUENCE: 64

Ile Pro Ala Val Gly Ile Pro Ala Val Gly Ile Pro Ala Val Gly Ile
1               5                   10                  15

Pro Ala Val Gly Ile Pro Ala Val Gly
            20                  25

<210> SEQ ID NO 65
<211> LENGTH: 30
<212> TYPE: PRT
<213> ORGANISM: Artificial Sequence
<220> FEATURE:
```

```
<223> OTHER INFORMATION: synthetic construct

<400> SEQUENCE: 65

Val Pro Ala Val Gly Ile Pro Ala Val Gly Ile Pro Ala Val Gly Ile
1               5                   10                  15

Pro Ala Val Gly Ile Pro Ala Val Gly Val Pro Ala Val Gly
            20                  25                  30

<210> SEQ ID NO 66
<211> LENGTH: 25
<212> TYPE: PRT
<213> ORGANISM: Artificial Sequence
<220> FEATURE:
<223> OTHER INFORMATION: synthetic construct

<400> SEQUENCE: 66

Val Pro Gly Val Gly Val Pro Gly Val Gly Val Pro Gly Glu Gly Val
1               5                   10                  15

Pro Gly Val Gly Val Pro Gly Val Gly
            20                  25

<210> SEQ ID NO 67
<211> LENGTH: 50
<212> TYPE: PRT
<213> ORGANISM: Artificial Sequence
<220> FEATURE:
<223> OTHER INFORMATION: synthetic construct

<400> SEQUENCE: 67

Val Pro Ala Val Gly Ile Pro Ala Val Gly Ile Pro Ala Val Gly Ile
1               5                   10                  15

Pro Ala Val Gly Ile Pro Ala Val Gly Ile Pro Ala Val Gly Ile Pro
            20                  25                  30

Ala Val Gly Ile Pro Ala Val Gly Ile Pro Ala Val Gly Ile Pro Ala
        35                  40                  45

Val Gly
    50

<210> SEQ ID NO 68
<211> LENGTH: 25
<212> TYPE: PRT
<213> ORGANISM: Artificial Sequence
<220> FEATURE:
<223> OTHER INFORMATION: synthetic construct

<400> SEQUENCE: 68

Val Pro Gly Ala Gly Val Pro Gly Ala Gly Val Pro Gly Glu Gly Val
1               5                   10                  15

Pro Gly Ala Gly Val Pro Gly Ala Gly
            20                  25

<210> SEQ ID NO 69
<211> LENGTH: 25
<212> TYPE: PRT
<213> ORGANISM: Artificial Sequence
<220> FEATURE:
<223> OTHER INFORMATION: synthetic construct

<400> SEQUENCE: 69

Ile Pro Gly Ala Gly Val Pro Gly Ala Gly Val Pro Gly Glu Gly Val
1               5                   10                  15

Pro Gly Ala Gly Val Pro Gly Ala Gly
            20                  25
```

<210> SEQ ID NO 70
<211> LENGTH: 50
<212> TYPE: PRT
<213> ORGANISM: Artificial Sequence
<220> FEATURE:
<223> OTHER INFORMATION: synthetic construct

<400> SEQUENCE: 70

Val Pro Gly Ala Gly Val Pro Gly Ala Gly Val Pro Gly Glu Gly Val
1               5                   10                  15

Pro Gly Ala Gly Val Pro Gly Ala Gly Ile Pro Gly Ala Gly Val Pro
            20                  25                  30

Gly Ala Gly Val Pro Gly Glu Gly Val Pro Gly Ala Gly Val Pro Gly
        35                  40                  45

Ala Gly
    50

<210> SEQ ID NO 71
<211> LENGTH: 3692
<212> TYPE: PRT
<213> ORGANISM: Artificial Sequence
<220> FEATURE:
<223> OTHER INFORMATION: synthetic construct

<400> SEQUENCE: 71

Val Pro Ala Val Gly Lys Val Pro Ala Val Gly Ile Pro Ala Val Gly
1               5                   10                  15

Ile Pro Ala Val Gly Ile Pro Ala Val Gly Ile Pro Ala Val Gly Ile
            20                  25                  30

Pro Ala Val Gly Ile Pro Ala Val Gly Ile Pro Ala Val Gly Ile Pro
        35                  40                  45

Ala Val Gly Ile Pro Ala Val Gly Ile Pro Ala Val Gly Ile Pro Ala
    50                  55                  60

Val Gly Ile Pro Ala Val Gly Ile Pro Ala Val Gly Ile Pro Ala Val
65                  70                  75                  80

Gly Ile Pro Ala Val Gly Ile Pro Ala Val Gly Ile Pro Ala Val Gly
                85                  90                  95

Ile Pro Ala Val Gly Ile Pro Ala Val Gly Ile Pro Ala Val Gly Ile
            100                 105                 110

Pro Ala Val Gly Ile Pro Ala Val Gly Ile Pro Ala Val Gly Ile Pro
        115                 120                 125

Ala Val Gly Ile Pro Ala Val Gly Ile Pro Ala Val Gly Ile Pro Ala
    130                 135                 140

Val Gly Ile Pro Ala Val Gly Ile Pro Ala Val Gly Ile Pro Ala Val
145                 150                 155                 160

Gly Ile Pro Ala Val Gly Ile Pro Ala Val Gly Ile Pro Ala Val Gly
                165                 170                 175

Ile Pro Ala Val Gly Ile Pro Ala Val Gly Ile Pro Ala Val Gly Ile
            180                 185                 190

Pro Ala Val Gly Ile Pro Ala Val Gly Ile Pro Ala Val Gly Ile Pro
        195                 200                 205

Ala Val Gly Ile Pro Ala Val Gly Ile Pro Ala Val Gly Ile Pro Ala
    210                 215                 220

Val Gly Ile Pro Ala Val Gly Ile Pro Ala Val Gly Ile Pro Ala Val
225                 230                 235                 240

Gly Ile Pro Ala Val Gly Ile Pro Ala Val Gly Ile Pro Ala Val Gly

-continued

```
                245                 250                 255
Ile Pro Ala Val Gly Ile Pro Ala Val Gly Ile Pro Ala Val Gly Ile
            260                 265                 270
Pro Ala Val Gly Ile Pro Ala Val Gly Ile Pro Ala Val Gly Ile Pro
            275                 280                 285
Ala Val Gly Ile Pro Ala Val Gly Ile Pro Ala Val Gly Ile Pro Ala
            290                 295                 300
Val Gly Ile Pro Ala Val Gly Ile Pro Ala Val Gly Ile Pro Ala Val
305                 310                 315                 320
Gly Ile Pro Ala Val Gly Ile Pro Ala Val Gly Ile Pro Ala Val Gly
            325                 330                 335
Ile Pro Ala Val Gly Ile Pro Ala Val Gly Ile Pro Ala Val Gly Ile
            340                 345                 350
Pro Ala Val Gly Ile Pro Ala Val Gly Ile Pro Ala Val Gly Ile Pro
            355                 360                 365
Ala Val Gly Ile Pro Ala Val Gly Ile Pro Ala Val Gly Ile Pro Ala
            370                 375                 380
Val Gly Ile Pro Ala Val Gly Ile Pro Ala Val Gly Ile Pro Ala Val
385                 390                 395                 400
Gly Ile Pro Ala Val Gly Ile Pro Ala Val Gly Ile Pro Ala Val Gly
            405                 410                 415
Ile Pro Ala Val Gly Ile Pro Ala Val Gly Ile Pro Ala Val Gly Ile
            420                 425                 430
Pro Ala Val Gly Ile Pro Ala Val Gly Ile Pro Ala Val Gly Ile Pro
            435                 440                 445
Ala Val Gly Ile Pro Ala Val Gly Ile Pro Ala Val Gly Ile Pro Ala
            450                 455                 460
Val Gly Ile Pro Ala Val Gly Ile Pro Ala Val Gly Ile Pro Ala Val
465                 470                 475                 480
Gly Ile Pro Ala Val Gly Ile Pro Ala Val Gly Ile Pro Ala Val Gly
            485                 490                 495
Ile Pro Ala Val Gly Ile Pro Ala Val Gly Ile Pro Ala Val Gly Ile
            500                 505                 510
Pro Ala Val Gly Ile Pro Ala Val Gly Ile Pro Ala Val Gly Ile Pro
            515                 520                 525
Ala Val Gly Ile Pro Ala Val Gly Ile Pro Ala Val Gly Ile Pro Ala
            530                 535                 540
Val Gly Ile Pro Ala Val Gly Ile Pro Ala Val Gly Ile Pro Ala Val
545                 550                 555                 560
Gly Ile Pro Ala Val Gly Ile Pro Ala Val Gly Ile Pro Ala Val Gly
            565                 570                 575
Ile Pro Ala Val Gly Ile Pro Ala Val Gly Ile Pro Ala Val Gly Ile
            580                 585                 590
Pro Ala Val Gly Ile Pro Ala Val Gly Ile Pro Ala Val Gly Ile Pro
            595                 600                 605
Ala Val Gly Ile Pro Ala Val Gly Ile Pro Ala Val Gly Ile Pro Ala
            610                 615                 620
Val Gly Ile Pro Ala Val Gly Ile Pro Ala Val Gly Ile Pro Ala Val
625                 630                 635                 640
Gly Ile Pro Ala Val Gly Ile Pro Ala Val Gly Ile Pro Ala Val Gly
            645                 650                 655
Ile Pro Ala Val Gly Ile Pro Ala Val Gly Ile Pro Ala Val Gly Ile
            660                 665                 670
```

-continued

Pro Ala Val Gly Ile Pro Ala Val Gly Ile Pro Ala Val Gly Ile Pro
         675                 680                 685

Ala Val Gly Ile Pro Ala Val Gly Ile Pro Ala Val Gly Ile Pro Ala
     690                 695                 700

Val Gly Ile Pro Ala Val Gly Ile Pro Ala Val Gly Ile Pro Ala Val
705                 710                 715                 720

Gly Ile Pro Ala Val Gly Ile Pro Ala Val Gly Ile Pro Ala Val Gly
             725                 730                 735

Ile Pro Ala Val Gly Ile Pro Ala Val Gly Ile Pro Ala Val Gly Ile
         740                 745                 750

Pro Ala Val Gly Ile Pro Ala Val Gly Ile Pro Ala Val Gly Ile Pro
             755                 760                 765

Ala Val Gly Ile Pro Ala Val Gly Ile Pro Ala Val Gly Ile Pro Ala
     770                 775                 780

Val Gly Ile Pro Ala Val Gly Ile Pro Ala Val Gly Ile Pro Ala Val
785                 790                 795                 800

Gly Ile Pro Ala Val Gly Ile Pro Ala Val Gly Ile Pro Ala Val Gly
             805                 810                 815

Ile Pro Ala Val Gly Ile Pro Ala Val Gly Ile Pro Ala Val Gly Ile
         820                 825                 830

Pro Ala Val Gly Ile Pro Ala Val Gly Ile Pro Ala Val Gly Ile Pro
             835                 840                 845

Ala Val Gly Ile Pro Ala Val Gly Ile Pro Ala Val Gly Lys Ala Ala
     850                 855                 860

Lys Val Pro Gly Ala Gly Val Pro Gly Ala Gly Val Pro Gly Ala Gly
865                 870                 875                 880

Val Pro Gly Glu Gly Val Pro Gly Ala Gly Val Pro Gly Ala Gly Val
             885                 890                 895

Pro Gly Ala Gly Val Pro Gly Ala Gly Val Pro Gly Glu Gly Val Pro
         900                 905                 910

Gly Ala Gly Val Pro Gly Ala Gly Val Pro Gly Ala Gly Val Pro Gly
     915                 920                 925

Ala Gly Val Pro Gly Glu Gly Val Pro Gly Ala Gly Val Pro Gly Ala
     930                 935                 940

Gly Val Pro Gly Ala Gly Val Pro Gly Ala Gly Val Pro Gly Glu Gly
945                 950                 955                 960

Val Pro Gly Ala Gly Val Pro Gly Ala Gly Val Pro Gly Ala Gly Val
             965                 970                 975

Pro Gly Ala Gly Val Pro Gly Glu Gly Val Pro Gly Ala Gly Val Pro
         980                 985                 990

Gly Ala Gly Val Pro Gly Ala Gly  Val Pro Gly Ala Gly  Val Pro Gly
     995                 1000                1005

Glu Gly  Val Pro Gly Ala Gly  Val Pro Gly Ala Gly  Val Pro Gly
    1010                1015                1020

Ala Gly  Val Pro Gly Ala Gly  Val Pro Gly Glu Gly  Val Pro Gly
    1025                1030                1035

Ala Gly  Val Pro Gly Ala Gly  Val Pro Gly Ala Gly  Val Pro Gly
    1040                1045                1050

Ala Gly  Val Pro Gly Glu Gly  Val Pro Gly Ala Gly  Val Pro Gly
    1055                1060                1065

Ala Gly  Val Pro Gly Ala Gly  Val Pro Gly Ala Gly  Val Pro Gly
    1070                1075                1080

```
Glu Gly Val Pro Gly Ala Gly Val Pro Gly Ala Gly Val Pro Gly
    1085                1090                1095

Ala Gly Val Pro Gly Ala Gly Val Pro Gly Glu Gly Val Pro Gly
    1100                1105                1110

Ala Gly Val Pro Gly Ala Gly Val Pro Gly Ala Gly Val Pro Gly
    1115                1120                1125

Ala Gly Val Pro Gly Glu Gly Val Pro Gly Ala Gly Val Pro Gly
    1130                1135                1140

Ala Gly Val Pro Gly Ala Gly Val Pro Gly Ala Gly Val Pro Gly
    1145                1150                1155

Glu Gly Val Pro Gly Ala Gly Val Pro Gly Ala Gly Val Pro Gly
    1160                1165                1170

Ala Gly Val Pro Gly Ala Gly Val Pro Gly Glu Gly Val Pro Gly
    1175                1180                1185

Ala Gly Val Pro Gly Ala Gly Val Pro Gly Ala Gly Val Pro Gly
    1190                1195                1200

Ala Gly Val Pro Gly Glu Gly Val Pro Gly Ala Gly Val Pro Gly
    1205                1210                1215

Ala Gly Val Pro Gly Ala Gly Val Pro Gly Ala Gly Val Pro Gly
    1220                1225                1230

Glu Gly Val Pro Gly Ala Gly Val Pro Gly Ala Gly Val Pro Gly
    1235                1240                1245

Ala Gly Val Pro Gly Ala Gly Val Pro Gly Glu Gly Val Pro Gly
    1250                1255                1260

Ala Gly Val Pro Gly Ala Gly Val Pro Gly Ala Gly Val Pro Gly
    1265                1270                1275

Ala Gly Val Pro Gly Glu Gly Val Pro Gly Ala Gly Val Pro Gly
    1280                1285                1290

Ala Gly Val Pro Gly Ala Gly Val Pro Gly Ala Gly Val Pro Gly
    1295                1300                1305

Glu Gly Val Pro Gly Ala Gly Val Pro Gly Ala Gly Val Pro Gly
    1310                1315                1320

Ala Gly Val Pro Gly Ala Gly Val Pro Gly Glu Gly Val Pro Gly
    1325                1330                1335

Ala Gly Val Pro Gly Ala Gly Val Pro Gly Ala Gly Val Pro Gly
    1340                1345                1350

Ala Gly Val Pro Gly Glu Gly Val Pro Gly Ala Gly Val Pro Gly
    1355                1360                1365

Ala Gly Val Pro Gly Ala Gly Val Pro Gly Ala Gly Val Pro Gly
    1370                1375                1380

Glu Gly Val Pro Gly Ala Gly Val Pro Gly Ala Gly Val Pro Gly
    1385                1390                1395

Ala Gly Val Pro Gly Ala Gly Val Pro Gly Glu Gly Val Pro Gly
    1400                1405                1410

Ala Gly Val Pro Gly Ala Gly Val Pro Gly Ala Gly Val Pro Gly
    1415                1420                1425

Ala Gly Val Pro Gly Glu Gly Val Pro Gly Ala Gly Val Pro Gly
    1430                1435                1440

Ala Gly Val Pro Gly Ala Gly Val Pro Gly Ala Gly Val Pro Gly
    1445                1450                1455

Glu Gly Val Pro Gly Ala Gly Val Pro Gly Ala Gly Val Pro Gly
    1460                1465                1470

Ala Gly Val Pro Gly Ala Gly Val Pro Gly Glu Gly Val Pro Gly
```

-continued

```
            1475                1480                1485

Ala Gly Val Pro Gly Ala Gly Val Pro Gly Ala Gly Val Pro Gly
    1490                1495                1500

Ala Gly Val Pro Gly Glu Gly Val Pro Gly Ala Gly Val Pro Gly
    1505                1510                1515

Ala Gly Val Pro Gly Ala Gly Val Pro Gly Ala Gly Val Pro Gly
    1520                1525                1530

Glu Gly Val Pro Gly Ala Gly Val Pro Gly Ala Gly Val Pro Gly
    1535                1540                1545

Ala Gly Val Pro Gly Ala Gly Val Pro Gly Glu Gly Val Pro Gly
    1550                1555                1560

Ala Gly Val Pro Gly Ala Gly Val Pro Ala Val Gly Lys Ala Ala
    1565                1570                1575

Lys Val Pro Gly Ala Gly Val Pro Ala Val Gly Ile Pro Ala Val
    1580                1585                1590

Gly Ile Pro Ala Val Gly Ile Pro Ala Val Gly Ile Pro Ala Val
    1595                1600                1605

Gly Ile Pro Ala Val Gly Ile Pro Ala Val Gly Ile Pro Ala Val
    1610                1615                1620

Gly Ile Pro Ala Val Gly Ile Pro Ala Val Gly Val Pro Ala Val
    1625                1630                1635

Gly Lys Ala Ala Lys Val Pro Gly Ala Gly Val Pro Ala Val Gly
    1640                1645                1650

Ile Pro Ala Val Gly Ile Pro Ala Val Gly Ile Pro Ala Val Gly
    1655                1660                1665

Ile Pro Ala Val Gly Ile Pro Ala Val Gly Ile Pro Ala Val Gly
    1670                1675                1680

Ile Pro Ala Val Gly Ile Pro Ala Val Gly Ile Pro Ala Val Gly
    1685                1690                1695

Val Pro Ala Val Gly Lys Ala Ala Lys Val Pro Gly Ala Gly Val
    1700                1705                1710

Pro Ala Val Gly Ile Pro Ala Val Gly Ile Pro Ala Val Gly Ile
    1715                1720                1725

Pro Ala Val Gly Ile Pro Ala Val Gly Ile Pro Ala Val Gly Ile
    1730                1735                1740

Pro Ala Val Gly Ile Pro Ala Val Gly Ile Pro Ala Val Gly Ile
    1745                1750                1755

Pro Ala Val Gly Val Pro Ala Val Gly Lys Ala Ala Lys Val Pro
    1760                1765                1770

Gly Ala Gly Val Pro Ala Val Gly Ile Pro Ala Val Gly Ile Pro
    1775                1780                1785

Ala Val Gly Ile Pro Ala Val Gly Ile Pro Ala Val Gly Ile Pro
    1790                1795                1800

Ala Val Gly Ile Pro Ala Val Gly Ile Pro Ala Val Gly Ile Pro
    1805                1810                1815

Ala Val Gly Ile Pro Ala Val Gly Val Pro Ala Val Gly Lys Ala
    1820                1825                1830

Ala Lys Val Pro Gly Ala Gly Val Pro Ala Val Gly Ile Pro Ala
    1835                1840                1845

Val Gly Ile Pro Ala Val Gly Ile Pro Ala Val Gly Ile Pro Ala
    1850                1855                1860

Val Gly Ile Pro Ala Val Gly Ile Pro Ala Val Gly Ile Pro Ala
    1865                1870                1875
```

```
Val Gly Ile Pro Ala Val Gly Ile Pro Ala Val Gly Val Pro Ala
    1880            1885            1890

Val Gly Lys Ala Ala Lys Val Pro Gly Ala Gly Val Pro Ala Val
    1895            1900            1905

Gly Ile Pro Ala Val Gly Ile Pro Ala Val Gly Ile Pro Ala Val
    1910            1915            1920

Gly Ile Pro Ala Val Gly Ile Pro Ala Val Gly Ile Pro Ala Val
    1925            1930            1935

Gly Ile Pro Ala Val Gly Ile Pro Ala Val Gly Ile Pro Ala Val
    1940            1945            1950

Gly Val Pro Ala Val Gly Lys Ala Ala Lys Val Pro Gly Ala Gly
    1955            1960            1965

Val Pro Ala Val Gly Ile Pro Ala Val Gly Ile Pro Ala Val Gly
    1970            1975            1980

Ile Pro Ala Val Gly Ile Pro Ala Val Gly Ile Pro Ala Val Gly
    1985            1990            1995

Ile Pro Ala Val Gly Ile Pro Ala Val Gly Ile Pro Ala Val Gly
    2000            2005            2010

Ile Pro Ala Val Gly Val Pro Ala Val Gly Lys Ala Ala Lys Val
    2015            2020            2025

Pro Gly Ala Gly Val Pro Ala Val Gly Ile Pro Ala Val Gly Ile
    2030            2035            2040

Pro Ala Val Gly Ile Pro Ala Val Gly Ile Pro Ala Val Gly Ile
    2045            2050            2055

Pro Ala Val Gly Ile Pro Ala Val Gly Ile Pro Ala Val Gly Ile
    2060            2065            2070

Pro Ala Val Gly Ile Pro Ala Val Gly Val Pro Ala Val Gly Lys
    2075            2080            2085

Ala Ala Lys Val Pro Gly Ala Gly Val Pro Ala Val Gly Ile Pro
    2090            2095            2100

Ala Val Gly Ile Pro Ala Val Gly Ile Pro Ala Val Gly Ile Pro
    2105            2110            2115

Ala Val Gly Ile Pro Ala Val Gly Ile Pro Ala Val Gly Ile Pro
    2120            2125            2130

Ala Val Gly Ile Pro Ala Val Gly Ile Pro Ala Val Gly Val Pro
    2135            2140            2145

Ala Val Gly Lys Ala Ala Lys Val Pro Gly Ala Gly Val Pro Ala
    2150            2155            2160

Val Gly Ile Pro Ala Val Gly Ile Pro Ala Val Gly Ile Pro Ala
    2165            2170            2175

Val Gly Ile Pro Ala Val Gly Ile Pro Ala Val Gly Ile Pro Ala
    2180            2185            2190

Val Gly Ile Pro Ala Val Gly Ile Pro Ala Val Gly Ile Pro Ala
    2195            2200            2205

Val Gly Val Pro Ala Val Gly Lys Ala Ala Lys Val Pro Gly Ala
    2210            2215            2220

Gly Val Pro Ala Val Gly Ile Pro Ala Val Gly Ile Pro Ala Val
    2225            2230            2235

Gly Ile Pro Ala Val Gly Ile Pro Ala Val Gly Ile Pro Ala Val
    2240            2245            2250

Gly Ile Pro Ala Val Gly Ile Pro Ala Val Gly Ile Pro Ala Val
    2255            2260            2265
```

```
Gly Ile Pro Ala Val Gly Val Pro Ala Val Gly Lys Ala Ala Lys
    2270                2275                2280

Val Pro Gly Ala Gly Val Pro Ala Val Gly Ile Pro Ala Val Gly
    2285                2290                2295

Ile Pro Ala Val Gly Ile Pro Ala Val Gly Ile Pro Ala Val Gly
    2300                2305                2310

Ile Pro Ala Val Gly Ile Pro Ala Val Gly Ile Pro Ala Val Gly
    2315                2320                2325

Ile Pro Ala Val Gly Ile Pro Ala Val Gly Val Pro Ala Val Gly
    2330                2335                2340

Lys Ala Ala Lys Val Pro Gly Ala Gly Val Pro Ala Val Gly Ile
    2345                2350                2355

Pro Ala Val Gly Ile Pro Ala Val Gly Ile Pro Ala Val Gly Ile
    2360                2365                2370

Pro Ala Val Gly Ile Pro Ala Val Gly Ile Pro Ala Val Gly Ile
    2375                2380                2385

Pro Ala Val Gly Ile Pro Ala Val Gly Ile Pro Ala Val Gly Val
    2390                2395                2400

Pro Ala Val Gly Lys Ala Ala Lys Val Pro Gly Ala Gly Val Pro
    2405                2410                2415

Ala Val Gly Ile Pro Ala Val Gly Ile Pro Ala Val Gly Ile Pro
    2420                2425                2430

Ala Val Gly Ile Pro Ala Val Gly Ile Pro Ala Val Gly Ile Pro
    2435                2440                2445

Ala Val Gly Ile Pro Ala Val Gly Ile Pro Ala Val Gly Ile Pro
    2450                2455                2460

Ala Val Gly Val Pro Ala Val Gly Lys Ala Ala Lys Val Pro Gly
    2465                2470                2475

Ala Gly Val Pro Ala Val Gly Ile Pro Ala Val Gly Ile Pro Ala
    2480                2485                2490

Val Gly Ile Pro Ala Val Gly Ile Pro Ala Val Gly Ile Pro Ala
    2495                2500                2505

Val Gly Ile Pro Ala Val Gly Ile Pro Ala Val Gly Ile Pro Ala
    2510                2515                2520

Val Gly Ile Pro Ala Val Gly Val Pro Ala Val Gly Lys Ala Ala
    2525                2530                2535

Lys Val Pro Gly Ala Gly Val Pro Ala Val Gly Ile Pro Ala Val
    2540                2545                2550

Gly Ile Pro Ala Val Gly Ile Pro Ala Val Gly Ile Pro Ala Val
    2555                2560                2565

Gly Ile Pro Ala Val Gly Ile Pro Ala Val Gly Ile Pro Ala Val
    2570                2575                2580

Gly Ile Pro Ala Val Gly Ile Pro Ala Val Gly Val Pro Ala Val
    2585                2590                2595

Gly Lys Ala Ala Lys Val Pro Gly Ala Gly Val Pro Ala Val Gly
    2600                2605                2610

Ile Pro Ala Val Gly Ile Pro Ala Val Gly Ile Pro Ala Val Gly
    2615                2620                2625

Ile Pro Ala Val Gly Ile Pro Ala Val Gly Ile Pro Ala Val Gly
    2630                2635                2640

Ile Pro Ala Val Gly Ile Pro Ala Val Gly Ile Pro Ala Val Gly
    2645                2650                2655

Val Pro Ala Val Gly Lys Ala Ala Lys Val Pro Gly Ala Gly Val
```

```
            2660                2665                2670

Pro Ala Val Gly Ile Pro Ala Val Gly Ile Pro Ala Val Gly Ile
            2675                2680                2685

Pro Ala Val Gly Ile Pro Ala Val Gly Ile Pro Ala Val Gly Ile
            2690                2695                2700

Pro Ala Val Gly Ile Pro Ala Val Gly Ile Pro Ala Val Gly Ile
            2705                2710                2715

Pro Ala Val Gly Val Pro Ala Val Gly Lys Ala Ala Lys Val Pro
            2720                2725                2730

Gly Ala Gly Val Pro Ala Val Gly Ile Pro Ala Val Gly Ile Pro
            2735                2740                2745

Ala Val Gly Ile Pro Ala Val Gly Ile Pro Ala Val Gly Ile Pro
            2750                2755                2760

Ala Val Gly Ile Pro Ala Val Gly Ile Pro Ala Val Gly Ile Pro
            2765                2770                2775

Ala Val Gly Ile Pro Ala Val Gly Val Pro Ala Val Gly Lys Ala
            2780                2785                2790

Ala Lys Val Pro Gly Ala Gly Val Pro Ala Val Gly Ile Pro Ala
            2795                2800                2805

Val Gly Ile Pro Ala Val Gly Ile Pro Ala Val Gly Ile Pro Ala
            2810                2815                2820

Val Gly Ile Pro Ala Val Gly Ile Pro Ala Val Gly Ile Pro Ala
            2825                2830                2835

Val Gly Ile Pro Ala Val Gly Ile Pro Ala Val Gly Val Pro Ala
            2840                2845                2850

Val Gly Lys Ala Ala Lys Val Pro Gly Ala Gly Val Pro Ala Val
            2855                2860                2865

Gly Ile Pro Ala Val Gly Ile Pro Ala Val Gly Ile Pro Ala Val
            2870                2875                2880

Gly Ile Pro Ala Val Gly Ile Pro Ala Val Gly Ile Pro Ala Val
            2885                2890                2895

Gly Ile Pro Ala Val Gly Ile Pro Ala Val Gly Ile Pro Ala Val
            2900                2905                2910

Gly Val Pro Ala Val Gly Lys Ala Ala Lys Val Pro Gly Ala Gly
            2915                2920                2925

Val Pro Ala Val Gly Ile Pro Ala Val Gly Ile Pro Ala Val Gly
            2930                2935                2940

Ile Pro Ala Val Gly Ile Pro Ala Val Gly Ile Pro Ala Val Gly
            2945                2950                2955

Ile Pro Ala Val Gly Ile Pro Ala Val Gly Ile Pro Ala Val Gly
            2960                2965                2970

Ile Pro Ala Val Gly Val Pro Ala Val Gly Lys Ala Ala Lys Val
            2975                2980                2985

Pro Gly Ala Gly Val Pro Ala Val Gly Ile Pro Ala Val Gly Ile
            2990                2995                3000

Pro Ala Val Gly Ile Pro Ala Val Gly Ile Pro Ala Val Gly Ile
            3005                3010                3015

Pro Ala Val Gly Ile Pro Ala Val Gly Ile Pro Ala Val Gly Ile
            3020                3025                3030

Pro Ala Val Gly Ile Pro Ala Val Gly Val Pro Ala Val Gly Lys
            3035                3040                3045

Ala Ala Lys Val Pro Gly Ala Gly Val Pro Ala Val Gly Ile Pro
            3050                3055                3060
```

-continued

```
Ala Val Gly Ile Pro Ala Val Gly Ile Pro Ala Val Gly Ile Pro
3065                3070                3075

Ala Val Gly Ile Pro Ala Val Gly Ile Pro Ala Val Gly Ile Pro
3080                3085                3090

Ala Val Gly Ile Pro Ala Val Gly Ile Pro Ala Val Gly Val Pro
3095                3100                3105

Ala Val Gly Lys Ala Ala Lys Val Pro Gly Ala Gly Val Pro Ala
3110                3115                3120

Val Gly Ile Pro Ala Val Gly Ile Pro Ala Val Gly Ile Pro Ala
3125                3130                3135

Val Gly Ile Pro Ala Val Gly Ile Pro Ala Val Gly Ile Pro Ala
3140                3145                3150

Val Gly Ile Pro Ala Val Gly Ile Pro Ala Val Gly Ile Pro Ala
3155                3160                3165

Val Gly Val Pro Ala Val Gly Lys Ala Ala Lys Val Pro Gly Ala
3170                3175                3180

Gly Val Pro Ala Val Gly Ile Pro Ala Val Gly Ile Pro Ala Val
3185                3190                3195

Gly Ile Pro Ala Val Gly Ile Pro Ala Val Gly Ile Pro Ala Val
3200                3205                3210

Gly Ile Pro Ala Val Gly Ile Pro Ala Val Gly Ile Pro Ala Val
3215                3220                3225

Gly Ile Pro Ala Val Gly Val Pro Ala Val Gly Lys Ala Ala Lys
3230                3235                3240

Val Pro Gly Ala Gly Val Pro Ala Val Gly Ile Pro Ala Val Gly
3245                3250                3255

Ile Pro Ala Val Gly Ile Pro Ala Val Gly Ile Pro Ala Val Gly
3260                3265                3270

Ile Pro Ala Val Gly Ile Pro Ala Val Gly Ile Pro Ala Val Gly
3275                3280                3285

Ile Pro Ala Val Gly Ile Pro Ala Val Gly Val Pro Ala Val Gly
3290                3295                3300

Lys Ala Ala Lys Val Pro Gly Ala Gly Val Pro Ala Val Gly Ile
3305                3310                3315

Pro Ala Val Gly Ile Pro Ala Val Gly Ile Pro Ala Val Gly Ile
3320                3325                3330

Pro Ala Val Gly Ile Pro Ala Val Gly Ile Pro Ala Val Gly Ile
3335                3340                3345

Pro Ala Val Gly Ile Pro Ala Val Gly Ile Pro Ala Val Gly Val
3350                3355                3360

Pro Ala Val Gly Lys Ala Ala Lys Val Pro Gly Ala Gly Val Pro
3365                3370                3375

Ala Val Gly Ile Pro Ala Val Gly Ile Pro Ala Val Gly Ile Pro
3380                3385                3390

Ala Val Gly Ile Pro Ala Val Gly Ile Pro Ala Val Gly Ile Pro
3395                3400                3405

Ala Val Gly Ile Pro Ala Val Gly Ile Pro Ala Val Gly Ile Pro
3410                3415                3420

Ala Val Gly Val Pro Ala Val Gly Lys Ala Ala Lys Val Pro Gly
3425                3430                3435

Ala Gly Val Pro Ala Val Gly Ile Pro Ala Val Gly Ile Pro Ala
3440                3445                3450
```

```
Val Gly Ile Pro Ala Val Gly Ile Pro Ala Val Gly Ile Pro Ala
    3455                3460                3465
Val Gly Ile Pro Ala Val Gly Ile Pro Ala Val Gly Ile Pro Ala
    3470                3475                3480
Val Gly Ile Pro Ala Val Gly Val Pro Ala Val Gly Lys Ala Ala
    3485                3490                3495
Lys Val Pro Gly Ala Gly Val Pro Ala Val Gly Ile Pro Ala Val
    3500                3505                3510
Gly Ile Pro Ala Val Gly Ile Pro Ala Val Gly Ile Pro Ala Val
    3515                3520                3525
Gly Ile Pro Ala Val Gly Ile Pro Ala Val Gly Ile Pro Ala Val
    3530                3535                3540
Gly Ile Pro Ala Val Gly Ile Pro Ala Val Gly Val Pro Ala Val
    3545                3550                3555
Gly Lys Ala Ala Lys Val Pro Gly Ala Gly Val Pro Ala Val Gly
    3560                3565                3570
Ile Pro Ala Val Gly Ile Pro Ala Val Gly Ile Pro Ala Val Gly
    3575                3580                3585
Ile Pro Ala Val Gly Ile Pro Ala Val Gly Ile Pro Ala Val Gly
    3590                3595                3600
Ile Pro Ala Val Gly Ile Pro Ala Val Gly Ile Pro Ala Val Gly
    3605                3610                3615
Val Pro Ala Val Gly Lys Ala Ala Lys Val Pro Gly Ala Gly Val
    3620                3625                3630
Pro Ala Val Gly Ile Pro Ala Val Gly Ile Pro Ala Val Gly Ile
    3635                3640                3645
Pro Ala Val Gly Ile Pro Ala Val Gly Ile Pro Ala Val Gly Ile
    3650                3655                3660
Pro Ala Val Gly Ile Pro Ala Val Gly Ile Pro Ala Val Gly Ile
    3665                3670                3675
Pro Ala Val Gly Ile Pro Ala Val Gly Lys Ala Ala Lys Ala
    3680                3685                3690
```